United States Patent
Lu et al.

(10) Patent No.: US 9,598,389 B2
(45) Date of Patent: Mar. 21, 2017

(54) DIHYDROBENZOFURAN DERIVATIVES AS INSECTICIDAL COMPOUNDS

(71) Applicant: SYNGENTA PARTICIPATIONS AG, Basel (CH)

(72) Inventors: Long Lu, Shanghai (CN); Jerome Yves Cassayre, Stein (CH); Torsten Luksch, Stein (CH); Myriem El Qacemi, Stein (CH); Guillaume Berthon, Stein (CH); Yaming Wu, Shanghai (CN)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 14/771,600

(22) PCT Filed: Mar. 6, 2014

(86) PCT No.: PCT/CN2014/072966
§ 371 (c)(1),
(2) Date: Aug. 31, 2015

(87) PCT Pub. No.: WO2014/135095
PCT Pub. Date: Sep. 12, 2014

(65) Prior Publication Data
US 2016/0016927 A1    Jan. 21, 2016

(30) Foreign Application Priority Data
Mar. 6, 2013 (WO) ............... PCT/CN2013/072227

(51) Int. Cl.
| | | |
|---|---|---|
| C07D 307/79 | (2006.01) | |
| C07C 233/33 | (2006.01) | |
| A01N 43/10 | (2006.01) | |
| C07D 405/12 | (2006.01) | |
| C07D 413/12 | (2006.01) | |
| A01N 43/80 | (2006.01) | |
| C07D 409/12 | (2006.01) | |
| A01N 43/40 | (2006.01) | |
| A01N 43/60 | (2006.01) | |
| C07C 233/25 | (2006.01) | |
| C07D 405/10 | (2006.01) | |
| A01N 43/90 | (2006.01) | |
| A01N 43/12 | (2006.01) | |
| C07D 333/54 | (2006.01) | |
| C07D 405/04 | (2006.01) | |
| A01N 37/22 | (2006.01) | |
| A01N 43/20 | (2006.01) | |
| A01N 43/54 | (2006.01) | |
| A01N 43/713 | (2006.01) | |

(52) U.S. Cl.
CPC .......... *C07D 307/79* (2013.01); *A01N 37/22* (2013.01); *A01N 43/10* (2013.01); *A01N 43/12* (2013.01); *A01N 43/20* (2013.01); *A01N 43/40* (2013.01); *A01N 43/54* (2013.01); *A01N 43/60* (2013.01); *A01N 43/713* (2013.01); *A01N 43/80* (2013.01); *A01N 43/90* (2013.01); *C07C 233/25* (2013.01); *C07C 233/33* (2013.01); *C07D 333/54* (2013.01); *C07D 405/04* (2013.01); *C07D 405/10* (2013.01); *C07D 405/12* (2013.01); *C07D 409/12* (2013.01); *C07D 413/12* (2013.01)

(58) Field of Classification Search
CPC .. C07D 307/79; C07D 233/33; C07D 405/12; C07D 413/12; C07D 409/12; C07D 405/10; A01N 43/10; A01N 43/80; A01N 43/40; A01N 43/60; A01N 43/54; A01N 43/20; A01N 43/713; A01N 37/22; C07C 233/25
See application file for complete search history.

(56) References Cited

U.S. PATENT DOCUMENTS

2016/0016927 A1* 1/2016 Lu .................. A01N 43/12
                                                     514/30

FOREIGN PATENT DOCUMENTS

| CN | 101190905 A | 6/2008 | |
|---|---|---|---|
| CN | 102010406 A | 4/2011 | |
| EP | 0383318 A2 | 8/1990 | |
| EP | 1731512 A1 * | 12/2006 | ............. A01N 43/80 |

(Continued)

OTHER PUBLICATIONS

International Search Report and Written Opinion for International Patent Application No. PCT/CN2014/072966 mailed on Jun. 5, 2014.

(Continued)

*Primary Examiner* — Samantha Shterengarts
*Assistant Examiner* — Matt Mauro
(74) *Attorney, Agent, or Firm* — Brian D. McAlhaney

(57) ABSTRACT

Provided are compounds of formula (I) and methods of controlling insects, acarines, nematodes or molluscs, which comprises applying to a pest, to a locus of a pest, or to a plant susceptible to attack by a pest an insecticidally, acaricidally, nematicidally or molluscicidally effective amount of a compound of formula (I).

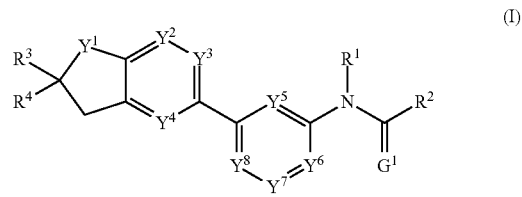

(I)

14 Claims, No Drawings

(56) References Cited

FOREIGN PATENT DOCUMENTS

| WO | 97/47615 A1 | 12/1997 |
| WO | 2009112275 A1 | 9/2009 |
| WO | 2010020522 A1 | 2/2010 |
| WO | 2010084067 A2 | 7/2010 |

OTHER PUBLICATIONS

Kuethe, Jeffrey T. et al: A Rapid Synthesis of 2-Aryl-5-substituted-2,3-dihydrobenzofurans, 2005, 70(9): 3727-3729; The Journal of Organic Chemistry (XP055285300).
Extended European Search Report and European Search Opinion for International Patent Application No. PCT/CN2014/072966 mailed Sep. 26, 2016.

\* cited by examiner

DIHYDROBENZOFURAN DERIVATIVES AS INSECTICIDAL COMPOUNDS

RELATED APPLICATION INFORMATION

This application is a 371 of International Application No. PCT/CN2014/072966, filed 6 Mar. 2014, which claims priority to PCT/CN2013/072227, filed 6 Mar. 2013, the contents of all of which are incorporated herein by reference herein.

The present invention relates to certain dihydrobenzofuran derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in EP 1,731,512. However there is a continuing need to find new biologically active compounds as well as new biologically active compounds displaying superior properties for use as agrochemical active ingredients, for example greater biological activity, different spectrum of activity, increased safety profile, or increased biodegradability.

It has now surprisingly been found that certain dihydrobenzofuranderivatives have highly potent insecticidal properties.

The present invention provides compounds of formula (I)

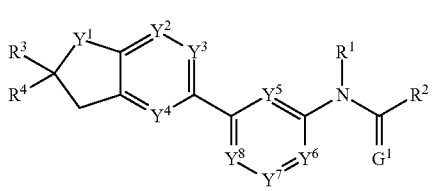

(I)

wherein
$G^1$ is oxygen or sulfur;
$Y^1$ is oxygen, sulfur, C(O), CHOR or $CH_2$;
$Y^2$, $Y^3$ and $Y^4$ are each independently C—H, C—$R^5$ or nitrogen, wherein no more than one of $Y^2$, $Y^3$ and $Y^4$ is C—$R^5$;
$Y^5$ is C—H, C—F or nitrogen;
$Y^6$ is C—H, C—$R^{6a}$ or nitrogen;
$Y^7$ is C—H, C—$R^{6b}$ or nitrogen;
$Y^8$ is C—H, C—$R^{6c}$ or nitrogen;
R is hydrogen, $C_1$-$C_8$alkyl;
$R^1$ is hydrogen, $C_1$-$C_8$alkyl, $C_1$-$C_8$alkoxy, $C_1$-$C_8$alkylcarbonyl, $C_3$-$C_8$cycloalkylcarbonyl, or $C_1$-$C_8$alkoxycarbonyl;
$R^2$ is $C_1$-$C_8$alkyl or $C_1$-$C_8$alkyl substituted by one to five $R^7$, $C_2$-$C_8$alkenyl or $C_2$-$C_8$alkenyl substituted by one to five $R^7$, $C_2$-$C_8$alkynyl or $C_2$-$C_8$alkynyl substituted by one to five $R^7$, $C_1$-$C_8$alkoxy-$C_1$-$C_8$alkyl or $C_1$-$C_8$alkoxy-$C_1$-$C_8$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-$C_1$-$C_4$alkylene or $C_3$-$C_{10}$cycloalkyl-$C_1$-$C_4$alkylene substituted by one to five $R^8$, aryl-$C_1$-$C_4$alkylene- or aryl-$C_1$-$C_4$alkylene-substituted by one to five $R^9$, heterocyclyl-$C_1$-$C_4$alkylene- or heterocyclyl-$C_1$-$C_4$alkylene-substituted by one to five $R^9$, aryl or aryl substituted by one to five $R^9$, heterocyclyl or heterocyclyl substituted by one to five $R^9$;
or $R^1$ and $R^2$ form a four to six membered ringtogether with the atoms to which they are attached substituted by one to five $R^7$
$R^3$ is $C_1$-$C_8$haloalkyl;
$R^4$ is aryl or aryl substituted by one to five $R^{10}$, or heteroaryl or heteroaryl substituted by one to five $R^{10}$;
each $R^5$ is independently halogen, cyano, $C_1$-$C_4$alkyl, $C_1$-$C_4$haloalkyl, $C_1$-$C_4$alkoxy or $C_1$-$C_4$haloalkoxy;
$R^{6a}$ is halogen, cyano, $C_1$-$C_4$alkyl, $C_1$-$C_4$haloalkyl, $C_1$-$C_4$alkoxy or $C_1$-$C_4$haloalkoxy;
$R^{6b}$ is fluoro or chloro;
$R^{6c}$ is halogen, cyano, $C_1$-$C_4$alkyl, $C_1$-$C_4$haloalkyl, $C_1$-$C_4$alkoxy or $C_1$-$C_4$haloalkoxy;
each $R^7$ is independently halogen, cyano, nitro, hydroxy, amino, $C_1$-$C_8$alkylamino, $(C_1$-$C_8$alkyl$)_2$amino, $C_1$-$C_8$alkylcarbonylamino, $C_1$-$C_8$haloalkylcarbonylamino, carbonylamino, (carbonyl)$(C_1$-$C_8$alkyl)amino, $(C_1$-$C_8$alkylcarbonyl$)(C_1$-$C_8$alkyl)amino, $(C_1$-$C_8$haloalkylcarbonyl$)(C_1$-$C_8$alkyl)amino, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, aryl-$C_1$-$C_4$alkylthio or aryl-$C_1$-$C_4$alkylthio wherein the aryl moiety is substituted by one to five $R^{11}$, or two $R^7$ are together OH—N= or $C_1$-$C_6$alkoxy-N=.

each $R^8$ is independently halogen, cyano, $C_1$-$C_8$alkyl, $C_2$-$C_8$alkenyl, $C_2$-$C_8$alkynyl, $C_1$-$C_8$alkoxy, or $C_1$-$C_8$alkoxycarbonyl;
each $R^9$ is independently halogen, cyano, nitro, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylaminosulfonyl, $(C_1$-$C_8$alkyl$)_2$aminosulfonyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl;
each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;
each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy;
or a salt or N-oxide thereof.

The compounds of formula (I) may exist in different geometric or optical isomers or tautomeric forms. In particular, the compounds of the invention may contain one or more asymmetric carbon atoms and may exist as enantiomers (or as pairs of diastereoisomers) or as mixtures of such. This invention covers all such isomers and tautomers and mixtures thereof in all proportions as well as isotopic forms such as deuterated compounds. The compounds of the invention include N-oxides and salts.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are preferably $C_1$-$C_3$, more preferably $C_1$-$C_2$, most preferably $C_1$ alkylene groups. Where an alkylene moiety is said to be substituted, the alkyl moiety is preferably substituted by one to four substituents, most preferably by one to three substituents.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups. Where an alkenyl moiety is said to be substituted, the alkyl moiety is preferably substituted by one to four substituents, most preferably by one to three substituents.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups. Where an alkynyl moiety is said to be substituted, the alkyl moiety is preferably substituted by one to four substituents, most preferably by one to three substituents.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazolyl), furanyl, thiophenyl, oxazolyl, isoxazolyl, oxadiazolyl, thiazolyl, isothiazolyl, tetrazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, dihydrofuranyl, tetrahydrofuranyl, dihydropyranyl, tetrahydropyranyl, dihydrothiophene, [1,3]dioxolanyl, piperidinyl, piperazinyl, [1,4]dioxanyl, morpholinyl, thiophene, oxetanyl, tetrahydropyranyl, 3-oxo-isoxazolidinyl-, 2,5-dioxo-1-pyrrolidinyl-, 2-oxo-1-pyrrolidinyl-, 4-oxo-1,3-oxazinanyl, 1-oxa-3,4-diazolyl, including their oxidised versions such as 1-oxo-thietanyl and 1,1-dioxothietanyl, thiophene 1-oxide, thiophene 1,1-dioxide, dihydrothiophene, dihydrothiophene 1-oxide, or dihydrothiophene 1,1-dioxide. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Heterocyclyl groups (and heteroaryl groups) according to the present invention do not contain adjacent oxygen atoms, adjacent sulphur atoms, or adjacent sulphur and oxygen atoms. Preferred heterocyclyl groups are thiophene, thiophene 1-oxide, thiophene 1,1-dioxide, dihydrothiophene, dihydrothiophene 1-oxide, dihydrothiophene 1,1-dioxide, pyridyl, pyrazinyl, pyrimidinyl, pyrrolyl, imidazolyl, pyrazolyl, triazolyl, and tetrazoyl.

In a further embodiment the present invention provides compounds of formula (I) wherein $G^1$ is oxygen or sulfur;

$Y^1$ is oxygen, sulfur, C(O), CHOR or $CH_2$;

$Y^2$ and $Y^3$ are independently C—H, C—$R^5$ or nitrogen, and $Y^4$ is C—H, C—$R^5$ wherein no more than one of $Y^2$, $Y^3$ and $Y^4$ is C—$R^5$;

$Y^5$ is C—H, C—F or nitrogen;

$Y^6$ is C—H, C—$R^{6a}$ or nitrogen;

$Y^7$ is C—H, C—$R^{6b}$ or nitrogen;

$Y^8$ is C—H, C—$R^{6c}$ or nitrogen;

R is hydrogen, $C_1$-$C_8$alkyl;

$R^1$ is hydrogen, $C_1$-$C_8$alkyl, $C_1$-$C_8$alkoxy, $C_1$-$C_8$alkylcarbonyl, $C_3$-$C_8$cycloalkylcarbonyl or $C_1$-$C_8$alkoxycarbonyl;

$R^2$ is $C_1$-$C_8$alkyl or $C_1$-$C_8$alkyl substituted by one to five $R^7$, $C_2$-$C_8$alkenyl or $C_2$-$C_8$alkenyl substituted by one to five $R^7$, $C_2$-$C_8$alkynyl or $C_2$-$C_8$alkynyl substituted by one to five $R^7$, $C_1$-$C_8$alkoxy-$C_1$-$C_8$alkyl or $C_1$-$C_8$alkoxy-$C_1$-$C_8$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-$C_1$-$C_4$alkylene or $C_3$-$C_{10}$cycloalkyl-$C_1$-$C_4$alkylene substituted by one to five $R^8$, aryl-$C_1$-$C_4$alkylene- or aryl-$C_1$-$C_4$alkylene-substituted by one to five $R^9$, heterocyclyl-$C_1$-$C_4$alkylene- or heterocyclyl-$C_1$-$C_4$alkylene-substituted by one to five $R^9$, aryl or aryl substituted by one to five $R^9$, heterocyclyl or heterocyclyl substituted by one to five $R^9$; or $R^1$ and $R^2$ form a four to six membered ring together with the atoms to which they are attached substituted by one to five $R^7$ $R^3$ is $C_1$-$C_8$haloalkyl;

$R^4$ is aryl or aryl substituted by one to five $R^{10}$, or heteroaryl or heteroaryl substituted by one to five $R^{10}$;

each $R^5$ is independently halogen, cyano, $C_1$-$C_4$alkyl, $C_1$-$C_4$haloalkyl, $C_1$-$C_4$alkoxy or $C_1$-$C_4$haloalkoxy;

$R^{6a}$ is halogen, cyano, $C_1$-$C_4$alkyl, $C_1$-$C_4$haloalkyl, $C_1$-$C_4$alkoxy or $C_1$-$C_4$haloalkoxy;

$R^{6b}$ is fluoro or chloro;

$R^{6c}$ is halogen, cyano, $C_1$-$C_4$alkyl, $C_1$-$C_4$haloalkyl, $C_1$-$C_4$alkoxy or $C_1$-$C_4$haloalkoxy;

each $R^7$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, carbonylamino, (carbonyl)($C_1$-$C_8$alkyl)amino, ($C_1$-$C_8$alkylcarbonyl)($C_1$-$C_8$alkyl)amino, ($C_1$-$C_8$haloalkylcarbonyl)($C_1$-$C_8$alkyl)amino, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, aryl-$C_1$-$C_4$alkylthio or aryl-$C_1$-$C_4$alkylthio wherein the aryl moiety is substituted by one to five $R^{11}$, or two $R^7$ are together OH—N= or $C_1$-$C_6$alkoxy-N=.

each $R^8$ is independently halogen, cyano, $C_1$-$C_8$alkyl, $C_2$-$C_8$alkenyl, $C_2$-$C_8$alkynyl, $C_1$-$C_8$alkoxy, or $C_1$-$C_8$alkoxycarbonyl;

each $R^9$ is independently halogen, cyano, nitro, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylaminosulfonyl, ($C_1$-$C_8$alkyl)$_2$aminosulfonyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl;

each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;

each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

or a salt or N-oxide thereof.

Preferred values of $Y^1$, $Y^2$, $Y^3$, $Y^4$, $Y^5$, $Y^6$, $Y^7$, $Y^8$, $G^1$, $R^1$, $R^2$, $R^3$, $R^4$, $R^5$, $R^6$, $R^7$, $R^8$, $R^9$, $R^{10}$, $R^{11}$ are, in any combination (including combinations of preferred values with the original values) as set out below.

Preferably $G^1$ is oxygen.

Preferably $Y^1$ is oxygen.

Preferably no more than two of $Y^2$, $Y^3$ and $Y^4$ are nitrogen.

Preferably $Y^3$ is C—H or C—$R^5$, more preferably C—H.

Preferably $Y^4$ is C—H or C—$R^5$, more preferably C—H.

Preferably no more than two of $Y^5$, $Y^6$, $Y^7$ and $Y^8$ are nitrogen.

Preferably $Y^5$ is C—H.

Preferably $Y^6$ is C—H, C—$R^{6a}$ or nitrogen.

Preferably $Y^7$ is C—H or nitrogen, more preferably C—H.

Preferably $Y^8$ is C—H or nitrogen, more preferably C—H.

Preferably R is hydrogen, methyl.

Preferably $R^1$ is hydrogen, methyl, ethyl, methylcarbonyl, cyclopropylcarbonyl, or methoxycarbonyl, more preferably hydrogen, methyl or ethyl, most preferably hydrogen.

Preferably $R^2$ is $C_1$-$C_6$alkyl or $C_1$-$C_6$alkyl substituted by one to five $R^7$, $C_2$-$C_6$alkenyl or $C_2$-$C_6$alkenyl substituted by one to five $R^7$, $C_2$-$C_6$alkynyl or $C_2$-$C_6$alkynyl substituted by one to five $R^7$, $C_1$-$C_6$alkoxy-$C_1$-$C_6$alkyl or $C_1$-$C_6$alkoxy-$C_1$-$C_6$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-C($R^{12}$)($R^{13}$)— or $C_3$-$C_{10}$cycloalkyl-C($R^{12}$)($R^{13}$)-substituted by one to five $R^8$, aryl-C($R^{12}$)($R^{13}$)— or aryl-C($R^{12}$)($R^{13}$)— substituted by one to five $R^9$, heterocyclyl-C($R^{12}$)($R^{13}$)— or heterocyclyl-C($R^{12}$)($R^{13}$)— substituted by one to five $R^9$, aryl or aryl substituted by one to five $R^9$, heterocyclyl or heterocyclyl substituted by one to five $R^9$; Or preferably $R^1$ and $R^2$ form a four to six membered ring together with the atoms to which they are attached wherein aryl is phenyl;

wherein heterocyclyl is a 4- to 7-membered heterocyclic ring containing one to four heteroatoms independently selected from O, S, SO, SO$_2$, N and N($R^{14}$) as ring atoms;

wherein $R^{12}$ and $R^{13}$ are independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl; and wherein $R^{14}$ is hydrogen or $R^9$.

More preferably $R^2$ is $C_1$-$C_6$alkyl or $C_1$-$C_6$alkyl substituted by one to three $R^7$, $C_2$-$C_6$alkenyl or $C_2$-$C_6$alkenyl substituted by one to three $R^7$, $C_2$-$C_6$alkynyl or $C_2$-$C_6$alkynyl substituted by one to three $R^7$, $C_1$-$C_4$alkoxy-$C_1$-$C_2$alkyl or $C_1$-$C_4$alkoxy-$C_1$-$C_2$alkyl substituted by one to five $R^7$, $C_3$-$C_8$cycloalkyl or $C_3$-$C_8$cycloalkyl substituted by one to five $R^8$, $C_3$-$C_8$cycloalkyl-C($R^{12}$)($R^{13}$)— or $C_3$-$C_8$cycloalkyl-C($R^{12}$)($R^{13}$)— substituted by one to five $R^8$, aryl-C($R^{12}$)($R^{13}$)— or aryl-C($R^{12}$)($R^{13}$)— substituted by one to five $R^9$, heterocyclyl-C($R^{12}$)($R^{13}$)— or heterocyclyl-C($R^{12}$)($R^{13}$)— substituted by one to five $R^9$, aryl or aryl substituted by one to five $R^9$, heterocyclyl or heterocyclyl substituted by one to five $R^9$;

Or $R^1$ and $R^2$ form a five membered ring together with the atoms to which they are attached wherein aryl is phenyl;

wherein heterocyclyl is a 4- to 6-membered saturated or partially saturated heterocyclic ring containing one or two heteroatoms independently selected from O, S, SO, SO$_2$, N and N($R^{14}$) as ring atoms; or wherein heterocyclyl is a 5- to 6-membered heteroaryl ring containing one to four heteroatoms selected from O, S, N and N($R^{14}$) as ring members;

wherein $R^{12}$ is hydrogen;

wherein $R^{13}$ is hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl; and wherein $R^{14}$ is hydrogen or $R^9$.

Most preferably $R^2$ is $C_1$-$C_6$alkyl or $C_1$-$C_6$alkyl substituted by one to three $R^7$, $C_2$-$C_6$alkenyl or $C_2$-$C_6$alkenyl substituted by one to three $R^7$, $C_1$-$C_4$alkoxy-$C_1$-$C_2$alkyl or $C_1$-$C_4$alkoxy-$C_1$-$C_2$alkyl substituted by one to five $R^7$, $C_3$-$C_6$cycloalkyl or $C_3$-$C_6$cycloalkyl substituted by one to five $R^8$, $C_3$-$C_6$cycloalkyl-C($R^{12}$)($R^{13}$)— or $C_3$-$C_6$cycloalkyl-C($R^{12}$)($R^{13}$)— substituted by one to five $R^8$, aryl-C($R^{12}$)($R^{13}$)— or aryl-C($R^{12}$)($R^{13}$)— substituted by one to three $R^9$, heterocyclyl-$C(R^{12})(R^{13})$—, or aryl or aryl substituted by one to three $R^9$;

wherein aryl is phenyl;

wherein heterocyclyl is oxetanyl, dihydrofuranyl, tetrahydrofuranyl, dihydropyranyl, tetrahydropyranyl, thietanyl, 1-oxo-thietanyl, 1,1,-dioxothietanyl, thiophene, thiophene 1-oxide, thiophene 1,1-dioxide, dihydrothiophene, dihydrothiophene 1-oxide, or dihydrothiophene 1,1-dioxide, each optionally substituted by one to three methyl (said heterocycles are preferably connected to the compound of formula I at the 3' position); or wherein heterocycle is pyridyl, pyrazinyl, pyrimidinyl, pyrrolyl, imidazolyl, pyrazolyl, triazolyl, tetrazoyl, each optionally substituted by one to three $R^9$.

wherein $R^{12}$ is hydrogen; and wherein $R^{13}$ is hydrogen or methyl.

Preferably $R^3$ is trifluoromethyl, difluoromethyl or chlorodifluoromethyl, most preferably trifluoromethyl.

Preferably $R^4$ is aryl or aryl substituted by one to five $R^{10}$, more preferably aryl substituted by one to three $R^{10}$, more preferably phenyl substituted by one to three $R^{10}$.

In one group of compounds $R^4$ is group (A)

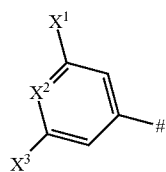

(A)

wherein $X^2$ is C—$X^4$ or nitrogen (preferably C—$X^4$); $X^1$, $X^3$ and $X^4$ are independently hydrogen, halogen or trihalomethyl, e.g. wherein at least two of $X^1$, $X^3$ and $X^4$ are not hydrogen.

Preferably $R^4$ is 3,5-dichlorophenyl, 3-chloro-4-fluorophenyl, 3-fluoro-4-chlorophenyl, 3,4-dichlorophenyl, 3-chloro-4-bromophenyl, 3,5-dichloro-4-fluorophenyl, 3,4,5-trichlorophenyl, 3,5-dichloro-4-iodophenyl, 3,4,5-trifluorophenyl, 3-chloro-5-bromophenyl, 3-chloro-5-fluorophenyl, 3-chloro-5-(trifluoromethyl)phenyl, 3-bromo-5-(trifluoromethyl)phenyl, 3,4-dichloro-5-(trifluoromethyl)phenyl, 3,5-bis(trifluoromethyl)phenyl, 4-chloro-3,5-bis(trifluoromethyl)phenyl, 3-(trifluoromethyl)phenyl, 2,6-dichloro-4-pyridyl, 2,6-bis(trifluoromethyl)-4-pyridyl,2-chloro-4-pyridyl-, 2-trifluoromethyl-4-pyridyl, more preferably 3,5-dichloro-phenyl, 3-chloro-5-bromophenyl,3-chloro-5-(trifluoromethyl)phenyl,3,5-dichloro-4-fluorophenyl,3,4,5-trichlorophenyl,3,5-bis(trifluoromethyl)phenyl,3-(trifluoromethyl)phenyl,2,6-dichloro-4-pyridyl,2,6-bis(trifluoromethyl)-4-pyridyl,3,5-dichloro-4-bromophenyl,3-bromo-5-(trifluoromethyl)phenyl,3,5-dibromophenyl, or 3,4-dichlorophenyl,2-chloro-4-pyridyl-, 2-trifluoromethyl-4-pyridyl, even more preferably 3,5-dichloro-phenyl, 3,5-dichloro-4-fluorophenyl,3,4,5-trichlorophenyl,3-(trifluoromethyl)phenyl,3,5-bis(trifluoromethyl)phenyl, most preferably 3,5-dichloro-phenyl, 3,5-dichloro-4-fluorophenyl, or 3,4,5-trichlorophenyl-. In one group of compounds $R^4$ is 3,5-dichloro-phenyl. In one group of compounds $R^4$ is 3,5-dichloro-4-fluorophenyl-. In one group of compounds $R^4$ is 3,4,5-trichlorophenyl-. In one group of compounds $R^4$ is 3,5-bis(trifluoromethyl)phenyl.

Preferably each $R^5$ is independently halogen, cyano, methyl, halomethyl, methoxy or halomethoxy, more preferably chloro, fluoro, cyano or methyl.

Preferably $R^{6a}$ is halogen, cyano, methyl, halomethyl, methoxy or halomethoxy, most preferably chloro, fluoro, cyano or methyl.

Preferably $R^{6b}$ is fluoro.

Preferably $R^{6c}$ is halogen, cyano, methyl, halomethyl, methoxy or halomethoxy, more preferably chloro, fluoro, cyano or methyl.

Preferably each $R^7$ is independently halogen, cyano, nitro, hydroxy, carbonylamino, (carbonyl)($C_1$-$C_8$)amino, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl, or two $R^7$ are together OH—N= or $C_1$-$C_6$alkoxy-N=, more preferably halogen, cyano, nitro, hydroxy, carbonylamino, (carbonyl)($C_1$-$C_8$)amino, $C_1$-$C_8$alkoxy, $C_1$-$C_8$haloalkoxy, mercapto, $C_1$-$C_8$alkylthio, or $C_1$-$C_8$haloalkylthio, or two $R^{12}$ are together OH—N=, even more preferably halogen, carbonylamino, (carbonyl)($C_1$-$C_4$)amino, $C_1$-$C_4$alkoxy, $C_1$-$C_4$alkylthio, $C_1$-$C_4$ alkylsulfinyl or $C_1$-$C_4$alkylsulfonyl, most preferably halogen, carbonylamino, (carbonyl)(methyl)amino, methoxy, methylthio, methylsulfinyl or methylsulfonyl.

Preferably each $R^8$ is independently halogen, cyano, $C_1$-$C_4$alkyl or $C_1$-$C_4$alkoxy, more preferably halogen, cyano or methyl, more preferably chloro, fluoro, cyano or methyl, most preferably fluoro, cyano or methyl.

Preferably each $R^9$ is independently halogen, cyano, nitro, $C_1$-$C_8$alkyl, $C_1$-$C_8$haloalkyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, more preferably halogen, cyano, nitro, $C_1$-$C_4$alkyl, $C_1$-$C_4$haloalkyl, $C_1$-$C_4$alkoxy, or $C_1$-$C_4$haloalkoxy, most preferably halogen, cyano, methyl, halomethyl, methoxy, or halomethoxy.

Preferably each $R^{10}$ is independently halogen, $C_1$-$C_8$alkyl, $C_1$-$C_8$haloalkyl, $C_1$-$C_8$alkoxy, $C_1$-$C_8$haloalkoxy, $C_1$-$C_8$alkylthio, or $C_1$-$C_8$haloalkylthio, more preferably bromo, chloro, fluoro, trifluoromethyl, methoxy, or methylthio, most preferably trifluoromethyl, fluoro or chloro.

Preferably each $R^{11}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

The following represent preferred embodiments of the invention, which may be combined with each other and with the preferred definitions where possible.

In one embodiment (E1) $Y^2$ is C—H and $Y^3$ and $Y^4$ are C—H or C—$R^5$ wherein no more than one of $Y^3$ and $Y^4$ is C—$R^5$.

In another embodiment (E2) $Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen.

In another Embodiment (E3) $Y^2$ is C—H, $Y^3$ and $Y^4$ are C—H or C—$R^5$ wherein no more than one of $Y^3$ and $Y^4$ is C—$R^5$, $Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen.

Embodiment E4 is embodiment E1 wherein $Y^1$ is oxygen
Embodiment E5 is embodiment E2 wherein $Y^1$ is oxygen
Embodiment E6 is embodiment E3 wherein $Y^1$ is oxygen
Embodiment E7 is embodiment E4 wherein $G^1$ is oxygen
Embodiment E8 is embodiment E5 wherein $G^1$ is oxygen
Embodiment E9 is embodiment E6 wherein $G^1$ is oxygen Embodiment E10 is embodiment E7 wherein $R^1$ is hydrogen, methyl or ethyl.

Embodiment E11 is embodiment E8 wherein $R^1$ is hydrogen, methyl or ethyl.

Embodiment E12 is embodiment E9 wherein $R^1$ is hydrogen, methyl or ethyl.

Embodiment E13 is embodiment E1 wherein $R^3$ is trifluoromethyl, difluoromethyl or chlorodifluoromethyl Embodiment E14 is embodiment E2 wherein $R^3$ is trifluoromethyl, difluoromethyl or chlorodifluoromethyl Embodiment E15 is embodiment E3 wherein $R^3$ is trifluoromethyl, difluoromethyl or chlorodifluoromethyl Embodiment E16 is embodiment E4 wherein $R^3$ is trifluoromethyl, difluoromethyl or chlorodifluoromethyl Embodiment E17 is embodiment E5 wherein $R^3$ is trifluoromethyl, difluoromethyl or chlorodifluoromethyl Embodiment E18 is embodiment E6 wherein $R^3$ is trifluoromethyl, difluoromethyl or chlorodifluoromethyl Embodiment E19 is embodiment E7 wherein $R^3$ is trifluoromethyl, difluoromethyl or chlorodifluoromethyl Embodiment E20 is embodiment E8 wherein $R^3$ is trifluoromethyl, difluoromethyl or chlorodifluoromethyl Embodiment E21 is embodiment E9 wherein $R^3$ is trifluoromethyl, difluoromethyl or chlorodifluoromethyl Embodiment E22 is embodiment E10 wherein $R^3$ is trifluoromethyl, difluoromethyl or chlorodifluoromethyl Embodiment E23 is embodiment E11 wherein $R^3$ is trifluoromethyl, difluoromethyl or chlorodifluoromethyl Embodiment E24 is embodiment E12 wherein $R^3$ is trifluoromethyl, difluoromethyl or chlorodifluoromethyl Embodiment 25 is embodiment E13 wherein $R^4$ is group A.

Embodiment E26 is embodiment E14 wherein $R^4$ is group A.

Embodiment E27 is embodiment E15 wherein $R^4$ is group A.

Embodiment E28 is embodiment E16 wherein $R^4$ is group A.

Embodiment E29 is embodiment E17 wherein $R^4$ is group A.

Embodiment E30 is embodiment E18 wherein $R^4$ is group A.

Embodiment E31 is embodiment E19 wherein $R^4$ is group A.

Embodiment E32 is embodiment E20 wherein $R^4$ is group A.

Embodiment E33 is embodiment E21 wherein $R^4$ is group A.

Embodiment E34 is embodiment E22 wherein $R^4$ is group A.

Embodiment E35 is embodiment E23 wherein $R^4$ is group A.

Embodiment E36 is embodiment E24 wherein $R^4$ is group A.

In another embodiment (E37):
$G^1$ is oxygen;
$Y^1$ is oxygen;
$Y^2$ is C—H, $Y^3$ and $Y^4$ are C—H or C—$R^5$, wherein no more than one of $Y^3$ and $Y^4$ is C—$R^5$;
$Y^5$ is C—H;
$Y^6$ is C—H, C—$R^{6a}$ or nitrogen;
$Y^7$ is C—H, C—$R^{6b}$ or nitrogen;
$Y^8$ is C—H, C—$R^{6c}$ or nitrogen, wherein no more than two of $Y^5$, $Y^6$, $Y^7$ and $Y^8$ are nitrogen;
$R^1$ is hydrogen, methyl or ethyl;
$R^2$ is $C_1$-$C_6$alkyl or $C_1$-$C_6$alkyl substituted by one to five $R^7$, $C_2$-$C_6$alkenyl or $C_2$-$C_6$alkenyl substituted by one to five $R^{12}$, $C_2$-$C_6$alkynyl or $C_2$-$C_6$alkynyl substituted by one to five $R^7$, $C_1$-$C_6$alkoxy-$C_1$-$C_6$alkyl or $C_1$-$C_6$alkoxy-$C_1$-$C_6$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-C($R^{12}$)($R^{13}$)— or $C_3$-$C_{10}$cycloalkyl-C($R^{12}$)($R^{13}$)-substituted by one to five $R^8$, aryl-C($R^{12}$)($R^{13}$)— or aryl-C($R^{12}$)($R^{13}$)— substituted by one to five $R^9$, heterocyclyl-C($R^{12}$)($R^{13}$)— or heterocyclyl-C($R^{12}$)($R^{13}$)— substituted by one to five $R^9$, aryl or aryl substituted by one to five $R^9$, heterocyclyl or heterocyclyl substituted by one to five $R^9$;

wherein aryl is phenyl;

wherein heterocyclyl is a 4- to 7-membered heterocyclic ring containing one to four heteroatoms independently selected from O, S, SO, $SO_2$, N and N($R^{14}$) as ring atoms;

wherein $R^{12}$ and $R^{13}$ are independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl; and wherein $R^{14}$ is hydrogen or $R^9$;

$R^3$ is trifluoromethyl, difluoromethyl or chlorodifluoromethyl;

$R^4$ is group A, wherein $X^2$ is C—$X^4$ or nitrogen and $X^1$, $X^3$ and $X^4$ are independently hydrogen, halogen or trihalomethyl, providing that at least one of $X^1$, $X^3$ and $X^4$ is not hydrogen;

$R^5$ is halogen, cyano, $C_1$-$C_4$alkyl, $C_1$-$C_4$haloalkyl, $C_1$-$C_4$alkoxy or $C_1$-$C_4$haloalkoxy;

$R^{6a}$ is halogen, cyano, $C_1$-$C_4$alkyl, $C_1$-$C_4$haloalkyl, $C_1$-$C_4$alkoxy or $C_1$-$C_4$haloalkoxy;

$R^{6b}$ is fluoro;

$R^{6c}$ is halogen, cyano, $C_1$-$C_4$alkyl, $C_1$-$C_4$haloalkyl, $C_1$-$C_4$alkoxy or $C_1$-$C_4$haloalkoxy;

each $R^7$ is independently halogen, cyano, nitro, hydroxy, carbonylamino, (carbonyl)($C_1$-$C_8$)amino, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl, or two $R^7$ are together OH—N= or $C_1$-$C_6$alkoxy-N=;

each $R^8$ is independently halogen, cyano, $C_1$-$C_4$alkyl or $C_1$-$C_4$alkoxy; and each $R^9$ is independently halogen, cyano, nitro, $C_1$-$C_8$alkyl, $C_1$-$C_8$haloalkyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl.

In another embodiment (E38):
$G^1$ is oxygen;
$Y^1$ is oxygen;
$Y^2$ is C—H, $Y^3$ and $Y^4$ are C—H or C—$R^5$, wherein no more than one of $Y^3$ and $Y^4$ is C—$R^5$;
$Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen;
$R^1$ is hydrogen, methyl or ethyl;
$R^2$ is $C_1$-$C_6$alkyl or $C_1$-$C_6$alkyl substituted by one to three $R^7$, $C_2$-$C_6$alkenyl or $C_2$-$C_6$alkenyl substituted by one to three $R^7$, $C_2$-$C_6$alkynyl or $C_2$-$C_6$alkynyl substituted by one to three $R^7$, $C_1$-$C_4$alkoxy-$C_1$-$C_2$alkyl or $C_1$-$C_4$alkoxy-$C_1$-$C_2$alkyl substituted by one to five $R^7$, $C_3$-$C_8$cycloalkyl or $C_3$-$C_8$cycloalkyl substituted by one to five $R^8$, $C_3$-$C_8$cycloalkyl-C($R^{12}$)($R^{13}$)— or $C_3$-$C_8$cycloalkyl-C($R^{12}$)($R^{13}$)— substituted by one to five $R^8$, aryl-C($R^{12}$)($R^{13}$)— or aryl-C($R^{12}$)($R^{13}$)— substituted by one to five $R^9$, heterocyclyl-C($R^{12}$)($R^{13}$)— or heterocyclyl-C($R^{12}$)($R^{13}$)— substituted by one to five $R^9$, aryl or aryl substituted by one to five $R^9$, heterocyclyl or heterocyclyl substituted by one to five $R^9$.

wherein aryl is phenyl;

wherein heterocyclyl is a 4- to 6-membered saturated or partially saturated heterocyclic ring containing one or two heteroatoms independently selected from O, S, SO, $SO_2$, N and $N(R^{14})$ as ring atoms; or wherein heterocyclyl is a 5- to 6-membered heteroaryl ring containing one to four heteroatoms selected from O, S, N and $N(R^{14})$ as ring members;

wherein $R^{12}$ is hydrogen;

wherein $R^{13}$ is hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl; and wherein $R^{14}$ is hydrogen or $R^9$;

$R^3$ is trifluoromethyl, difluoromethyl or chlorodifluoromethyl;

$R^4$ is group A, wherein $X^2$ is C—$X^4$ or nitrogen and $X^1$, $X^3$ and $X^4$ are independently hydrogen, halogen or trihalomethyl, proving that at least one of $X^1$, $X^3$ and $X^4$ is not hydrogen;

$R^5$ is halogen, cyano, methyl, halomethyl, methoxy or halomethoxy;

$R^{6a}$ is halogen, cyano, $C_1$-$C_4$alkyl, $C_1$-$C_4$haloalkyl, $C_1$-$C_4$alkoxy or $C_1$-$C_4$haloalkoxy;

each $R^7$ is independently halogen, cyano, nitro, hydroxy, carbonylamino, (carbonyl)($C_1$-$C_8$)amino, $C_1$-$C_8$alkoxy, $C_1$-$C_8$haloalkoxy, mercapto, $C_1$-$C_8$alkylthio, or $C_1$-$C_8$haloalkylthio, or two $R^{12}$ are together OH—N=;

each $R^8$ is independently halogen, cyano or methyl; and each $R^9$ is independently halogen, cyano, nitro, $C_1$-$C_4$alkyl, $C_1$-$C_4$haloalkyl, $C_1$-$C_4$alkoxy, or $C_1$-$C_4$haloalkoxy.

In another embodiment (E39):

$G^1$ is oxygen;

$Y^1$ is oxygen;

$Y^2$, $Y^3$ and $Y^4$ are C—H;

$Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen;

$R^1$ is hydrogen, methyl or ethyl;

$R^2$ is $C_1$-$C_6$alkyl or $C_1$-$C_6$alkyl substituted by one to three $R^7$, $C_2$-$C_6$alkenyl or $C_2$-$C_6$alkenyl substituted by one to three $R^7$, $C_1$-$C_4$alkoxy-$C_1$-$C_2$alkyl or $C_1$-$C_4$alkoxy-$C_1$-$C_2$alkyl substituted by one to five $R^7$, $C_3$-$C_6$cycloalkyl or $C_3$-$C_6$cycloalkyl substituted by one to five $R^8$, $C_3$-$C_6$cycloalkyl-$C(R^{12})(R^{13})$— or $C_3$-$C_6$cycloalkyl-$C(R^{12})(R^{13})$— substituted by one to five $R^8$, aryl-$C(R^{12})(R^{13})$— or aryl-$C(R^{12})(R^{13})$— substituted by one to three $R^9$, heterocyclyl-$C(R^{12})(R^{13})$—, or aryl or aryl substituted by one to three $R^9$;

wherein aryl is phenyl;

wherein heterocyclyl is oxetanyl, dihydrofuranyl, tetrahydrofuranyl, dihydropyranyl, tetrahydropyranyl, thietanyl, 1-oxo-thietanyl, 1,1,-dioxothietanyl, thiophene, thiophene 1-oxide, thiophene 1,1-dioxide, dihydrothiophene, dihydrothiophene 1-oxide, or dihydrothiophene 1,1-dioxide, each optionally substituted by one to three methyl; or wherein is heterocycle pyridyl, pyrazinyl, pyrimidinyl, pyrrolyl, imidazolyl, pyrazolyl, triazolyl, tetrazoyl, each optionally substituted by one to three $R^9$;

wherein $R^{12}$ is hydrogen;

wherein $R^{13}$ is hydrogen or methyl;

$R^3$ is trifluoromethyl;

$R^4$ is group A, wherein $X^2$ is C—$X^4$ and $X^1$, $X^3$ and $X^4$ are independently hydrogen, halogen or trihalomethyl, proving that at least one of $X^1$, $X^3$ and $X^4$ is not hydrogen;

$R^5$ is methyl;

$R^{6a}$ is chloro, fluoro, cyano, methyl or halomethyl;

each $R^7$ is independently halogen, carbonylamino, (carbonyl)(methyl)amino, methoxy, methylthio, methylsulfinyl or methysulfonyl;

each $R^8$ is independently fluoro, cyano or methyl;

each $R^9$ is independently halogen, cyano, methyl, halomethyl, methoxy, or halomethoxy.

In another embodiment (E40) $Y^1$ is oxygen.

In another embodiment (E41) $Y^1$ is sulfur.

In another embodiment (E42) $Y^1$ is $CH_2$.

In another embodiment (E43) $R^2$ is $C_1$-$C_8$alkyl or $C_1$-$C_8$alkyl substituted by one to five $R^7$, $C_2$-$C_8$alkenyl or $C_2$-$C_8$alkenyl substituted by one to five $R^7$, $C_2$-$C_8$alkynyl or $C_2$-$C_8$alkynyl substituted by one to five $R^7$, $C_1$-$C_8$alkoxy-$C_1$-$C_8$alkyl or $C_1$-$C_8$alkoxy-$C_1$-$C_8$alkyl substituted by one to five $R^7$.

In another embodiment (E44) $R^2$ is $C_3$-$C_{10}$cycloalkyl or $C_3$-$C_{10}$cycloalkyl substituted by one to five $R^8$, $C_3$-$C_{10}$cycloalkyl-$C_1$-$C_4$alkylene or $C_3$-$C_{10}$cycloalkyl-$C_1$-$C_4$alkylene substituted by one to five W.

In another embodiment (E45) $R^2$ is aryl-$C_1$-$C_4$alkylene- or aryl-$C_1$-$C_4$alkylene-substituted by one to five $R^9$, or aryl or aryl substituted by one to five $R^9$.

In another embodiment (E46) $R^2$ is heterocyclyl-$C_1$-$C_4$alkylene- or heterocyclyl-$C_1$-$C_4$alkylene-substituted by one to five $R^{14}$, or heterocyclyl or heterocyclyl substituted by one to five $R^9$.

In another embodiment (E47) $Y^2$ is C—H, and $Y^3$ and $Y^4$ are C—H or C—$R^5$ and $R^5$ is halogen, cyano, methyl, halomethyl, methoxy or halomethoxy, wherein no more than one of $Y^3$ and $Y^4$ is C—$R^5$.

In another embodiment (E48) $Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen, and $R^{6a}$ is halogen, cyano, methyl, halomethyl, methoxy or halomethoxy.

In another embodiment (E49) $Y^2$, $Y^3$, $Y^4$, $Y^5$, $Y^6$, $Y^7$, $Y^8$, $R^5$ and $R^{6a}$ are as defined in embodiments E47 and E48.

The present invention also provides intermediates useful for the preparation of compounds of formula I.

One group of novel intermediates are compounds of formula Int-I

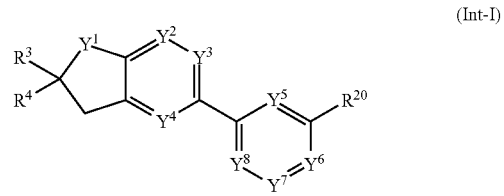

(Int-I)

wherein $R^{20}$ is —NH($R^1$), —N($R^{21}$)($R^{22}$) or nitro, $R^{21}$ and $R^{22}$ are independently $C_1$-$C_8$alkylcarbonyl, $C_1$-$C_8$alkoxycarbonyl, or $R^{21}$ and $R^{22}$ together are —C(=O)—$(CH_2)_r$—C(=O)— wherein r is 1 to 4, —C($C_1$-$C_3$alkyl)=C—C=($C_1$-$C_3$alkyl)C—, or group B

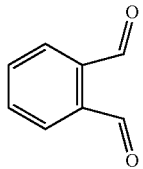

(B)

and $Y^1$, $Y^2$, $Y^3$, $Y^4$, $Y^5$, $Y^6$, $Y^7$, $Y^8$, $R^1$, $R^3$ and $R^4$ are as defined for compounds of formula I. The preferred definitions of $Y^1$, $Y^2$, $Y^3$, $Y^4$, $Y^5$, $Y^6$, $Y^7$, $Y^8$, $R^1$, $R^3$ and $R^4$ are as defined for compounds of formula I, or a salt or N-oxide thereof.

In one group of compounds of formula Int-I $R^{20}$ is —NH($R^1$). In another group of compounds of formula Int-I $R^{20}$ is —N($R^{21}$)($R^{22}$). In another group of compounds of formula Int-I $R^{20}$ is nitro.

Another group of novel intermediates are compounds of formula Int-II

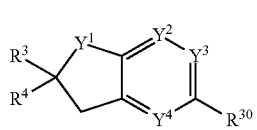

(Int-II)

wherein $R^{30}$ is $NH_2$, nitro, $X^C$, wherein $X^C$ is a leaving group, M, wherein M is a derivative of B, Si, Sn, Zn suitable for performing Suzuki, Sille, Hiyama, or Negishi coupling reaction, or $R^{31}$, wherein $R^{31}$ is cyano, chloro, bromo, 3-nitrophenyl or C(O)R' wherein R' is $C_1$-$C_{15}$alkoxy and $Y^1$, $Y^2$, $Y^3$, $Y^4$, $R^3$ and $R^4$ are as defined for compounds of formula I, or a salt or N-oxide thereof. The preferred definitions of $Y^1$, $Y^2$, $Y^3$, $Y^4$, $R^3$ and $R^4$ are as defined for compounds of formula I. $X^C$ is for example halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. the leaving group may be selected from —$N_2^+$ Cl$^-$, —$N_2^+$ BF$_4^-$, —$N_2^+$ Br$^-$, —$N_2^+$ PF$_6^-$) and phosphonate esters (e.g. —OP(O)(OR)$_2$, wherein R is methyl or ethyl), preferably bromo, iodo, chloro, trifluoromethylsulfoxy, p-toluenesulfoxy, or diazonium chloride, most preferably bromo, iodo or chloro. M is for example boronic acid, boronic ester, trifluoroborate, dialkylhydroxysilane, trialkyltin, ZnCl, ZnBr.

In one group of compounds of formula Int-II $R^{30}$ is $NH_2$. In another group of compounds of formula Int-II $R^{30}$ is nitro. In another group of compounds of formula Int-II $R^{30}$ is $X^C$. In another group of compounds of formula Int-II $R^{30}$ is MIn another group of compounds of formula Int-II $R^{30}$ is $R^{31}$.

Another group of novel intermediates are compounds of formula Int-III

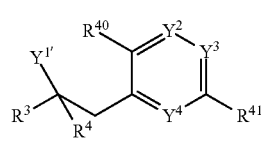

(Int-III)

wherein $R^{40}$ is nitro or $X^C$, wherein $X^C$ is as defined for compounds of formula Int-II, $R^{41}$ is nitro or $R^{31}$, wherein $R^{31}$ is as defined for compounds of formula Int-II and wherein $R^{40}$ is not $X^C$ when $R^{41}$ is nitro, $Y^{1'}$ is OH and $Y^2$, $Y^3$, $Y^4$, $R^3$ and $R^4$ are as defined for compounds of formula I, or a salt or N-oxide thereof. The preferred definitions of $Y^2$, $Y^3$, $Y^4$, $R^3$ and $R^4$ are as defined for compounds of formula I. The preferred definitions of $X^C$ and $R^{31}$ are as defined for compounds of formula Int-II.

In one group of compounds of formula Int-III $R^{40}$ is nitro and $R^{41}$ is $R^{31}$. In another group of compounds $R^{40}$ is $X^C$ and $R^{41}$ is $R^{31}$. In another group of compounds $R^{40}$ is nitro and $R^{41}$ is nitro.

Compounds of formula I include at least one chiral centre and may exist as compounds of formula I* or compounds of formula I**:

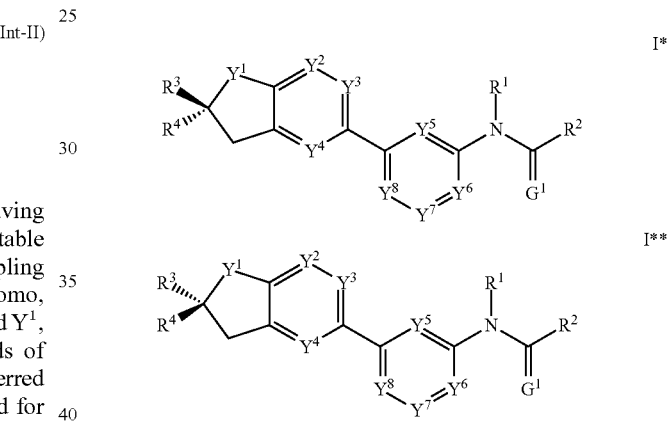

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound disclosed in Tables 1 to 84 represents a disclosure of a compound according to the compound of formula I*, and a disclosure according to the compound of formula I**. The tables below illustrate compounds of the invention.

TABLE P

| | R4 | Y3 | Y4 | Y6 | Y7 | Y8 |
|---|---|---|---|---|---|---|
| 1 | 3,5-dichlorophenyl- | C—H | C—H | CH | C—H | N |
| 2 | 3,4,5-trichlorophenyl- | C—H | C—H | CH | C—H | N |

TABLE P-continued

|   | R4 | Y3 | Y4 | Y6 | Y7 | Y8 |
|---|---|---|---|---|---|---|
| 3 | 3,5-dichloro-4-fluorophenyl- | C—H | C—H | CH | C—H | N |
| 4 | 3-trifluoromethylphenyl- | C—H | C—H | CH | C—H | N |
| 5 | 3,5-bis(trifluoromethyl)phenyl- | C—H | C—H | CH | C—H | N |
| 6 | 3,5-dichlorophenyl- | C—F | C—H | CH | C—H | N |
| 7 | 3,4,5-trichlorophenyl- | C—F | C—H | CH | C—H | N |
| 8 | 3,5-dichloro-4-fluorophenyl- | C—F | C—H | CH | C—H | N |
| 9 | 3-trifluoromethylphenyl- | C—F | C—H | CH | C—H | N |
| 10 | 3,5-bis(trifluoromethyl)phenyl- | C—F | C—H | CH | C—H | N |
| 11 | 3,5-dichlorophenyl- | C—H | C—F | CH | C—H | N |
| 12 | 3,4,5-trichlorophenyl- | C—H | C—F | CH | C—H | N |
| 13 | 3,5-dichloro-4-fluorophenyl- | C—H | C—F | CH | C—H | N |
| 14 | 3-trifluoromethylphenyl- | C—H | C—F | CH | C—H | N |
| 15 | 3,5-bis(trifluoromethyl)phenyl- | C—H | C—F | CH | C—H | N |
| 16 | 3,5-dichlorophenyl- | C—H | C—H | C—CN | C—H | N |
| 17 | 3,4,5-trichlorophenyl- | C—H | C—H | C—CN | C—H | N |
| 18 | 3,5-dichloro-4-fluorophenyl- | C—H | C—H | C—CN | C—H | N |
| 19 | 3-trifluoromethylphenyl- | C—H | C—H | C—CN | C—H | N |
| 20 | 3,5-bis(trifluoromethyl)phenyl- | C—H | C—H | C—CN | C—H | N |
| 21 | 3,5-dichlorophenyl- | C—F | C—H | C—CN | C—H | N |
| 22 | 3,4,5-trichlorophenyl- | C—F | C—H | C—CN | C—H | N |
| 23 | 3,5-dichloro-4-fluorophenyl- | C—F | C—H | C—CN | C—H | N |
| 24 | 3-trifluoromethylphenyl- | C—F | C—H | C—CN | C—H | N |
| 25 | 3,5-bis(trifluoromethyl)phenyl- | C—F | C—H | C—CN | C—H | N |
| 26 | 3,5-dichlorophenyl- | C—H | C—F | C—CN | C—H | N |
| 27 | 3,4,5-trichlorophenyl- | C—H | C—F | C—CN | C—H | N |
| 28 | 3,5-dichloro-4-fluorophenyl- | C—H | C—F | C—CN | C—H | N |
| 29 | 3-trifluoromethylphenyl- | C—H | C—F | C—CN | C—H | N |
| 30 | 3,5-bis(trifluoromethyl)phenyl- | C—H | C—F | C—CN | C—H | N |
| 31 | 3,5-dichlorophenyl- | C—H | C—H | C—Cl | C—H | N |
| 32 | 3,4,5-trichlorophenyl- | C—H | C—H | C—Cl | C—H | N |
| 33 | 3,5-dichloro-4-fluorophenyl- | C—H | C—H | C—Cl | C—H | N |
| 34 | 3-trifluoromethylphenyl- | C—H | C—H | C—Cl | C—H | N |
| 35 | 3,5-bis(trifluoromethyl)phenyl- | C—H | C—H | C—Cl | C—H | N |
| 36 | 3,5-dichlorophenyl- | C—F | C—H | C—Cl | C—H | N |
| 37 | 3,4,5-trichlorophenyl- | C—F | C—H | C—Cl | C—H | N |
| 38 | 3,5-dichloro-4-fluorophenyl- | C—F | C—H | C—Cl | C—H | N |
| 39 | 3-trifluoromethylphenyl- | C—F | C—H | C—Cl | C—H | N |
| 40 | 3,5-bis(trifluoromethyl)phenyl- | C—F | C—H | C—Cl | C—H | N |
| 41 | 3,5-dichlorophenyl- | C—H | C—F | C—Cl | C—H | N |
| 42 | 3,4,5-trichlorophenyl- | C—H | C—F | C—Cl | C—H | N |
| 43 | 3,5-dichloro-4-fluorophenyl- | C—H | C—F | C—Cl | C—H | N |
| 44 | 3-trifluoromethylphenyl- | C—H | C—F | C—Cl | C—H | N |
| 45 | 3,5-bis(trifluoromethyl)phenyl- | C—H | C—F | C—Cl | C—H | N |
| 46 | 3,5-dichlorophenyl- | C—H | C—H | C—F | C—H | N |
| 47 | 3,4,5-trichlorophenyl- | C—H | C—H | C—F | C—H | N |
| 48 | 3,5-dichloro-4-fluorophenyl- | C—H | C—H | C—F | C—H | N |
| 49 | 3-trifluoromethylphenyl- | C—H | C—H | C—F | C—H | N |
| 50 | 3,5-bis(trifluoromethyl)phenyl- | C—H | C—H | C—F | C—H | N |
| 51 | 3,5-dichlorophenyl- | C—F | C—H | C—F | C—H | N |
| 52 | 3,4,5-trichlorophenyl- | C—F | C—H | C—F | C—H | N |
| 53 | 3,5-dichloro-4-fluorophenyl- | C—F | C—H | C—F | C—H | N |
| 54 | 3-trifluoromethylphenyl- | C—F | C—H | C—F | C—H | N |
| 55 | 3,5-bis(trifluoromethyl)phenyl- | C—F | C—H | C—F | C—H | N |
| 56 | 3,5-dichlorophenyl- | C—H | C—F | C—F | C—H | N |
| 57 | 3,4,5-trichlorophenyl- | C—H | C—F | C—F | C—H | N |
| 58 | 3,5-dichloro-4-fluorophenyl- | C—H | C—F | C—F | C—H | N |
| 59 | 3-trifluoromethylphenyl- | C—H | C—F | C—F | C—H | N |
| 60 | 3,5-bis(trifluoromethyl)phenyl- | C—H | C—F | C—F | C—H | N |
| 61 | 3,5-dichlorophenyl- | C—H | C—H | C—CH3 | C—H | N |
| 62 | 3,4,5-trichlorophenyl- | C—H | C—H | C—CH3 | C—H | N |
| 63 | 3,5-dichloro-4-fluorophenyl- | C—H | C—H | C—CH3 | C—H | N |
| 64 | 3-trifluoromethylphenyl- | C—H | C—H | C—CH3 | C—H | N |
| 65 | 3,5-bis(trifluoromethyl)phenyl- | C—H | C—H | C—CH3 | C—H | N |
| 66 | 3,5-dichlorophenyl- | C—F | C—H | C—CH3 | C—H | N |
| 67 | 3,4,5-trichlorophenyl- | C—F | C—H | C—CH3 | C—H | N |
| 68 | 3,5-dichloro-4-fluorophenyl- | C—F | C—H | C—CH3 | C—H | N |
| 69 | 3-trifluoromethylphenyl- | C—F | C—H | C—CH3 | C—H | N |
| 70 | 3,5-bis(trifluoromethyl)phenyl- | C—F | C—H | C—CH3 | C—H | N |
| 71 | 3,5-dichlorophenyl- | C—H | C—F | C—CH3 | C—H | N |
| 72 | 3,4,5-trichlorophenyl- | C—H | C—F | C—CH3 | C—H | N |
| 73 | 3,5-dichloro-4-fluorophenyl- | C—H | C—F | C—CH3 | C—H | N |
| 74 | 3-trifluoromethylphenyl- | C—H | C—F | C—CH3 | C—H | N |
| 75 | 3,5-bis(trifluoromethyl)phenyl- | C—H | C—F | C—CH3 | C—H | N |
| 76 | 3,5-dichlorophenyl- | C—H | C—H | CH | C—F | N |
| 77 | 3,4,5-trichlorophenyl- | C—H | C—H | CH | C—F | N |
| 78 | 3,5-dichloro-4-fluorophenyl- | C—H | C—H | CH | C—F | N |
| 79 | 3-trifluoromethylphenyl- | C—H | C—H | CH | C—F | N |
| 80 | 3,5-bis(trifluoromethyl)phenyl- | C—H | C—H | CH | C—F | N |

TABLE P-continued

|  | R4 | Y3 | Y4 | Y6 | Y7 | Y8 |
|---|---|---|---|---|---|---|
| 81 | 3,5-dichlorophenyl- | C—F | C—H | CH | C—F | N |
| 82 | 3,4,5-trichlorophenyl- | C—F | C—H | CH | C—F | N |
| 83 | 3,5-dichloro-4-fluorophenyl- | C—F | C—H | CH | C—F | N |
| 84 | 3-trifluoromethylphenyl- | C—F | C—H | CH | C—F | N |
| 85 | 3,5-bis(trifluoromethyl)phenyl- | C—F | C—H | CH | C—F | N |
| 86 | 3,5-dichlorophenyl- | C—H | C—F | CH | C—F | N |
| 87 | 3,4,5-trichlorophenyl- | C—H | C—F | CH | C—F | N |
| 88 | 3,5-dichloro-4-fluorophenyl- | C—H | C—F | CH | C—F | N |
| 89 | 3-trifluoromethylphenyl- | C—H | C—F | CH | C—F | N |
| 90 | 3,5-bis(trifluoromethyl)phenyl- | C—H | C—F | CH | C—F | N |
| 91 | 3,5-dichlorophenyl- | C—H | C—H | C—CN | C—F | N |
| 92 | 3,4,5-trichlorophenyl- | C—H | C—H | C—CN | C—F | N |
| 93 | 3,5-dichloro-4-fluorophenyl- | C—H | C—H | C—CN | C—F | N |
| 94 | 3-trifluoromethylphenyl- | C—H | C—H | C—CN | C—F | N |
| 95 | 3,5-bis(trifluoromethyl)phenyl- | C—H | C—H | C—CN | C—F | N |
| 96 | 3,5-dichlorophenyl- | C—F | C—H | C—CN | C—F | N |
| 97 | 3,4,5-trichlorophenyl- | C—F | C—H | C—CN | C—F | N |
| 98 | 3,5-dichloro-4-fluorophenyl- | C—F | C—H | C—CN | C—F | N |
| 99 | 3-trifluoromethylphenyl- | C—F | C—H | C—CN | C—F | N |
| 100 | 3,5-bis(trifluoromethyl)phenyl- | C—F | C—H | C—CN | C—F | N |
| 101 | 3,5-dichlorophenyl- | C—H | C—F | C—CN | C—F | N |
| 102 | 3,4,5-trichlorophenyl- | C—H | C—F | C—CN | C—F | N |
| 103 | 3,5-dichloro-4-fluorophenyl- | C—H | C—F | C—CN | C—F | N |
| 104 | 3-trifluoromethylphenyl- | C—H | C—F | C—CN | C—F | N |
| 105 | 3,5-bis(trifluoromethyl)phenyl- | C—H | C—F | C—CN | C—F | N |
| 106 | 3,5-dichlorophenyl- | C—H | C—H | C—Cl | C—F | N |
| 107 | 3,4,5-trichlorophenyl- | C—H | C—H | C—Cl | C—F | N |
| 108 | 3,5-dichloro-4-fluorophenyl- | C—H | C—H | C—Cl | C—F | N |
| 109 | 3-trifluoromethylphenyl- | C—H | C—H | C—Cl | C—F | N |
| 110 | 3,5-bis(trifluoromethyl)phenyl- | C—H | C—H | C—Cl | C—F | N |
| 111 | 3,5-dichlorophenyl- | C—F | C—H | C—Cl | C—F | N |
| 112 | 3,4,5-trichlorophenyl- | C—F | C—H | C—Cl | C—F | N |
| 113 | 3,5-dichloro-4-fluorophenyl- | C—F | C—H | C—Cl | C—F | N |
| 114 | 3-trifluoromethylphenyl- | C—F | C—H | C—Cl | C—F | N |
| 115 | 3,5-bis(trifluoromethyl)phenyl- | C—F | C—H | C—Cl | C—F | N |
| 116 | 3,5-dichlorophenyl- | C—H | C—F | C—Cl | C—F | N |
| 117 | 3,4,5-trichlorophenyl- | C—H | C—F | C—Cl | C—F | N |
| 118 | 3,5-dichloro-4-fluorophenyl- | C—H | C—F | C—Cl | C—F | N |
| 119 | 3-trifluoromethylphenyl- | C—H | C—F | C—Cl | C—F | N |
| 120 | 3,5-bis(trifluoromethyl)phenyl- | C—H | C—F | C—Cl | C—F | N |
| 121 | 3,5-dichlorophenyl- | C—H | C—H | C—F | C—F | N |
| 122 | 3,4,5-trichlorophenyl- | C—H | C—H | C—F | C—F | N |
| 123 | 3,5-dichloro-4-fluorophenyl- | C—H | C—H | C—F | C—F | N |
| 124 | 3-trifluoromethylphenyl- | C—H | C—H | C—F | C—F | N |
| 125 | 3,5-bis(trifluoromethyl)phenyl- | C—H | C—H | C—F | C—F | N |
| 126 | 3,5-dichlorophenyl- | C—F | C—H | C—F | C—F | N |
| 127 | 3,4,5-trichlorophenyl- | C—F | C—H | C—F | C—F | N |
| 128 | 3,5-dichloro-4-fluorophenyl- | C—F | C—H | C—F | C—F | N |
| 129 | 3-trifluoromethylphenyl- | C—F | C—H | C—F | C—F | N |
| 130 | 3,5-bis(trifluoromethyl)phenyl- | C—F | C—H | C—F | C—F | N |
| 131 | 3,5-dichlorophenyl- | C—H | C—F | C—F | C—F | N |
| 132 | 3,4,5-trichlorophenyl- | C—H | C—F | C—F | C—F | N |
| 133 | 3,5-dichloro-4-fluorophenyl- | C—H | C—F | C—F | C—F | N |
| 134 | 3-trifluoromethylphenyl- | C—H | C—F | C—F | C—F | N |
| 135 | 3,5-bis(trifluoromethyl)phenyl- | C—H | C—F | C—F | C—F | N |
| 136 | 3,5-dichlorophenyl- | C—H | C—H | C—CH3 | C—F | N |
| 137 | 3,4,5-trichlorophenyl- | C—H | C—H | C—CH3 | C—F | N |
| 138 | 3,5-dichloro-4-fluorophenyl- | C—H | C—H | C—CH3 | C—F | N |
| 139 | 3-trifluoromethylphenyl- | C—H | C—H | C—CH3 | C—F | N |
| 140 | 3,5-bis(trifluoromethyl)phenyl- | C—H | C—H | C—CH3 | C—F | N |
| 141 | 3,5-dichlorophenyl- | C—F | C—H | C—CH3 | C—F | N |
| 142 | 3,4,5-trichlorophenyl- | C—F | C—H | C—CH3 | C—F | N |
| 143 | 3,5-dichloro-4-fluorophenyl- | C—F | C—H | C—CH3 | C—F | N |
| 144 | 3-trifluoromethylphenyl- | C—F | C—H | C—CH3 | C—F | N |
| 145 | 3,5-bis(trifluoromethyl)phenyl- | C—F | C—H | C—CH3 | C—F | N |
| 146 | 3,5-dichlorophenyl- | C—H | C—F | C—CH3 | C—F | N |
| 147 | 3,4,5-trichlorophenyl- | C—H | C—F | C—CH3 | C—F | N |
| 148 | 3,5-dichloro-4-fluorophenyl- | C—H | C—F | C—CH3 | C—F | N |
| 149 | 3-trifluoromethylphenyl- | C—H | C—F | C—CH3 | C—F | N |
| 150 | 3,5-bis(trifluoromethyl)phenyl- | C—H | C—F | C—CH3 | C—F | N |
| 151 | 3,5-dichlorophenyl- | C—H | C—H | CH | C—H | CH |
| 152 | 3,4,5-trichlorophenyl- | C—H | C—H | CH | C—H | CH |
| 153 | 3,5-dichloro-4-fluorophenyl- | C—H | C—H | CH | C—H | CH |
| 154 | 3-trifluoromethylphenyl- | C—H | C—H | CH | C—H | CH |
| 155 | 3,5-bis(trifluoromethyl)phenyl- | C—H | C—H | CH | C—H | CH |
| 156 | 3,5-dichlorophenyl- | C—F | C—H | CH | C—H | CH |
| 157 | 3,4,5-trichlorophenyl- | C—F | C—H | CH | C—H | CH |
| 158 | 3,5-dichloro-4-fluorophenyl- | C—F | C—H | CH | C—H | CH |

TABLE P-continued

|  | R4 | Y3 | Y4 | Y6 | Y7 | Y8 |
|---|---|---|---|---|---|---|
| 159 | 3-trifluoromethylphenyl- | C—F | C—H | CH | C—H | CH |
| 160 | 3,5-bis(trifluoromethyl)phenyl- | C—F | C—H | CH | C—H | CH |
| 161 | 3,5-dichlorophenyl- | C—H | C—F | CH | C—H | CH |
| 162 | 3,4,5-trichlorophenyl- | C—H | C—F | CH | C—H | CH |
| 163 | 3,5-dichloro-4-fluorophenyl- | C—H | C—F | CH | C—H | CH |
| 164 | 3-trifluoromethylphenyl- | C—H | C—F | CH | C—H | CH |
| 165 | 3,5-bis(trifluoromethyl)phenyl- | C—H | C—F | CH | C—H | CH |
| 166 | 3,5-dichlorophenyl- | C—H | C—H | C—CN | C—H | CH |
| 167 | 3,4,5-trichlorophenyl- | C—H | C—H | C—CN | C—H | CH |
| 168 | 3,5-dichloro-4-fluorophenyl- | C—H | C—H | C—CN | C—H | CH |
| 169 | 3-trifluoromethylphenyl- | C—H | C—H | C—CN | C—H | CH |
| 170 | 3,5-bis(trifluoromethyl)phenyl- | C—H | C—H | C—CN | C—H | CH |
| 171 | 3,5-dichlorophenyl- | C—F | C—H | C—CN | C—H | CH |
| 172 | 3,4,5-trichlorophenyl- | C—F | C—H | C—CN | C—H | CH |
| 173 | 3,5-dichloro-4-fluorophenyl- | C—F | C—H | C—CN | C—H | CH |
| 174 | 3-trifluoromethylphenyl- | C—F | C—H | C—CN | C—H | CH |
| 175 | 3,5-bis(trifluoromethyl)phenyl- | C—F | C—H | C—CN | C—H | CH |
| 176 | 3,5-dichlorophenyl- | C—H | C—F | C—CN | C—H | CH |
| 177 | 3,4,5-trichlorophenyl- | C—H | C—F | C—CN | C—H | CH |
| 178 | 3,5-dichloro-4-fluorophenyl- | C—H | C—F | C—CN | C—H | CH |
| 179 | 3-trifluoromethylphenyl- | C—H | C—F | C—CN | C—H | CH |
| 180 | 3,5-bis(trifluoromethyl)phenyl- | C—H | C—F | C—CN | C—H | CH |
| 181 | 3,5-dichlorophenyl- | C—H | C—H | C—Cl | C—H | CH |
| 182 | 3,4,5-trichlorophenyl- | C—H | C—H | C—Cl | C—H | CH |
| 183 | 3,5-dichloro-4-fluorophenyl- | C—H | C—H | C—Cl | C—H | CH |
| 184 | 3-trifluoromethylphenyl- | C—H | C—H | C—Cl | C—H | CH |
| 185 | 3,5-bis(trifluoromethyl)phenyl- | C—H | C—H | C—Cl | C—H | CH |
| 186 | 3,5-dichlorophenyl- | C—F | C—H | C—Cl | C—H | CH |
| 187 | 3,4,5-trichlorophenyl- | C—F | C—H | C—Cl | C—H | CH |
| 188 | 3,5-dichloro-4-fluorophenyl- | C—F | C—H | C—Cl | C—H | CH |
| 189 | 3-trifluoromethylphenyl- | C—F | C—H | C—Cl | C—H | CH |
| 190 | 3,5-bis(trifluoromethyl)phenyl- | C—F | C—H | C—Cl | C—H | CH |
| 191 | 3,5-dichlorophenyl- | C—H | C—F | C—Cl | C—H | CH |
| 192 | 3,4,5-trichlorophenyl- | C—H | C—F | C—Cl | C—H | CH |
| 193 | 3,5-dichloro-4-fluorophenyl- | C—H | C—F | C—Cl | C—H | CH |
| 194 | 3-trifluoromethylphenyl- | C—H | C—F | C—Cl | C—H | CH |
| 195 | 3,5-bis(trifluoromethyl)phenyl- | C—H | C—F | C—Cl | C—H | CH |
| 196 | 3,5-dichlorophenyl- | C—H | C—H | C—F | C—H | CH |
| 197 | 3,4,5-trichlorophenyl- | C—H | C—H | C—F | C—H | CH |
| 198 | 3,5-dichloro-4-fluorophenyl- | C—H | C—H | C—F | C—H | CH |
| 199 | 3-trifluoromethylphenyl- | C—H | C—H | C—F | C—H | CH |
| 200 | 3,5-bis(trifluoromethyl)phenyl- | C—H | C—H | C—F | C—H | CH |
| 201 | 3,5-dichlorophenyl- | C—F | C—H | C—F | C—H | CH |
| 202 | 3,4,5-trichlorophenyl- | C—F | C—H | C—F | C—H | CH |
| 203 | 3,5-dichloro-4-fluorophenyl- | C—F | C—H | C—F | C—H | CH |
| 204 | 3-trifluoromethylphenyl- | C—F | C—H | C—F | C—H | CH |
| 205 | 3,5-bis(trifluoromethyl)phenyl- | C—F | C—H | C—F | C—H | CH |
| 206 | 3,5-dichlorophenyl- | C—H | C—F | C—F | C—H | CH |
| 207 | 3,4,5-trichlorophenyl- | C—H | C—F | C—F | C—H | CH |
| 208 | 3,5-dichloro-4-fluorophenyl- | C—H | C—F | C—F | C—H | CH |
| 209 | 3-trifluoromethylphenyl- | C—H | C—F | C—F | C—H | CH |
| 210 | 3,5-bis(trifluoromethyl)phenyl- | C—H | C—F | C—F | C—H | CH |
| 211 | 3,5-dichlorophenyl- | C—H | C—H | C—CH3 | C—H | CH |
| 212 | 3,4,5-trichlorophenyl- | C—H | C—H | C—CH3 | C—H | CH |
| 213 | 3,5-dichloro-4-fluorophenyl- | C—H | C—H | C—CH3 | C—H | CH |
| 214 | 3-trifluoromethylphenyl- | C—H | C—H | C—CH3 | C—H | CH |
| 215 | 3,5-bis(trifluoromethyl)phenyl- | C—H | C—H | C—CH3 | C—H | CH |
| 216 | 3,5-dichlorophenyl- | C—F | C—H | C—CH3 | C—H | CH |
| 217 | 3,4,5-trichlorophenyl- | C—F | C—H | C—CH3 | C—H | CH |
| 218 | 3,5-dichloro-4-fluorophenyl- | C—F | C—H | C—CH3 | C—H | CH |
| 219 | 3-trifluoromethylphenyl- | C—F | C—H | C—CH3 | C—H | CH |
| 220 | 3,5-bis(trifluoromethyl)phenyl- | C—F | C—H | C—CH3 | C—H | CH |
| 221 | 3,5-dichlorophenyl- | C—H | C—F | C—CH3 | C—H | CH |
| 222 | 3,4,5-trichlorophenyl- | C—H | C—F | C—CH3 | C—H | CH |
| 223 | 3,5-dichloro-4-fluorophenyl- | C—H | C—F | C—CH3 | C—H | CH |
| 224 | 3-trifluoromethylphenyl- | C—H | C—F | C—CH3 | C—H | CH |
| 225 | 3,5-bis(trifluoromethyl)phenyl- | C—H | C—F | C—CH3 | C—H | CH |
| 226 | 3,5-dichlorophenyl- | C—H | C—H | CH | C—F | CH |
| 227 | 3,4,5-trichlorophenyl- | C—H | C—H | CH | C—F | CH |
| 228 | 3,5-dichloro-4-fluorophenyl- | C—H | C—H | CH | C—F | CH |
| 229 | 3-trifluoromethylphenyl- | C—H | C—H | CH | C—F | CH |
| 230 | 3,5-bis(trifluoromethyl)phenyl- | C—H | C—H | CH | C—F | CH |
| 231 | 3,5-dichlorophenyl- | C—F | C—H | CH | C—F | CH |
| 232 | 3,4,5-trichlorophenyl- | C—F | C—H | CH | C—F | CH |
| 233 | 3,5-dichloro-4-fluorophenyl- | C—F | C—H | CH | C—F | CH |
| 234 | 3-trifluoromethylphenyl- | C—F | C—H | CH | C—F | CH |
| 235 | 3,5-bis(trifluoromethyl)phenyl- | C—F | C—H | CH | C—F | CH |
| 236 | 3,5-dichlorophenyl- | C—H | C—F | CH | C—F | CH |

TABLE P-continued

| | R4 | Y3 | Y4 | Y6 | Y7 | Y8 |
|---|---|---|---|---|---|---|
| 237 | 3,4,5-trichlorophenyl- | C—H | C—F | CH | C—F | CH |
| 238 | 3,5-dichloro-4-fluorophenyl- | C—H | C—F | CH | C—F | CH |
| 239 | 3-trifluoromethylphenyl- | C—H | C—F | CH | C—F | CH |
| 240 | 3,5-bis(trifluoromethyl)phenyl- | C—H | C—F | CH | C—F | CH |
| 241 | 3,5-dichlorophenyl- | C—H | C—H | C—CN | C—F | CH |
| 242 | 3,4,5-trichlorophenyl- | C—H | C—H | C—CN | C—F | CH |
| 243 | 3,5-dichloro-4-fluorophenyl- | C—H | C—H | C—CN | C—F | CH |
| 244 | 3-trifluoromethylphenyl- | C—H | C—H | C—CN | C—F | CH |
| 245 | 3,5-bis(trifluoromethyl)phenyl- | C—H | C—H | C—CN | C—F | CH |
| 246 | 3,5-dichlorophenyl- | C—F | C—H | C—CN | C—F | CH |
| 247 | 3,4,5-trichlorophenyl- | C—F | C—H | C—CN | C—F | CH |
| 248 | 3,5-dichloro-4-fluorophenyl- | C—F | C—H | C—CN | C—F | CH |
| 249 | 3-trifluoromethylphenyl- | C—F | C—H | C—CN | C—F | CH |
| 250 | 3,5-bis(trifluoromethyl)phenyl- | C—F | C—H | C—CN | C—F | CH |
| 251 | 3,5-dichlorophenyl- | C—H | C—F | C—CN | C—F | CH |
| 252 | 3,4,5-trichlorophenyl- | C—H | C—F | C—CN | C—F | CH |
| 253 | 3,5-dichloro-4-fluorophenyl- | C—H | C—F | C—CN | C—F | CH |
| 254 | 3-trifluoromethylphenyl- | C—H | C—F | C—CN | C—F | CH |
| 255 | 3,5-bis(trifluoromethyl)phenyl- | C—H | C—F | C—CN | C—F | CH |
| 256 | 3,5-dichlorophenyl- | C—H | C—H | C—Cl | C—F | CH |
| 257 | 3,4,5-trichlorophenyl- | C—H | C—H | C—Cl | C—F | CH |
| 258 | 3,5-dichloro-4-fluorophenyl- | C—H | C—H | C—Cl | C—F | CH |
| 259 | 3-trifluoromethylphenyl- | C—H | C—H | C—Cl | C—F | CH |
| 260 | 3,5-bis(trifluoromethyl)phenyl- | C—H | C—H | C—Cl | C—F | CH |
| 261 | 3,5-dichlorophenyl- | C—F | C—H | C—Cl | C—F | CH |
| 262 | 3,4,5-trichlorophenyl- | C—F | C—H | C—Cl | C—F | CH |
| 263 | 3,5-dichloro-4-fluorophenyl- | C—F | C—H | C—Cl | C—F | CH |
| 264 | 3-trifluoromethylphenyl- | C—F | C—H | C—Cl | C—F | CH |
| 265 | 3,5-bis(trifluoromethyl)phenyl- | C—F | C—H | C—Cl | C—F | CH |
| 266 | 3,5-dichlorophenyl- | C—H | C—F | C—Cl | C—F | CH |
| 267 | 3,4,5-trichlorophenyl- | C—H | C—F | C—Cl | C—F | CH |
| 268 | 3,5-dichloro-4-fluorophenyl- | C—H | C—F | C—Cl | C—F | CH |
| 269 | 3-trifluoromethylphenyl- | C—H | C—F | C—Cl | C—F | CH |
| 270 | 3,5-bis(trifluoromethyl)phenyl- | C—H | C—F | C—Cl | C—F | CH |
| 271 | 3,5-dichlorophenyl- | C—H | C—H | C—F | C—F | CH |
| 272 | 3,4,5-trichlorophenyl- | C—H | C—H | C—F | C—F | CH |
| 273 | 3,5-dichloro-4-fluorophenyl- | C—H | C—H | C—F | C—F | CH |
| 274 | 3-trifluoromethylphenyl- | C—H | C—H | C—F | C—F | CH |
| 275 | 3,5-bis(trifluoromethyl)phenyl- | C—H | C—H | C—F | C—F | CH |
| 276 | 3,5-dichlorophenyl- | C—F | C—H | C—F | C—F | CH |
| 277 | 3,4,5-trichlorophenyl- | C—F | C—H | C—F | C—F | CH |
| 278 | 3,5-dichloro-4-fluorophenyl- | C—F | C—H | C—F | C—F | CH |
| 279 | 3-trifluoromethylphenyl- | C—F | C—H | C—F | C—F | CH |
| 280 | 3,5-bis(trifluoromethyl)phenyl- | C—F | C—H | C—F | C—F | CH |
| 281 | 3,5-dichlorophenyl- | C—H | C—F | C—F | C—F | CH |
| 282 | 3,4,5-trichlorophenyl- | C—H | C—F | C—F | C—F | CH |
| 283 | 3,5-dichloro-4-fluorophenyl- | C—H | C—F | C—F | C—F | CH |
| 284 | 3-trifluoromethylphenyl- | C—H | C—F | C—F | C—F | CH |
| 285 | 3,5-bis(trifluoromethyl)phenyl- | C—H | C—F | C—F | C—F | CH |
| 286 | 3,5-dichlorophenyl- | C—H | C—H | C—CH3 | C—F | CH |
| 287 | 3,4,5-trichlorophenyl- | C—H | C—H | C—CH3 | C—F | CH |
| 288 | 3,5-dichloro-4-fluorophenyl- | C—H | C—H | C—CH3 | C—F | CH |
| 289 | 3-trifluoromethylphenyl- | C—H | C—H | C—CH3 | C—F | CH |
| 290 | 3,5-bis(trifluoromethyl)phenyl- | C—H | C—H | C—CH3 | C—F | CH |
| 291 | 3,5-dichlorophenyl- | C—F | C—H | C—CH3 | C—F | CH |
| 292 | 3,4,5-trichlorophenyl- | C—F | C—H | C—CH3 | C—F | CH |
| 293 | 3,5-dichloro-4-fluorophenyl- | C—F | C—H | C—CH3 | C—F | CH |
| 294 | 3-trifluoromethylphenyl- | C—F | C—H | C—CH3 | C—F | CH |
| 295 | 3,5-bis(trifluoromethyl)phenyl- | C—F | C—H | C—CH3 | C—F | CH |
| 296 | 3,5-dichlorophenyl- | C—H | C—F | C—CH3 | C—F | CH |
| 297 | 3,4,5-trichlorophenyl- | C—H | C—F | C—CH3 | C—F | CH |
| 298 | 3,5-dichloro-4-fluorophenyl- | C—H | C—F | C—CH3 | C—F | CH |
| 299 | 3-trifluoromethylphenyl- | C—H | C—F | C—CH3 | C—F | CH |
| 300 | 3,5-bis(trifluoromethyl)phenyl- | C—H | C—F | C—CH3 | C—F | CH |
| 301 | 3,5-dichlorophenyl- | C—H | C—H | CH | C—H | C—F |
| 302 | 3,4,5-trichlorophenyl- | C—H | C—H | CH | C—H | C—F |
| 303 | 3,5-dichloro-4-fluorophenyl- | C—H | C—H | CH | C—H | C—F |
| 304 | 3-trifluoromethylphenyl- | C—H | C—H | CH | C—H | C—F |
| 305 | 3,5-bis(trifluoromethyl)phenyl- | C—H | C—H | CH | C—H | C—F |
| 306 | 3,5-dichlorophenyl- | C—F | C—H | CH | C—H | C—F |
| 307 | 3,4,5-trichlorophenyl- | C—F | C—H | CH | C—H | C—F |
| 308 | 3,5-dichloro-4-fluorophenyl- | C—F | C—H | CH | C—H | C—F |
| 309 | 3-trifluoromethylphenyl- | C—F | C—H | CH | C—H | C—F |
| 310 | 3,5-bis(trifluoromethyl)phenyl- | C—F | C—H | CH | C—H | C—F |
| 311 | 3,5-dichlorophenyl- | C—H | C—F | CH | C—H | C—F |
| 312 | 3,4,5-trichlorophenyl- | C—H | C—F | CH | C—H | C—F |
| 313 | 3,5-dichloro-4-fluorophenyl- | C—H | C—F | CH | C—H | C—F |
| 314 | 3-trifluoromethylphenyl- | C—H | C—F | CH | C—H | C—F |

TABLE P-continued

|  | R4 | Y3 | Y4 | Y6 | Y7 | Y8 |
|---|---|---|---|---|---|---|
| 315 | 3,5-bis(trifluoromethyl)phenyl- | C—H | C—F | CH | C—H | C—F |
| 316 | 3,5-dichlorophenyl- | C—H | C—H | C—CN | C—H | C—F |
| 317 | 3,4,5-trichlorophenyl- | C—H | C—H | C—CN | C—H | C—F |
| 318 | 3,5-dichloro-4-fluorophenyl- | C—H | C—H | C—CN | C—H | C—F |
| 319 | 3-trifluoromethylphenyl- | C—H | C—H | C—CN | C—H | C—F |
| 320 | 3,5-bis(trifluoromethyl)phenyl- | C—H | C—H | C—CN | C—H | C—F |
| 321 | 3,5-dichlorophenyl- | C—F | C—H | C—CN | C—H | C—F |
| 322 | 3,4,5-trichlorophenyl- | C—F | C—H | C—CN | C—H | C—F |
| 323 | 3,5-dichloro-4-fluorophenyl- | C—F | C—H | C—CN | C—H | C—F |
| 324 | 3-trifluoromethylphenyl- | C—F | C—H | C—CN | C—H | C—F |
| 325 | 3,5-bis(trifluoromethyl)phenyl- | C—F | C—H | C—CN | C—H | C—F |
| 326 | 3,5-dichlorophenyl- | C—H | C—F | C—CN | C—H | C—F |
| 327 | 3,4,5-trichlorophenyl- | C—H | C—F | C—CN | C—H | C—F |
| 328 | 3,5-dichloro-4-fluorophenyl- | C—H | C—F | C—CN | C—H | C—F |
| 329 | 3-trifluoromethylphenyl- | C—H | C—F | C—CN | C—H | C—F |
| 330 | 3,5-bis(trifluoromethyl)phenyl- | C—H | C—F | C—CN | C—H | C—F |
| 331 | 3,5-dichlorophenyl- | C—H | C—H | C—Cl | C—H | C—F |
| 332 | 3,4,5-trichlorophenyl- | C—H | C—H | C—Cl | C—H | C—F |
| 333 | 3,5-dichloro-4-fluorophenyl- | C—H | C—H | C—Cl | C—H | C—F |
| 334 | 3-trifluoromethylphenyl- | C—H | C—H | C—Cl | C—H | C—F |
| 335 | 3,5-bis(trifluoromethyl)phenyl- | C—H | C—H | C—Cl | C—H | C—F |
| 336 | 3,5-dichlorophenyl- | C—F | C—H | C—Cl | C—H | C—F |
| 337 | 3,4,5-trichlorophenyl- | C—F | C—H | C—Cl | C—H | C—F |
| 338 | 3,5-dichloro-4-fluorophenyl- | C—F | C—H | C—Cl | C—H | C—F |
| 339 | 3-trifluoromethylphenyl- | C—F | C—H | C—Cl | C—H | C—F |
| 340 | 3,5-bis(trifluoromethyl)phenyl- | C—F | C—H | C—Cl | C—H | C—F |
| 341 | 3,5-dichlorophenyl- | C—H | C—F | C—Cl | C—H | C—F |
| 342 | 3,4,5-trichlorophenyl- | C—H | C—F | C—Cl | C—H | C—F |
| 343 | 3,5-dichloro-4-fluorophenyl- | C—H | C—F | C—Cl | C—H | C—F |
| 344 | 3-trifluoromethylphenyl- | C—H | C—F | C—Cl | C—H | C—F |
| 345 | 3,5-bis(trifluoromethyl)phenyl- | C—H | C—F | C—Cl | C—H | C—F |
| 346 | 3,5-dichlorophenyl- | C—H | C—H | C—F | C—H | C—F |
| 347 | 3,4,5-trichlorophenyl- | C—H | C—H | C—F | C—H | C—F |
| 348 | 3,5-dichloro-4-fluorophenyl- | C—H | C—H | C—F | C—H | C—F |
| 349 | 3-trifluoromethylphenyl- | C—H | C—H | C—F | C—H | C—F |
| 350 | 3,5-bis(trifluoromethyl)phenyl- | C—H | C—H | C—F | C—H | C—F |
| 351 | 3,5-dichlorophenyl- | C—F | C—H | C—F | C—H | C—F |
| 352 | 3,4,5-trichlorophenyl- | C—F | C—H | C—F | C—H | C—F |
| 353 | 3,5-dichloro-4-fluorophenyl- | C—F | C—H | C—F | C—H | C—F |
| 354 | 3-trifluoromethylphenyl- | C—F | C—H | C—F | C—H | C—F |
| 355 | 3,5-bis(trifluoromethyl)phenyl- | C—F | C—H | C—F | C—H | C—F |
| 356 | 3,5-dichlorophenyl- | C—H | C—F | C—F | C—H | C—F |
| 357 | 3,4,5-trichlorophenyl- | C—H | C—F | C—F | C—H | C—F |
| 358 | 3,5-dichloro-4-fluorophenyl- | C—H | C—F | C—F | C—H | C—F |
| 359 | 3-trifluoromethylphenyl- | C—H | C—F | C—F | C—H | C—F |
| 360 | 3,5-bis(trifluoromethyl)phenyl- | C—H | C—F | C—F | C—H | C—F |
| 361 | 3,5-dichlorophenyl- | C—H | C—H | C—CH3 | C—H | C—F |
| 362 | 3,4,5-trichlorophenyl- | C—H | C—H | C—CH3 | C—H | C—F |
| 363 | 3,5-dichloro-4-fluorophenyl- | C—H | C—H | C—CH3 | C—H | C—F |
| 364 | 3-trifluoromethylphenyl- | C—H | C—H | C—CH3 | C—H | C—F |
| 365 | 3,5-bis(trifluoromethyl)phenyl- | C—H | C—H | C—CH3 | C—H | C—F |
| 366 | 3,5-dichlorophenyl- | C—F | C—H | C—CH3 | C—H | C—F |
| 367 | 3,4,5-trichlorophenyl- | C—F | C—H | C—CH3 | C—H | C—F |
| 368 | 3,5-dichloro-4-fluorophenyl- | C—F | C—H | C—CH3 | C—H | C—F |
| 369 | 3-trifluoromethylphenyl- | C—F | C—H | C—CH3 | C—H | C—F |
| 370 | 3,5-bis(trifluoromethyl)phenyl- | C—F | C—H | C—CH3 | C—H | C—F |
| 371 | 3,5-dichlorophenyl- | C—H | C—F | C—CH3 | C—H | C—F |
| 372 | 3,4,5-trichlorophenyl- | C—H | C—F | C—CH3 | C—H | C—F |
| 373 | 3,5-dichloro-4-fluorophenyl- | C—H | C—F | C—CH3 | C—H | C—F |
| 374 | 3-trifluoromethylphenyl- | C—H | C—F | C—CH3 | C—H | C—F |
| 375 | 3,5-bis(trifluoromethyl)phenyl- | C—H | C—F | C—CH3 | C—H | C—F |
| 376 | 3,5-dichlorophenyl- | C—H | C—H | CH | C—F | C—F |
| 377 | 3,4,5-trichlorophenyl- | C—H | C—H | CH | C—F | C—F |
| 378 | 3,5-dichloro-4-fluorophenyl- | C—H | C—H | CH | C—F | C—F |
| 379 | 3-trifluoromethylphenyl- | C—H | C—H | CH | C—F | C—F |
| 380 | 3,5-bis(trifluoromethyl)phenyl- | C—H | C—H | CH | C—F | C—F |
| 381 | 3,5-dichlorophenyl- | C—F | C—H | CH | C—F | C—F |
| 382 | 3,4,5-trichlorophenyl- | C—F | C—H | CH | C—F | C—F |
| 383 | 3,5-dichloro-4-fluorophenyl- | C—F | C—H | CH | C—F | C—F |
| 384 | 3-trifluoromethylphenyl- | C—F | C—H | CH | C—F | C—F |
| 385 | 3,5-bis(trifluoromethyl)phenyl- | C—F | C—H | CH | C—F | C—F |
| 386 | 3,5-dichlorophenyl- | C—H | C—F | CH | C—F | C—F |
| 387 | 3,4,5-trichlorophenyl- | C—H | C—F | CH | C—F | C—F |
| 388 | 3,5-dichloro-4-fluorophenyl- | C—H | C—F | CH | C—F | C—F |
| 389 | 3-trifluoromethylphenyl- | C—H | C—F | CH | C—F | C—F |
| 390 | 3,5-bis(trifluoromethyl)phenyl- | C—H | C—F | CH | C—F | C—F |
| 391 | 3,5-dichlorophenyl- | C—H | C—H | C—CN | C—F | C—F |
| 392 | 3,4,5-trichlorophenyl- | C—H | C—H | C—CN | C—F | C—F |

TABLE P-continued

| | R4 | Y3 | Y4 | Y6 | Y7 | Y8 |
|---|---|---|---|---|---|---|
| 393 | 3,5-dichloro-4-fluorophenyl- | C—H | C—H | C—CN | C—F | C—F |
| 394 | 3-trifluoromethylphenyl- | C—H | C—H | C—CN | C—F | C—F |
| 395 | 3,5-bis(trifluoromethyl)phenyl- | C—H | C—H | C—CN | C—F | C—F |
| 396 | 3,5-dichlorophenyl- | C—F | C—H | C—CN | C—F | C—F |
| 397 | 3,4,5-trichlorophenyl- | C—F | C—H | C—CN | C—F | C—F |
| 398 | 3,5-dichloro-4-fluorophenyl- | C—F | C—H | C—CN | C—F | C—F |
| 399 | 3-trifluoromethylphenyl- | C—F | C—H | C—CN | C—F | C—F |
| 400 | 3,5-bis(trifluoromethyl)phenyl- | C—F | C—H | C—CN | C—F | C—F |
| 401 | 3,5-dichlorophenyl- | C—H | C—F | C—CN | C—F | C—F |
| 402 | 3,4,5-trichlorophenyl- | C—H | C—F | C—CN | C—F | C—F |
| 403 | 3,5-dichloro-4-fluorophenyl- | C—H | C—F | C—CN | C—F | C—F |
| 404 | 3-trifluoromethylphenyl- | C—H | C—F | C—CN | C—F | C—F |
| 405 | 3,5-bis(trifluoromethyl)phenyl- | C—H | C—F | C—CN | C—F | C—F |
| 406 | 3,5-dichlorophenyl- | C—H | C—H | C—Cl | C—F | C—F |
| 407 | 3,4,5-trichlorophenyl- | C—H | C—H | C—Cl | C—F | C—F |
| 408 | 3,5-dichloro-4-fluorophenyl- | C—H | C—H | C—Cl | C—F | C—F |
| 409 | 3-trifluoromethylphenyl- | C—H | C—H | C—Cl | C—F | C—F |
| 410 | 3,5-bis(trifluoromethyl)phenyl- | C—H | C—H | C—Cl | C—F | C—F |
| 411 | 3,5-dichlorophenyl- | C—F | C—H | C—Cl | C—F | C—F |
| 412 | 3,4,5-trichlorophenyl- | C—F | C—H | C—Cl | C—F | C—F |
| 413 | 3,5-dichloro-4-fluorophenyl- | C—F | C—H | C—Cl | C—F | C—F |
| 414 | 3-trifluoromethylphenyl- | C—F | C—H | C—Cl | C—F | C—F |
| 415 | 3,5-bis(trifluoromethyl)phenyl- | C—F | C—H | C—Cl | C—F | C—F |
| 416 | 3,5-dichlorophenyl- | C—H | C—F | C—Cl | C—F | C—F |
| 417 | 3,4,5-trichlorophenyl- | C—H | C—F | C—Cl | C—F | C—F |
| 418 | 3,5-dichloro-4-fluorophenyl- | C—H | C—F | C—Cl | C—F | C—F |
| 419 | 3-trifluoromethylphenyl- | C—H | C—F | C—Cl | C—F | C—F |
| 420 | 3,5-bis(trifluoromethyl)phenyl- | C—H | C—F | C—Cl | C—F | C—F |
| 421 | 3,5-dichlorophenyl- | C—H | C—H | C—F | C—F | C—F |
| 422 | 3,4,5-trichlorophenyl- | C—H | C—H | C—F | C—F | C—F |
| 423 | 3,5-dichloro-4-fluorophenyl- | C—H | C—H | C—F | C—F | C—F |
| 424 | 3-trifluoromethylphenyl- | C—H | C—H | C—F | C—F | C—F |
| 425 | 3,5-bis(trifluoromethyl)phenyl- | C—H | C—H | C—F | C—F | C—F |
| 426 | 3,5-dichlorophenyl- | C—F | C—H | C—F | C—F | C—F |
| 427 | 3,4,5-trichlorophenyl- | C—F | C—H | C—F | C—F | C—F |
| 428 | 3,5-dichloro-4-fluorophenyl- | C—F | C—H | C—F | C—F | C—F |
| 429 | 3-trifluoromethylphenyl- | C—F | C—H | C—F | C—F | C—F |
| 430 | 3,5-bis(trifluoromethyl)phenyl- | C—F | C—H | C—F | C—F | C—F |
| 431 | 3,5-dichlorophenyl- | C—H | C—F | C—F | C—F | C—F |
| 432 | 3,4,5-trichlorophenyl- | C—H | C—F | C—F | C—F | C—F |
| 433 | 3,5-dichloro-4-fluorophenyl- | C—H | C—F | C—F | C—F | C—F |
| 434 | 3-trifluoromethylphenyl- | C—H | C—F | C—F | C—F | C—F |
| 435 | 3,5-bis(trifluoromethyl)phenyl- | C—H | C—F | C—F | C—F | C—F |
| 436 | 3,5-dichlorophenyl- | C—H | C—H | C—CH3 | C—F | C—F |
| 437 | 3,4,5-trichlorophenyl- | C—H | C—H | C—CH3 | C—F | C—F |
| 438 | 3,5-dichloro-4-fluorophenyl- | C—H | C—H | C—CH3 | C—F | C—F |
| 439 | 3-trifluoromethylphenyl- | C—H | C—H | C—CH3 | C—F | C—F |
| 440 | 3,5-bis(trifluoromethyl)phenyl- | C—H | C—H | C—CH3 | C—F | C—F |
| 441 | 3,5-dichlorophenyl- | C—F | C—H | C—CH3 | C—F | C—F |
| 442 | 3,4,5-trichlorophenyl- | C—F | C—H | C—CH3 | C—F | C—F |
| 443 | 3,5-dichloro-4-fluorophenyl- | C—F | C—H | C—CH3 | C—F | C—F |
| 444 | 3-trifluoromethylphenyl- | C—F | C—H | C—CH3 | C—F | C—F |
| 445 | 3,5-bis(trifluoromethyl)phenyl- | C—F | C—H | C—CH3 | C—F | C—F |
| 446 | 3,5-dichlorophenyl- | C—H | C—F | C—CH3 | C—F | C—F |
| 447 | 3,4,5-trichlorophenyl- | C—H | C—F | C—CH3 | C—F | C—F |
| 448 | 3,5-dichloro-4-fluorophenyl- | C—H | C—F | C—CH3 | C—F | C—F |
| 449 | 3-trifluoromethylphenyl- | C—H | C—F | C—CH3 | C—F | C—F |
| 450 | 3,5-bis(trifluoromethyl)phenyl- | C—H | C—F | C—CH3 | C—F | C—F |

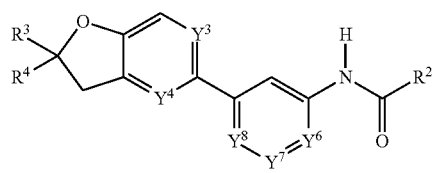

(IA)

Table IA-1

Table IA-1 provides 450 compounds of formula (IA) wherein $R^2$ is ethyl-, wherein $R^2$ is trifluoromethyl, and $R^4$, $Y^3$, $Y^4$, $Y^6$, $Y^7$ and $Y^8$ are as defined in Table P.

Table IA-2

Table IA-2 provides 450 compounds of formula (IA) wherein $R^2$ is 2,2,2-trifluoro-ethyl-, wherein $R^2$ is trifluoromethyl, and $R^4$, $Y^3$, $Y^4$, $Y^6$, $Y^7$ and $Y^8$ are as defined in Table P.

Table IA-3

Table IA-3 provides 450 compounds of formula (IA) wherein $R^2$ is prop-2-yl-, wherein $R^2$ is trifluoromethyl, and $R^4$, $Y^3$, $Y^4$, $Y^6$, $Y^7$ and $Y^8$ are as defined in Table P.

Table IA-4

Table IA-4 provides 450 compounds of formula (IA) wherein $R^2$ is methyl-, wherein $R^2$ is trifluoromethyl, and $R^4$, $Y^3$, $Y^4$, $Y^6$, $Y^7$ and $Y^8$ are as defined in Table P.

Table IA-5

Table IA-5 provides 450 compounds of formula (IA) wherein $R^2$ is 2-fluoro-cycloprop-1-yl-, wherein $R^2$ is trifluoromethyl, and $R^4$, $Y^3$, $Y^4$, $Y^6$, $Y^7$ and $Y^8$ are as defined in Table P.

Table IA-6

Table IA-6 provides 450 compounds of formula (IA) wherein $R^2$ is prop-1-yl, wherein $R^2$ is trifluoromethyl, and $R^4$, $Y^3$, $Y^4$, $Y^6$, $Y^7$ and $Y^8$ are as defined in Table P.

Table IA-7

Table IA-7 provides 450 compounds of formula (IA) wherein $R^2$ is 2-fluoro-ethyl-, wherein $R^2$ is trifluoromethyl, and $R^4$, $Y^3$, $Y^4$, $Y^6$, $Y^7$ and $Y^8$ are as defined in Table P.

Table IA-8

Table IA-8 provides 450 compounds of formula (IA) wherein $R^2$ is 2-cyano-ethyl-, wherein $R^2$ is trifluoromethyl, and $R^4$, $Y^3$, $Y^4$, $Y^6$, $Y^7$ and $Y^8$ are as defined in Table P.

Table IA-9

Table IA-9 provides 450 compounds of formula (IA) wherein $R^2$ is 1-fluoroethyl-, wherein $R^2$ is trifluoromethyl, and $R^4$, $Y^3$, $Y^4$, $Y^6$, $Y^7$ and $Y^8$ are as defined in Table P.

Table IA-10

Table IA-10 provides 450 compounds of formula (IA) wherein $R^2$ is 2-methylprop-1-yl-, wherein $R^2$ is trifluoromethyl, and $R^4$, $Y^3$, $Y^4$, $Y^6$, $Y^7$ and $Y^8$ are as defined in Table P.

Table IA-11

Table IA-11 provides 450 compounds of formula (IA) wherein $R^2$ is propen-2-yl-, wherein $R^2$ is trifluoromethyl, and $R^4$, $Y^3$, $Y^4$, $Y^6$, $Y^7$ and $Y^8$ are as defined in Table P.

Table IA-12

Table IA-12 provides 450 compounds of formula (IA) wherein $R^2$ is cyclopropylmethyl-, wherein $R^2$ is trifluoromethyl, and $R^4$, $Y^3$, $Y^4$, $Y^6$, $Y^7$ and $Y^8$ are as defined in Table P.

Table IA-13

Table IA-13 provides 450 compounds of formula (IA) wherein $R^2$ is 2-methoxy-ethyl-, wherein $R^2$ is trifluoromethyl, and $R^4$, $Y^3$, $Y^4$, $Y^6$, $Y^7$ and $Y^8$ are as defined in Table P.

Table IA-14

Table IA-14 provides 450 compounds of formula (IA) wherein $R^2$ is 3-methyloxetan-3-yl-, wherein $R^2$ is trifluoromethyl, and $R^4$, $Y^3$, $Y^4$, $Y^6$, $Y^7$ and $Y^8$ are as defined in Table P.

Table IA-15

Table IA-15 provides 450 compounds of formula (IA) wherein $R^2$ is 1-methylcyclopropyl-, wherein $R^2$ is trifluoromethyl, and $R^4$, $Y^3$, $Y^4$, $Y^6$, $Y^7$ and $Y^8$ are as defined in Table P.

Table IA-16

Table IA-16 provides 450 compounds of formula (IA) wherein $R^2$ is dihydrofuran-4-yl-, wherein $R^2$ is trifluoromethyl, and $R^4$, $Y^3$, $Y^4$, $Y^6$, $Y^7$ and $Y^8$ are as defined in Table P.

Table IA-17

Table IA-17 provides 450 compounds of formula (IA) wherein $R^2$ is cyclopropyl-, wherein $R^2$ is trifluoromethyl, and $R^4$, $Y^3$, $Y^4$, $Y^6$, $Y^7$ and $Y^8$ are as defined in Table P.

Table IA-18

Table IA-18 provides 450 compounds of formula (IA) wherein $R^2$ is cyclobutyl-, wherein $R^2$ is trifluoromethyl, and $R^4$, $Y^3$, $Y^4$, $Y^6$, $Y^7$ and $Y^8$ are as defined in Table P.

Table IA-19

Table IA-19 provides 450 compounds of formula (IA) wherein $R^2$ is methylsulfonylmethyl-, wherein $R^2$ is trifluoromethyl, and $R^4$, $Y^3$, $Y^4$, $Y^6$, $Y^7$ and $Y^8$ are as defined in Table P.

Table IA-20

Table IA-20 provides 450 compounds of formula (IA) wherein $R^2$ is propen-1-yl-, wherein $R^2$ is trifluoromethyl, and $R^4$, $Y^3$, $Y^4$, $Y^6$, $Y^7$ and $Y^8$ are as defined in Table P.

Table IA-21

Table IA-21 provides 450 compounds of formula (IA) wherein $R^2$ is methylsulfanylmethyl-, wherein $R^2$ is trifluoromethyl, and $R^4$, $Y^3$, $Y^4$, $Y^6$, $Y^7$ and $Y^8$ are as defined in Table P.

Table IA-22

Table IA-22 provides 450 compounds of formula (IA) wherein $R^2$ is 1-methoxyeth-1-yl-, wherein $R^2$ is trifluoromethyl, and $R^4$, $Y^3$, $Y^4$, $Y^6$, $Y^7$ and $Y^8$ are as defined in Table P.

Table IA-23

Table IA-23 provides 450 compounds of formula (IA) wherein $R^2$ is 5-pyrimidyl-, wherein $R^2$ is trifluoromethyl, and $R^4$, $Y^3$, $Y^4$, $Y^6$, $Y^7$ and $Y^8$ are as defined in Table P.

Table IA-24

Table IA-24 provides 450 compounds of formula (IA) wherein $R^2$ is but-2-yl-, wherein $R^2$ is trifluoromethyl, and $R^4$, $Y^3$, $Y^4$, $Y^6$, $Y^7$ and $Y^8$ are as defined in Table P.

Table IA-25

Table IA-25 provides 450 compounds of formula (IA) wherein $R^2$ is 1-fluoroprop-2-yl-, wherein $R^2$ is trifluoromethyl, and $R^4$, $Y^3$, $Y^4$, $Y^6$, $Y^7$ and $Y^8$ are as defined in Table P.

Table IA-26

Table IA-26 provides 450 compounds of formula (IA) wherein $R^2$ is 2-methylpropen-1-yl-, wherein $R^2$ is trifluoromethyl, and $R^4$, $Y^3$, $Y^4$, $Y^6$, $Y^7$ and $Y^8$ are as defined in Table P.

Table IA-27

Table IA-27 provides 450 compounds of formula (IA) wherein $R^2$ is 1-cyanocyclopropyl-, wherein $R^2$ is trifluoromethyl, and $R^4$, $Y^3$, $Y^4$, $Y^6$, $Y^7$ and $Y^8$ are as defined in Table P.

Table IA-28

Table IA-28 provides 450 compounds of formula (IA) wherein $R^2$ is N-formylaminomethyl-, wherein $R^2$ is trifluoromethyl, and $R^4$, $Y^3$, $Y^4$, $Y^6$, $Y^7$ and $Y^8$ are as defined in Table P.

Table IA-29

Table IA-29 provides 450 compounds of formula (IA) wherein $R^2$ is 2-methylsulfinyl-ethyl-, wherein $R^2$ is trifluoromethyl, and $R^4$, $Y^3$, $Y^4$, $Y^6$, $Y^7$ and $Y^8$ are as defined in Table P.

Table IA-30

Table IA-30 provides 450 compounds of formula (IA) wherein $R^2$ is 2-(methylsulfonyl)-ethyl-, wherein $R^2$ is trifluoromethyl, and $R^4$, $Y^3$, $Y^4$, $Y^6$, $Y^7$ and $Y^8$ are as defined in Table P.

Table IA-31

Table IA-31 provides 450 compounds of formula (IA) wherein $R^2$ is 1-oxo-tetrahydrofuran-3-yl-, wherein $R^2$ is trifluoromethyl, and $R^4$, $Y^3$, $Y^4$, $Y^6$, $Y^7$ and $Y^8$ are as defined in Table P.

Table IA-32

Table IA-32 provides 450 compounds of formula (IA) wherein $R^2$ is 1-oxo-thietan-3-yl-, wherein $R^2$ is trifluoromethyl, and $R^4$, $Y^3$, $Y^4$, $Y^6$, $Y^7$ and $Y^8$ are as defined in Table P.

Table IA-33
Table IA-33 provides 450 compounds of formula (IA) wherein $R^2$ is 1,1-dioxo-tetrahydrofuran-3-yl-, wherein $R^2$ is trifluoromethyl, and $R^4$, $Y^3$, $Y^4$, $Y^6$, $Y^7$ and $Y^8$ are as defined in Table P.

Table IA-34
Table IA-34 provides 450 compounds of formula (IA) wherein $R^2$ is 1,1-dioxo-thietan-3-yl-, wherein $R^2$ is trifluoromethyl, and $R^4$, $Y^3$, $Y^4$, $Y^6$, $Y^7$ and $Y^8$ are as defined in Table P.

Table IA-35
Table IA-35 provides 450 compounds of formula (IA) wherein $R^2$ is 3-chloroprop-1-yl-, wherein $R^2$ is trifluoromethyl, and $R^4$, $Y^3$, $Y^4$, $Y^6$, $Y^7$ and $Y^8$ are as defined in Table P.

Table IA-36
Table IA-36 provides 450 compounds of formula (IA) wherein $R^2$ is 3,3,3-trifluoro-propyl-, wherein $R^2$ is trifluoromethyl, and $R^4$, $Y^3$, $Y^4$, $Y^6$, $Y^7$ and $Y^8$ are as defined in Table P.

Table IA-37
Table IA-37 provides 450 compounds of formula (IA) wherein $R^2$ is thietan-3-yl-, wherein $R^2$ is trifluoromethyl, and $R^4$, $Y^3$, $Y^4$, $Y^6$, $Y^7$ and $Y^8$ are as defined in Table P.

Table IA-38
Table IA-38 provides 450 compounds of formula (IA) wherein $R^2$ is 3-oxetanyl-, wherein $R^2$ is trifluoromethyl, and $R^4$, $Y^3$, $Y^4$, $Y^6$, $Y^7$ and $Y^8$ are as defined in Table P.

Table IA-39
Table IA-39 provides 450 compounds of formula (IA) wherein $R^2$ is tetrahydrofuran-2-yl-, wherein $R^2$ is trifluoromethyl, and $R^4$, $Y^3$, $Y^4$, $Y^6$, $Y^7$ and $Y^8$ are as defined in Table P.

Table IA-40
Table IA-40 provides 450 compounds of formula (IA) wherein $R^2$ is 1,1,1-trifluoroprop-2-yl-, wherein $R^2$ is trifluoromethyl, and $R^4$, $Y^3$, $Y^4$, $Y^6$, $Y^7$ and $Y^8$ are as defined in Table P.

Table IA-41
Table IA-41 provides 450 compounds of formula (IA) wherein $R^2$ is but-1-yl-, wherein $R^2$ is trifluoromethyl, and $R^4$, $Y^3$, $Y^4$, $Y^6$, $Y^7$ and $Y^8$ are as defined in Table P.

Table IA-42
Table IA-42 provides 450 compounds of formula (IA) wherein $R^2$ is 2,2-difluoro-ethyl-, wherein $R^2$ is trifluoromethyl, and $R^4$, $Y^3$, $Y^4$, $Y^6$, $Y^7$ and $Y^8$ are as defined in Table P.

Table IA-43
Table IA-43 provides 450 compounds of formula (IA) wherein $R^2$ is ethyl-, wherein $R^2$ is chlorodifluoromethyl, and $R^4$, $Y^3$, $Y^4$, $Y^6$, $Y^7$ and $Y^8$ are as defined in Table P.

Table IA-44
Table IA-44 provides 450 compounds of formula (IA) wherein $R^2$ is 2,2,2-trifluoro-ethyl-, wherein $R^2$ is chlorodifluoromethyl, and $R^4$, $Y^3$, $Y^4$, $Y^6$, $Y^7$ and $Y^8$ are as defined in Table P.

Table IA-45
Table IA-45 provides 450 compounds of formula (IA) wherein $R^2$ is prop-2-yl-, wherein $R^2$ is chlorodifluoromethyl, and $R^4$, $Y^3$, $Y^4$, $Y^6$, $Y^7$ and $Y^8$ are as defined in Table P.

Table IA-46
Table IA-46 provides 450 compounds of formula (IA) wherein $R^2$ is methyl-, wherein $R^2$ is chlorodifluoromethyl, and $R^4$, $Y^3$, $Y^4$, $Y^6$, $Y^7$ and $Y^8$ are as defined in Table P.

Table IA-47
Table IA-47 provides 450 compounds of formula (IA) wherein $R^2$ is 2-fluoro-cycloprop-1-yl-, wherein $R^2$ is chlorodifluoromethyl, and $R^4$, $Y^3$, $Y^4$, $Y^6$, $Y^7$ and $Y^8$ are as defined in Table P.

Table IA-48
Table IA-48 provides 450 compounds of formula (IA) wherein $R^2$ is prop-1-yl, wherein $R^2$ is chlorodifluoromethyl, and $R^4$, $Y^3$, $Y^4$, $Y^6$, $Y^7$ and $Y^8$ are as defined in Table P.

Table IA-49
Table IA-49 provides 450 compounds of formula (IA) wherein $R^2$ is 2-fluoro-ethyl-, wherein $R^2$ is chlorodifluoromethyl, and $R^4$, $Y^3$, $Y^4$, $Y^6$, $Y^7$ and $Y^8$ are as defined in Table P.

Table IA-50
Table IA-50 provides 450 compounds of formula (IA) wherein $R^2$ is 2-cyano-ethyl-, wherein $R^2$ is chlorodifluoromethyl, and $R^4$, $Y^3$, $Y^4$, $Y^6$, $Y^7$ and $Y^8$ are as defined in Table P.

Table IA-51
Table IA-51 provides 450 compounds of formula (IA) wherein $R^2$ is 1-fluoroethyl-, wherein $R^2$ ischlorodifluoromethyl, and $R^4$, $Y^3$, $Y^4$, $Y^6$, $Y^7$ and $Y^8$ are as defined in Table P.

Table IA-52
Table IA-52 provides 450 compounds of formula (IA) wherein $R^2$ is 2-methylprop-1-yl-, wherein $R^2$ is chlorodifluoromethyl, and $R^4$, $Y^3$, $Y^4$, $Y^6$, $Y^7$ and $Y^8$ are as defined in Table P.

Table IA-53
Table IA-53 provides 450 compounds of formula (IA) wherein $R^2$ is propen-2-yl-, wherein $R^2$ is chlorodifluoromethyl, and $R^4$, $Y^3$, $Y^4$, $Y^6$, $Y^7$ and $Y^8$ are as defined in Table P.

Table IA-54
Table IA-54 provides 450 compounds of formula (IA) wherein $R^2$ is cyclopropylmethyl-, wherein $R^2$ is chlorodifluoromethyl, and $R^4$, $Y^3$, $Y^4$, $Y^6$, $Y^7$ and $Y^8$ are as defined in Table P.

Table IA-55
Table IA-55 provides 450 compounds of formula (IA) wherein $R^2$ is 2-methoxy-ethyl-, wherein $R^2$ is chlorodifluoromethyl, and $R^4$, $Y^3$, $Y^4$, $Y^6$, $Y^7$ and $Y^8$ are as defined in Table P.

Table IA-56
Table IA-56 provides 450 compounds of formula (IA) wherein $R^2$ is 3-methyloxetan-3-yl-, wherein $R^2$ is chlorodifluoromethyl, and $R^4$, $Y^3$, $Y^4$, $Y^6$, $Y^7$ and $Y^8$ are as defined in Table P.

Table IA-57
Table IA-57 provides 450 compounds of formula (IA) wherein $R^2$ is 1-methylcyclopropyl-, wherein $R^2$ is chlorodifluoromethyl, and $R^4$, $Y^3$, $Y^4$, $Y^6$, $Y^7$ and $Y^8$ are as defined in Table P.

Table IA-58
Table IA-58 provides 450 compounds of formula (IA) wherein $R^2$ is dihydrofuran-4-yl-, wherein $R^2$ is chlorodifluoromethyl, and $R^4$, $Y^3$, $Y^4$, $Y^6$, $Y^7$ and $Y^8$ are as defined in Table P.

Table IA-59
Table IA-59 provides 450 compounds of formula (IA) wherein $R^2$ is cyclopropyl-, wherein $R^2$ is chlorodifluoromethyl, and $R^4$, $Y^3$, $Y^4$, $Y^6$, $Y^7$ and $Y^8$ are as defined in Table P.

Table IA-60
Table IA-60 provides 450 compounds of formula (IA) wherein $R^2$ is cyclobutyl-, wherein $R^2$ is chlorodifluoromethyl, and $R^4$, $Y^3$, $Y^4$, $Y^6$, $Y^7$ and $Y^8$ are as defined in Table P.

Table IA-61
Table IA-61 provides 450 compounds of formula (IA) wherein $R^2$ is methylsulfonylmethyl-, wherein $R^2$ is chlorodifluoromethyl, and $R^4$, $Y^3$, $Y^4$, $Y^6$, $Y^7$ and $Y^8$ are as defined in Table P.

Table IA-62
Table IA-62 provides 450 compounds of formula (IA) wherein $R^2$ is propen-1-yl-, wherein $R^2$ is chlorodifluoromethyl, and $R^4$, $Y^3$, $Y^4$, $Y^6$, $Y^7$ and $Y^8$ are as defined in Table P.

Table IA-63
Table IA-63 provides 450 compounds of formula (IA) wherein $R^2$ is methylsulfanylmethyl-, wherein $R^2$ is chlorodifluoromethyl, and $R^4$, $Y^3$, $Y^4$, $Y^6$, $Y^7$ and $Y^8$ are as defined in Table P.

Table IA-64
Table IA-64 provides 450 compounds of formula (IA) wherein $R^2$ is 1-methoxyeth-1-yl-, wherein $R^2$ is chlorodifluoromethyl, and $R^4$, $Y^3$, $Y^4$, $Y^6$, $Y^7$ and $Y^8$ are as defined in Table P.

Table IA-65
Table IA-65 provides 450 compounds of formula (IA) wherein $R^2$ is 5-pyrimidyl-, wherein $R^2$ is chlorodifluoromethyl, and $R^4$, $Y^3$, $Y^4$, $Y^6$, $Y^7$ and $Y^8$ are as defined in Table P.

Table IA-66
Table IA-66 provides 450 compounds of formula (IA) wherein $R^2$ is but-2-yl-, wherein $R^2$ is chlorodifluoromethyl, and $R^4$, $Y^3$, $Y^4$, $Y^6$, $Y^7$ and $Y^8$ are as defined in Table P.

Table IA-67
Table IA-67 provides 450 compounds of formula (IA) wherein $R^2$ is 1-fluoroprop-2-yl-, wherein $R^2$ is chlorodifluoromethyl, and $R^4$, $Y^3$, $Y^4$, $Y^6$, $Y^7$ and $Y^8$ are as defined in Table P.

Table IA-68
Table IA-68 provides 450 compounds of formula (IA) wherein $R^2$ is 2-methylpropen-1-yl-, wherein $R^2$ is chlorodifluoromethyl, and $R^4$, $Y^3$, $Y^4$, $Y^6$, $Y^7$ and $Y^8$ are as defined in Table P.

Table IA-69
Table IA-69 provides 450 compounds of formula (IA) wherein $R^2$ is 1-cyanocyclopropyl-, wherein $R^2$ is chlorodifluoromethyl, and $R^4$, $Y^3$, $Y^4$, $Y^6$, $Y^7$ and $Y^8$ are as defined in Table P.

Table IA-70
Table IA-70 provides 450 compounds of formula (IA) wherein $R^2$ is N-formylaminomethyl-, wherein $R^2$ is chlorodifluoromethyl, and $R^4$, $Y^3$, $Y^4$, $Y^6$, $Y^7$ and $Y^8$ are as defined in Table P.

Table IA-71
Table IA-71 provides 450 compounds of formula (IA) wherein $R^2$ is 2-methylsulfinyl-ethyl-, wherein $R^2$ is chlorodifluoromethyl, and $R^4$, $Y^3$, $Y^4$, $Y^6$, $Y^7$ and $Y^8$ are as defined in Table P.

Table IA-72
Table IA-72 provides 450 compounds of formula (IA) wherein $R^2$ is 2-(methylsulfonyl)-ethyl-, wherein $R^2$ is chlorodifluoromethyl, and $R^4$, $Y^3$, $Y^4$, $Y^6$, $Y^7$ and $Y^8$ are as defined in Table P.

Table IA-73
Table IA-73 provides 450 compounds of formula (IA) wherein $R^2$ is 1-oxo-tetrahydrofuran-3-yl-, wherein $R^2$ is chlorodifluoromethyl, and $R^4$, $Y^3$, $Y^4$, $Y^6$, $Y^7$ and $Y^8$ are as defined in Table P.

Table IA-74
Table IA-74 provides 450 compounds of formula (IA) wherein $R^2$ is 1-oxo-thietan-3-yl-, wherein $R^2$ is chlorodifluoromethyl, and $R^4$, $Y^3$, $Y^4$, $Y^6$, $Y^7$ and $Y^8$ are as defined in Table P.

Table IA-75
Table IA-75 provides 450 compounds of formula (IA) wherein $R^2$ is 1,1-dioxo-tetrahydrofuran-3-yl-, wherein $R^2$ is chlorodifluoromethyl, and $R^4$, $Y^3$, $Y^4$, $Y^6$, $Y^7$ and $Y^8$ are as defined in Table P.

Table IA-76
Table IA-76 provides 450 compounds of formula (IA) wherein $R^2$ is 1,1-dioxo-thietan-3-yl-, wherein $R^2$ is chlorodifluoromethyl, and $R^4$, $Y^3$, $Y^4$, $Y^6$, $Y^7$ and $Y^8$ are as defined in Table P.

Table IA-77
Table IA-77 provides 450 compounds of formula (IA) wherein $R^2$ is 3-chloroprop-1-yl-, wherein $R^2$ is chlorodifluoromethyl, and $R^4$, $Y^3$, $Y^4$, $Y^6$, $Y^7$ and $Y^8$ are as defined in Table P.

Table IA-78
Table IA-78 provides 450 compounds of formula (IA) wherein $R^2$ is 3,3,3-trifluoro-propyl-, wherein $R^2$ is chlorodifluoromethyl, and $R^4$, $Y^3$, $Y^4$, $Y^6$, $Y^7$ and $Y^8$ are as defined in Table P.

Table IA-79
Table IA-79 provides 450 compounds of formula (IA) wherein $R^2$ is thietan-3-yl-, wherein $R^2$ is chlorodifluoromethyl, and $R^4$, $Y^3$, $Y^4$, $Y^6$, $Y^7$ and $Y^8$ are as defined in Table P.

Table IA-80
Table IA-80 provides 450 compounds of formula (IA) wherein $R^2$ is 3-oxetanyl-, wherein $R^2$ is chlorodifluoromethyl, and $R^4$, $Y^3$, $Y^4$, $Y^6$, $Y^7$ and $Y^8$ are as defined in Table P.

Table IA-81
Table IA-81 provides 450 compounds of formula (IA) wherein $R^2$ is tetrahydrofuran-2-yl-, wherein $R^2$ is chlorodifluoromethyl, and $R^4$, $Y^3$, $Y^4$, $Y^6$, $Y^7$ and $Y^8$ are as defined in Table P.

Table IA-82
Table IA-82 provides 450 compounds of formula (IA) wherein $R^2$ is 1,1,1-trifluoroprop-2-yl-, wherein $R^2$ is chlorodifluoromethyl, and $R^4$, $Y^3$, $Y^4$, $Y^6$, $Y^7$ and $Y^8$ are as defined in Table P.

Table IA-83
Table IA-83 provides 450 compounds of formula (IA) wherein $R^2$ is but-1-yl-, wherein $R^2$ is chlorodifluoromethyl, and $R^4$, $Y^3$, $Y^4$, $Y^6$, $Y^7$ and $Y^8$ are as defined in Table P.

Table IA-84
Table IA-84 provides 450 compounds of formula (IA) wherein $R^2$ is 2,2-difluoro-ethyl-, wherein $R^2$ is chlorodifluoromethyl, and $R^4$, $Y^3$, $Y^4$, $Y^6$, $Y^7$ and $Y^8$ are as defined in Table P.

Table IB-1

Table IB-1 provides 450 compounds of formula (IB) wherein $R^2$ is ethyl-, $R^3$ is trifluoromethyl, and $R^4$, $Y^3$, $Y^4$, $Y^6$, $Y^7$ and $Y^8$ are as defined in Table P.

Table IB-2

Table IB-2 provides 450 compounds of formula (IB) wherein $R^2$ is 2,2,2-trifluoro-ethyl-, $R^3$ is trifluoromethyl, and $R^4$, $Y^3$, $Y^4$, $Y^6$, $Y^7$ and $Y^8$ are as defined in Table P.

Table IB-3

Table IB-3 provides 450 compounds of formula (IB) wherein $R^2$ is prop-2-yl-, $R^3$ is trifluoromethyl, and $R^4$, $Y^3$, $Y^4$, $Y^6$, $Y^7$ and $Y^8$ are as defined in Table P.

Table IB-4

Table IB-4 provides 450 compounds of formula (IB) wherein $R^2$ is methyl-, $R^3$ is trifluoromethyl, and $R^4$, $Y^3$, $Y^4$, $Y^6$, $Y^7$ and $Y^8$ are as defined in Table P.

Table IB-5

Table IB-5 provides 450 compounds of formula (IB) wherein $R^2$ is 2-fluoro-cycloprop-1-yl-, $R^3$ is trifluoromethyl, and $R^4$, $Y^3$, $Y^4$, $Y^6$, $Y^7$ and $Y^8$ are as defined in Table P.

Table IB-6

Table IB-6 provides 450 compounds of formula (IB) wherein $R^2$ is prop-1-yl, $R^3$ is trifluoromethyl, and $R^4$, $Y^3$, $Y^4$, $Y^6$, $Y^7$ and $Y^8$ are as defined in Table P.

Table IB-7

Table IB-7 provides 450 compounds of formula (IB) wherein $R^2$ is 2-fluoro-ethyl-, $R^3$ is trifluoromethyl, and $R^4$, $Y^3$, $Y^4$, $Y^6$, $Y^7$ and $Y^8$ are as defined in Table P.

Table IB-8

Table IB-8 provides 450 compounds of formula (IB) wherein $R^2$ is 2-cyano-ethyl-, $R^3$ is trifluoromethyl, and $R^4$, $Y^3$, $Y^4$, $Y^6$, $Y^7$ and $Y^8$ are as defined in Table P.

Table IB-9

Table IB-9 provides 450 compounds of formula (IB) wherein $R^2$ is 1-fluoroethyl-, $R^3$ is trifluoromethyl, and $R^4$, $Y^3$, $Y^4$, $Y^6$, $Y^7$ and $Y^8$ are as defined in Table P.

Table IB-10

Table IB-10 provides 450 compounds of formula (IB) wherein $R^2$ is 2-methylprop-1-yl-, $R^3$ is trifluoromethyl, and $R^4$, $Y^3$, $Y^4$, $Y^6$, $Y^7$ and $Y^8$ are as defined in Table P.

Table IB-11

Table IB-11 provides 450 compounds of formula (IB) wherein $R^2$ is propen-2-yl-, $R^3$ is trifluoromethyl, and $R^4$, $Y^3$, $Y^4$, $Y^6$, $Y^7$ and $Y^8$ are as defined in Table P.

Table IB-12

Table IB-12 provides 450 compounds of formula (IB) wherein $R^2$ is cyclopropylmethyl-, $R^3$ is trifluoromethyl, and $R^4$, $Y^3$, $Y^4$, $Y^6$, $Y^7$ and $Y^8$ are as defined in Table P.

Table IB-13

Table IB-13 provides 450 compounds of formula (IB) wherein $R^2$ is 2-methoxy-ethyl-, $R^3$ is trifluoromethyl, and $R^4$, $Y^3$, $Y^4$, $Y^6$, $Y^7$ and $Y^8$ are as defined in Table P.

Table IB-14

Table IB-14 provides 450 compounds of formula (IB) wherein $R^2$ is 3-methyloxetan-3-yl-, $R^3$ is trifluoromethyl, and $R^4$, $Y^3$, $Y^4$, $Y^6$, $Y^7$ and $Y^8$ are as defined in Table P.

Table IB-15

Table IB-15 provides 450 compounds of formula (IB) wherein $R^2$ is 1-methylcyclopropyl-, $R^3$ is trifluoromethyl, and $R^4$, $Y^3$, $Y^4$, $Y^6$, $Y^7$ and $Y^8$ are as defined in Table P.

Table IB-16

Table IB-16 provides 450 compounds of formula (IB) wherein $R^2$ is dihydrofuran-4-yl-, $R^3$ is trifluoromethyl, and $R^4$, $Y^3$, $Y^4$, $Y^6$, $Y^7$ and $Y^8$ are as defined in Table P.

Table IB-17

Table IB-17 provides 450 compounds of formula (IB) wherein $R^2$ is cyclopropyl-, $R^3$ is trifluoromethyl, and $R^4$, $Y^3$, $Y^4$, $Y^6$, $Y^7$ and $Y^8$ are as defined in Table P.

Table IB-18

Table IB-18 provides 450 compounds of formula (IB) wherein $R^2$ is cyclobutyl-, $R^3$ is trifluoromethyl, and $R^4$, $Y^3$, $Y^4$, $Y^6$, $Y^7$ and $Y^8$ are as defined in Table P.

Table IB-19

Table IB-19 provides 450 compounds of formula (IB) wherein $R^2$ is methylsulfonylmethyl-, $R^3$ is trifluoromethyl, and $R^4$, $Y^3$, $Y^4$, $Y^6$, $Y^7$ and $Y^8$ are as defined in Table P.

Table IB-20

Table IB-20 provides 450 compounds of formula (IB) wherein $R^2$ is propen-1-yl-, $R^3$ is trifluoromethyl, and $R^4$, $Y^3$, $Y^4$, $Y^6$, $Y^7$ and $Y^8$ are as defined in Table P.

Table IB-21

Table IB-21 provides 450 compounds of formula (IB) wherein $R^2$ is methylsulfanylmethyl-, $R^3$ is trifluoromethyl, and $R^4$, $Y^3$, $Y^4$, $Y^6$, $Y^7$ and $Y^8$ are as defined in Table P.

Table IB-22

Table IB-22 provides 450 compounds of formula (IB) wherein $R^2$ is 1-methoxyeth-1-yl-, $R^3$ is trifluoromethyl, and $R^4$, $Y^3$, $Y^4$, $Y^6$, $Y^7$ and $Y^8$ are as defined in Table P.

Table IB-23

Table IB-23 provides 450 compounds of formula (IB) wherein $R^2$ is 5-pyrimidyl-, $R^3$ is trifluoromethyl, and $R^4$, $Y^3$, $Y^4$, $Y^6$, $Y^7$ and $Y^8$ are as defined in Table P.

Table IB-24

Table IB-24 provides 450 compounds of formula (IB) wherein $R^2$ is but-2-yl-, $R^3$ is trifluoromethyl, and $R^4$, $Y^3$, $Y^4$, $Y^6$, $Y^7$ and $Y^8$ are as defined in Table P.

Table IB-25

Table IB-25 provides 450 compounds of formula (IB) wherein $R^2$ is 1-fluoroprop-2-yl-, $R^3$ is trifluoromethyl, and $R^4$, $Y^3$, $Y^4$, $Y^6$, $Y^7$ and $Y^8$ are as defined in Table P.

Table IB-26

Table IB-26 provides 450 compounds of formula (IB) wherein $R^2$ is 2-methylpropen-1-yl-, $R^3$ is trifluoromethyl, and $R^4$, $Y^3$, $Y^4$, $Y^6$, $Y^7$ and $Y^8$ are as defined in Table P.

Table IB-27

Table IB-27 provides 450 compounds of formula (IB) wherein $R^2$ is 1-cyanocyclopropyl-, $R^3$ is trifluoromethyl, and $R^4$, $Y^3$, $Y^4$, $Y^6$, $Y^7$ and $Y^8$ are as defined in Table P.

Table IB-28

Table IB-28 provides 450 compounds of formula (IB) wherein $R^2$ is N-formylaminomethyl-, $R^3$ is trifluoromethyl, and $R^4$, $Y^3$, $Y^4$, $Y^6$, $Y^7$ and $Y^8$ are as defined in Table P.

Table IB-29

Table IB-29 provides 450 compounds of formula (IB) wherein $R^2$ is 2-methylsulfinyl-ethyl-, $R^3$ is trifluoromethyl, and $R^4$, $Y^3$, $Y^4$, $Y^6$, $Y^7$ and $Y^8$ are as defined in Table P.

Table IB-30

Table IB-30 provides 450 compounds of formula (IB) wherein $R^2$ is 2-(methylsulfonyl)-ethyl-, $R^3$ is trifluoromethyl, and $R^4$, $Y^3$, $Y^4$, $Y^6$, $Y^7$ and $Y^8$ are as defined in Table P.

Table IB-31

Table IB-31 provides 450 compounds of formula (IB) wherein $R^2$ is 1-oxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table IB-32

Table IB-32 provides 450 compounds of formula (IB) wherein $R^2$ is 1-oxo-thietan-3-yl-, $R^3$ is trifluoromethyl, and $R^4$, $Y^3$, $Y^4$, $Y^6$, $Y^7$ and $Y^8$ are as defined in Table P.

Table IB-33

Table IB-33 provides 450 compounds of formula (IB) wherein $R^2$ is 1,1-dioxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table IB-34

Table IB-34 provides 450 compounds of formula (IB) wherein $R^2$ is 1,1-dioxo-thietan-3-yl-, $R^3$ is trifluoromethyl, and $R^4$, $Y^3$, $Y^4$, $Y^6$, $Y^7$ and $Y^8$ are as defined in Table P.

Table IB-35

Table IB-35 provides 450 compounds of formula (IB) wherein $R^2$ is 3-chloroprop-1-yl-, $R^3$ is trifluoromethyl, and $R^4$, $Y^3$, $Y^4$, $Y^6$, $Y^7$ and $Y^8$ are as defined in Table P.

Table IB-36

Table IB-36 provides 450 compounds of formula (IB) wherein $R^2$ is 3,3,3-trifluoro-propyl-, $R^3$ is trifluoromethyl, and $R^4$, $Y^3$, $Y^4$, $Y^6$, $Y^7$ and $Y^8$ are as defined in Table P.

Table IB-37

Table IB-37 provides 450 compounds of formula (IB) wherein $R^2$ is thietan-3-yl-, $R^3$ is trifluoromethyl, and $R^4$, $Y^3$, $Y^4$, $Y^6$, $Y^7$ and $Y^8$ are as defined in Table P.

Table IB-38

Table IB-38 provides 450 compounds of formula (IB) wherein $R^2$ is 3-oxetanyl-, $R^3$ is trifluoromethyl, and $R^4$, $Y^3$, $Y^4$, $Y^6$, $Y^7$ and $Y^8$ are as defined in Table P.

Table IB-39

Table IB-39 provides 450 compounds of formula (IB) wherein $R^2$ is tetrahydrofuran-2-yl-, $R^3$ is trifluoromethyl, and $R^4$, $Y^3$, $Y^4$, $Y^6$, $Y^7$ and $Y^8$ are as defined in Table P.

Table IB-40

Table IB-40 provides 450 compounds of formula (IB) wherein $R^2$ is 1,1,1-trifluoroprop-2-yl-, $R^3$ is trifluoromethyl, and $R^4$, $Y^3$, $Y^4$, $Y^6$, $Y^7$ and $Y^8$ are as defined in Table P.

Table IB-41

Table IB-41 provides 450 compounds of formula (IB) wherein $R^2$ is but-1-yl-, $R^3$ is trifluoromethyl, and $R^4$, $Y^3$, $Y^4$, $Y^6$, $Y^7$ and $Y^8$ are as defined in Table P.

Table IB-42

Table IB-42 provides 450 compounds of formula (IB) wherein $R^2$ is 2,2-difluoro-ethyl-, $R^3$ is trifluoromethyl, and $R^4$, $Y^3$, $Y^4$, $Y^6$, $Y^7$ and $Y^8$ are as defined in Table P.

Table IB-43

Table IB-43 provides 450 compounds of formula (IB) wherein $R^2$ is ethyl-, $R^3$ is chlorodifluoromethyl, and $R^4$, $Y^3$, $Y^4$, $Y^6$, $Y^7$ and $Y^8$ are as defined in Table P.

Table IB-44

Table IB-44 provides 450 compounds of formula (IB) wherein $R^2$ is 2,2,2-trifluoro-ethyl-, $R^3$ is chlorodifluoromethyl, and $R^4$, $Y^3$, $Y^4$, $Y^6$, $Y^7$ and $Y^8$ are as defined in Table P.

Table IB-45

Table IB-45 provides 450 compounds of formula (IB) wherein $R^2$ is prop-2-yl-, $R^3$ is chlorodifluoromethyl, and $R^4$, $Y^3$, $Y^4$, $Y^6$, $Y^7$ and $Y^8$ are as defined in Table P.

Table IB-46

Table IB-46 provides 450 compounds of formula (IB) wherein $R^2$ is methyl-, $R^3$ is chlorodifluoromethyl, and $R^4$, $Y^3$, $Y^4$, $Y^6$, $Y^7$ and $Y^8$ are as defined in Table P.

Table IB-47

Table IB-47 provides 450 compounds of formula (IB) wherein $R^2$ is 2-fluoro-cycloprop-1-yl-, $R^3$ is chlorodifluoromethyl, and $R^4$, $Y^3$, $Y^4$, $Y^6$, $Y^7$ and $Y^8$ are as defined in Table P.

Table IB-48

Table IB-48 provides 450 compounds of formula (IB) wherein $R^2$ is prop-1-yl, $R^3$ is chlorodifluoromethyl, and $R^4$, $Y^3$, $Y^4$, $Y^6$, $Y^7$ and $Y^8$ are as defined in Table P.

Table IB-49

Table IB-49 provides 450 compounds of formula (IB) wherein $R^2$ is 2-fluoro-ethyl-, $R^3$ is chlorodifluoromethyl, and $R^4$, $Y^3$, $Y^4$, $Y^6$, $Y^7$ and $Y^8$ are as defined in Table P.

Table IB-50

Table IB-50 provides 450 compounds of formula (IB) wherein $R^2$ is 2-cyano-ethyl-, $R^3$ is chlorodifluoromethyl, and $R^4$, $Y^3$, $Y^4$, $Y^6$, $Y^7$ and $Y^8$ are as defined in Table P.

Table IB-51

Table IB-51 provides 450 compounds of formula (IB) wherein $R^2$ is 1-fluoroethyl-, $R^3$ is chlorodifluoromethyl, and $R^4$, $Y^3$, $Y^4$, $Y^6$, $Y^7$ and $Y^8$ are as defined in Table P.

Table IB-52

Table IB-52 provides 450 compounds of formula (IB) wherein $R^2$ is 2-methylprop-1-yl-, $R^3$ is chlorodifluoromethyl, and $R^4$, $Y^3$, $Y^4$, $Y^6$, $Y^7$ and $Y^8$ are as defined in Table P.

Table IB-53

Table IB-53 provides 450 compounds of formula (IB) wherein $R^2$ is propen-2-yl-, $R^3$ is chlorodifluoromethyl, and $R^4$, $Y^3$, $Y^4$, $Y^6$, $Y^7$ and $Y^8$ are as defined in Table P.

Table IB-54

Table IB-54 provides 450 compounds of formula (IB) wherein $R^2$ is cyclopropylmethyl-, $R^3$ is chlorodifluoromethyl, and $R^4$, $Y^3$, $Y^4$, $Y^6$, $Y^7$ and $Y^8$ are as defined in Table P.

Table IB-55

Table IB-55 provides 450 compounds of formula (IB) wherein $R^2$ is 2-methoxy-ethyl-, $R^3$ is chlorodifluoromethyl, and $R^4$, $Y^3$, $Y^4$, $Y^6$, $Y^7$ and $Y^8$ are as defined in Table P.

Table IB-56

Table IB-56 provides 450 compounds of formula (IB) wherein $R^2$ is 3-methyloxetan-3-yl-, $R^3$ is chlorodifluoromethyl, and $R^4$, $Y^3$, $Y^4$, $Y^6$, $Y^7$ and $Y^8$ are as defined in Table P.

Table IB-57

Table IB-57 provides 450 compounds of formula (IB) wherein $R^2$ is 1-methylcyclopropyl-, $R^3$ is chlorodifluoromethyl, and $R^4$, $Y^3$, $Y^4$, $Y^6$, $Y^7$ and $Y^8$ are as defined in Table P.

Table IB-58

Table IB-58 provides 450 compounds of formula (IB) wherein $R^2$ is dihydrofuran-4-yl-, $R^3$ is chlorodifluoromethyl, and $R^4$, $Y^3$, $Y^4$, $Y^6$, $Y^7$ and $Y^8$ are as defined in Table P.

Table IB-59

Table IB-59 provides 450 compounds of formula (IB) wherein $R^2$ is cyclopropyl-, $R^3$ is chlorodifluoromethyl, and $R^4$, $Y^3$, $Y^4$, $Y^6$, $Y^7$ and $Y^8$ are as defined in Table P.

Table IB-60

Table IB-60 provides 450 compounds of formula (IB) wherein $R^2$ is cyclobutyl-, $R^3$ is chlorodifluoromethyl, and $R^4$, $Y^3$, $Y^4$, $Y^6$, $Y^7$ and $Y^8$ are as defined in Table P.

Table IB-61

Table IB-61 provides 450 compounds of formula (IB) wherein $R^2$ is methylsulfonylmethyl-, $R^3$ is chlorodifluoromethyl, and $R^4$, $Y^3$, $Y^4$, $Y^6$, $Y^7$ and $Y^8$ are as defined in Table P.

Table IB-62

Table IB-62 provides 450 compounds of formula (IB) wherein $R^2$ is propen-1-yl-, $R^3$ is chlorodifluoromethyl, and $R^4$, $Y^3$, $Y^4$, $Y^6$, $Y^7$ and $Y^8$ are as defined in Table P.

Table IB-63

Table IB-63 provides 450 compounds of formula (IB) wherein $R^2$ is methylsulfanylmethyl-, $R^3$ is chlorodifluoromethyl, and $R^4$, $Y^3$, $Y^4$, $Y^6$, $Y^7$ and $Y^8$ are as defined in Table P.

Table IB-64

Table IB-64 provides 450 compounds of formula (IB) wherein $R^2$ is 1-methoxyeth-1-yl-, $R^3$ is chlorodifluoromethyl, and $R^4$, $Y^3$, $Y^4$, $Y^6$, $Y^7$ and $Y^8$ are as defined in Table P.

Table IB-65

Table IB-65 provides 450 compounds of formula (IB) wherein $R^2$ is 5-pyrimidyl-, $R^3$ is chlorodifluoromethyl, and $R^4$, $Y^3$, $Y^4$, $Y^6$, $Y^7$ and $Y^8$ are as defined in Table P.

Table IB-66

Table IB-66 provides 450 compounds of formula (IB) wherein $R^2$ is but-2-yl-, $R^3$ is chlorodifluoromethyl, and $R^4$, $Y^3$, $Y^4$, $Y^6$, $Y^7$ and $Y^8$ are as defined in Table P.

Table IB-67

Table IB-67 provides 450 compounds of formula (IB) wherein $R^2$ is 1-fluoroprop-2-yl-, $R^3$ is chlorodifluoromethyl, and $R^4$, $Y^3$, $Y^4$, $Y^6$, $Y^7$ and $Y^8$ are as defined in Table P.

Table IB-68

Table IB-68 provides 450 compounds of formula (IB) wherein $R^2$ is 2-methylpropen-1-yl-, $R^3$ is chlorodifluoromethyl, and $R^4$, $Y^3$, $Y^4$, $Y^6$, $Y^7$ and $Y^8$ are as defined in Table P.

Table IB-69

Table IB-69 provides 450 compounds of formula (IB) wherein $R^2$ is 1-cyanocyclopropyl-, $R^3$ is chlorodifluoromethyl, and $R^4$, $Y^3$, $Y^4$, $Y^6$, $Y^7$ and $Y^8$ are as defined in Table P.

Table IB-70

Table IB-70 provides 450 compounds of formula (IB) wherein $R^2$ is N-formylaminomethyl-, $R^3$ is chlorodifluoromethyl, and $R^4$, $Y^3$, $Y^4$, $Y^6$, $Y^7$ and $Y^8$ are as defined in Table P.

Table IB-71

Table IB-71 provides 450 compounds of formula (IB) wherein $R^2$ is 2-methylsulfinyl-ethyl-, $R^3$ is chlorodifluoromethyl, and $R^4$, $Y^3$, $Y^4$, $Y^6$, $Y^7$ and $Y^8$ are as defined in Table P.

Table IB-72

Table IB-72 provides 450 compounds of formula (IB) wherein $R^2$ is 2-(methylsulfonyl)-ethyl-, $R^3$ is chlorodifluoromethyl, and $R^4$, $Y^3$, $Y^4$, $Y^6$, $Y^7$ and $Y^8$ are as defined in Table P.

Table IB-73

Table IB-73 provides 450 compounds of formula (IB) wherein $R^2$ is 1-oxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table IB-74

Table IB-74 provides 450 compounds of formula (IB) wherein $R^2$ is 1-oxo-thietan-3-yl-, $R^3$ is chlorodifluoromethyl, and $R^4$, $Y^3$, $Y^4$, $Y^6$, $Y^7$ and $Y^8$ are as defined in Table P.

Table IB-75

Table IB-75 provides 450 compounds of formula (IB) wherein $R^2$ is 1,1-dioxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table IB-76

Table IB-76 provides 450 compounds of formula (IB) wherein $R^2$ is 1,1-dioxo-thietan-3-yl-, $R^3$ is chlorodifluoromethyl, and $R^4$, $Y^3$, $Y^4$, $Y^6$, $Y^7$ and $Y^8$ are as defined in Table P.

Table IB-77

Table IB-77 provides 450 compounds of formula (IB) wherein $R^2$ is 3-chloroprop-1-yl-, $R^3$ is chlorodifluoromethyl, and $R^4$, $Y^3$, $Y^4$, $Y^6$, $Y^7$ and $Y^8$ are as defined in Table P.

Table IB-78

Table IB-78 provides 450 compounds of formula (IB) wherein $R^2$ is 3,3,3-trifluoro-propyl-, $R^3$ is chlorodifluoromethyl, and $R^4$, $Y^3$, $Y^4$, $Y^6$, $Y^7$ and $Y^8$ are as defined in Table P.

Table IB-79

Table IB-79 provides 450 compounds of formula (IB) wherein $R^2$ is thietan-3-yl-, $R^3$ is chlorodifluoromethyl, and $R^4$, $Y^3$, $Y^4$, $Y^6$, $Y^7$ and $Y^8$ are as defined in Table P.

Table IB-80

Table IB-80 provides 450 compounds of formula (IB) wherein $R^2$ is 3-oxetanyl-, $R^3$ is chlorodifluoromethyl, and $R^4$, $Y^3$, $Y^4$, $Y^6$, $Y^7$ and $Y^8$ are as defined in Table P.

Table IB-81

Table IB-81 provides 450 compounds of formula (IB) wherein $R^2$ is tetrahydrofuran-2-yl-, $R^3$ is chlorodifluoromethyl, and $R^4$, $Y^3$, $Y^4$, $Y^6$, $Y^7$ and $Y^8$ are as defined in Table P.

Table IB-82

Table IB-82 provides 450 compounds of formula (IB) wherein $R^2$ is 1,1,1-trifluoroprop-2-yl-, $R^3$ is chlorodifluoromethyl, and $R^4$, $Y^3$, $Y^4$, $Y^6$, $Y^7$ and $Y^8$ are as defined in Table P.

Table IB-83

Table IB-83 provides 450 compounds of formula (IB) wherein $R^2$ is but-1-yl-, $R^3$ is chlorodifluoromethyl, and $R^4$, $Y^3$, $Y^4$, $Y^6$, $Y^7$ and $Y^8$ are as defined in Table P.

Table IB-84

Table IB-84 provides 450 compounds of formula (IB) wherein $R^2$ is 2,2-difluoro-ethyl-, $R^3$ is chlorodifluoromethyl, and $R^4$, $Y^3$, $Y^4$, $Y^6$, $Y^7$ and $Y^8$ are as defined in Table P.

(IC)

Table IC-1

Table IC-1 provides 450 compounds of formula (IC) wherein $R^2$ is ethyl-, $R^3$ is trifluoromethyl, and $R^4$, $Y^3$, $Y^4$, $Y^6$, $Y^7$ and $Y^8$ are as defined in Table P.

Table IC-2

Table IC-2 provides 450 compounds of formula (IC) wherein $R^2$ is 2,2,2-trifluoro-ethyl-, $R^3$ is trifluoromethyl, and $R^4$, $Y^3$, $Y^4$, $Y^6$, $Y^7$ and $Y^8$ are as defined in Table P.

Table IC-3

Table IC-3 provides 450 compounds of formula (IC) wherein $R^2$ is prop-2-yl-, $R^3$ is trifluoromethyl, and $R^4$, $Y^3$, $Y^4$, $Y^6$, $Y^7$ and $Y^8$ are as defined in Table P.

Table IC-4

Table IC-4 provides 450 compounds of formula (IC) wherein $R^2$ is methyl-, $R^3$ is trifluoromethyl, and $R^4$, $Y^3$, $Y^4$, $Y^6$, $Y^7$ and $Y^8$ are as defined in Table P.

Table IC-5

Table IC-5 provides 450 compounds of formula (IC) wherein $R^2$ is 2-fluoro-cycloprop-1-yl-, $R^3$ is trifluoromethyl, and $R^4$, $Y^3$, $Y^4$, $Y^6$, $Y^7$ and $Y^8$ are as defined in Table P.

Table IC-6

Table IC-6 provides 450 compounds of formula (IC) wherein $R^2$ is prop-1-yl, $R^3$ is trifluoromethyl, and $R^4$, $Y^3$, $Y^4$, $Y^6$, $Y^7$ and $Y^8$ are as defined in Table P.

Table IC-7

Table IC-7 provides 450 compounds of formula (IC) wherein $R^2$ is 2-fluoro-ethyl-, $R^3$ is trifluoromethyl, and $R^4$, $Y^3$, $Y^4$, $Y^6$, $Y^7$ and $Y^8$ are as defined in Table P.

Table IC-8

Table IC-8 provides 450 compounds of formula (IC) wherein $R^2$ is 2-cyano-ethyl-, $R^3$ is trifluoromethyl, and $R^4$, $Y^3$, $Y^4$, $Y^6$, $Y^7$ and $Y^8$ are as defined in Table P.

Table IC-9

Table IC-9 provides 450 compounds of formula (IC) wherein $R^2$ is 1-fluoroethyl-, $R^3$ is trifluoromethyl, and $R^4$, $Y^3$, $Y^4$, $Y^6$, $Y^7$ and $Y^8$ are as defined in Table P.

Table IC-10

Table IC-10 provides 450 compounds of formula (IC) wherein $R^2$ is 2-methylprop-1-yl-, $R^3$ is trifluoromethyl, and $R^4$, $Y^3$, $Y^4$, $Y^6$, $Y^7$ and $Y^8$ are as defined in Table P.

Table IC-11

Table IC-11 provides 450 compounds of formula (IC) wherein $R^2$ is propen-2-yl-, $R^3$ is trifluoromethyl, and $R^4$, $Y^3$, $Y^4$, $Y^6$, $Y^7$ and $Y^8$ are as defined in Table P.

Table IC-12

Table IC-12 provides 450 compounds of formula (IC) wherein $R^2$ is cyclopropylmethyl-, $R^3$ is trifluoromethyl, and $R^4$, $Y^3$, $Y^4$, $Y^6$, $Y^7$ and $Y^8$ are as defined in Table P.

Table IC-13

Table IC-13 provides 450 compounds of formula (IC) wherein $R^2$ is 2-methoxy-ethyl-, $R^3$ is trifluoromethyl, and $R^4$, $Y^3$, $Y^4$, $Y^6$, $Y^7$ and $Y^8$ are as defined in Table P.

Table IC-14

Table IC-14 provides 450 compounds of formula (IC) wherein $R^2$ is 3-methyloxetan-3-yl-, $R^3$ is trifluoromethyl, and $R^4$, $Y^3$, $Y^4$, $Y^6$, $Y^7$ and $Y^8$ are as defined in Table P.

Table IC-15

Table IC-15 provides 450 compounds of formula (IC) wherein $R^2$ is 1-methylcyclopropyl-, $R^3$ is trifluoromethyl, and $R^4$, $Y^3$, $Y^4$, $Y^6$, $Y^7$ and $Y^8$ are as defined in Table P.

Table IC-16

Table IC-16 provides 450 compounds of formula (IC) wherein $R^2$ is dihydrofuran-4-yl-, $R^3$ is trifluoromethyl, and $R^4$, $Y^3$, $Y^4$, $Y^6$, $Y^7$ and $Y^8$ are as defined in Table P.

Table IC-17

Table IC-17 provides 450 compounds of formula (IC) wherein $R^2$ is cyclopropyl-, $R^3$ is trifluoromethyl, and $R^4$, $Y^3$, $Y^4$, $Y^6$, $Y^7$ and $Y^8$ are as defined in Table P.

Table IC-18

Table IC-18 provides 450 compounds of formula (IC) wherein $R^2$ is cyclobutyl-, $R^3$ is trifluoromethyl, and $R^4$, $Y^3$, $Y^4$, $Y^6$, $Y^7$ and $Y^8$ are as defined in Table P.

Table IC-19

Table IC-19 provides 450 compounds of formula (IC) wherein $R^2$ is methylsulfonylmethyl-, $R^3$ is trifluoromethyl, and $R^4$, $Y^3$, $Y^4$, $Y^6$, $Y^7$ and $Y^8$ are as defined in Table P.

Table IC-20

Table IC-20 provides 450 compounds of formula (IC) wherein $R^2$ is propen-1-yl-, $R^3$ is trifluoromethyl, and $R^4$, $Y^3$, $Y^4$, $Y^6$, $Y^7$ and $Y^8$ are as defined in Table P.

Table IC-21

Table IC-21 provides 450 compounds of formula (IC) wherein $R^2$ is methylsulfanylmethyl-, $R^3$ is trifluoromethyl, and $R^4$, $Y^3$, $Y^4$, $Y^6$, $Y^7$ and $Y^8$ are as defined in Table P.

Table IC-22

Table IC-22 provides 450 compounds of formula (IC) wherein $R^2$ is 1-methoxyeth-1-yl-, $R^3$ is trifluoromethyl, and $R^4$, $Y^3$, $Y^4$, $Y^6$, $Y^7$ and $Y^8$ are as defined in Table P.

Table IC-23

Table IC-23 provides 450 compounds of formula (IC) wherein $R^2$ is 5-pyrimidyl-, $R^3$ is trifluoromethyl, and $R^4$, $Y^3$, $Y^4$, $Y^6$, $Y^7$ and $Y^8$ are as defined in Table P.

Table IC-24

Table IC-24 provides 450 compounds of formula (IC) wherein $R^2$ is but-2-yl-, $R^3$ is trifluoromethyl, and $R^4$, $Y^3$, $Y^4$, $Y^6$, $Y^7$ and $Y^8$ are as defined in Table P.

Table IC-25

Table IC-25 provides 450 compounds of formula (IC) wherein $R^2$ is 1-fluoroprop-2-yl-, $R^3$ is trifluoromethyl, and $R^4$, $Y^3$, $Y^4$, $Y^6$, $Y^7$ and $Y^8$ are as defined in Table P.

Table IC-26

Table IC-26 provides 450 compounds of formula (IC) wherein $R^2$ is 2-methylpropen-1-yl-, $R^3$ is trifluoromethyl, and $R^4$, $Y^3$, $Y^4$, $Y^6$, $Y^7$ and $Y^8$ are as defined in Table P.

Table IC-27

Table IC-27 provides 450 compounds of formula (IC) wherein $R^2$ is 1-cyanocyclopropyl-, $R^3$ is trifluoromethyl, and $R^4$, $Y^3$, $Y^4$, $Y^6$, $Y^7$ and $Y^8$ are as defined in Table P.

Table IC-28

Table IC-28 provides 450 compounds of formula (IC) wherein $R^2$ is N-formylaminomethyl-, $R^3$ is trifluoromethyl, and $R^4$, $Y^3$, $Y^4$, $Y^6$, $Y^7$ and $Y^8$ are as defined in Table P.

Table IC-29

Table IC-29 provides 450 compounds of formula (IC) wherein $R^2$ is 2-methylsulfinyl-ethyl-, $R^3$ is trifluoromethyl, and $R^4$, $Y^3$, $Y^4$, $Y^6$, $Y^7$ and $Y^8$ are as defined in Table P.

Table IC-30

Table IC-30 provides 450 compounds of formula (IC) wherein $R^2$ is 2-(methylsulfonyl)-ethyl-, $R^3$ is trifluoromethyl, and $R^4$, $Y^3$, $Y^4$, $Y^6$, $Y^7$ and $Y^8$ are as defined in Table P.

Table IC-31

Table IC-31 provides 450 compounds of formula (IC) wherein $R^2$ is 1-oxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table IC-32

Table IC-32 provides 450 compounds of formula (IC) wherein $R^2$ is 1-oxo-thietan-3-yl-, $R^3$ is trifluoromethyl, and $R^4$, $Y^3$, $Y^4$, $Y^6$, $Y^7$ and $Y^8$ are as defined in Table P.

Table IC-33

Table IC-33 provides 450 compounds of formula (IC) wherein $R^2$ is 1,1-dioxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table IC-34

Table IC-34 provides 450 compounds of formula (IC) wherein $R^2$ is 1,1-dioxo-thietan-3-yl-, $R^3$ is trifluoromethyl, and $R^4$, $Y^3$, $Y^4$, $Y^6$, $Y^7$ and $Y^8$ are as defined in Table P.

Table IC-35

Table IC-35 provides 450 compounds of formula (IC) wherein $R^2$ is 3-chloroprop-1-yl-, $R^3$ is trifluoromethyl, and $R^4$, $Y^3$, $Y^4$, $Y^6$, $Y^7$ and $Y^8$ are as defined in Table P.

Table IC-36
Table IC-36 provides 450 compounds of formula (IC) wherein $R^2$ is 3,3,3-trifluoro-propyl-, $R^3$ is trifluoromethyl, and $R^4$, $Y^3$, $Y^4$, $Y^6$, $Y^7$ and $Y^8$ are as defined in Table P.

Table IC-37
Table IC-37 provides 450 compounds of formula (IC) wherein $R^2$ is thietan-3-yl-, $R^3$ is trifluoromethyl, and $R^4$, $Y^3$, $Y^4$, $Y^6$, $Y^7$ and $Y^8$ are as defined in Table P.

Table IC-38
Table IC-38 provides 450 compounds of formula (IC) wherein $R^2$ is 3-oxetanyl-, $R^3$ is trifluoromethyl, and $R^4$, $Y^3$, $Y^4$, $Y^6$, $Y^7$ and $Y^8$ are as defined in Table P.

Table IC-39
Table IC-39 provides 450 compounds of formula (IC) wherein $R^2$ is tetrahydrofuran-2-yl-, $R^3$ is trifluoromethyl, and $R^4$, $Y^3$, $Y^4$, $Y^6$, $Y^7$ and $Y^8$ are as defined in Table P.

Table IC-40
Table IC-40 provides 450 compounds of formula (IC) wherein $R^2$ is 1,1,1-trifluoroprop-2-yl-, $R^3$ is trifluoromethyl, and $R^4$, $Y^3$, $Y^4$, $Y^6$, $Y^7$ and $Y^8$ are as defined in Table P.

Table IC-41
Table IC-41 provides 450 compounds of formula (IC) wherein $R^2$ is but-1-yl-, $R^3$ is trifluoromethyl, and $R^4$, $Y^3$, $Y^4$, $Y^6$, $Y^7$ and $Y^8$ are as defined in Table P.

Table IC-42
Table IC-42 provides 450 compounds of formula (IC) wherein $R^2$ is 2,2-difluoro-ethyl-, $R^3$ is trifluoromethyl, and $R^4$, $Y^3$, $Y^4$, $Y^6$, $Y^7$ and $Y^8$ are as defined in Table P.

Table IC-43
Table IC-43 provides 450 compounds of formula (IC) wherein $R^2$ is ethyl-, $R^3$ is chlorodifluoromethyl, and $R^4$, $Y^3$, $Y^4$, $Y^6$, $Y^7$ and $Y^8$ are as defined in Table P.

Table IC-44
Table IC-44 provides 450 compounds of formula (IC) wherein $R^2$ is 2,2,2-trifluoro-ethyl-, $R^3$ is chlorodifluoromethyl, and $R^4$, $Y^3$, $Y^4$, $Y^6$, $Y^7$ and $Y^8$ are as defined in Table P.

Table IC-45
Table IC-45 provides 450 compounds of formula (IC) wherein $R^2$ is prop-2-yl-, $R^3$ is chlorodifluoromethyl, and $R^4$, $Y^3$, $Y^4$, $Y^6$, $Y^7$ and $Y^8$ are as defined in Table P.

Table IC-46
Table IC-46 provides 450 compounds of formula (IC) wherein $R^2$ is methyl-, $R^3$ is chlorodifluoromethyl, and $R^4$, $Y^3$, $Y^4$, $Y^6$, $Y^7$ and $Y^8$ are as defined in Table P.

Table IC-47
Table IC-47 provides 450 compounds of formula (IC) wherein $R^2$ is 2-fluoro-cycloprop-1-yl-, $R^3$ is chlorodifluoromethyl, and $R^4$, $Y^3$, $Y^4$, $Y^6$, $Y^7$ and $Y^8$ are as defined in Table P.

Table IC-48
Table IC-48 provides 450 compounds of formula (IC) wherein $R^2$ is prop-1-yl, $R^3$ is chlorodifluoromethyl, and $R^4$, $Y^3$, $Y^4$, $Y^6$, $Y^7$ and $Y^8$ are as defined in Table P.

Table IC-49
Table IC-49 provides 450 compounds of formula (IC) wherein $R^2$ is 2-fluoro-ethyl-, $R^3$ is chlorodifluoromethyl, and $R^4$, $Y^3$, $Y^4$, $Y^6$, $Y^7$ and $Y^8$ are as defined in Table P.

Table IC-50
Table IC-50 provides 450 compounds of formula (IC) wherein $R^2$ is 2-cyano-ethyl-, $R^3$ is chlorodifluoromethyl, and $R^4$, $Y^3$, $Y^4$, $Y^6$, $Y^7$ and $Y^8$ are as defined in Table P.

Table IC-51
Table IC-51 provides 450 compounds of formula (IC) wherein $R^2$ is 1-fluoroethyl-, $R^3$ is chlorodifluoromethyl, and $R^4$, $Y^3$, $Y^4$, $Y^6$, $Y^7$ and $Y^8$ are as defined in Table P.

Table IC-52
Table IC-52 provides 450 compounds of formula (IC) wherein $R^2$ is 2-methylprop-1-yl-, $R^3$ is chlorodifluoromethyl, and $R^4$, $Y^3$, $Y^4$, $Y^6$, $Y^7$ and $Y^8$ are as defined in Table P.

Table IC-53
Table IC-53 provides 450 compounds of formula (IC) wherein $R^2$ is propen-2-yl-, $R^3$ is chlorodifluoromethyl, and $R^4$, $Y^3$, $Y^4$, $Y^6$, $Y^7$ and $Y^8$ are as defined in Table P.

Table IC-54
Table IC-54 provides 450 compounds of formula (IC) wherein $R^2$ is cyclopropylmethyl-, $R^3$ is chlorodifluoromethyl, and $R^4$, $Y^3$, $Y^4$, $Y^6$, $Y^7$ and $Y^8$ are as defined in Table P.

Table IC-55
Table IC-55 provides 450 compounds of formula (IC) wherein $R^2$ is 2-methoxy-ethyl-, $R^3$ is chlorodifluoromethyl, and $R^4$, $Y^3$, $Y^4$, $Y^6$, $Y^7$ and $Y^8$ are as defined in Table P.

Table IC-56
Table IC-56 provides 450 compounds of formula (IC) wherein $R^2$ is 3-methyloxetan-3-yl-, $R^3$ is chlorodifluoromethyl, and $R^4$, $Y^3$, $Y^4$, $Y^6$, $Y^7$ and $Y^8$ are as defined in Table P.

Table IC-57
Table IC-57 provides 450 compounds of formula (IC) wherein $R^2$ is 1-methylcyclopropyl-, $R^3$ is chlorodifluoromethyl, and $R^4$, $Y^3$, $Y^4$, $Y^6$, $Y^7$ and $Y^8$ are as defined in Table P.

Table IC-58
Table IC-58 provides 450 compounds of formula (IC) wherein $R^2$ is dihydrofuran-4-yl-, $R^3$ is chlorodifluoromethyl, and $R^4$, $Y^3$, $Y^4$, $Y^6$, $Y^7$ and $Y^8$ are as defined in Table P.

Table IC-59
Table IC-59 provides 450 compounds of formula (IC) wherein $R^2$ is cyclopropyl-, $R^3$ is chlorodifluoromethyl, and $R^4$, $Y^3$, $Y^4$, $Y^6$, $Y^7$ and $Y^8$ are as defined in Table P.

Table IC-60
Table IC-60 provides 450 compounds of formula (IC) wherein $R^2$ is cyclobutyl-, $R^3$ is chlorodifluoromethyl, and $R^4$, $Y^3$, $Y^4$, $Y^6$, $Y^7$ and $Y^8$ are as defined in Table P.

Table IC-61
Table IC-61 provides 450 compounds of formula (IC) wherein $R^2$ is methylsulfonylmethyl-, $R^3$ is chlorodifluoromethyl, and $R^4$, $Y^3$, $Y^4$, $Y^6$, $Y^7$ and $Y^8$ are as defined in Table P.

Table IC-62
Table IC-62 provides 450 compounds of formula (IC) wherein $R^2$ is propen-1-yl-, $R^3$ is chlorodifluoromethyl, and $R^4$, $Y^3$, $Y^4$, $Y^6$, $Y^7$ and $Y^8$ are as defined in Table P.

Table IC-63
Table IC-63 provides 450 compounds of formula (IC) wherein $R^2$ is methylsulfanylmethyl-, $R^3$ is chlorodifluoromethyl, and $R^4$, $Y^3$, $Y^4$, $Y^6$, $Y^7$ and $Y^8$ are as defined in Table P.

Table IC-64
Table IC-64 provides 450 compounds of formula (IC) wherein $R^2$ is 1-methoxyeth-1-yl-, $R^3$ is chlorodifluoromethyl, and $R^4$, $Y^3$, $Y^4$, $Y^6$, $Y^7$ and $Y^8$ are as defined in Table P.

Table IC-65
Table IC-65 provides 450 compounds of formula (IC) wherein $R^2$ is 5-pyrimidyl-, $R^3$ is chlorodifluoromethyl, and $R^4$, $Y^3$, $Y^4$, $Y^6$, $Y^7$ and $Y^8$ are as defined in Table P.

Table IC-66

Table IC-66 provides 450 compounds of formula (IC) wherein $R^2$ is but-2-yl-, $R^3$ is chlorodifluoromethyl, and $R^4$, $Y^3$, $Y^4$, $Y^6$, $Y^7$ and $Y^8$ are as defined in Table P.

Table IC-67

Table IC-67 provides 450 compounds of formula (IC) wherein $R^2$ is 1-fluoroprop-2-yl-, $R^3$ is chlorodifluoromethyl, and $R^4$, $Y^3$, $Y^4$, $Y^6$, $Y^7$ and $Y^8$ are as defined in Table P.

Table IC-68

Table IC-68 provides 450 compounds of formula (IC) wherein $R^2$ is 2-methylpropen-1-yl-, $R^3$ is chlorodifluoromethyl, and $R^4$, $Y^3$, $Y^4$, $Y^6$, $Y^7$ and $Y^8$ are as defined in Table P.

Table IC-69

Table IC-69 provides 450 compounds of formula (IC) wherein $R^2$ is 1-cyanocyclopropyl-, $R^3$ is chlorodifluoromethyl, and $R^4$, $Y^3$, $Y^4$, $Y^6$, $Y^7$ and $Y^8$ are as defined in Table P.

Table IC-70

Table IC-70 provides 450 compounds of formula (IC) wherein $R^2$ is N-formylaminomethyl-, $R^3$ is chlorodifluoromethyl, and $R^4$, $Y^3$, $Y^4$, $Y^6$, $Y^7$ and $Y^8$ are as defined in Table P.

Table IC-71

Table IC-71 provides 450 compounds of formula (IC) wherein $R^2$ is 2-methylsulfinyl-ethyl-, $R^3$ is chlorodifluoromethyl, and $R^4$, $Y^3$, $Y^4$, $Y^6$, $Y^7$ and $Y^8$ are as defined in Table P.

Table IC-72

Table IC-72 provides 450 compounds of formula (IC) wherein $R^2$ is 2-(methylsulfonyl)-ethyl-, $R^3$ is chlorodifluoromethyl, and $R^4$, $Y^3$, $Y^4$, $Y^6$, $Y^7$ and $Y^8$ are as defined in Table P.

Table IC-73

Table IC-73 provides 450 compounds of formula (IC) wherein $R^2$ is 1-oxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table IC-74

Table IC-74 provides 450 compounds of formula (IC) wherein $R^2$ is 1-oxo-thietan-3-yl-, $R^3$ is chlorodifluoromethyl, and $R^4$, $Y^3$, $Y^4$, $Y^6$, $Y^7$ and $Y^8$ are as defined in Table P.

Table IC-75

Table IC-75 provides 450 compounds of formula (IC) wherein $R^2$ is 1,1-dioxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table IC-76

Table IC-76 provides 450 compounds of formula (IC) wherein $R^2$ is 1,1-dioxo-thietan-3-yl-, $R^3$ is chlorodifluoromethyl, and $R^4$, $Y^3$, $Y^4$, $Y^6$, $Y^7$ and $Y^8$ are as defined in Table P.

Table IC-77

Table IC-77 provides 450 compounds of formula (IC) wherein $R^2$ is 3-chloroprop-1-yl-, $R^3$ is chlorodifluoromethyl, and $R^4$, $Y^3$, $Y^4$, $Y^6$, $Y^7$ and $Y^8$ are as defined in Table P.

Table IC-78

Table IC-78 provides 450 compounds of formula (IC) wherein $R^2$ is 3,3,3-trifluoro-propyl-, $R^3$ is chlorodifluoromethyl, and $R^4$, $Y^3$, $Y^4$, $Y^6$, $Y^7$ and $Y^8$ are as defined in Table P.

Table IC-79

Table IC-79 provides 450 compounds of formula (IC) wherein $R^2$ is thietan-3-yl-, $R^3$ is chlorodifluoromethyl, and $R^4$, $Y^3$, $Y^4$, $Y^6$, $Y^7$ and $Y^8$ are as defined in Table P.

Table IC-80

Table IC-80 provides 450 compounds of formula (IC) wherein $R^2$ is 3-oxetanyl-, $R^3$ is chlorodifluoromethyl, and $R^4$, $Y^3$, $Y^4$, $Y^6$, $Y^7$ and $Y^8$ are as defined in Table P.

Table IC-81

Table IC-81 provides 450 compounds of formula (IC) wherein $R^2$ is tetrahydrofuran-2-yl-, $R^3$ is chlorodifluoromethyl, and $R^4$, $Y^3$, $Y^4$, $Y^6$, $Y^7$ and $Y^8$ are as defined in Table P.

Table IC-82

Table IC-82 provides 450 compounds of formula (IC) wherein $R^2$ is 1,1,1-trifluoroprop-2-yl-, $R^3$ is chlorodifluoromethyl, and $R^4$, $Y^3$, $Y^4$, $Y^6$, $Y^7$ and $Y^8$ are as defined in Table P.

Table IC-83

Table IC-83 provides 450 compounds of formula (IC) wherein $R^2$ is but-1-yl-, $R^3$ is chlorodifluoromethyl, and $R^4$, $Y^3$, $Y^4$, $Y^6$, $Y^7$ and $Y^8$ are as defined in Table P.

Table IC-84

Table IC-84 provides 450 compounds of formula (IC) wherein $R^2$ is 2,2-difluoro-ethyl-, $R^3$ is chlorodifluoromethyl, and $R^4$, $Y^3$, $Y^4$, $Y^6$, $Y^7$ and $Y^8$ are as defined in Table P.

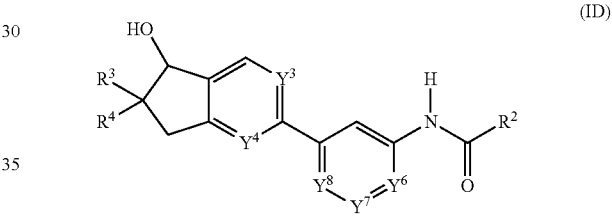

(ID)

Table ID-1

Table ID-1 provides 450 compounds of formula (ID) wherein $R^2$ is ethyl-, $R^3$ is trifluoromethyl, and $R^4$, $Y^3$, $Y^4$, $Y^6$, $Y^7$ and $Y^8$ are as defined in Table P.

Table ID-2

Table ID-2 provides 450 compounds of formula (ID) wherein $R^2$ is 2,2,2-trifluoro-ethyl-, $R^3$ is trifluoromethyl, and $R^4$, $Y^3$, $Y^4$, $Y^6$, $Y^7$ and $Y^8$ are as defined in Table P.

Table ID-3

Table ID-3 provides 450 compounds of formula (ID) wherein $R^2$ is prop-2-yl-, $R^3$ is trifluoromethyl, and $R^4$, $Y^3$, $Y^4$, $Y^6$, $Y^7$ and $Y^8$ are as defined in Table P.

Table ID-4

Table ID-4 provides 450 compounds of formula (ID) wherein $R^2$ is methyl-, $R^3$ is trifluoromethyl, and $R^4$, $Y^3$, $Y^4$, $Y^6$, $Y^7$ and $Y^8$ are as defined in Table P.

Table ID-5

Table ID-5 provides 450 compounds of formula (ID) wherein $R^2$ is 2-fluoro-cycloprop-1-yl-, $R^3$ is trifluoromethyl, and $R^4$, $Y^3$, $Y^4$, $Y^6$, $Y^7$ and $Y^8$ are as defined in Table P.

Table ID-6

Table ID-6 provides 450 compounds of formula (ID) wherein $R^2$ is prop-1-yl, $R^3$ is trifluoromethyl, and $R^4$, $Y^3$, $Y^4$, $Y^6$, $Y^7$ and $Y^8$ are as defined in Table P.

Table ID-7

Table ID-7 provides 450 compounds of formula (ID) wherein $R^2$ is 2-fluoro-ethyl-, $R^3$ is trifluoromethyl, and $R^4$, $Y^3$, $Y^4$, $Y^6$, $Y^7$ and $Y^8$ are as defined in Table P.

Table ID-8
Table ID-8 provides 450 compounds of formula (ID) wherein $R^2$ is 2-cyano-ethyl-, $R^3$ is trifluoromethyl, and $R^4$, $Y^3$, $Y^4$, $Y^6$, $Y^7$ and $Y^8$ are as defined in Table P.

Table ID-9
Table ID-9 provides 450 compounds of formula (ID) wherein $R^2$ is 1-fluoroethyl-, $R^3$ is trifluoromethyl, and $R^4$, $Y^3$, $Y^4$, $Y^6$, $Y^7$ and $Y^8$ are as defined in Table P.

Table ID-10
Table ID-10 provides 450 compounds of formula (ID) wherein $R^2$ is 2-methylprop-1-yl-, $R^3$ is trifluoromethyl, and $R^4$, $Y^3$, $Y^4$, $Y^6$, $Y^7$ and $Y^8$ are as defined in Table P.

Table ID-11
Table ID-11 provides 450 compounds of formula (ID) wherein $R^2$ is propen-2-yl-, $R^3$ is trifluoromethyl, and $R^4$, $Y^3$, $Y^4$, $Y^6$, $Y^7$ and $Y^8$ are as defined in Table P.

Table ID-12
Table ID-12 provides 450 compounds of formula (ID) wherein $R^2$ is cyclopropylmethyl-, $R^3$ is trifluoromethyl, and $R^4$, $Y^3$, $Y^4$, $Y^6$, $Y^7$ and $Y^8$ are as defined in Table P.

Table ID-13
Table ID-13 provides 450 compounds of formula (ID) wherein $R^2$ is 2-methoxy-ethyl-, $R^3$ is trifluoromethyl, and $R^4$, $Y^3$, $Y^4$, $Y^6$, $Y^7$ and $Y^8$ are as defined in Table P.

Table ID-14
Table ID-14 provides 450 compounds of formula (ID) wherein $R^2$ is 3-methyloxetan-3-yl-, $R^3$ is trifluoromethyl, and $R^4$, $Y^3$, $Y^4$, $Y^6$, $Y^7$ and $Y^8$ are as defined in Table P.

Table ID-15
Table ID-15 provides 450 compounds of formula (ID) wherein $R^2$ is 1-methylcyclopropyl-, $R^3$ is trifluoromethyl, and $R^4$, $Y^3$, $Y^4$, $Y^6$, $Y^7$ and $Y^8$ are as defined in Table P.

Table ID-16
Table ID-16 provides 450 compounds of formula (ID) wherein $R^2$ is dihydrofuran-4-yl-, $R^3$ is trifluoromethyl, and $R^4$, $Y^3$, $Y^4$, $Y^6$, $Y^7$ and $Y^8$ are as defined in Table P.

Table ID-17
Table ID-17 provides 450 compounds of formula (ID) wherein $R^2$ is cyclopropyl-, $R^3$ is trifluoromethyl, and $R^4$, $Y^3$, $Y^4$, $Y^6$, $Y^7$ and $Y^8$ are as defined in Table P.

Table ID-18
Table ID-18 provides 450 compounds of formula (ID) wherein $R^2$ is cyclobutyl-, $R^3$ is trifluoromethyl, and $R^4$, $Y^3$, $Y^4$, $Y^6$, $Y^7$ and $Y^8$ are as defined in Table P.

Table ID-19
Table ID-19 provides 450 compounds of formula (ID) wherein $R^2$ is methylsulfonylmethyl-, $R^3$ is trifluoromethyl, and $R^4$, $Y^3$, $Y^4$, $Y^6$, $Y^7$ and $Y^8$ are as defined in Table P.

Table ID-20
Table ID-20 provides 450 compounds of formula (ID) wherein $R^2$ is propen-1-yl-, $R^3$ is trifluoromethyl, and $R^4$, $Y^3$, $Y^4$, $Y^6$, $Y^7$ and $Y^8$ are as defined in Table P.

Table ID-21
Table ID-21 provides 450 compounds of formula (ID) wherein $R^2$ is methylsulfanylmethyl-, $R^3$ is trifluoromethyl, and $R^4$, $Y^3$, $Y^4$, $Y^6$, $Y^7$ and $Y^8$ are as defined in Table P.

Table ID-22
Table ID-22 provides 450 compounds of formula (ID) wherein $R^2$ is 1-methoxyeth-1-yl-, $R^3$ is trifluoromethyl, and $R^4$, $Y^3$, $Y^4$, $Y^6$, $Y^7$ and $Y^8$ are as defined in Table P.

Table ID-23
Table ID-23 provides 450 compounds of formula (ID) wherein $R^2$ is 5-pyrimidyl-, $R^3$ is trifluoromethyl, and $R^4$, $Y^3$, $Y^4$, $Y^6$, $Y^7$ and $Y^8$ are as defined in Table P.

Table ID-24
Table ID-24 provides 450 compounds of formula (ID) wherein $R^2$ is but-2-yl-, $R^3$ is trifluoromethyl, and $R^4$, $Y^3$, $Y^4$, $Y^6$, $Y^7$ and $Y^8$ are as defined in Table P.

Table ID-25
Table ID-25 provides 450 compounds of formula (ID) wherein $R^2$ is 1-fluoroprop-2-yl-, $R^3$ is trifluoromethyl, and $R^4$, $Y^3$, $Y^4$, $Y^6$, $Y^7$ and $Y^8$ are as defined in Table P.

Table ID-26
Table ID-26 provides 450 compounds of formula (ID) wherein $R^2$ is 2-methylpropen-1-yl-, $R^3$ is trifluoromethyl, and $R^4$, $Y^3$, $Y^4$, $Y^6$, $Y^7$ and $Y^8$ are as defined in Table P.

Table ID-27
Table ID-27 provides 450 compounds of formula (ID) wherein $R^2$ is 1-cyanocyclopropyl-, $R^3$ is trifluoromethyl, and $R^4$, $Y^3$, $Y^4$, $Y^6$, $Y^7$ and $Y^8$ are as defined in Table P.

Table ID-28
Table ID-28 provides 450 compounds of formula (ID) wherein $R^2$ is N-formylaminomethyl-, $R^3$ is trifluoromethyl, and $R^4$, $Y^3$, $Y^4$, $Y^6$, $Y^7$ and $Y^8$ are as defined in Table P.

Table ID-29
Table ID-29 provides 450 compounds of formula (ID) wherein $R^2$ is 2-methylsulfinyl-ethyl-, $R^3$ is trifluoromethyl, and $R^4$, $Y^3$, $Y^4$, $Y^6$, $Y^7$ and $Y^8$ are as defined in Table P.

Table ID-30
Table ID-30 provides 450 compounds of formula (ID) wherein $R^2$ is 2-(methylsulfonyl)-ethyl-, $R^3$ is trifluoromethyl, and $R^4$, $Y^3$, $Y^4$, $Y^6$, $Y^7$ and $Y^8$ are as defined in Table P.

Table ID-31
Table ID-31 provides 450 compounds of formula (ID) wherein $R^2$ is 1-oxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table ID-32
Table ID-32 provides 450 compounds of formula (ID) wherein $R^2$ is 1-oxo-thietan-3-yl-, $R^3$ is trifluoromethyl, and $R^4$, $Y^3$, $Y^4$, $Y^6$, $Y^7$ and $Y^8$ are as defined in Table P.

Table ID-33
Table ID-33 provides 450 compounds of formula (ID) wherein $R^2$ is 1,1-dioxo-tetrahydrofuran-3-yl-, $R^3$ is trifluoromethyl, and $R^4$, $Y^3$, $Y^4$, $Y^6$, $Y^7$ and $Y^8$ are as defined in Table P.

Table ID-34
Table ID-34 provides 450 compounds of formula (ID) wherein $R^2$ is 1,1-dioxo-thietan-3-yl-, $R^3$ is trifluoromethyl, and $R^4$, $Y^3$, $Y^4$, $Y^6$, $Y^7$ and $Y^8$ are as defined in Table P.

Table ID-35
Table ID-35 provides 450 compounds of formula (ID) wherein $R^2$ is 3-chloroprop-1-yl-, $R^3$ is trifluoromethyl, and $R^4$, $Y^3$, $Y^4$, $Y^6$, $Y^7$ and $Y^8$ are as defined in Table P.

Table ID-36
Table ID-36 provides 450 compounds of formula (ID) wherein $R^2$ is 3,3,3-trifluoro-propyl-, $R^3$ is trifluoromethyl, and $R^4$, $Y^3$, $Y^4$, $Y^6$, $Y^7$ and $Y^8$ are as defined in Table P.

Table ID-37
Table ID-37 provides 450 compounds of formula (ID) wherein $R^2$ is thietan-3-yl-, $R^3$ is trifluoromethyl, and $R^4$, $Y^3$, $Y^4$, $Y^6$, $Y^7$ and $Y^8$ are as defined in Table P.

Table ID-38
Table ID-38 provides 450 compounds of formula (ID) wherein $R^2$ is 3-oxetanyl-, $R^3$ is trifluoromethyl, and $R^4$, $Y^3$, $Y^4$, $Y^6$, $Y^7$ and $Y^8$ are as defined in Table P.

Table ID-39
Table ID-39 provides 450 compounds of formula (ID) wherein $R^2$ is tetrahydrofuran-2-yl-, $R^3$ is trifluoromethyl, and $R^4$, $Y^3$, $Y^4$, $Y^6$, $Y^7$ and $Y^8$ are as defined in Table P.

Table ID-40

Table ID-40 provides 450 compounds of formula (ID) wherein $R^2$ is 1,1,1-trifluoroprop-2-yl-, $R^3$ is trifluoromethyl, and $R^4$, $Y^3$, $Y^4$, $Y^6$, $Y^7$ and $Y^8$ are as defined in Table P.

Table ID-41

Table ID-41 provides 450 compounds of formula (ID) wherein $R^2$ is but-1-yl-, $R^3$ is trifluoromethyl, and $R^4$, $Y^3$, $Y^4$, $Y^6$, $Y^7$ and $Y^8$ are as defined in Table P.

Table ID-42

Table ID-42 provides 450 compounds of formula (ID) wherein $R^2$ is 2,2-difluoro-ethyl-, $R^3$ is trifluoromethyl, and $R^4$, $Y^3$, $Y^4$, $Y^6$, $Y^7$ and $Y^8$ are as defined in Table P.

Table ID-43

Table ID-43 provides 450 compounds of formula (ID) wherein $R^2$ is ethyl-, $R^3$ is chlorodifluoromethyl, and $R^4$, $Y^3$, $Y^4$, $Y^6$, $Y^7$ and $Y^8$ are as defined in Table P.

Table ID-44

Table ID-44 provides 450 compounds of formula (ID) wherein $R^2$ is 2,2,2-trifluoro-ethyl-, $R^3$ is chlorodifluoromethyl, and $R^4$, $Y^3$, $Y^4$, $Y^6$, $Y^7$ and $Y^8$ are as defined in Table P.

Table ID-45

Table ID-45 provides 450 compounds of formula (ID) wherein $R^2$ is prop-2-yl-, $R^3$ is chlorodifluoromethyl, and $R^4$, $Y^3$, $Y^4$, $Y^6$, $Y^7$ and $Y^8$ are as defined in Table P.

Table ID-46

Table ID-46 provides 450 compounds of formula (ID) wherein $R^2$ is methyl-, $R^3$ is chlorodifluoromethyl, and $R^4$, $Y^3$, $Y^4$, $Y^6$, $Y^7$ and $Y^8$ are as defined in Table P.

Table ID-47

Table ID-47 provides 450 compounds of formula (ID) wherein $R^2$ is 2-fluoro-cycloprop-1-yl-, $R^3$ is chlorodifluoromethyl, and $R^4$, $Y^3$, $Y^4$, $Y^6$, $Y^7$ and $Y^8$ are as defined in Table P.

Table ID-48

Table ID-48 provides 450 compounds of formula (ID) wherein $R^2$ is prop-1-yl, $R^3$ is chlorodifluoromethyl, and $R^4$, $Y^3$, $Y^4$, $Y^6$, $Y^7$ and $Y^8$ are as defined in Table P.

Table ID-49

Table ID-49 provides 450 compounds of formula (ID) wherein $R^2$ is 2-fluoro-ethyl-, $R^3$ is chlorodifluoromethyl, and $R^4$, $Y^3$, $Y^4$, $Y^6$, $Y^7$ and $Y^8$ are as defined in Table P.

Table ID-50

Table ID-50 provides 450 compounds of formula (ID) wherein $R^2$ is 2-cyano-ethyl-, $R^3$ is chlorodifluoromethyl, and $R^4$, $Y^3$, $Y^4$, $Y^6$, $Y^7$ and $Y^8$ are as defined in Table P.

Table ID-51

Table ID-51 provides 450 compounds of formula (ID) wherein $R^2$ is 1-fluoroethyl-, $R^3$ is chlorodifluoromethyl, and $R^4$, $Y^3$, $Y^4$, $Y^6$, $Y^7$ and $Y^8$ are as defined in Table P.

Table ID-52

Table ID-52 provides 450 compounds of formula (ID) wherein $R^2$ is 2-methylprop-1-yl-, $R^3$ is chlorodifluoromethyl, and $R^4$, $Y^3$, $Y^4$, $Y^6$, $Y^7$ and $Y^8$ are as defined in Table P.

Table ID-53

Table ID-53 provides 450 compounds of formula (ID) wherein $R^2$ is propen-2-yl-, $R^3$ is chlorodifluoromethyl, and $R^4$, $Y^3$, $Y^4$, $Y^6$, $Y^7$ and $Y^8$ are as defined in Table P.

Table ID-54

Table ID-54 provides 450 compounds of formula (ID) wherein $R^2$ is cyclopropylmethyl-, $R^3$ is chlorodifluoromethyl, and $R^4$, $Y^3$, $Y^4$, $Y^6$, $Y^7$ and $Y^8$ are as defined in Table P.

Table ID-55

Table ID-55 provides 450 compounds of formula (ID) wherein $R^2$ is 2-methoxy-ethyl-, $R^3$ is chlorodifluoromethyl, and $R^4$, $Y^3$, $Y^4$, $Y^6$, $Y^7$ and $Y^8$ are as defined in Table P.

Table ID-56

Table ID-56 provides 450 compounds of formula (ID) wherein $R^2$ is 3-methyloxetan-3-yl-, $R^3$ is chlorodifluoromethyl, and $R^4$, $Y^3$, $Y^4$, $Y^6$, $Y^7$ and $Y^8$ are as defined in Table P.

Table ID-57

Table ID-57 provides 450 compounds of formula (ID) wherein $R^2$ is 1-methylcyclopropyl-, $R^3$ is chlorodifluoromethyl, and $R^4$, $Y^3$, $Y^4$, $Y^6$, $Y^7$ and $Y^8$ are as defined in Table P.

Table ID-58

Table ID-58 provides 450 compounds of formula (ID) wherein $R^2$ is dihydrofuran-4-yl-, $R^3$ is chlorodifluoromethyl, and $R^4$, $Y^3$, $Y^4$, $Y^6$, $Y^7$ and $Y^8$ are as defined in Table P.

Table ID-59

Table ID-59 provides 450 compounds of formula (ID) wherein $R^2$ is cyclopropyl-, $R^3$ is chlorodifluoromethyl, and $R^4$, $Y^3$, $Y^4$, $Y^6$, $Y^7$ and $Y^8$ are as defined in Table P.

Table ID-60

Table ID-60 provides 450 compounds of formula (ID) wherein $R^2$ is cyclobutyl-, $R^3$ is chlorodifluoromethyl, and $R^4$, $Y^3$, $Y^4$, $Y^6$, $Y^7$ and $Y^8$ are as defined in Table P.

Table ID-61

Table ID-61 provides 450 compounds of formula (ID) wherein $R^2$ is methylsulfonylmethyl-, $R^3$ is chlorodifluoromethyl, and $R^4$, $Y^3$, $Y^4$, $Y^6$, $Y^7$ and $Y^8$ are as defined in Table P.

Table ID-62

Table ID-62 provides 450 compounds of formula (ID) wherein $R^2$ is propen-1-yl-, $R^3$ is chlorodifluoromethyl, and $R^4$, $Y^3$, $Y^4$, $Y^6$, $Y^7$ and $Y^8$ are as defined in Table P.

Table ID-63

Table ID-63 provides 450 compounds of formula (ID) wherein $R^2$ is methylsulfanylmethyl-, $R^3$ is chlorodifluoromethyl, and $R^4$, $Y^3$, $Y^4$, $Y^6$, $Y^7$ and $Y^8$ are as defined in Table P.

Table ID-64

Table ID-64 provides 450 compounds of formula (ID) wherein $R^2$ is 1-methoxyeth-1-yl-, $R^3$ is chlorodifluoromethyl, and $R^4$, $Y^3$, $Y^4$, $Y^6$, $Y^7$ and $Y^8$ are as defined in Table P.

Table ID-65

Table ID-65 provides 450 compounds of formula (ID) wherein $R^2$ is 5-pyrimidyl-, $R^3$ is chlorodifluoromethyl, and $R^4$, $Y^3$, $Y^4$, $Y^6$, $Y^7$ and $Y^8$ are as defined in Table P.

Table ID-66

Table ID-66 provides 450 compounds of formula (ID) wherein $R^2$ is but-2-yl-, $R^3$ is chlorodifluoromethyl, and $R^4$, $Y^3$, $Y^4$, $Y^6$, $Y^7$ and $Y^8$ are as defined in Table P.

Table ID-67

Table ID-67 provides 450 compounds of formula (ID) wherein $R^2$ is 1-fluoroprop-2-yl-, $R^3$ is chlorodifluoromethyl, and $R^4$, $Y^3$, $Y^4$, $Y^6$, $Y^7$ and $Y^8$ are as defined in Table P.

Table ID-68

Table ID-68 provides 450 compounds of formula (ID) wherein $R^2$ is 2-methylpropen-1-yl-, $R^3$ is chlorodifluoromethyl, and $R^4$, $Y^3$, $Y^4$, $Y^6$, $Y^7$ and $Y^8$ are as defined in Table P.

Table ID-69

Table ID-69 provides 450 compounds of formula (ID) wherein $R^2$ is 1-cyanocyclopropyl-, $R^3$ is chlorodifluoromethyl, and $R^4$, $Y^3$, $Y^4$, $Y^6$, $Y^7$ and $Y^8$ are as defined in Table P.

Table ID-70

Table ID-70 provides 450 compounds of formula (ID) wherein $R^2$ is N-formylaminomethyl-, $R^3$ is chlorodifluoromethyl, and $R^4$, $Y^3$, $Y^4$, $Y^6$, $Y^7$ and $Y^8$ are as defined in Table P.

Table ID-71

Table ID-71 provides 450 compounds of formula (ID) wherein $R^2$ is 2-methylsulfinyl-ethyl-, $R^3$ is chlorodifluoromethyl, and $R^4$, $Y^3$, $Y^4$, $Y^6$, $Y^7$ and $Y^8$ are as defined in Table P.

Table ID-72

Table ID-72 provides 450 compounds of formula (ID) wherein $R^2$ is 2-(methylsulfonyl)-ethyl-, $R^3$ is chlorodifluoromethyl, and $R^4$, $Y^3$, $Y^4$, $Y^6$, $Y^7$ and $Y^8$ are as defined in Table P.

Table ID-73

Table ID-73 provides 450 compounds of formula (ID) wherein $R^2$ is 1-oxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table ID-74

Table ID-74 provides 450 compounds of formula (ID) wherein $R^2$ is 1-oxo-thietan-3-yl-, $R^3$ is chlorodifluoromethyl, and $R^4$, $Y^3$, $Y^4$, $Y^6$, $Y^7$ and $Y^8$ are as defined in Table P.

Table ID-75

Table ID-75 provides 450 compounds of formula (ID) wherein $R^2$ is 1,1-dioxo-tetrahydrofuran-3-yl-, $R^3$ is chlorodifluoromethyl, and $R^4$, $Y^3$, $Y^4$, $Y^6$, $Y^7$ and $Y^8$ are as defined in Table P.

Table ID-76

Table ID-76 provides 450 compounds of formula (ID) wherein $R^2$ is 1,1-dioxo-thietan-3-yl-, $R^3$ is chlorodifluoromethyl, and $R^4$, $Y^3$, $Y^4$, $Y^6$, $Y^7$ and $Y^8$ are as defined in Table P.

Table ID-77

Table ID-77 provides 450 compounds of formula (ID) wherein $R^2$ is 3-chloroprop-1-yl-, $R^3$ is chlorodifluoromethyl, and $R^4$, $Y^3$, $Y^4$, $Y^6$, $Y^7$ and $Y^8$ are as defined in Table P.

Table ID-78

Table ID-78 provides 450 compounds of formula (ID) wherein $R^2$ is 3,3,3-trifluoro-propyl-, $R^3$ is chlorodifluoromethyl, and $R^4$, $Y^3$, $Y^4$, $Y^6$, $Y^7$ and $Y^8$ are as defined in Table P.

Table ID-79

Table ID-79 provides 450 compounds of formula (ID) wherein $R^2$ is thietan-3-yl-, $R^3$ is chlorodifluoromethyl, and $R^4$, $Y^3$, $Y^4$, $Y^6$, $Y^7$ and $Y^8$ are as defined in Table P.

Table ID-80

Table ID-80 provides 450 compounds of formula (ID) wherein $R^2$ is 3-oxetanyl-, $R^3$ is chlorodifluoromethyl, and $R^4$, $Y^3$, $Y^4$, $Y^6$, $Y^7$ and $Y^8$ are as defined in Table P.

Table ID-81

Table ID-81 provides 450 compounds of formula (ID) wherein $R^2$ is tetrahydrofuran-2-yl-, $R^3$ is chlorodifluoromethyl, and $R^4$, $Y^3$, $Y^4$, $Y^6$, $Y^7$ and $Y^8$ are as defined in Table P.

Table ID-82

Table ID-82 provides 450 compounds of formula (ID) wherein $R^2$ is 1,1,1-trifluoroprop-2-yl-, $R^3$ is chlorodifluoromethyl, and $R^4$, $Y^3$, $Y^4$, $Y^6$, $Y^7$ and $Y^8$ are as defined in Table P.

Table ID-83

Table ID-83 provides 450 compounds of formula (ID) wherein $R^2$ is but-1-yl-, $R^3$ is chlorodifluoromethyl, and $R^4$, $Y^3$, $Y^4$, $Y^6$, $Y^7$ and $Y^8$ are as defined in Table P.

Table ID-84

Table ID-84 provides 450 compounds of formula (ID) wherein $R^2$ is 2,2-difluoro-ethyl-, $R^3$ is chlorodifluoromethyl, and $R^4$, $Y^3$, $Y^4$, $Y^6$, $Y^7$ and $Y^8$ are as defined in Table P.

The compounds of the invention may be made by a variety of methods as shown in the following Schemes.

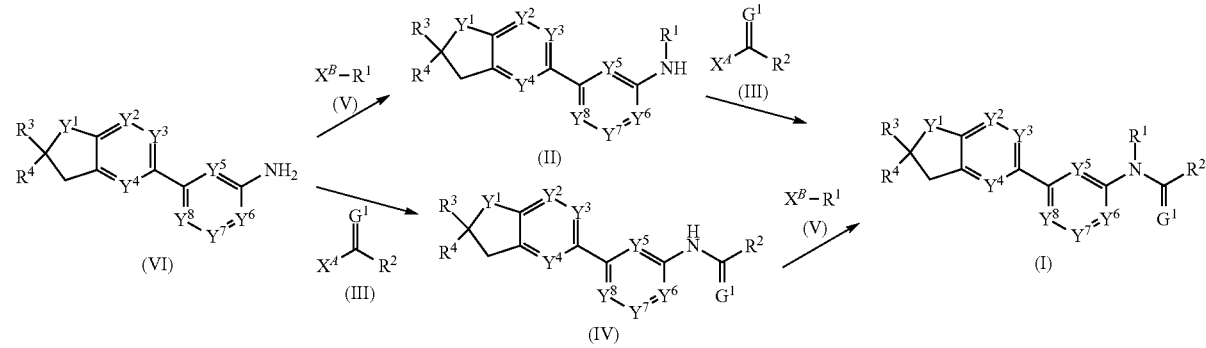

Scheme 1

1) Compounds of formula (I) wherein $G^1$ is oxygen, can be prepared by reacting an amine of formula (II) with a compound of formula (III) wherein $G^1$ is oxygen and $X^A$ is OH, $C_1$-$C_6$alkoxy or Cl, F or Br. When $X^A$ is OH such reactions are usually carried out in the presence of a coupling reagent, such as N,N'-dicyclohexyl-carbo-diimide ("DCC"), 1-ethyl-3-(3-dimethyl-amino-propyl)-carbodiimide hydrochloride ("EDC") or bis(2-oxo-3-oxazolidinyl) phosphonic chloride ("BOP-Cl"), in the presence of a base, and optionally in the presence of a nucleophilic catalyst, such as hydroxybenzo-triazole ("HOBT"). When $X^A$ is Cl, such reactions are usually carried out in the presence of a base, and optionally in the presence of a nucleophilic catalyst for example dimethylaminopyridine. Alternatively, it is possible to conduct the reaction in a biphasic system comprising an organic solvent, preferably ethyl acetate, and an aqueous solvent, preferably a solution of sodium hydrogen carbonate. When $X^A$ is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Compounds of formula (III) are either known in the literature or can be prepared using methods known to a person skilled in the art. Some of these methods are described in the preparation Examples.

2) Compounds of formula (I), wherein $G^1$ is sulfur, may be made by treatment of a compound of formula (III), wherein $G^1$ is oxygen and $X^A$ is OH, $C_1$-$C_6$alkoxy or Cl, F or Br, with a thio-transfer reagent such as Lawesson's reagent or phosphorus pentasulfide prior to elaborating to compounds of formula (I), as described under 1).

3) Alternatively compounds of formula (I), wherein $G^1$ is sulfur, may be made by treatment of a compound of formula (I), wherein $G^1$ is oxygen, with a thio-transfer reagent such as Lawesson's reagent or phosphorus pentasulfide.

4) Compound of formula (II) wherein $R^1$ is $C_1$-$C_6$alkyl, can be prepared by alkylation of an intermediate of formula (VI) with a reagent of formula (V) wherein $X^B$ is chloro, bromo, iodo, mesylate, triflate in presence of a base such a butyl lithium, KH, NaH, $K_2CO_3$, $Cs_2CO_3$, $NaHCO_3$ in a solvent such as dimethylsulfoxide, acetonitrile, tetrahydrofuran, dimethylformamide or toluene. Such reactions can be carried out under well established methods, described for example in Tetrahedron, 36(9), 1223-6; 1980 and Bioorganic & Medicinal Chemistry Letters, 21(11), 3457-3461; 2011.

5) Compounds of formula (I) wherein $G^1$ is oxygen can be prepared by alkylation of an intermediate of formula (IV) with a reagent of formula (V) wherein $X^B$ is chloro, bromo, iodo, mesylate or triflate in presence of a strong base such as sodium hydride, lithium diisopropyl amide, or butyl lithium in a polar aprotic solvent such as dimethylsulfoxide, acetonitrile, tetrahydrofuran or dimethylformamide. Such reactions can be carried out under well established methods, described for example in Bioorganic & Medicinal Chemistry Letters, 22(2), 1237-1241; 2012.

6) Compounds of formula (IV) wherein $G^1$ is oxygen, can be prepared by reacting an amine of formula (VI) with a compound of formula (III) using conditions described in 1).

Scheme 2

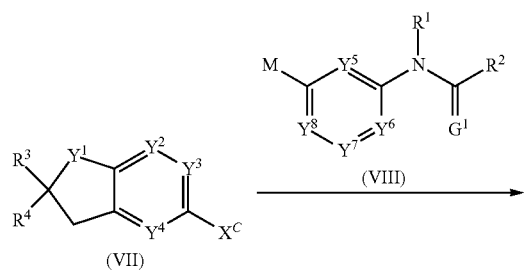

(VII)

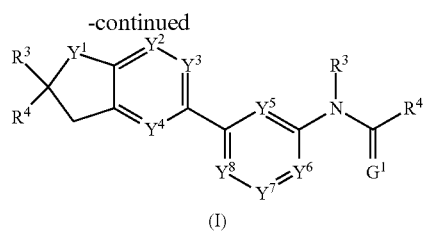

(I)

7) Compounds of formula (I) can be obtained from compounds of formula (VII) via a coupling reaction (e.g. Suzuki, Stille, Hiyama, Negishi) e.g. by treating compounds of formula (VII) wherein $X^C$ represents a leaving group such as halogen, activated alcohols, diazonium salt, with a reactant (VIII), wherein M represents a suitable derivative of B, Si, Sn, Zn (e.g. boronic acid, boronic ester, trifluoroborate, dialkyl-hydroxysilane, trialkyltin, ZnCl, ZnBr) in presence of a catalyst and optionally in the presence of a suitable ligand, solvent and additive. Suitable $X^C$ are for example Br, Cl, I. Suitable catalysts are for example palladium catalysts such as $Pd(OAc)_2$, $PdCl_2$, $Pd_2(dba)_3$, $Pd_2(dba)_3.CHCl_3$, [Pd(PPh_3)_4], [Pd(Cl)_2(H_3CCN)_2)], [(allyl)Pd(Cl)]_2, [Pd(PPh_3)_2(Cl)_2], [Pd(DPPF)(Cl)_2], PEPPSI®, nickel catalysts such as $NiCl_2$, $Ni(OAc)_2$, $Ni(acac)_2$, [Ni(PPh_3)_2Cl_2], [Ni(DPPP)Cl_2]. Suitable ligands are for example phosphine ligands such as $P(tBu)_3$, tris(ortho-tolyl)phosphine, BINAP, $PPh_3$, $PCy_3$, S-Phos, X-Phos, Ru-Phos, trifuryl phosphine, tris(2,4-bis(1,1-dimethylethyl)phenyl)-phosphite, DPEphos, Josiphos and carbene ligands such as IMes, SIMes, IPr, SIPr. Suitable solvents include polar and non-polar organic solvents for example. dimethylformamide, dimethylacetamide, dimethoxyethane, dioxane, NMP, toluene, xylenes, water, acetonitrile, THF, ionic liquids, tert-butylalcohol, ethanol, methanol. Suitable additives are for example. Lithium halide, metal hydroxide, trialkyl amine, metal carbonate or acetate or phosphate or fluoride. Examples of additives are for example LiCl, KOH, NaOH, $Et_3N$, $Na_2CO_3$, $K_2CO_3$, $Cs_2CO_3$, $K_3PO_4$, KF, CsF. The reaction temperature is usually in the range 0° C. to 200° C., more preferably 20° C. to 150° C. The reaction time is usually in the range 1 hour to 100 hours.

Scheme 3

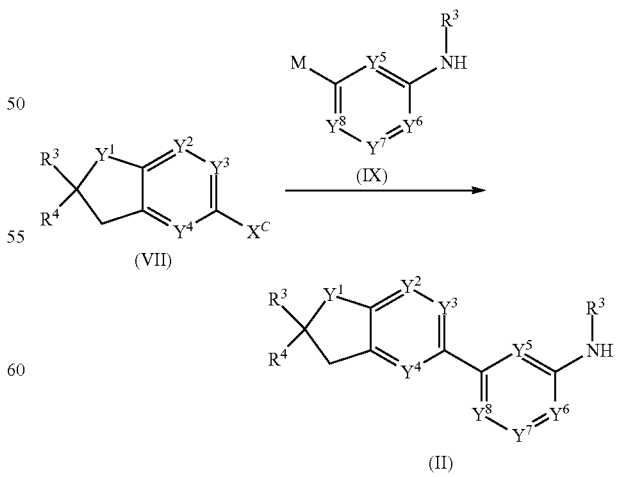

8) Compounds of formula (II) can be obtained from compounds of formula (VII) wherein $X^C$ is as described in 7) via a coupling reaction (e.g. Suzuki, Stille, Hiyama, Negishi) e.g. by treating compounds of formula (VII) with compounds of formula (IX) wherein M is suitable derivative of B, Si, Sn, Zn (e.g. boronic acid, boronic ester, trifluoroborate, dialkyl-hydroxysilane, trialkyltin, ZnCl, ZnBr) using conditions described in 7).

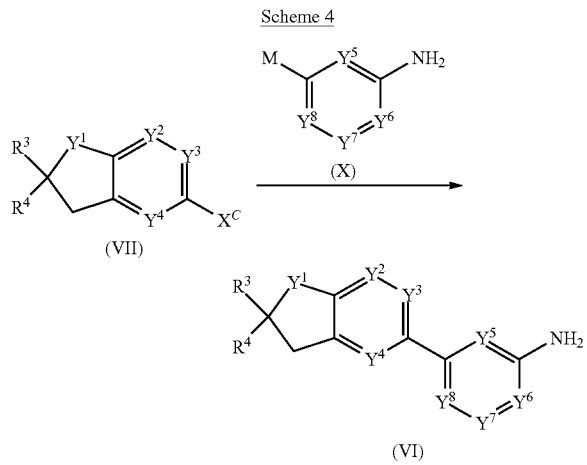

9) Compounds of formula (VI) can be obtained from compounds of formula (VII) via a coupling reaction (e.g. Suzuki, Stille, Hiyama, Negishi) e.g. by treating compounds of formula (VII) wherein $X^C$ is as described in 7), with a reactant (X) wherein M is as described in 7). Example of coupling of compounds of formula (VII) wherein $X^C$ is iodo with compounds of formula (X) wherein M is $B(OH)_2$ are given in the experimental section.

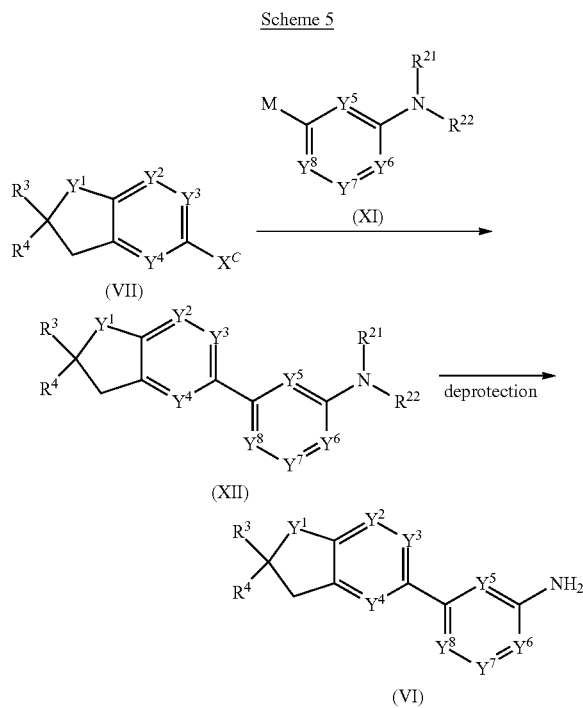

10) Compounds of formula (VI) can be obtained from compounds of formula (XII) wherein $R^{21}$ and $R^{22}$ are independently selected from hydrogen, $C_1$-$C_8$carbonyl, $C_1$-$C_8$alkoxycarbonyl, or $R^{21}$ and $R^{22}$ together are C(=O)—(CH$_2$)$_r$—C(=O)— wherein r is 1 to 4, —C($C_1$-$C_3$ alkyl)=C—C=($C_1$-$C_3$alkyl)C—, or group B

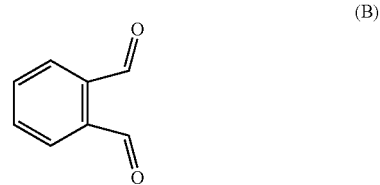

via a deprotection reaction using conditions described in the section on protecting groups for anilines in Wuts, P. G. M.; Greene, T. W., Protective Groups in Organic Synthesis 3rd ed. John Wiley & Sons: New York, 1999.

11) Compounds of formula (XII) can be obtained from compounds of formula (VII) via a coupling reaction (e.g. Suzuki, Stille, Hiyama, Negishi) e.g. by treating compounds of formula (VII) wherein $X^C$ is as described in 7), with a reactant (XI) wherein M is as described in 7) using conditions described in 7).

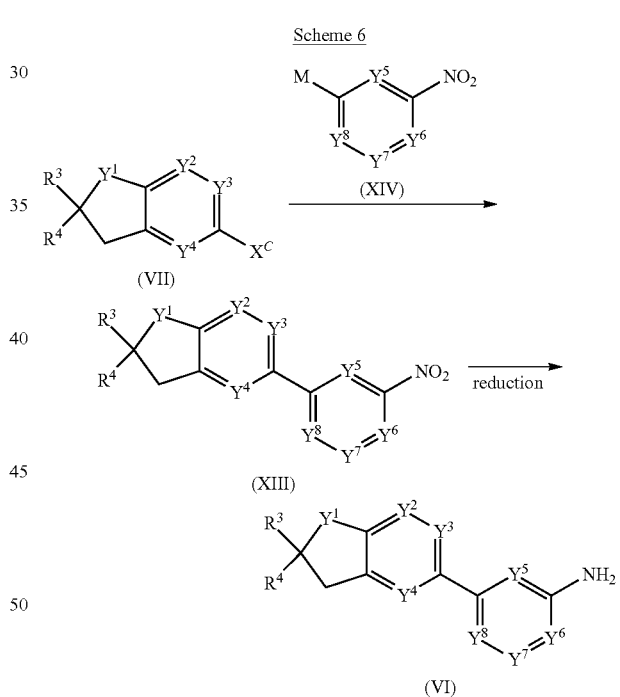

12) Compounds of formula (VI) can be obtained by reduction of compounds of formula (XIII) by using a suitable reducing agent as described extensively in Kabalka, G. W.; Varma, R. S., Reduction of Nitro and Nitroso Compounds. In Comprehensive Organic Synthesis, Trost, B. M.; Fleming, I., Eds. Pergamon Press: Oxford, 1991; Vol. 8, p 363. Suitable reducing agent can be for example iron, magnesium, zinc, tin(II)chloride in protic solvent for example water, ethanol, methanol, acetic acid, aqueous HCl. Alternatively the reduction can be carried using a transition metal catalyst for taken from Pd, Pt, Ni, such as Raney-nickel or palladium on charcoal in the presence of hydrogen pressure, formic acid or ammonium formate. Examples of such methods using Raney-nickel are described in the preparation Examples.

13) Compounds of formula (XIII) can be obtained from compounds of formula (VII) via a coupling reaction (e.g. Suzuki, Stille, Hiyama, Negishi) e.g. by treating compounds of formula (VII) wherein $X^C$ is as described in 7), with a reactant (XIV) wherein M is as described in 7), as described in 7). Example of coupling of compounds of formula (VII) wherein $X^C$ is iodo with compounds of formula (XIV) wherein M is B(pinacol) are given in the experimental section.

Scheme 7

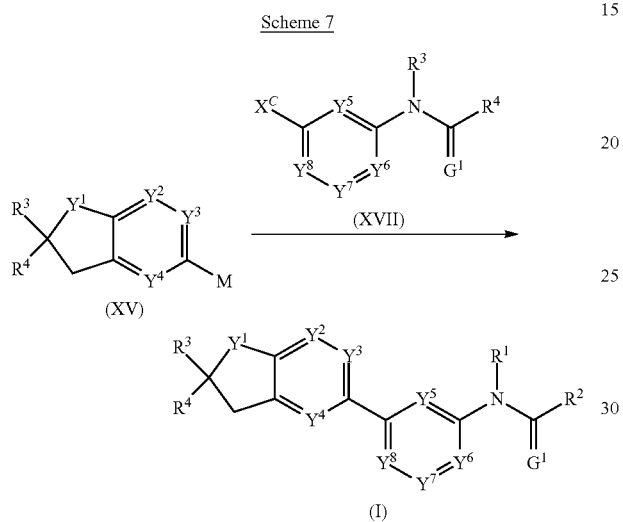

14) Compounds of formula (I) can be obtained from compounds of formula (XV) via a coupling reaction (e.g. Suzuki, Stille, Hiyama, Negishi) e.g. by treating compounds of formula (XVII) wherein $X^C$ represents a leaving group such as halogen, activated alcohols, diazonium salt, with a reactant (XV), wherein M represents a suitable derivative of B, Si, Sn, Zn (e.g. boronic acid, boronic ester, trifluoroborate, dialkyl-hydroxysilane, trialkyltin, ZnCl, ZnBr, ZnI, MnCl) in presence of a catalyst and optionally in the presence of a suitable ligand, solvent and additive. Suitable $X^C$ are for example Br, Cl, I, trifluromethylsulfonate, methylsulfonate, carboxylate, carbamate. Suitable catalysts are for example palladium catalysts such as Pd(OAc)$_2$, PdCl$_2$, Pd$_2$(dba)$_3$, Pd$_2$(dba)$_3$.CHCl$_3$, [Pd(PPh$_3$)$_4$], [Pd(Cl)$_2$(H$_3$CCN)$_2$)], [(allyl)Pd(Cl)]$_2$, [Pd(PPh$_3$)$_2$(Cl)$_2$], [Pd(DPPF)(Cl)$_2$], PEPPSI®, nickel catalysts such as NiCl$_2$, Ni(OAc)$_2$, Ni(acac)$_2$, [Ni(PPh$_3$)$_2$Cl$_2$], [Ni(DPPP)Cl$_2$]. Suitable ligands are for example phosphine ligands such as P(tBu)$_3$, tris(ortho-tolyl)phosphine, BINAP, PPh$_3$, PCy$_3$, S-Phos, X-Phos, Ru-Phos, trifuryl phosphine, tris(2,4-bis(1,1-dimethylethyl)phenyl)-phosphite, DPEphos, Josiphos and carbene ligands such as IMes, SIMes, IPr, SIPr. Suitable solvents include polar and non-polar organic solvents for example. DMF, DMA, DME, dioxane, NMP, toluene, xylenes, water, acetonitrile, THF, ionic liquids, tert-butylalcohol, ethanol, methanol. Suitable additives are for example. Lithium halide, metal hydroxide, trialkyl amine, metal carbonate or acetate or phosphate or fluoride. Examples of additives are for example LiCl, KOH, NaOH, Et$_3$N, Na$_2$CO$_3$, K$_2$CO$_3$, Cs$_2$CO$_3$, K$_3$PO$_4$, KF, CsF. The reaction temperature is usually in the range 0° C. to 200° C., more preferably 20° C. to 150° C. The reaction time is usually in the range 1 hour to 100 hours.

Scheme 8

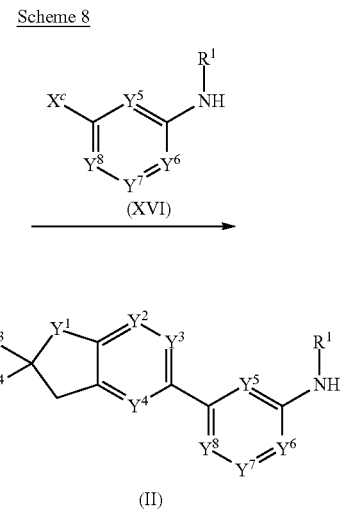

15) Compounds of formula (II) can be obtained from compounds of formula (XV) via a coupling reaction (e.g. Suzuki, Stille, Hiyama, Negishi) e.g. by treating compounds of formula (XV), with a reactant (XVI), as described in 14).

Scheme 9

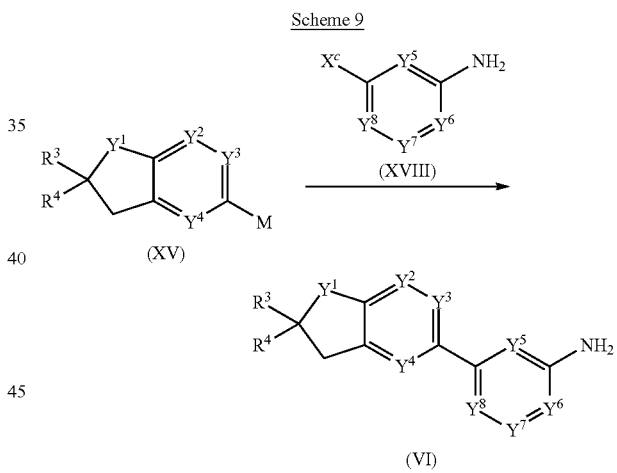

16) Compounds of formula (VI) can be obtained from compounds of formula (XV), (e.g. Suzuki, Stille, Hiyama, Negishi) e.g. by treating compounds of formula (XV), with a reactant (XVIII), as described in 14).

Scheme 10

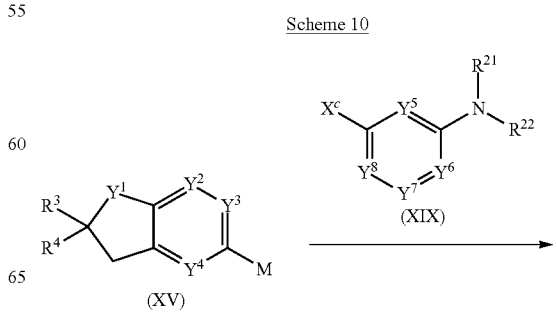

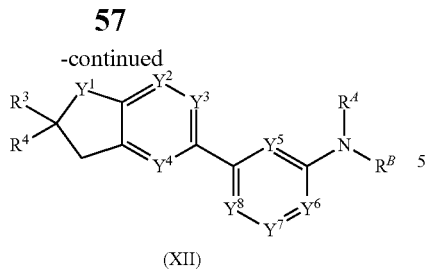

(XII)

17) Compounds of formula (XII) can be obtained from compounds of formula (XV) via a coupling reaction (e.g. Suzuki, Stille, Hiyama, Negishi) e.g. by treating compounds of formula (XV) with a reactant (XIX) wherein $R^{21}$ and $R^{22}$ are independently selected from hydrogen, $C_1$-$C_8$alkylcarbonyl, $C_1$-$C_8$alkoxycarbonyl, or $R^{21}$ and $R^{22}$ together are C(=O)—(CH$_2$)$_r$—C(=O)— wherein r is 1 to 4, —C($C_1$-$C_3$alkyl)=C—C=($C_1$-$C_3$alkyl)C—, or group B, as described in 14).

Scheme 11

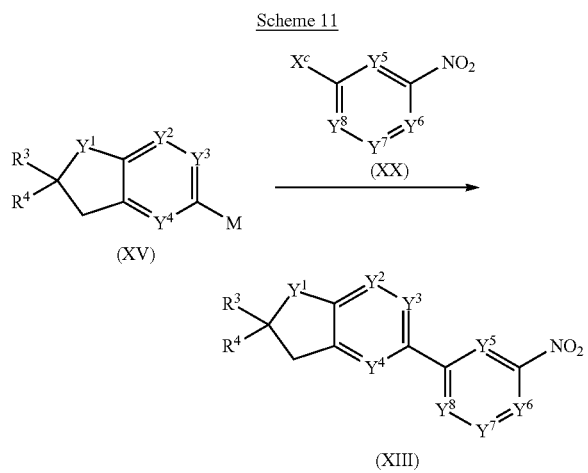

18) Compounds of formula (XIII) can be obtained from compounds of formula (XV) via a coupling reaction (e.g. Suzuki, Stille, Hiyama, Negishi) e.g. by treating compounds of formula (XV), with a reactant (XX), as described in 14).

Scheme 12

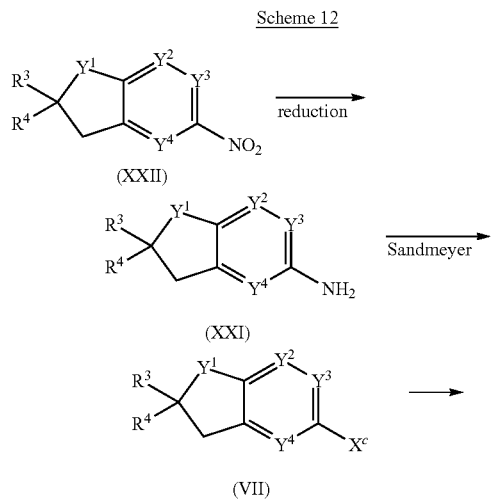

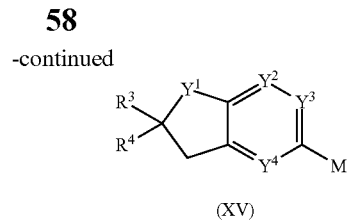

(XV)

19) Compounds of formula (XV) wherein M represents a suitable derivative of B, Si, Sn, Mg, Zn, (e.g. boronic acid, boronic ester, trifluoroborate, dialkyl-hydroxysilane, trialkyltin, ZnCl, ZnBr, ZnI), can be obtained from compounds of formula (VII) wherein $X^C$ is bromo, iodo, chloro via a halogen/metal exchange reaction by treating compounds of formula (VII) with an organolithium, for example butyllithium, or an organomagnesium, for example isopropylmagnesium chloride, isopropylmagnesium chloride lithium chloride complex, in an aprotic solvent for example tetrahydrofuran, diethyl ether, methyl tert-butyl ether and reaction with the appropriate electrophile such as a trialkyl tin halide for M=trialkylstannyl using conditions described in Journal of Organic Chemistry, 69(17), 5803-5806; 2004, a trialkylborate for M=dihydroxyboryl using conditions described in Tetrahedron, 62(12), 2831-2844; 2006 or dialkoxyboryl, a zinc(II) halide when M is zinc halide or a dialkyldialkoxysilanes when M is dialkylalkoxysilyl.

20) Alternatively compounds of formula (XV) wherein M is dialkoxyboryl, can be made by reacting compounds of formula (VII) wherein $X^C$ is a halogen for example bromo, iodo, chloro with tetraalkoxydiboron for example bis(pinacolato)diboron or tetrahydroxydiboron in presence of a transition metal salt such as palladium for example Pd(OAc)$_2$, PdCl$_2$, Pd$_2$(dba)$_3$, Pd$_2$(dba)$_3$.CHCl$_3$, [Pd(PPh$_3$)$_4$], [Pd(Cl)$_2$(H$_3$CCN)$_2$)], [(allyl)Pd(Cl)]$_2$, [Pd(PPh$_3$)$_2$(Cl)$_2$], [Pd(DPPF)(Cl)$_2$] and an activator such as a metal carboxylate for example sodium acetate in a polar or non-polar solvent for example 1,4-dioxane, toluene, tetrahydrofuran using conditions described in Ishiyama, T.; Miyaura, N. Chemical Record, 3, 271; 2004 and Organic & Biomolecular Chemistry, 10(39), 7980-7985; 2012.

21) Compounds of formula (VII) wherein $X^C$ is a halogen for example bromo, iodo, chloro with can be made by diazotation of compounds of formula (XXI) using NaNO$_2$ or alkyl nitrite in presence of an HX where X is Cl$^-$, Br$^-$, OAC$^-$ or BF$_4^-$ in an aqueous solvent followed by reaction with CuX$^C$ wherein $X^C$ is a halogen for example bromo, iodo, chloro. Alternatively KI can be employed when $X^C$ is iodo. Specific examples for compounds of formula (XV) wherein $X^C$ is iodo are described in the experimental section.

22) Compound of formula (XXI), can be made by reducing compounds of formula (XXII) as described in 12). Specific examples are described in the experimental section.

Scheme 13

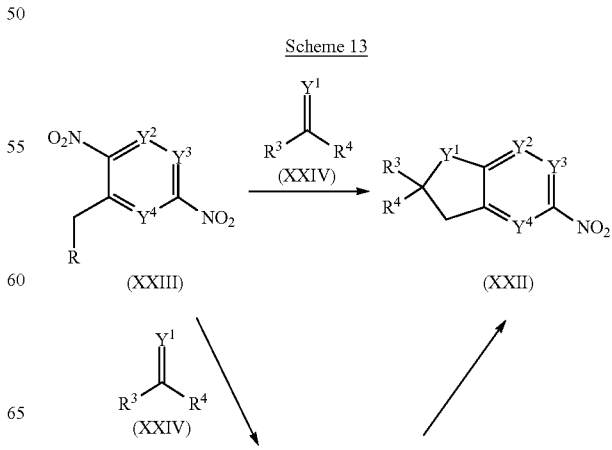

-continued

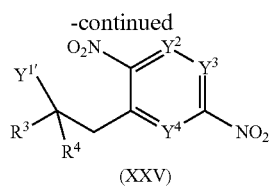

(XXV)

23) Compound of formula (XXII) wherein $Y^1$ is oxygen can be made by reacting compounds of formula (XXIII) wherein R is hydrogen or trialkylsilyl for example trimethylsilyl with a compound of formula (XXIV) wherein $Y^1$ is oxygen in presence of an activator such as a fluoride source for example tetrabutylammonium fluoride in presence of a base for example diisopropylethylamine in an aprotic solvent such tetrahydrofuran following conditions described in J. Org. Chem. 70, 3727-3729; 2005. Some of these methods are described in the preparation Examples.

24) Alternatively compound of formula (XXII) wherein $Y^1$ is oxygen can be made by reacting compounds of formula (XXV) wherein $Y^{1'}$ is OH in presence of a base for example diisopropylethylamine in an solvent such tetrahydrofuran as described in J. Org. Chem. 70, 3727-3729; 2005.

25) Compound of formula (XXV) wherein $Y^{1'}$ is OH can be made by reacting compounds of formula (XXIII) wherein R is hydrogen or trialkylsilyl for example trimethylsilyl with a compound of formula (XXIV) wherein $Y^1$ is oxygen in presence of catalytic amount an activator such as a fluoride source for example tetrabutylammonium fluoride in an aprotic solvent such tetrahydrofuran as described in J. Org. Chem. 70, 3727-3729; 2005, and J. Org. Chem. 51, 3694; 1986.

Scheme 14

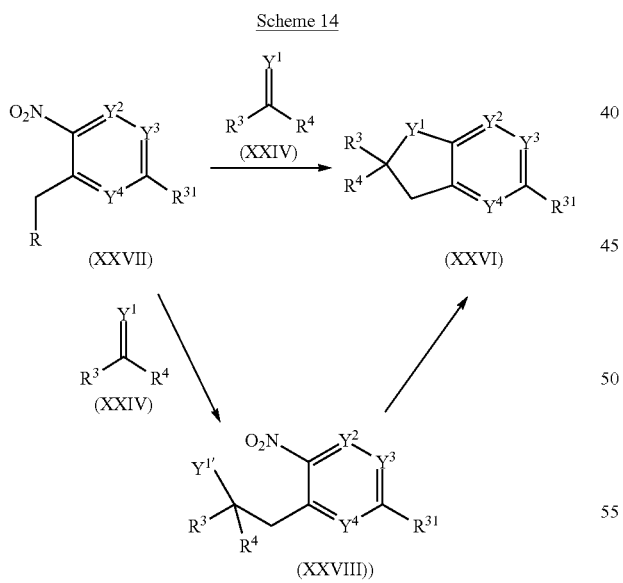

26) Compounds of formula (XXVI) wherein $Y^1$ is oxygen and $R^{31}$ is cyano, chloro, bromo, 3-nitrophenyl or C(O)R' wherein R' is $C_1$-$C_{15}$alkoxy, can be made by reacting compounds of formula (XXVII) wherein R is hydrogen or trialkylsilyl for example trimethylsilyl with a compound of formula (XXIV) wherein $Y^1$ is oxygenin presence of an activator such as a fluoride source for example tetrabutylammonium fluoride in presence of a base for example diisopropylethylamine in an aprotic solvent such tetrahydrofuran following conditions described in J. Org. Chem. 70, 3727-3729; 2005.

27) Alternatively compounds of formula (XXVI) wherein $Y^1$ is oxygen and $R^{31}$ is cyano, chloro, bromo, 3-nitrophenyl or C(O)R' wherein R' is $C_1$-$C_{15}$alkoxy can be made by reacting compounds of formula (XXVIII) wherein $Y^{1'}$ is OH in presence of a base for example diisopropylethylamine in an solvent such tetrahydrofuran. Such reactions can be carried out using conditions, described in J. Org. Chem. 70, 3727-3729; 2005.

28) Compounds of formula (XXVIII) wherein $Y^{1'}$ is OH and $R^{31}$ is cyano, chloro, bromo, 3-nitrophenyl or C(O)R' wherein R' is $C_1$-$C_{15}$alkoxy can be made by reacting compounds of formula (XXVII) wherein R is hydrogen or trialkylsilyl for example trimethylsilyl with a compound of formula (XXIV) wherein $Y^1$ is oxygen in presence of catalytic amount an activator such as a fluoride source for example tetrabutylammonium fluoride in an aprotic solvent such tetrahydrofuran. Such reactions can be carried out using condition, described in J. Org. Chem. 70, 3727-3729; 2005 and J. Org. Chem. 51, 3694; 1986.

Scheme 15

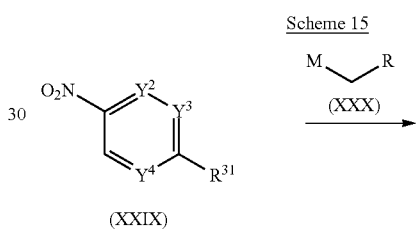

(XXIX)

(XXVI)

29) Compounds of formula (XXVI) wherein $R^{31}$ is cyano, chloro, bromo, 3-nitrophenyl or C(O)R' wherein R' is $C_1$-$C_{15}$alkoxy can be made by reacting a compound of formula (XXIX) with an organometallic reagent (XXX) where in R is H or trialkylsilyl such as an orgnomagesium for example trimethylsilylmethyl magnesium chloride followed by oxidation with a single electron oxidant such as 2,3-dichloro-5,6-dicyano-1,4-benzoquinone following conditions described in J. Org. Chem. 51, 3694; 1986.

Scheme 16

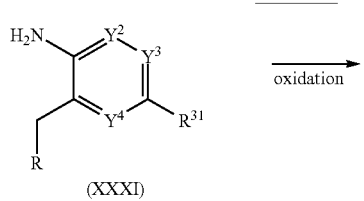

(XXXI)

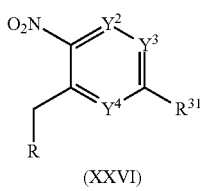

30) Alternatively compounds of formula (XXVI) wherein $R^{31}$ is nitro, cyano, chloro, bromo, 3-nitrophenyl or C(O)R' wherein R' is $C_1$-$C_{15}$alkoxy and R is hydrogen can be prepared by oxidation of compounds of formula (XXXI) using an oxidant for example Oxone®, sodium perborate, potassium permanganate. Some of these methods are described in the preparation Examples.

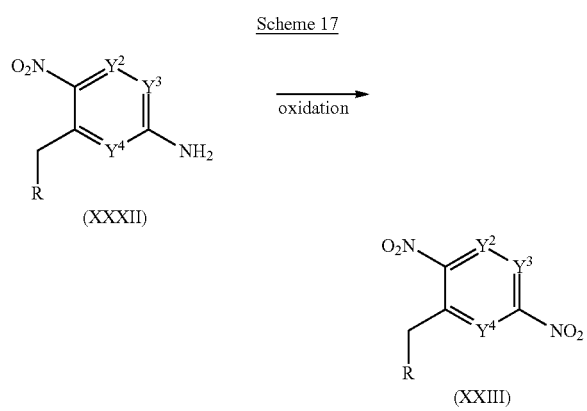

31) Compounds of formula (XXIII) wherein R is hydrogen can be prepared by oxidation of compounds of formula (XXXII) using conditions described in 30).

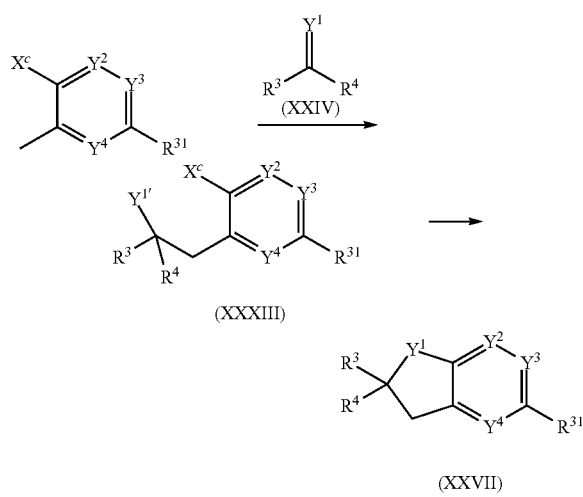

32) Alternatively compounds of formula (XXVII) wherein $Y^1$ is oxygen and $R^{31}$ is nitro, cyano, chloro, 3-nitrophenyl or C(O)R' wherein R' is $C_1$-$C_{15}$alkoxy can be prepared by coupling compounds of formula (XXXIII) wherein $Y^{1'}$ is OH and $X^C$ is halogen for example bromo or iodo in presence of a transition metal catalyst such palladium or copper for example a copper(I) halide and in presence of a ligand for example 8-quinolinol with a base such as alkali metal carbonate or alkali metal hydroxide or a alkali metal alkoxide for example $Cs_2CO_3$ in a aprotic solvent such as toluene.

33) Compounds of formula (XXXIII) wherein $Y^{1'}$ is OH and $R^{31}$ is nitro, cyano, chloro, 3-nitrophenyl or C(O)R' wherein R' is $C_1$-$C_{15}$alkoxy can be prepared by reaction compounds of formula (XXXIV) with a strong base such lithium amide or alkali metal hexamethyldisilazide for example lithium diisopropyl amide followed by addition of (XXIV) wherein $Y^1$ is oxygen.

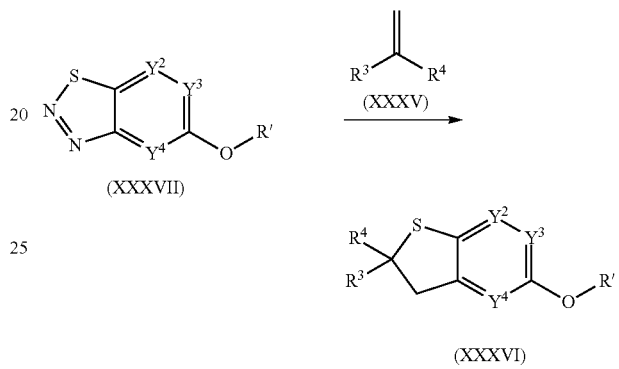

34) Compounds of formula (XXXVI) wherein R' is $C_1$-$C_{15}$alkoxy can be prepared by reaction of compound (XXXVII) with alkene (XXXV) in the presence of a radical initiator for example tert-butylhydroperoxide in the presence of a suitable solvent for example tert-butylalcohol. Alternatively the reaction can be run without solvent. Some of these methods are described in the preparation Examples.

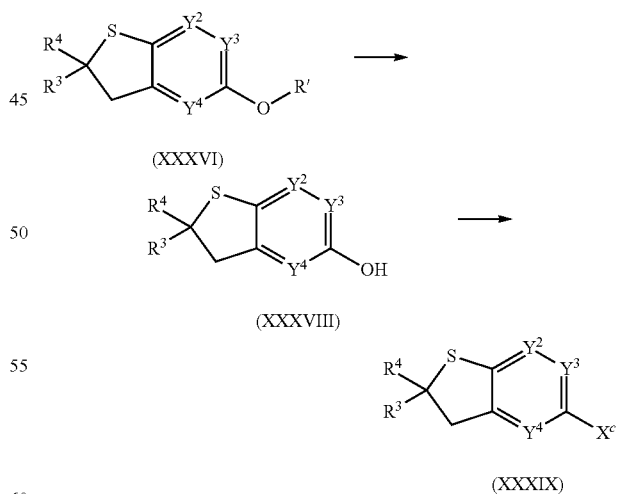

35) Compounds of formula (XXXIX) wherein $X^c$ is an activated alcohol for example a $C_1$-$C_8$alkylsulfonyloxy, $C_1$-$C_8$haloalkylsulfonyloxy, $C_1$-$C_8$arylsulfonyloxy, di($C_1$-$C_8$alkyl)sulfamoyloxy, or a di($C_1$-$C_8$alkyl)carbamoyloxy can be prepared by reacting phenol of formula (XXXVIII) with a suitable activating agent for example $C_1$-$C_8$alkylsulfonylchloride, $C_1$-$C_8$alkylsulfonylanhydride, $C_1$-$C_8$haloalkylsulfonylfluoride, $C_1$-$C_8$haloalkylsulfonylanhydride, $C_1$-$C_8$arylsulfonylchloride, di($C_1$-$C_8$alkyl)sulfamoylchloride or di($C_1$-$C_8$alkyl)carbamoylchloride. A specific example for compounds of formula (XXXIX) wherein $X^C$ is trifluoromethanesulfonyloxy is described in the experimental section.

36) Phenols of formula (XXXVIII) can be prepared by treating compounds of formula (XXXVI) wherein R' is $C_1$-$C_{15}$alkoxy with $BBr_3$, $BCl_3$, $AlCl_3$, or Me3SiI in a chlorinated solvent for example dichloromethane. Some of these methods are described in the preparation Examples.

37) Compounds of formula (XXXIX) wherein $X^c$ is an activated alcohol for example a $C_1$-$C_8$alkylsulfonyloxy, $C_1$-$C_8$haloalkylsulfonyloxy, $C_1$-$C_8$arylsulfonyloxy, di($C_1$-$C_8$alkyl)sulfamoyloxy, or a di($C_1$-$C_8$alkyl)carbamoyloxy can be elaborated into compounds of formula (I) wherein $Y^1$ is S using conditions described in 7).

Scheme 21

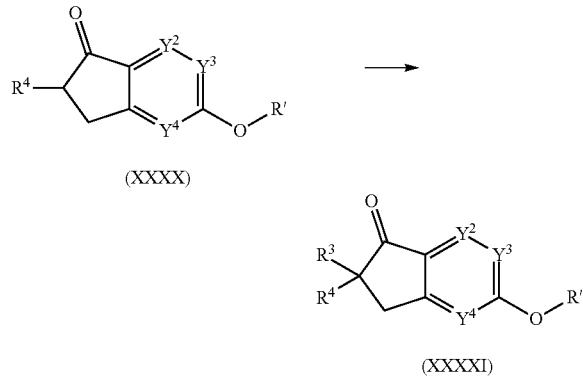

(XXXX)

(XXXXI)

38)) Compounds of formula (XXXXI) wherein R' is $C_1$-$C_{15}$alkoxy can be prepared by deprotonation of compound (XXXX) with a suitably strong organic base for example 1,8-diazabicyclo[5.4.0]undec-7-ene in a suitable organic solvent for example acetonitrile, followed by sequential addition of a $C_1$-$C_8$haloalkyliodide, $CF_3I$ where in $R^3$ is $CF_3$, and a suitable reducing agent for example $Na_2S_2O_4$.

Scheme 21

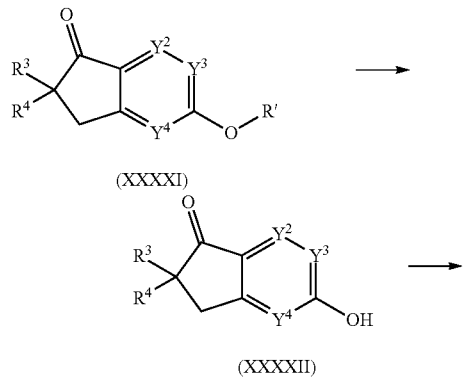

(XXXXI)

(XXXXII)

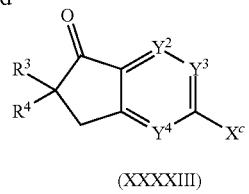

(XXXXIII)

39) Compounds of formula (XXXXIII) wherein $X^c$ is an activated alcohol for example a $C_1$-$C_8$alkylsulfonyloxy, $C_1$-$C_8$haloalkylsulfonyloxy, $C_1$-$C_8$arylsulfonyloxy, di($C_1$-$C_8$alkyl)sulfamoyloxy, or a di($C_1$-$C_8$alkyl)carbamoyloxy can be prepared by reacting phenol of formula (XXXXII) with a suitable activating agent for example $C_1$-$C_8$alkylsulfonylchloride, $C_1$-$C_8$alkylsulfonylanhydride, $C_1$-$C_8$haloalkylsulfonylfluoride, $C_1$-$C_8$haloalkylsulfonylanhydride, $C_1$-$C_8$arylsulfonylchloride, di($C_1$-$C_8$alkyl)sulfamoylchloride or di($C_1$-$C_8$alkyl)carbamoylchloride. A specific example for compounds of formula (XXXXIII) wherein $X^C$ is trifluoromethanesulfonyloxy is described in the experimental section.

40) Phenols of formula (XXXXII) can be prepared by treating compounds of formula (XXXXI) wherein R' is $C_1$-$C_{15}$alkoxy with $BBr_3$, $BCl_3$, $AlCl_3$, or Me3SiI in a chlorinated solvent for example dichloromethane. Some of these methods are described in the preparation Examples.

41) Compounds of formula (XXXXIII) wherein $X^c$ is an activated alcohol for example a $C_1$-$C_8$alkylsulfonyloxy, $C_1$-$C_8$haloalkylsulfonyloxy, $C_1$-$C_8$arylsulfonyloxy, di($C_1$-$C_8$alkyl)sulfamoyloxy, or a di($C_1$-$C_8$alkyl)carbamoyloxy can be elaborated into compounds of formula (I) wherein $Y^1$ is C=O using conditions described in 7).

In the above descriptions reference to leaving groups includes leaving groups such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, di($C_1$-$C_8$alkyl)sulfamoyloxy, di($C_1$-$C_8$alkyl)carbamoyloxy, optionally substituted $C_1$-$C_8$arylsulfonyloxy (aryl is preferably phenyl), diazonium salts (e.g. the leaving group may be selected from —$N_2^+$ $Cl^-$, —$N_2^+BF_4^-$, —$N_2^+$ $Br^-$, —$N_2^+$ $PF_6^-$), phosphonate esters (e.g. —OP(O)(OR)$_2$, wherein R is methyl or ethyl).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus otyzophilus, Lyctus bruneus, Aulacophora femoralis;* lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;* hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental;* orthopterans, for example, *Blatella germanica, Periplaneta americana, Gtyllotalpa Africana, Locusta migratoria migratoriodes;* isopterans, for example, *Reticulitermes speratus, Coptotermes formosanus;* dipterans, for example, *Musca domestica, Aedes aegypti, Hylemia platura, Culex pipiens, Anopheles sinensis, Culex tritaeniorhynchus, Liriomyza trifolii;* acari, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya et Kiyohara, Aphelenchoides besseyi, Heterodera glycines, Pratylenchus* spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Blyobia praetiosa, Chorioptes* spp., *Dermanyssus gallinae, Eotetranychus* spp., *Epitrimerus Pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;* from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Ctyptorhynchus lapathi, Dermestes* spp., *Diabrotica* spp., *Epilachna* spp., *Faustinus cubae, Gibbium psylloides, Heteronychus orator, Hylamorpha elegans, Hylotrupes bajulus, Hypera postica, Hypothenemus* spp., *Lachnosterna consanguinea, Leptinotarsa decemlineata, Lissorhoptrus otyzophilus, Lixus* spp., *Lyctus* spp., *Meligethes aeneus, Melolontha melolontha, Migdolus* spp., *Monochamus* spp., *Naupactus xanthographus, Niptus hololeucus, Otyctes rhinoceros, Otyzaephilus surinamensis, Otiorrhynchus sulcatus, Oxycetonia jucunda, Phaedon cochleariae, Phyllophaga* spp., *Popillia japonica, Premnottypes* spp., *Psylliodes chtysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus;* from the order of the Dermaptera, for example, *Forficula auricularia;* from the order of the Diplopoda, for example, *Blaniulus guttulatus;* from the order of the Diptera, for example, *Aedes* spp., *Anopheles* spp., *Bibio hortulanus, Calliphora etythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella Pegomyia hyoscyami, Phorbia* spp., *Stomoxys* spp., *Tabanus* spp., *Tannia* spp., *Tipula paludosa, Wohlfahrtia* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* ft may be furthermore possible to control protozoa, such as *Eimeria;* from the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eutygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.; from the order of the Homoptera, for example, *Acyrthosipon* spp., *Aeneolamia* spp., *Agonoscena* spp., *Aleurodes* spp.,

*Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicotyne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chtysomphalus ficus, Cicadulina mbila, Coccomytilus halli, Coccus* spp., *Ctyptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Etythroneura* spp., *Euscelis bilobatus, Geococcus coffeae, Homalodisca coagulata, Hyalopterus arundinis,* ketya spp., *Idiocerus* spp., *Idioscopus* spp., *Laodelphax striatellus, Lecanium* spp., *Lepidosaphes* spp., *Lipaphis etysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis catyaefoliae, Tomaspis* spp., *Toxoptera* spp., *Trialeurodes vaporariorum, Trioza* spp., *Typhlocyba* spp., *Unaspis* spp., *Viteus vitifolii;* from the order of the Hymenoptera, for example, *Diprion* spp., *Hoplocampa* spp., *Lasius* spp., Mono-*morium pharaonis, Vespa* spp.; from the order of the *Isopoda,* for example, *Armadillidium vulgare, Oniscus asellus, Porcellio scaber;* from the order of the Isoptera, for example, *Reticulitermes* spp., *Odontotermes* spp.; from the order of the *Lepidoptera,* for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chtysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema otyzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.; from the order of the Orthoptera, for example, *Acheta domesticus, Blatta orientalis, Blattella germanica, Gtyllotalpa* spp., *Leucophaea maderae, Locusta* spp., *Melanoplus* spp., *Periplaneta americana, Schistocerca gregaria;* from the order of the Siphonaptera, for example, *Ceratophyllus* spp., *Xenopsylla cheopis*. From the order of the Symphyla, for example, *Scutigerella immaculata;* from the order of the Thysanoptera, for example, *Baliothrips biformis, Enneothrips flavens, Frankliniella* spp., *Helio-thrips* spp., *Hercinothrips femoralis, Kakothrips* spp., *Rhipiphorothrips cruentatus, Scirtothrips* spp., *Taeniothrips cardamoni, Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In particular, the compounds of the invention may be used to control the following pest spcies:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Franklinielaoccidentalis* (thrip), *Thrips* spp. (thrips), *Leptinotarsadecemlineata* (Colorado potato beetle), *Anthonomusgrandis* (boll weevil), *Aonidiella* spp. (scale insects), *Trialeurodes* spp. (white flies), *Bemisia tabaci* (white fly), *Ostrinianubilalis* (European corn borer), *Spodopteralittoralis* (cotton leafworm), *Heliothisvirescens* (tobacco budworm), *Helicoverpaarmigera* (cotton bollworm), *Helicoverpazea* (cotton bollworm), *Sylepta derogata* (cotton leaf roller), *Pierisbrassicae* (white butterfly), *Plutellaxylostella* (diamond back moth), *Agrotis* spp. (cutworms), *Chilosuppressalis* (rice stem borer), *Locustamigratoria* (locust), *Chortiocetesterminifera* (locust), *Diabrotica* spp. (rootworms), *Panonychusulmi* (European red mite), *Panonychuscitri* (citrus red mite), *Tetranychusurticae* (two-spotted spider mite), *Tetranychuscinnabarinus* (carmine spider mite), *Phyllocoptrutaoleivora* (citrus rust mite), *Polyphagotarsonemuslatus* (broad mite), *Brevipalpus* spp. (flat mites), *Boophilus microplus* (cattle tick), *Dermacentorvariabilis* (American dog tick), *Ctenocephalidesfelis* (cat flea), *Liriomyza* spp. (leafminer), *Muscadomestica* (housefly), *Aedesaegypti* (mosquito), *Anopheles* spp. (mosquitoes), *Culex* spp. (mosquitoes), *Lucillia* spp. (blowflies), *Blattellagermanica* (cockroach), *Periplanetaamericana* (cockroach), *Blattaorientalis* (cockroach), termites of the Mastotermitidae (for example *Mastotermes* spp.), the Kalotermitidae (for example *Neotermes* spp.), the Rhinotermitidae (for example *Coptotermesformosanus, Reticulitermes flavipes, R. speratu, R. virginicus, R. hesperus, and R. santonensis*) and the Termitidae (for example *Globitermessulfureus*), *Solenopsisgeminata* (fire ant), *Monomoriumpharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*(vinegar eelworm), *Trichostrongylus* spp. (gastro intestinal nematodes) and *Deroceras reticulatum* (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, *Elasmopalpus lignosellus, Diloboderus abderus, Diabrotica speciosa, Trialeurodes* spp., *Bemisia* spp., aphids, *Sternechus subsignatus, Formicidae, Agrotis ipsilon, Julus* spp., *Murgantia* spp., *Halyomorpha* spp., *Thyanta* spp., *Megascelis* ssp., *Procornitermes* ssp., *Gtyllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euschistus heros*, stalk borer, *Scaptocoris castanea, phyllophaga* spp., *Migdolus* spp., *Pseudoplusia includens, Anticarsia gemmatalis, Epinotia* spp., *Rachiplusia* spp., *Spodoptera* spp., *Bemisia tabaci, Tetranychus* spp., *Agriotes* spp., *Euschistus* spp. The compounds of the invention are preferably used on soybean to control *Diloboderus abderus, Diabrotica speciosa, Trialeurodes* spp., *Bemisia* spp., *Nezara viridula, Piezodorus* spp., *Acrosternum* spp., *Cerotoma trifurcata, Popillia japonica, Euschistus heros, Scaptocoris castanea, phyllophaga* spp., *Migdolus* spp., *Agriotes* spp., *Euschistus* spp.

The compounds of the invention may be used on corn to control, for example, *Euschistus heros, Euschistus* spp., *Dichelops furcatus, Diloboderus abderus, Thyanta* spp., *Elasmopalpus lignosellus, Halyomorpha* spp., *Spodoptera frugiperda, Nezara viridula, Cerotoma trifurcata, Popillia japonica, Agrotis ipsilon, Diabrotica speciosa*, aphids, Heteroptera, *Procornitermes* spp., *Scaptocoris castanea, Formicidae, Julus* ssp., *Dalbulus maidis, Diabrotica virgifera, Diabrotica* spp., *Mocis latipes, Bemisia tabaci, heliothis* spp., *Tetranychus* spp., thrips spp., *phyllophaga* spp., *Migdolus* spp., *scaptocoris* spp., *Liogenys fuscus, Spodoptera* spp., *Ostrinia* spp., *Sesamia* spp., wireworms, *Agriotes* spp., *Halotydeus destructor*. The compounds of the invention are preferably used on corn to control *Euschistus heros, Euschistus* spp., *Dichelops furcatus, Diloboderus abderus, Nezara viridula, Cerotoma trifurcata, Popillia japonica, Diabrotica speciosa, Diabrotica virgifera, Diabrotica* spp., *Tetranychus* spp., Thrips spp., *Phyllophaga* spp., *Migdolus* spp., *Scaptocoris* spp., *Agriotes* spp.

The compounds of the invention may be used on sugar cane to control, for example, *Sphenophorus* spp., termites, *Migdolus* spp., *Diloboderus* spp., *Telchin hem, Diatrea saccharalis, Mahanarva* spp., Mealybugs.

The compounds of the invention may be used on alfalfa to control, for example, *Hypera brunneipennis, Hypera postica, Colias eutytheme, Collops* spp., *Empoasca solana, Epitrix* spp., *Geocoris* spp., *Lygus hesperus, Lygus lineolaris, Spissistilus* spp., *Spodoptera* spp., Aphids, *Trichoplusia ni*. The compounds of the invention are preferably used on alfalfa to control *Hypera brunneipennis, Hypera postica, Empoasca solana, Epitrix* spp., *Lygus hesperus, Lygus lineolaris, Trichoplusia ni*.

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca* spp., thrips spp., *Delia* spp., *Murgantia* spp., *Trialeurodes* spp., *Bemisia* spp., *Microtheca* spp., Aphids. The compounds of the invention are preferably used on brassicas to control *Plutella xylostella, Pieris* spp., *Plusia* spp., *Trichoplusia ni, Phyllotreta* spp., *Thrips* spp.

The compounds of the invention may be used on oil seed rape, e.g. canola, to control, for example, *Meligethes* spp., *Ceutorhynchus napi, Halotydeus destructor, Psylloides* spp.

The compounds of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp., Aphids, wireworms. The compounds of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The compounds of the invention may be used on cotton to control, for example, *Anthonomus grandis, Pectinophora* spp., *heliothis* spp., *Spodoptera* spp., *Tetranychus* spp., *Empoasca* spp., *Thrips* spp., *Bemisia tabaci, Trialeurodes* spp., Aphids, *Lygus* spp., *phyllophaga* spp., *Scaptocoris* spp., *Austroasca viridigrisea, Creontiades* spp., *Nezara* spp., *Piezodorus* spp., *Halotydeus destructor, Oxycaraenus hyalinipennis, Dysdercus cingulatus*. The compounds of the invention are preferably used on cotton to control *Anthonomus grandis, Tetranychus* spp., *Empoasca* spp., thrips spp., *Lygus* spp., *phyllophaga* spp., *Scaptocoris* spp.

The compounds of the invention may be used on rice to control, for example, *Leptocorisa* spp., *Cnaphalocrosis* spp., *Chilo* spp., *Scirpophaga* spp., *Lissorhoptrus* spp., *Oebalus pugnax, Scotinophara* spp., *Nephotettix malayanus, Nephotettix nigropictus, Nephottetix parvus, Nephottetix virescens, Nephotettix* spp., Mealybugs, *Sogatella furcifera, Nilaparvata lugens, Orseolia* spp., *Cnaphalocrocis medinalis, Marasmia* spp., *Stenchaetothrips biformis, Thrips* spp., *Hydrellia philippina*, Grasshoppers, *Pomacea canaliculata, Scirpophaga innotata, Chilo suppressalis, Chilo auricilius, Chilo polychtysus, Sesamia inferens, Laodelphax striatellus, Nymphula depunctalis, Oulema otyzae*, Stinkbugs. The compounds of the invention are preferably used on rice to control *Leptocorisa* spp., *Lissorhoptrus* spp., *Oebalus pugnax, Nephotettix malayanus, Nephotettix nigropictus, Nephotettix parvus, Nephottetix virescens, Nephotettix* spp., *Sogatella furcifera, Stenchaetothrips biformis, Thrips* spp., *Hydrellia philippina*, Grasshoppers, *Pomacea canaliculata, Scirpophaga innotata, Chilo suppressalis, Chilo polychtysus, Oulema otyzae*.

The compounds of the invention may be used on coffee to control, for example, Hypothenemus *Hampei, Perileucoptera Coffeella, Tetranychus* spp., *Brevipalpus* spp., Mealybugs. The compounds of the invention are preferably used on coffee to control *Hypothenemus Hampei, Perileucoptera Coffeella*.

The compounds of the invention may be used on citrus to control, for example, *Panonychus citri, Phyllocoptruta oleivora, Brevipalpus* spp., *Diaphorina citri, Scirtothrips* spp., *Thrips* spp., *Unaspis* spp., *Ceratitis capitata, Phyllocnistis* spp., Aphids, Hardscales, Softscales, Mealybugs. The compounds of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The compounds of the invention may be used on almonds to control, for example, *Amyelois transitella, Tetranychus* spp.

The compounds of the invention may be used on fruiting vegetables, cucurbits and pulses, including tomatoes, pepper, chili, eggplant, cucumber, squash etc., to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., Aphids, *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp., Fruit flies, Stinkbugs, Lepidopteras, Coleopteras. The compounds of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora, Tetranychus* spp. The compounds of the invention are preferably used on tea to control *Empoasca* spp., *Scirtothrips* spp.

The compounds of the invention may be used on bulb vegetables, including onion, leek etc. to control, for example, *Thrips* spp., *Spodoptera* spp., *heliothis* spp. The compounds of the invention are preferably used on bulb vegetables, including onion, leek etc. to control *Thrips* spp.

The compounds of the invention may be used on grapes to control, for example, *Empoasca* spp., *Lobesia* spp., *Eupoecilia ambiguella, Frankliniella* spp., *Thrips* spp., *Tetranychus* spp., *Rhipiphorothrips Cruentatus, Eotetranychus Willamettei, Etythroneura Elegantula, Scaphoides* spp., *Scelodonta strigicollis*, Mealybugs. The compounds of the invention are preferably used on grapes to control *Frankliniella* spp., *Thrips* spp., *Tetranychus* spp., *Rhipiphorothrips Cruentatus, Scaphoides* spp.

The compounds of the invention may be used on pome fruit, including apples, pears etc., to control, for example, *Cacopsylla* spp., *Psylla* spp., *Panonychus ulmi, Cydia pomonella, Lepidopteras*, Aphids, Hardscales, Softscales. The compounds of the invention are preferably used on pome fruit, including apples, pears etc., to control *Cacopsylla* spp., *Psylla* spp., *Panonychus ulmi*.

The compounds of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eutygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis (Thrips), Chilo* spp. (e.g. *Chilo polychtysus* (Dark headed striped borer), *Chilo suppressalis* (Rice stemborer), *Chilo indicus* (Paddy stem borer), *Chilo polychtysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema otyzae* (Rice leafbeetle), *Leptocorsia acuta* (Rice bug), *Leptocorsia oratorius* (rice bug), *Lissorhoptrus otyzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia otyzae* (Rice Gall midge), *Oulema otyzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, Thrips, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, thrips, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on *lepidoptera*, such as *spodoptera, cutworms, elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp Hipnodes bicolor; *Ctenicera destructor; Limonius canu; Limonius californicus*; rice water weevil: *Lissorhoptrus otyzophilus*; Red Legged earth mites: *Halotydeus destructor.*

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in super-additive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A. 105; or vegetative insiciticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.*

62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A. 105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Further examples of transgenic plants, and of very high interest, are those carrying traits conferring resistance to 2.4D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

Examples of cotton transgenic events include MON 531/ 757/1076 (Bollgard I®—Monsanto), MON1445 (Roundup ready Cotton®—Monsanto), MON531×MON1445 (Bollgard I+RR® Monsanto), MON15985 (Genuity Bollgard II Cotton®—Monsanto), MON88913 (Genuity RR FLEX Cotton®—Monsanto), MON15985×MON1445 (Genuity Bollgard II+RR FELX Cotton®—Monsanto), MON15983× MON88913 (Genuity Bollgard II+RR FLEX Cotton®— Monsanto), MON15985 (FibreMax Bollgard II Cotton®— Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton® BCS Stoneville/Monsanto), GHB614×LL25 (FibreMax LL GlyTol Cotton®—BCS Stoneville), GHB614× LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX®—Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701×MON89788 (Genuity Roundup ready 2 Yield Soybeans®—Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience), DHT-1 (Dow), TC1507 (Herculex I®—Dow), DAS59122-7 (Herculex RW®—Dow), TC1507+DAS59122-7 Herculex Xtra®—Dow), TC1507×DAS-59122-7×NK603 (Herculex Xtra+RR® Dow), TC1507×DAS-59122-×MON88017×MON89034 (Genuity Smartstax Corn®, Genuity Smartstax RIB Complete®—Monsanto/Dow), MON89034×NK603 (Genuity VT double PRO® Monsanto), MON89034+MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monasnto), MON810×MON863 (YieldGard Plus® Monsanto), MON863×MON810×NK603 (YieldGard Plus+RR Corn2®/YieldGard RR Maize® Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW® Monsanto), MON810+MON88017 (YieldGard VT Triple®—Monsanto), MON88017+MON89034 (YieldGard VT Triple Pro®—Monsanto), Bt11+MIR604+GA21 (Agrisure 3000®—Syngenta), Bt11+TC1507+MIR604+5307+GA21 (Syngenta), Bt11+TC1507+MIR604+DAS59122+GA21 (Agrisure 3122®—Syngenta), BT11 (Agrisure CB®—Syngenta), GA21 (Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure™ 3100® Syngenta), Event3272+BT11+MIR604+GA21 (Syngenta), BT11+MIR1692+MIR604+GA21 (Agrisure Viptera 3111®—Syngenta), BT11+MIR162+TC1507+GA21 (Agrisure Viptera 3220® Syngenta), BT11+MIR162+TC1507+MIR604+5307+GA21 (Agrisure Viptera 3222®—Syngenta), MIR162 (Syngenta), BT11+GA21+MIR162+MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefin sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer.

The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methy 1, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;

f) Pyrazoles, such as tebufenpyrad, tolfenpyrad, ethiprole, pyriprole, fipronil, and fenpyroximate;

g) Macrolides, such as avermectins or milbemycins, for example abamectin, emamectin benzoate, ivermectin, milbemycin, spinosad, azadirachtin, milbemectin, lepimectin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, or nithiazine;

m) Diacylhydrazines, such as tebufenozide, chromafenozide or methoxyfenozide;

n) Diphenyl ethers, such as diofenolan or pyriproxifen;

o) Pyrazolines such as Indoxacarb or metaflumizone;

p) Ketoenols, such as Spirotetramat, spirodiclofen or spiromesifen;

q) Diamides, such as flubendiamide, chlorantraniliprole (Rynaxypyr®) or cyantraniliprole;

r) Essential oils such as Bugoil®—(PlantImpact); or s) a comopund selected from buprofezine, flonicamid, acequinocy 1, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone,4-[(6-Chloropyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap) or hopper specific insecticides (combinations such as buprofezin) for use in rice may be employed. Alternatively insecticides or acaricides specific for particular insect species/stages may also be included in the compositions (for example acaricidal ovo-larvicides, to give combinations such as clofentezine, flubenzimine, hexythiazox or tetradifon; acaricidal motilicides, to give combinations such as dicofol or propargite; acaricides, to give combinations such as bromopropylate or chlorobenzilate; or growth regulators, such as hydramethylnon, cyromazine, methoprene, chlorfluazuron or diflubenzuron).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim, chlorhydrate, carboxin, carpropamid, carvone, CGA41396, CGA41397, chinomethionate, chlorothalonil, chlorozolinate, clozylacon, copper containing compounds to give combintations such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimo 1, ethyl-(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-A1, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide[1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

The active ingredients combinations described above comprising a compound selected of the invention, in particularly from the Tables IA1 to IA84, IB1 to IB84, IC1 to IC8 or ID1 to ID84 and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Baciullus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*. Also of interest are *Metarhizium* spp. such as *M. anisopliae; Pochonia* spp. such as *P. chlamydosporia*.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, Bacillus thuringiensis, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: Bacillus thuringiensis ssp aizawai, kurstaki, Bacillus thuringiensis delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following: imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Examples of ratios of the compound of formula I to any mixing partner described herein include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus*, *Dermacentor variabilis*, *Dermacentor andersoni*, *Amblyomma americanum*, *Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felts*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis*, *Hypoderma lineatum*, *Lucilia sericata*, *Lucilia cuprina* (green blowfly), *Calliphora* spp. (blowfly), *Protophormia* spp., *Oestrus ovis* (nasal botfly), *Culicoides* spp. (midges), *Hippobosca equine*, *Gastrophilus intestinalis*, *Gastrophilus haemorrhoidalis* and *Gastrophilus nasalis*; lice such as *Bovicola* (*Damalinia*) *bovis*, *Bovicola equi*, *Haematopinus asini*, *Felicola subrostratus*, *Heterodoxus spiniger*, *Lignonathus setosus* and *Trichodectes canis*; keds such as *Melophagus ovinus*; and mites such as *Psoroptes* spp., *Sarcoptes scabei*, *Chorioptes bovis*, *Demodex equi*, *Cheyletiella* spp., *Notoedres cati*, *Trombicula* spp. and *Otodectes cyanotis* (ear mites).

Examples of species of animal health pesets include those from the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eutysternus*, *Haematopinus suis*, *Pediculus humanus capitis*, *Pediculus humanus corporis*, *Phylloera vastatrix*, *Phthirus pubis*, *Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora etythrocephala*, *Chtysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora etythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chtysomya chloropyga*, *Chtysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorroidalis*, *Gasterophilus inermis*, *Gasterophilus nasalis*, *Gasterophilus nigricornis*, *Gasterophilus pecorum*, *Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis*, *Ctenocephalides felis*, *Pulex irritans*, *Tunga penetrans*, *Xenopsylla cheopis*; from the order of the Heteropterida, for example *Cimex* spp., *Triatoma* spp., *Rhodnius* spp., *Panstrongylus* spp; from the order of the Blattarida, for example

*Blatta orientalis, Periplaneta americana, Blattela germanica, Supella* spp. (e.g. *Suppella longipalpa*); from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp., *Ctenocephalides canis, Cimx lecturius, Ctenocephalides felis, Lucilia cuprina*, examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasitical composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasitical compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, [M+H]⁺=molecular mass of the molecular cation, [M−H]⁻=molecular mass of the molecular *anion*.

The following LC-MS methods were used to characterize the compounds:

Method A

| | |
|---|---|
| MS | Shimadzu LCMS-2010EV Mass Spectrometer (Single quadrupole mass spectrometer) |
| | Ionisation method: Electrospray |
| | Polarity: positive and negative ions |
| | Capillary (kV) 1.50, Extractor (V) 5.00, Source Temperature (° C.) 200, Desolvation Temperature (° C.) 250, Cone Gas Flow (L/Hr) 90, Desolvation Gas Flow (L/Hr) 90 |
| | Mass range: 50 to 1000 Da |
| LC | LC-20AD Method Waters ACQUITY UPLC with the following HPLC gradient conditions |
| | Detector: 254 nm |
| | Diamonsil C18(2) 4.6*150 mm 5 μm |
| | (Solvent A: Water, 0.1% trifluoroacetic acid and Solvent B: Acetonitrile, 0.1% trifluoroacetic acid) |

| Time (min) | A % | B % | Flow (mL/min) |
|---|---|---|---|
| 0 | 90 | 10 | 1.00 |
| 15.00 | 0 | 100 | 1.00 |
| 25.00 | 0 | 100 | 1.00 |
| 27.00 | 90 | 10 | 1.00 |
| 36.00 | 90 | 10 | 1.00 |

Method B

| | |
|---|---|
| MS | ACQUITY SQD Mass Spectrometer from Waters (Single quadrupole mass spectrometer) |
| | Ionisation method: Electrospray |
| | Polarity: positive ions |
| | Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 |
| | Mass range: 100 to 800 Da |
| | DAD Wavelength range (nm): 210 to 400 |
| LC | Method Waters ACQUITY UPLC with the following HPLC gradient conditions (Solvent A: Water/Methanol 9:1, 0.1% formic acid and Solvent B: Acetonitrile, 0.1% formic acid) |

| Time (min) | A % | B % | Flow (mL/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

N-(3-(2-(3,5-dichlorophenyl)-2-(trifluoromethyl)-2,3-dihydrobenzofuran-5-yl)phenyl)cyclopropanecarboxamide (141)

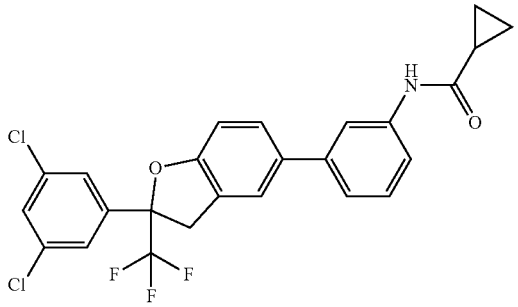 [SMILES: O=C(Nc1cccc(-c2ccc3c(c2)CC(c2cc(Cl)cc(Cl)c2)(C(F)(F)F)O3)c1)C1CC1]

Step A: Synthesis of 2-methyl-1,4-dinitrobenzene

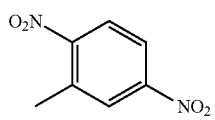

At 50-60° C., 2-methyl-4-nitroaniline (30.4 g) was slowly added to a stirred solution of sodium peroxyboratetetrahydrate (154 g) in 250 mL of acetic acid. After the addition, the mixture was stirred at the same temperature for another 16 h. Then, it was poured into ice water and filtered. The filter cake was purified by flash chromatography on silica gel to give the title compound (17.8 g). ¹H NMR (300 MHz, CDCl₃): δ 2.69 (s, 3H), 8.06 (d, 1H), 8.18 (d, 1H), 8.22 (s, 1H).

Step B: Synthesis of 2-(3,5-dichlorophenyl)-5-nitro-2-(trifluoromethyl)-2,3-dihydrobenzofuran

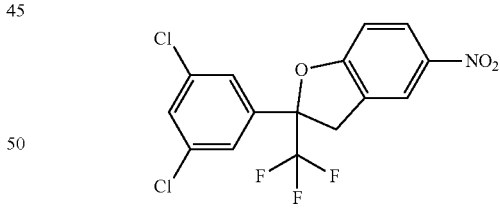

To a mixture of compound 2-methyl-1,4-dinitrobenzene (22 g), compound 1-(3,5-dichlorophenyl)-2,2,2-trifluoroethanone (34.85 g), and i-Pr₂NEt (31 g) in 100 mL of dry THF was added tetrabutyl ammonium fluoride (47 g) at room temperature. After the addition, the mixture was refluxed for 16 h under nitrogen. Then the reaction mixture was poured into water and extracted with ethyl acetate three times. The combined organic layers were dried over sodium sulfate, filtered and concentrated under vacuum. The residue was purified by recrystallization with petroleum ether to give the title compound (24.88 g). ¹H NMR (300 MHz, CDCl₃): δ 3.66 (d, 1H), 4.04 (d, 1H), 7.09 (d, 1H), 7.43 (m, 1H), 7.49 (s, 2H), 8.12 (s, 1H), 8.20 (d, 1H).

Step C: Synthesis of 2-(3,5-dichlorophenyl)-2-(trifluoromethyl)-2,3-dihydrobenzofuran-5-amine

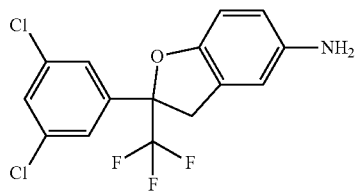 [SMILES: Nc1ccc2c(c1)CC(c1cc(Cl)cc(Cl)c1)(C(F)(F)F)O2]

A mixture of compound 2-(3,5-dichlorophenyl)-5-nitro-2-(trifluoromethyl)-2,3-dihydrobenzofuran (20 g) and Raney-nickel (3 g) in 100 mL of MeOH and 100 mL of THF was hydrogenated at 1 bar of hydrogen pressure at room temperature for 3 h. Then, the mixture was filtered. The filtrate was concentrated under vacuum. The residue was purified by flash chromatography on silica gel to give the title compound (18 g). $^1$H NMR (300 MHz, DMSO-d$_6$): δ 3.64 (d, 1H), 3.85 (d, 1H), 4.74 (br s, 2H), 6.40 (dd, 1H), 6.46 (s, 1H), 6.75 (d, 1H), 7.62 (s, 2H), 7.73 (s, 1H); ESI-MS: 348 (M+H)$^+$, 380 (M+Na)$^+$.

Step D: Synthesis of 2-(3,5-dichlorophenyl)-5-iodo-2-(trifluoromethyl)-2,3-dihydrobenzofuran

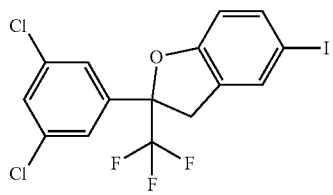 [SMILES: FC(F)(F)C1(c2cc(Cl)cc(Cl)c2)Cc2cc(I)ccc2O1]

Compound 2-(3,5-dichlorophenyl)-2-(trifluoromethyl)-2,3-dihydrobenzofuran-5-amine (5.4 g) was dissolved in 105 mL of water and 30 mL of concentrated sulphuric acid. After the solution was cooled to 0° C., sodium nitrite (1.176 g) in 30 mL of water was added and stirring was continued for 1 h at 0-5° C. Then, potassium iodide (3.345 g) in 45 mL of water was slowly added to the mixture. After the addition, the mixture was allowed to warm to the room temperature and extracted with ethyl acetate three times. The combined organic phases were washed with Na$_2$S$_2$O$_3$ three times, dried over Na$_2$SO$_4$, filtered and concentrated under vacuum. The residue was purified by flash chromatography on silica gel to give the title compound (4 g). $^1$H NMR (300 MHz, DMSO-d$_6$): δ 3.81 (d, 1H), 4.00 (d, 1H), 6.96 (d, 1H), 7.54 (d, 1H), 7.60 (s, 1H), 7.65 (s, 2H), 7.76 (m, 1H).

Step E: Synthesis of 3-(2-(3,5-dichlorophenyl)-2-(trifluoromethyl)-2,3-dihydrobenzofuran-5-yl)aniline

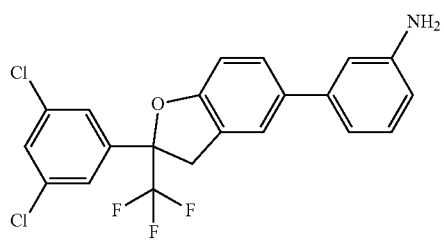 [SMILES: Nc1cccc(-c2ccc3c(c2)CC(c2cc(Cl)cc(Cl)c2)(C(F)(F)F)O3)c1]

A mixture of compound 2-(3,5-dichlorophenyl)-5-iodo-2-(trifluoromethyl)-2,3-dihydrobenzofuran (1.374 g), 3-aminophenylboronic acid hydrate (558 mg), Pd(PPh$_3$)$_4$ (105 mg) and K$_2$CO$_3$ (1.242 g) in 56 mL of diemthoxyethane and 24 mL of H$_2$O was refluxed for 2 h under nitrogen. Then, the mixture was poured into water and extracted with ethyl acetate three times. The organic phase was dried over anhydrous sodium sulfate and concentrated in vacuo. The residue was purified by flash column chromatography on silica gel to give the title compound (0.72 g). $^1$H NMR (300 MHz, DMSO-d$_6$): δ 3.84 (d, 1H), 4.04 (d, 1H), 5.11 (br s, 2H), 6.50 (d, 1H), 6.68 (d, 1H), 6.74 (s, 1H), 7.04 (m, 1H), 7.13 (d, 1H), 7.38 (d, 1H), 7.42 (s, 1H), 7.69 (s, 2H), 7.76 (s, 1H).

Step F: Synthesis of N-(3-(2-(3,5-dichlorophenyl)-2-(trifluoromethyl)-2,3-dihydrobenzofuran-5-yl)phenyl)cyclopropanecarboxamide (141)

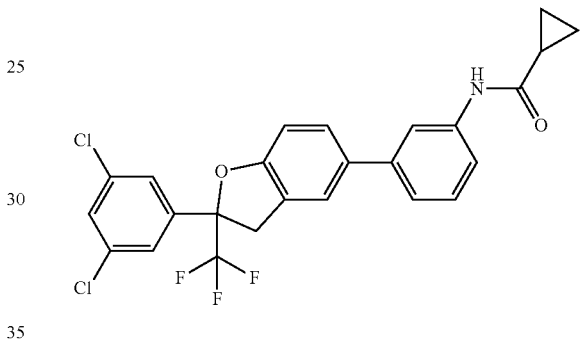

To a mixture of compound 3-(2-(3,5-dichlorophenyl)-2-(trifluoromethyl)-2,3-dihydrobenzofuran-5-yl)aniline (210 mg) and Et$_3$N (101 mg) in 25 mL of dry THF was slowly added cyclopropanecarbonyl chloride (624 mg) under nitrogen. After the addition, the mixture was stirred for another 2 h. Then, the mixture was poured into water and extracted with ethyl acetate three times. The organic phase was dried over anhydrous sodium sulfate and concentrated in vacuo. The residue was purified by flash column chromatography on silica gel to give the title compound 141 (200 mg). $^1$H NMR (300 MHz, DMSO-d$_6$): δ 0.79 (m, 4H), 1.73-1.83 (m, 1H), 3.87 (d, 1H), 4.06 (d, 1H), 7.19-7.50 (m, 6H), 7.69 (m, 2H), 7.76 (m, 1H), 7.87 (s, 1H), 10.26 (s, 1H); $^{19}$F NMR (282 MHz, DMSO-d$_6$): δ−74.16 (s, 3F); ESI-MS: 492 (M+H)$^+$, 514(M+Na)$^+$; m.p.: 220-222° C.; HPLC: 98.9%.

Synthesis of N-(3-(2-(3,5-dichlorophenyl)-2-(trifluoromethyl)-2,3-dihydrobenzofuran-5-yl)-2-fluorophenyl)cyclopropanecarboxamide (42)

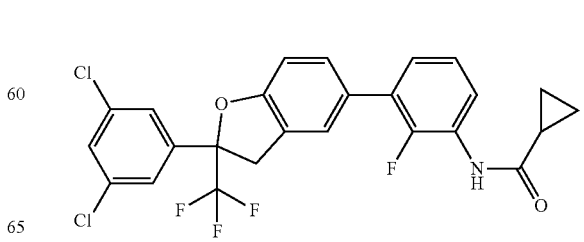

Step A: Synthesis of 2-(2-fluoro-3-nitrophenyl)-4,4,5,5-tetramethyl-1,3,2-dioxaborolane

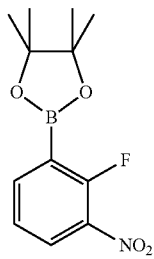 [SMILES: CC1(C)OB(c2cccc([N+](=O)[O-])c2F)OC1(C)C]

Compound 1-bromo-2-fluoro-3-nitrobenzene (440 mg) was dissolved in 10 mL of dry 1,4-dioxane. To this was added potassium acetate, followed by bis(pinacolato)diboron (759 mg). Nitrogen was bubbled through the reaction vessel for 1 min and PdCl$_2$(dppf) (164 mg) was added. The reaction mixture was sealed and heated to 90° C. for 16 h, then cooled to room temperature and poured into water and extracted with ethyl acetate three times. The combined organic layers were dried over sodium sulfate, filtered and concentrated under vacuum to give the title compound (488 mg). $^1$H NMR (300 MHz, CDCl$_3$): δ 1.37 (s, 12H), 7.27 (m, 1H), 7.99 (m, 1H), 8.09 (m, 1H).

Step B: Synthesis of 2-(3,5-dichlorophenyl)-5-(2-fluoro-3-nitrophenyl)-2-(trifluoromethyl)-2,3-dihydrobenzofuran

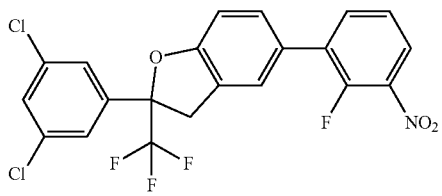

Under the protection of nitrogen, compound 2-(3,5-dichlorophenyl)-5-iodo-2-(trifluoromethyl)-2,3-dihydrobenzofuran (458 mg), PdCl$_2$(dppf) (80 mg), potassium carbonate (414 mg) and compound 2-(2-fluoro-3-nitrophenyl)-4,4,5,5-tetramethyl-1,3,2-dioxaborolane (400 mg) were dissolved in 20 mL of DME and 10 mL of H$_2$O. After the addition, the mixture was refluxed for 1 h. Then, it was filtered through silica gel, and concentrated under vacuum. The residue was purified by column chromatography on silica gel to give the title compound (400 mg). $^1$H NMR (300 MHz, DMSO-d6): δ 3.92 (d, 1H), 4.10 (d, 1H), 7.27 (d, 1H), 7.45-7.52 (m, 3H), 7.73 (s, 2H), 7.78 (s, 1H), 7.86 (t, 1H), 8.10 (t, 1H).

Step C: Synthesis of 3-(2-(3,5-dichlorophenyl)-2-(trifluoromethyl)-2,3-dihydrobenzofuran-5-yl)-2-fluoroaniline

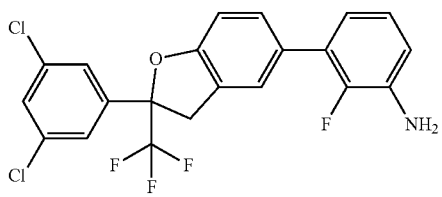 [SMILES: O=[N+]([O-])c1cccc(-c2ccc3c(c2)CC(c2cc(Cl)cc(Cl)c2)(C(F)(F)F)O3)c1F]

A mixture of compound 2-(3,5-dichlorophenyl)-5-(2-fluoro-3-nitrophenyl)-2-(trifluoromethyl)-2,3-dihydrobenzofuran (350 mg) and Raney-Nickel (150 mg) in 10 mL of MeOH and 10 mL of H$_2$O was hydrogenated at 1 bar of hydrogen pressure at room temperature for 30 min. Then, the mixture was filtered. The filtrate was concentrated under vacuum. The residue was purified by flash column chromatography on silica gel to give the title compound (320 mg). $^1$H NMR (300 MHz, DMSO-d$_6$): δ 3.86 (d, 1H), 4.05 (d, 1H), 5.15 (br s, 2H), 6.52 (t, 1H), 6.71 (t, 1H), 6.88 (t, 1H), 7.17 (d, 1H), 7.33 (d, 1H), 7.37 (s, 1H), 7.70 (s, 2H), 7.77 (s, 1H); ESI-MS: 440 (M–H)$^-$.

Step D: Synthesis of N-(3-(2-(3,5-dichlorophenyl)-2-(trifluoromethyl)-2,3-dihydrobenzofuran-5-yl)-2-fluorophenyl)cyclopropanecarboxamide (42)

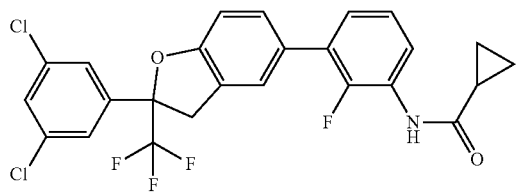 [SMILES: O=C(Nc1cccc(-c2ccc3c(c2)CC(c2cc(Cl)cc(Cl)c2)(C(F)(F)F)O3)c1F)C1CC1]

To a mixture of compound 3-(2-(3,5-dichlorophenyl)-2-(trifluoromethyl)-2,3-dihydrobenzofuran-5-yl)-2-fluoroaniline (380 mg) and Et$_3$N (173 mg) in 25 mL of dry THF was added cyclopropanecarbonyl chloride (108 mg) under nitrogen. After the addition, the mixture was stirred for another 2 h. Then, it was poured into water and extracted with ethyl acetate three times. The organic phase was dried over anhydrous sodium sulfate and concentrated under vacuum. The residue was purified by flash column chromatography on silica gel to give the title compound 42 (400 mg). $^1$H NMR (300 MHz, DMSO-d$_6$): δ 0.81-0.83 (m, 4H), 2.00-2.06 (m, 1H), 3.92 (d, 1H), 4.10 (d, 1H), 7.19 (s, 1H), 7.21 (s, 1H), 7.24 (d, 1H), 7.42 (d, 1H), 7.45 (s, 1H), 7.74 (s, 2H), 7.81 (s, 1H), 7.87 (q, 1H), 10.05 (s, 1H); $^{19}$F NMR (282 MHz, DMSO-d$_6$): δ−75.48 (s, 3F), −130.72 (s, 3F); ESI-MS: 508 [M−H]$^-$; m.p.: 230-232° C.; HPLC: 98.3%.

Synthesis of N-(3-(2-(trifluoromethyl)-2-(3-(trifluoromethyl)phenyl)-2,3-dihydrobenzofuran-5-yl)phenyl)cyclopropanecarboxamide (182)

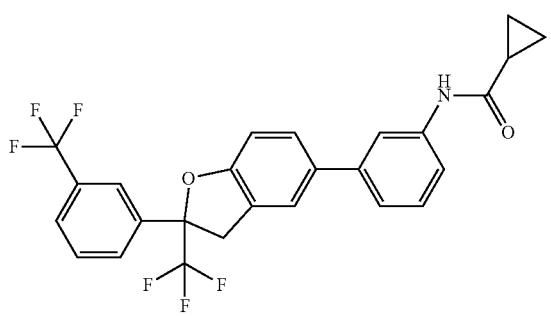 [SMILES: O=C(Nc1cccc(-c2ccc3c(c2)CC(c2cccc(C(F)(F)F)c2)(C(F)(F)F)O3)c1)C1CC1]

Step A: Synthesis of 5-nitro-2-(trifluoromethyl)-2-(3-(trifluoromethyl)phenyl)-2,3-dihydrobenzofuran

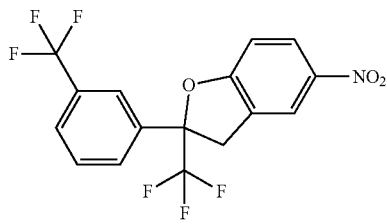 [SMILES: O=[N+]([O-])c1ccc2c(c1)CC(c1cccc(C(F)(F)F)c1)(C(F)(F)F)O2]

At room temperature, to a mixture of compound 2-methyl-1,4-dinitrobenzene (9.1 g), compound 2,2,2-trifluoro-1-(3-(trifluoromethyl)phenyl)ethanone (13.31 g), and i-Pr$_2$NEt (12.9 g, 0.1 mol) in 100 mL of dry THF was added tetrabutylammonium fluoride (52.2 g). After the addition, the mixture was refluxed for 16 h under nitrogen. Then the reaction mixture was poured into water and extracted with ethyl acetate three times. The combined organic layers were dried over sodium sulfate, filtered and concentrated under vacuum. The residue was purified by recrystallization with petroleum ether to give the title compound (12 g). $^1$H NMR (300 MHz, DMSO-d$_6$): δ 4.00 (d, 1H), 4.24 (d, 1H), 7.37 (d, 1H), 7.80-7.83 (m, 1H), 7.9-8.00 (m, 3H), 8.21 (m, 2H).

Step B: Synthesis of 2-(trifluoromethyl)-2-(3-(trifluoromethyl)phenyl)-2,3-dihydrobenzofuran-5-amine

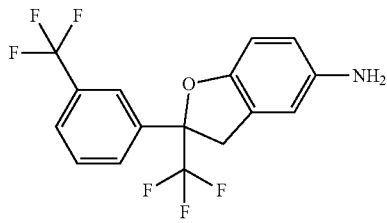 [SMILES: Nc1ccc2c(c1)CC(c1cccc(C(F)(F)F)c1)(C(F)(F)F)O2]

A mixture of compound 5-nitro-2-(trifluoromethyl)-2-(3-(trifluoromethyl)phenyl)-2,3-dihydrobenzofuran (0.7 g) and Raney-Nickel (0.2 g) in 25 mL of MeOH and 25 mL of THF was hydrogenated at 1 bar of hydrogen pressure at room temperature for 3 h. Then, the mixture was filtered and the filtrate was concentrated under vacuum. The residue was purified by column chromatography on silica gel to give the title compound (0.6 g). $^1$H NMR (300 MHz, DMSO-d$_6$): δ 3.66 (d, 1H), 3.90 (d, 1H), 4.74 (s, 2H), 6.39 (d, 1H), 6.49 (s, 1H), 6.75 (d, 1H), 7.69-7.93 (m, 4H).

Step C: Synthesis of 5-iodo-2-(trifluoromethyl)-2-(3-(trifluoromethyl)phenyl)-2,3-dihydrobenzofuran

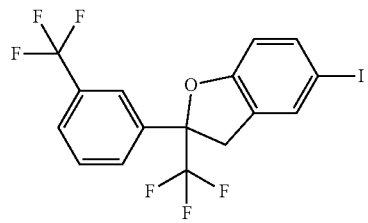 [SMILES: FC(F)(F)c1cccc(C2(C(F)(F)F)Cc3cc(I)ccc3O2)c1]

At 0° C., sodium nitrite (0.897 g) in 20 mL of water was slowly added to a mixture of compound 2-(trifluoromethyl)-2-(3-(trifluoromethyl)phenyl)-2,3-dihydrobenzofuran-5-amine (3.47 g) in 65 mL of water and 21 mL of concentrated sulphuric acid. After the addition, the mixture was stirred for another 0.5 h at the same temperature. Then, potassium iodide (2.158 g) dissolved in 30 mL of water was slowly added to the mixture and the resulting mixture was allowed to warm to the room temperature for 2 h. The aqueous phase was extracted with ethyl acetate three times. The combined organic phases were washed with Na$_2$S$_2$O$_3$ three times, dried over Na$_2$SO$_4$, filtered and concentrated under vacuum. The residue was purified by flash chromatography on silica gel to give the title compound (1.67 g). $^1$H NMR (300 MHz, CDCl$_3$): δ 3.60 (d, 1H), 4.01 (d, 1H), 6.80 (d, 1H), 7.50-7.86 (m, 6H).

Step D: Synthesis of 3-(2-(trifluoromethyl)-2-(3-(trifluoromethyl)phenyl)-2,3-dihydrobenzofuran-5-yl)aniline

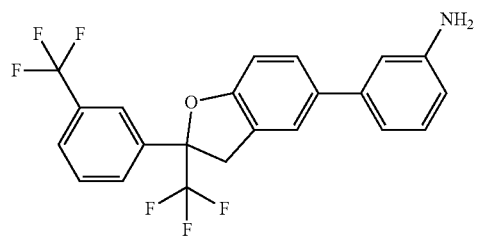 [SMILES: Nc1cccc(-c2ccc3c(c2)CC(c2cccc(C(F)(F)F)c2)(C(F)(F)F)O3)c1]

A mixture of compound 5-iodo-2-(trifluoromethyl)-2-(3-(trifluoromethyl)phenyl)-2,3-dihydrobenzofuran (916 mg), compound 3-aminophenylboronic acid hydrate (372 mg) Pd(PPh$_3$)$_4$(70 mg) and K$_2$CO$_3$(838 mg) in 60 mL of dimethoxyethane and 30 mL of H$_2$O was refluxed for 2 h under nitrogen. Then the mixture was poured into water and extracted with ethyl acetate three times. The organic phase was dried over anhydrous sodium sulfate and concentrated under vacuum. The residue was purified by flash column chromatography on silica gel to give the title compound (300 mg). $^1$H NMR (300 MHz, DMSO-d$_6$): δ 3.87 (d, 1H), 4.11 (d, 1H), 5.10 (s, 2H), 6.51 (d, 1H), 6.67 (d, 1H), 6.74 (s, 1H), 7.04 (m, 1H), 7.14 (d, 1H), 7.38 (d, 1H), 7.44 (s, 1H), 7.76 (m, 1H), 7.87 (d, 1H), 7.94 (s, 1H), 7.99 (d, 1H); ESI-MS: 424 (M+H)$^+$.

Step E: Synthesis of N-(3-(2-(trifluoromethyl)-2-(3-(trifluoromethyl)phenyl)-2,3-dihydrobenzofuran-5-yl)phenyl)cyclopropanecarboxamide (182)

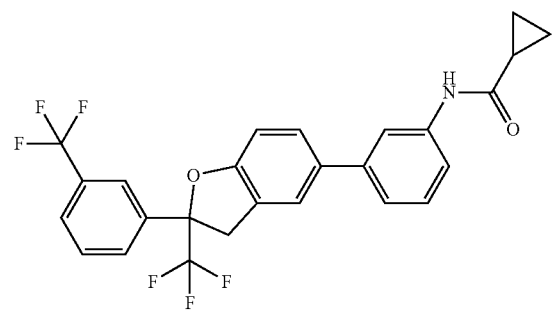 [SMILES: O=C(Nc1cccc(-c2ccc3c(c2)CC(c2cccc(C(F)(F)F)c2)(C(F)(F)F)O3)c1)C1CC1]

Under nitrogen, cyclopropanecarbonyl chloride (624 mg) was added to a mixture of 3-(2-(trifluoromethyl)-2-(3-(trifluoromethyl)phenyl)-2,3-dihydrobenzofuran-5-yl)aniline (210 mg) and Et$_3$N (101 mg) in 25 mL of dry THF. After the addition, the mixture was stirred for another 2 h. Then, the mixture was poured into water and extracted with ethyl acetate three times. The organic phase was dried over anhydrous sodium sulfate and concentrated under vacuum. The residue was purified by flash column chromatography on silica gel to give the title compound (200 mg). $^1$H NMR (300 MHz, DMSO-d$_6$): δ 0.79 (m, 4H), 1.73-1.77 (m, 1H), 3.90 (d, 1H), 4.13 (d, 1H), 7.21-7.23 (m, 2H), 7.29-7.34 (m, 1H), 7.42-7.49 (m, 3H), 7.77 (m, 1H), 7.86-7.99 (m, 4H), 10.26 (s, 1H); $^{19}$F NMR (282 MHz, DMSO-d$_6$): δ−56.08 (s, 3F), −74.54 (s, 3F); ESI-MS: 490 [M−H]$^-$; m.p.: 180-182° C.; HPLC: 99.9%.

Synthesis of N-[4-[2-(3,5-dichlorophenyl)-2-(trifluoromethyl)-3H-benzofuran-5-yl]-2-pyridyl]cyclopropanecarboxamide (137)

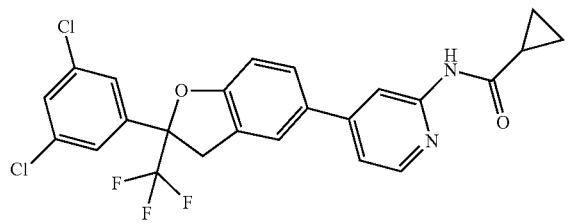 [SMILES: O=C(Nc1cc(-c2ccc3c(c2)CC(c2cc(Cl)cc(Cl)c2)(C(F)(F)F)O3)ccn1)C1CC1]

Step A: Synthesis of N-(4-bromo-2-pyridyl)cyclopropanecarboxamide

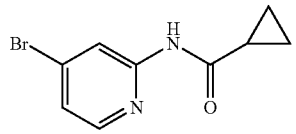 [SMILES: O=C(Nc1cc(Br)ccn1)C1CC1]

Cyclopropanecarboxylic acid chloride (104 mg, 1 mmol) was added to a solution of 4-bromopyridin-2-amine (173 mg, 1 mmol) in 10 mL of THF at 0° C. After the addition, the mixture was stirred at room temperature for 16 h. Then, the mixture was poured into water and extracted with ethyl acetate three times. The combined organic layers were dried over sodium sulfate, filtered and concentrated under reduced pressure. The residue was purified by column chromatography on silica gel to provide the title compound (100 mg, 41% yield). $^1$H NMR (300 MHz, CDCl$_3$): δ 0.88-0.95 (m, 2H), 1.06-1.14 (m, 2H), 1.60-1.68 (m, 1H), 7.18-7.20 (m, 1H), 8.03 (d, 1H), 8.54 (s, 1H), 9.43 (s, 1H).

Step B: Synthesis of 5-bromo-2-(3,5-dichlorophenyl)-2-(trifluoromethyl)-3H-benzofuran

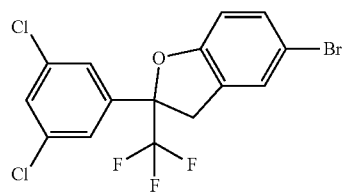 [SMILES: FC(F)(F)C1(c2cc(Cl)cc(Cl)c2)Cc2cc(Br)ccc2O1]

CuBr$_2$ (134 mg, 0.6 mmol) was added to a mixture of 2-(3,5-dichlorophenyl)-2-(trifluoromethyl)-2,3-dihydrobenzofuran-5-amine (2.0 g, 5.8 mmol), isoamyl nitrite (0.8 g, 6.8 mmol), p-TsOH (1.2 g, 7.0 mmol), tetrabutyl ammonium bromide (3.7 g, 11 mmol) in 55 mL of CH$_3$CN. After stirring at room temperature for 2 h, the mixture was filtered and concentrated under vacuum. The residue was purified by column chromatography on silica gel to give the title compound (1.5 g, 61% yield). $^1$H NMR (300 MHz, CDCl$_3$): δ3.53 (d, 1H), 3.93 (d, 1H), 6.87 (d, 1H), 7.26-7.34 (m, 2H), 7.41 (s, 1H), 7.48-7.52 (m, 2H).

Step C: Synthesis of 2-[2-(3,5-dichlorophenyl)-2-(trifluoromethyl)-3H-benzofuran-5-yl]-4,4,5,5-tetramethyl-1,3,2-dioxaborolane

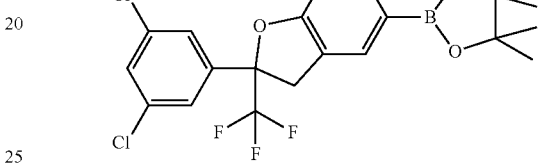

Under nitrogen, a mixture of 5-bromo-2-(3,5-dichlorophenyl)-2-(trifluoromethyl)-3H-benzofuran (4.0 g, 9.7 mmol), bis(pinacolato)diboron (3.7 g, 15 mmol), PdCl$_2$(dppf) (0.8 g, 1 mmol) and KOAc (4.8 g, 49 mmol) in 95 mL of 1,4-dioxane was stirred at 90° C. for 16 h. Then the mixture was filtered and concentrated under reduced pressure. The residue was purified by column chromatography on silica gel to give the title compound (4.0 g, 89% yield). $^1$H NMR (300 MHz, CDCl$_3$): δ 1.34 (s, 12H), 3.51 (d, 1H), 3.93 (d, 1H), 7.01 (d, 1H), 7.28 (s, 1H), 7.41 (s, 1H), 7.52 (s, 1H), 7.67 (s, 1H), 7.71 (d, 1H).

Step D: Synthesis of N-[4-[2-(3,5-dichlorophenyl)-2-(trifluoromethyl)-3H-benzofuran-5-yl]-2-pyridyl]cyclopropanecarboxamide (137)

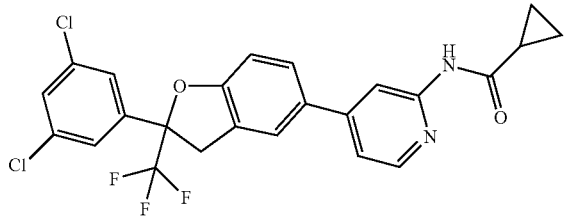 [SMILES: O=C(Nc1cc(-c2ccc3c(c2)CC(c2cc(Cl)cc(Cl)c2)(C(F)(F)F)O3)ccn1)C1CC1]

Under the protection of nitrogen, N-(4-bromopyridin-2-yl)cyclopropanecarboxamide (289 mg, 1.2 mmol), Pd(PPh$_3$)$_4$ (82 mg, 0.1 mmol), potassium carbonate (414 mg, 3 mmol) and 2-[2-(3,5-dichlorophenyl)-2-(trifluoromethyl)-3H-benzofuran-5-yl]-4,4,5,5-tetramethyl-1,3,2-dioxaborolane (458 mg, 1 mmol) were dissolved in 30 mL of DME and 10 mL of H$_2$O. The mixture was refluxed for 2 h. Then, it was poured into water and extracted with ethyl acetate three times. The combined organic layers were dried over sodium sulfate, filtered and concentrated under reduced pressure. The residue was purified by column chromatography on silica gel to provide compound 137 (156 mg, 32% yield). $^1$H NMR (300 MHz, DMSO-d$_6$): δ 0.80-0.83 (m, 4H), 2.00-2.04 (m, 1H), 3.88 (d, 1H), 4.07 (d, 1H), 7.23 (d, 1H), 7.32 (dd, 1H), 7.58-7.63 (m, 1H), 7.07 (s, 1H), 7.71 (d, 2H), 7.78-1.80 (m, 1H), 8.31-8.34 (m, 2H), 10.81 (s, 1H); $^{19}$F NMR (300 MHz, DMSO-d$_6$): δ−74.42 (s, 3F); ESI-MS(+): 514 (M+Na)$^+$.

Synthesis of N-[2-cyano-5-[2-(3,5-dichlorophenyl)-2-(trifluoromethyl)-3H-benzofuran-5-yl]phenyl]propanamide (198)

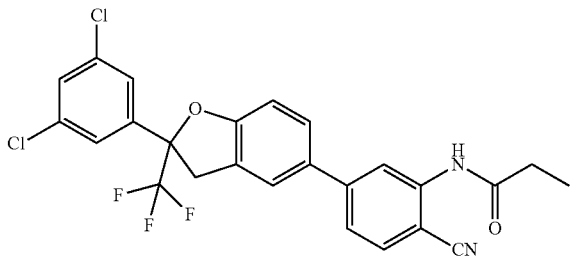 [SMILES: CCC(=O)Nc1cc(-c2ccc3c(c2)CC(c2cc(Cl)cc(Cl)c2)(C(F)(F)F)O3)ccc1C#N]

Step A: Synthesis of 2-amino-4-[2-(3,5-dichlorophenyl)-2-(trifluoromethyl)-3H-benzofuran-5-yl]benzonitrile

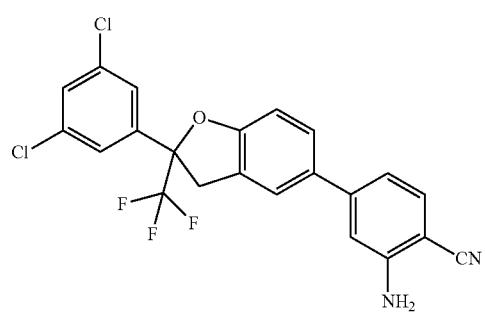 [SMILES: N#Cc1ccc(-c2ccc3c(c2)CC(c2cc(Cl)cc(Cl)c2)(C(F)(F)F)O3)cc1N]

Under the protection of nitrogen, compound 1 (418 mg, 0.91 mmol), Pd(PPh$_3$)$_4$ (88 mg, 0.08 mmol), potassium carbonate (635 g, 4.57 mmol) and 2-amino-4-bromobenzonitrile (150 mg, 0.76 mmol) were dissolved in 14 mL of DME and 6 mL of H$_2$O. After the addition, the mixture was refluxed for 2 h. Then, it was poured into water and extracted with ethyl acetate three times. The combined organic layers were dried over sodium sulfate, filtered and concentrated under reduced pressure. Then, get the crude compound 3 (259 mg, 74% yield). $^1$H NMR (300 MHz, DMSO-d$_6$): δ 3.87 (d, 1H), 4.06 (d, 1H), 6.10 (br s, 2H), 6.82-6.85 (m, 1H), 7.00 (s, 1H), 7.21 (d, 1H), 7.43-7.50 (m, 2H), 7.52 (s, 1H), 7.72 (s, 2H), 7.79-7.80 (m, 1H); $^{19}$F NMR (300 MHz, DMSO-d$_6$): δ −74.44 (s, 3F).

Step B: Synthesis of N-[2-cyano-5-[2-(3,5-dichlorophenyl)-2-(trifluoromethyl)-3H-benzofuran-5-yl]phenyl]propanamide (198)

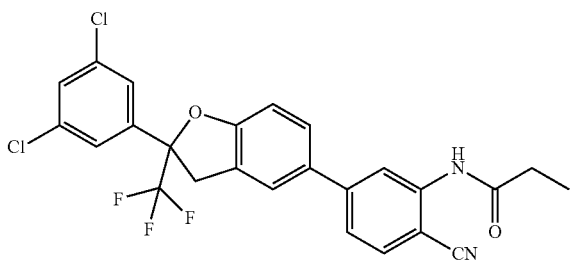 [SMILES: CCC(=O)Nc1cc(-c2ccc3c(c2)CC(c2cc(Cl)cc(Cl)c2)(C(F)(F)F)O3)ccc1C#N]

Propionyl chloride (69 mg, 0.75 mmol) was added to a solution of 2-amino-4-[2-(3,5-dichlorophenyl)-2-(trifluoromethyl)-3H-benzofuran-5-yl]benzonitrile (230 mg, 0.5 mmol) and potassium carbonate (206 mg, 1.5 mmol) in 10 mL of acetone at 0° C. After the addition, the mixture was stirred at the same temperature for 30 min. Then, the mixture was poured into water and extracted with ethyl acetate three times. The combined organic layers were dried over sodium sulfate, filtered and concentrated under reduced pressure. The residue was purified by column chromatography on silica gel to provide product 198 (287 mg, 93% yield). $^1$H NMR (300 MHz, DMSO-d$_6$): δ 1.10 (t, 3H), 2.38 (q, 2H), 3.88 (d, 1H), 4.07 (d, 1H), 7.24 (d, 1H), 7.57-7.62 (m, 2H), 7.64 (s, 1H), 7.74 (s, 2H), 7.79-7.80 (m, 1H), 7.84-7.87 (m, 2H), 10.14 (s, 1H); $^{19}$F NMR (300 MHz, DMSO-d$_6$): δ −74.43 (s, 3F); ESI-MS(−): 503 (M−1).

Synthesis of N-[2-[6-chloro-2-(3,5-dichlorophenyl)-2-(trifluoromethyl)-3H-benzofuran-5-yl]-4-pyridyl]propanamide (136)

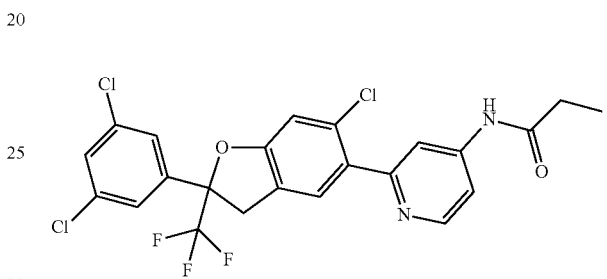

Step A: Synthesis of 1-chloro-4-methyl-2,5-dinitro-benzene

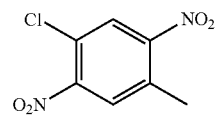

At 60° C., 5-chloro-2-methyl-4-nitrobenzenamine (18.6 g, 0.1 mol) was slowly added to a stirred solution of sodium peroxyboratetetrahydrate (77 g, 0.5 mol) in 300 mL of AcOH. After the addition, the mixture was stirred at the same temperature for another 16 h. Then, it was poured into ice water and filtered. The filter cake was purified by flash chromatography on silica gel to give the title compound (14.6 g, 68% yield). $^1$H NMR (300 MHz, CDCl$_3$): δ 2.54 (s, 3H), 8.32 (s, 1H), 8.43 (s, 1H).

Step B: Synthesis of 6-chloro-2-(3,5-dichlorophenyl)-5-nitro-2-(trifluoromethyl)-3H-benzofuran

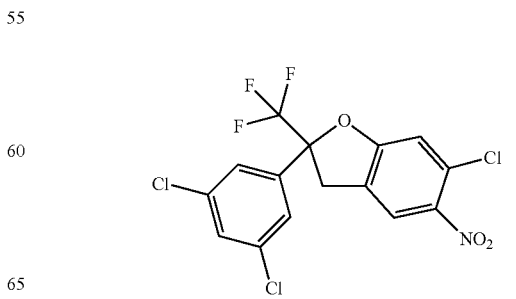

Under nitrogen, to a mixture of 1-chloro-4-methyl-2,5-dinitrobenzene (14 g, 65 mmol), 1-(3,5-dichlorophenyl)-2,2,2-trifluoroethanone (19.7 g, 81 mmol) and i-Pr$_2$NEt (13.97 g, 110 mmol) in 100 mL of dry THF was added TBAF (22.5 g, 98 mmol) at room temperature. After the addition, the mixture was refluxed for 16 h. Then the reaction mixture was poured into water and extracted with ethyl acetate three times. The combined organic layers were dried over sodium sulfate, filtered and concentrated under vacuum. The residue was purified by recrystallization with petroleum ether to give the title compound (9.89 g, 37% yield). $^1$H NMR (300 MHz, DMSO-d$_6$): δ 3.97 (d, 1H), 4.11 (d, 1H), 7.64 (s, 1H), 7.71 (s, 2H), 7.82 (s, 1H), 8.11 (s, 1H).

Step C: Synthesis of 6-chloro-2-(3,5-dichlorophenyl)-2-(trifluoromethyl)-3H-benzofuran-5-amine

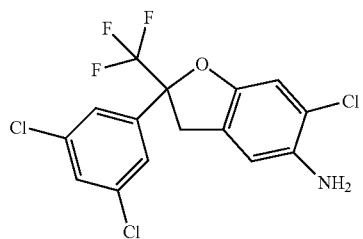 [SMILES: O=[N+]([O-])c1cc2c(cc1Cl)OC(c1cc(Cl)cc(Cl)c1)(C(F)(F)F)C2]

A mixture of compound 6-chloro-2-(3,5-dichlorophenyl)-5-nitro-2-(trifluoromethyl)-3H-benzofuran (4.11 g, 10 mmol), Raney-Nickel (500 mg) and hydrazine monohydrate (2.5 g, 50 mmol) in 60 mL of MeOH was stirred at room temperature for 3 h. Then, the mixture was filtered. The filtrate was concentrated under vacuum. The residue was purified by flash chromatography on silica gel to give the title compound (3.3 g, 86% yield). $^1$H NMR (300 MHz, DMSO-d$_6$): δ 3.72 (d, 1H), 3.84 (d, 1H), 4.98 (s, 2H), 6.72 (s, 1H), 7.01 (s, 1H), 7.62 (s, 2H), 7.74 (s, 1H).

Step D: Synthesis of 5-bromo-6-chloro-2-(3,5-dichlorophenyl)-2-(trifluoromethyl)-3H-benzofuran

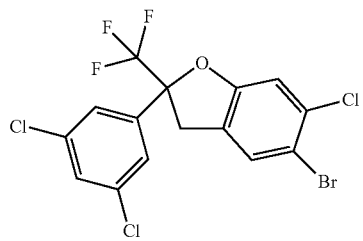 [SMILES: FC(F)(F)C1(c2cc(Cl)cc(Cl)c2)Cc2cc(Br)c(Cl)cc2O1]

CuBr$_2$ (223 mg, 1 mmol) was added to a mixture of 6-chloro-2-(3,5-dichlorophenyl)-2-(trifluoromethyl)-3H-benzofuran-5-amine (3.2 g, 8.4 mmol), isoamyl nitrite (1.18 g, 10.1 mol), p-TsOH (1.74 g, 10.1 mmol), tetrabutyl ammonium bromide (5.41 g, 16.8 mmol) in 150 mL of CH$_3$CN. After the mixture was stirred at room temperature for 2 h, the mixture was filtered and concentrated under vacuum. The crude product was purified by column chromatography on silica gel to give the title product (2.9 g, 79% yield). $^1$H NMR (300 MHz, DMSO-d$_6$): δ 3.88 (d, 1H), 4.02 (d, 1H), 7.51 (s, 1H), 7.69 (s, 3H), 7.80-7.82 (m, 1H); ESI-MS(−): 444 (M−H)$^-$.

Step E: Synthesis of [6-chloro-2-(3,5-dichlorophenyl)-2-(trifluoromethyl)-3H-benzofuran-5-yl]boronic acid

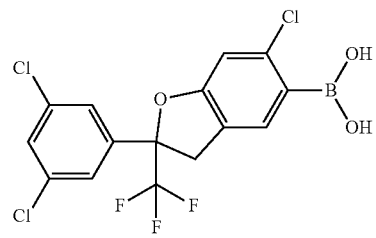 [SMILES: OB(O)c1cc2c(cc1Cl)OC(c1cc(Cl)cc(Cl)c1)(C(F)(F)F)C2]

n-BuLi (2.4 mL, 6 mmol, 2.5M in n-hexane) was added to a solution of 5-bromo-6-chloro-2-(3,5-dichlorophenyl)-2-(trifluoromethyl)-3H-benzofuran (1.3 g, 3 mmol) in 10 mL of anhydrous THF at −60° C. under nitrogen. After the addition, the mixture was stirred for 10 min, then (i-PrO)$_3$B (2.3 mL, 10 mmol) was added to the mixture and stirring was continued for another 30 min. The reaction mixture was poured into diluted hydrochloric acid and extracted with ethyl acetate three times. The combined organic layers were dried over sodium sulfate, filtered and concentrated under vacuum. The residue was purified by recrystallization with petroleum ether to give the crude title compound (541 mg, 44% yield) which was directly used for the next step without further purification.

Step F: Synthesis of N-(2-bromo-4-pyridyl)propanamide

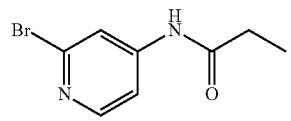

Propionyl chloride (460 mg, 5 mmol) was added to a mixture of 4-amino-2-bromopyridine (519 mg, 3 mmol) and potassium carbonate (1.38 g, 10 mmol) in 20 mL of acetone. After the addition, the mixture was stirred at room temperature for 2 h. Then the reaction mixture was poured into water and extracted with ethyl acetate three times. The combined organic layers were dried over anhydrous Na$_2$SO$_4$, filtered and concentrated under reduced pressure. The residue was purified by column chromatography on silica gel to give the title compound (460 mg, 67% yield).

Step G: Synthesis of N-[2-[6-chloro-2-(3,5-dichlorophenyl)-2-(trifluoromethyl)-3H-benzofuran-5-yl]-4-pyridyl]propanamide (136)

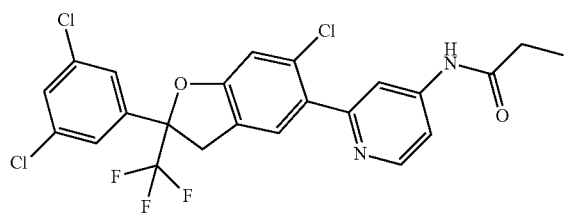 [SMILES: CCC(=O)Nc1ccnc(-c2cc3c(cc2Cl)OC(c2cc(Cl)cc(Cl)c2)(C(F)(F)F)C3)c1]

Under the protection of nitrogen, N-(2-bromopyridin-4-yl)propionamide (115 mg, 0.5 mmol), Pd(PPh₃)₄ (35 mg, 0.05 mmol), potassium carbonate (276 mg, 2 mmol) and [6-chloro-2-(3,5-dichlorophenyl)-2-(trifluoromethyl)-3H-benzofuran-5-yl]boronic acid (205 mg, 0.5 mmol) were dissolved in 5 mL of DME and 1 mL of H₂O. After the addition, the mixture was refluxed for 2 h. Then, it was poured into water and extracted with ethyl acetate three times. The combined organic layers were dried over sodium sulfate, filtered and concentrated under reduced pressure. The residue was purified by column chromatography on silica gel to provide the title compound 136 (167 mg, 65% yield). ¹H NMR (300 MHz, DMSO-d₆): δ 1.09 (t, 3H), 2.38 (q, 2H), 3.86 (d, 1H), 4.06 (d, 1H), 7.41 (s, 1H), 7.48 (s, 1H), 7.57 (dd, 1H), 7.72 (d, 2H), 7.81-7.82 (m, 1H), 7.84 (d, 1H), 8.47 (d, 1H), 10.36 (s, 1H); ¹⁹F NMR (300 MHz, DMSO-d₆): δ−74.52 (s, 3F); ESI-MS(+): 515 (M+H)⁺.

1-{3-[2-(3,5-Dichloro-phenyl)-2-trifluoromethyl-2,3-dihydro-benzofuran-5-yl]-phenyl}-pyrrolidin-2-one

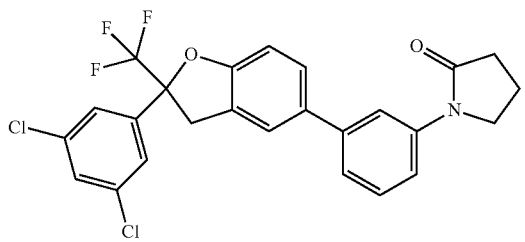 [SMILES: O=C1CCCN1c1cccc(-c2ccc3c(c2)CC(c2cc(Cl)cc(Cl)c2)(C(F)(F)F)O3)c1]

Step A: Synthesis of 4-chloro-N-{3-[2-(3,5-dichloro-phenyl)-2-trifluoromethyl-2,3-dihydro-benzofuran-5-yl]-phenyl}-butyramide

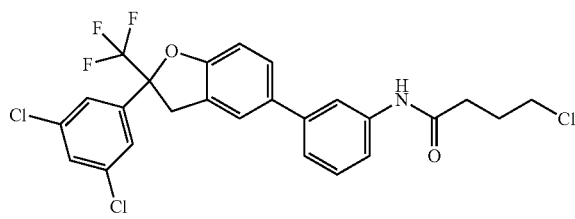 [SMILES: O=C(CCCCl)Nc1cccc(-c2ccc3c(c2)CC(c2cc(Cl)cc(Cl)c2)(C(F)(F)F)O3)c1]

4-Chlorobut 1 chloride (212 mg, 1.5 mmol) was added to a solution of 3-[2-(3,5-Dichloro-phenyl)-2-trifluoromethyl-2,3-dihydro-benzofuran-5-yl]-phenylamine (423 mg, 1 mmol) and Et₃N (303 mg, 0.42 ml, 3 mmol) in 10 mL of tetrahydrofuran at 0° C. After the addition, the mixture was stirred at the same temperature for 30 min. Then, the mixture was poured into water and extracted with ethyl acetate three times. The combined organic layers were dried over sodium sulfate, filtered and concentrated under reduced pressure. The residue was purified by column chromatography on silica gel to provide 4-chloro-N-{3-[2-(3,5-dichloro-phenyl)-2-trifluoromethyl-2,3-dihydro-benzofuran-5-yl]-phenyl}-butyramide (478 mg, 90% yield). ¹H NMR (300 Mz, DMSO-d₆): δ 1.99-2.07 (m, 2H), 2.48-2.53 (m, 2H), 3.69-3.73 (m, 2H), 3.87-3.93 (d, 1H), 4.06-4.12 (d, 1H), 7.19-7.27 (m, 2H), 7.32-7.38 (t, 1H), 7.45-7.51 (m, 3H), 7.72 (d, 2H), 7.79-7.80 (t, 1H), 7.89 (s, 1H), 10.06 (s, 1H); ¹⁹F NMR (282 Mz, CD₃OD): δ−82.60 (s, 3F); ESI-MS(+): 550 (M+Na)⁺.

Step B: Synthesis of 1-{3-[2-(3,5-Dichloro-phenyl)-2-trifluoromethyl-2,3-dihydro-benzofuran-5-yl]-phenyl}-pyrrolidin-2-one

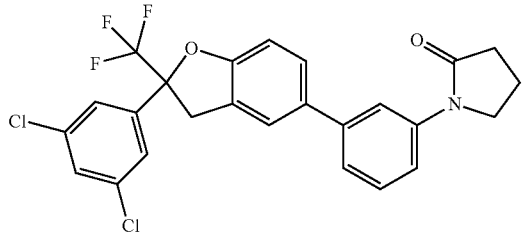 [SMILES: O=C1CCCN1c1cccc(-c2ccc3c(c2)CC(c2cc(Cl)cc(Cl)c2)(C(F)(F)F)O3)c1]

15 mL of NaOEt (1 mol/L in EtOH) was added to a mixture of 4-chloro-N-{3-[2-(3,5-dichloro-phenyl)-2-trifluoromethyl-2,3-dihydro-benzofuran-5-yl]-phenyl}-butyramide (200 mg, 0.38 mmol) in EtOH (2 mL). After stirring at room temperature for 2 h, the reaction mixture was poured into water and extracted with ethyl acetate three times. The combined organic layers were dried over sodium sulfate, filtered and concentrated under vacuum. The residue was purified by column chromatography on silica gel to provide 1-{3-[2-(3,5-Dichloro-phenyl)-2-trifluoromethyl-2,3-dihydro-benzofuran-5-yl]-phenyl}-pyrrolidin-2-one (160 mg, 86% yield). ¹H NMR (300 Mz, CD₃OD): δ 2.12-2.22 (m, 2H), 2.57-2.62 (t, 2H), 3.68-3.74 (d, 1H), 3.92-3.97 (t, 2H), 4.03-4.09 (d, 1H), 7.06-7.08 (d, 1H), 7.33-7.36 (d, 1H), 7.37-7.42 (t, 1H), 7.46-7.55 (m, 3H), 7.54-7.55 (t, 1H), 7.64 (s, 2H), 7.81 (s, 1H); ¹⁹F NMR (282 Mz, CD₃OD): δ−82.60 (s, 3F); ESI-MS(+): 490 (M+H)⁺, 514 (M+Na)⁺.

4-[2-(3,5-Dichloro-phenyl)-2-trifluoromethyl-2,3-dihydro-benzofuran-5-yl]-2-(2-oxo-pyrrolidin-1-yl)-benzonitrile

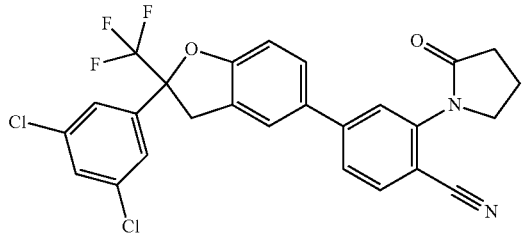 [SMILES: N#Cc1ccc(-c2ccc3c(c2)CC(c2cc(Cl)cc(Cl)c2)(C(F)(F)F)O3)cc1N1CCCC1=O]

0.5 mL of 50% NaOH was added to a mixture of 4-Chloro-N-{2-cyano-5-[2-(3,5-dichloro-phenyl)-2-trifluoromethyl-2,3-dihydro-benzofuran-5-yl]-phenyl}-butyramide (253 mg, 0.46 mmol, made) in MeCN (10 mL). After stirring at room temperature for 1 h, the reaction mixture was poured into water and extracted with ethyl acetate three times. The combined organic layers were dried over sodium sulfate, filtered and concentrated under vacuum. The residue was purified by column chromatography on silica gel to provide 4-[2-(3,5-Dichloro-phenyl)-2-trifluoromethyl-2,3-dihydro-benzo furan-5-yl]-2-(2-oxo-pyrrolidin-1-yl)-benzonitrile (182 mg, 77% yield). ¹H NMR (300 Mz, CD₃OD): δ 2.30-2.35 (m, 2H), 2.62-2.68 (t, 2H), 3.76-3.82 (d, 1H), 3.99-4.04 (t, 2H), 4.10-4.15 (d, 1H), 7.16-7.19 (d, 1H), 7.58-7.60 (d, 2H), 7.65-7.67 (d, 3H), 7.70-7.74 (d, 2H), 7.83-7.86 (d, 1H); $^{19}$F NMR (282 Mz, CD$_3$OD): −82.64 (s, 3F); ESI-MS(+): 539 (M+Na)$^+$; HPLC: 94.1%

The Table 1 below represents compounds of formula I wherein R$^3$ is trifluoromethyl, Y$^1$ and G$^1$ are oxygen and Y$^4$ is C—H.

| Entry | R4 | R1 | R2 | Y2 | Y3 | Y5 | Y6 | Y7 | Y8 | RT (min) | m/z | Method | MP (° C.) |
|---|---|---|---|---|---|---|---|---|---|---|---|---|---|
| 1 | 3,5-dichlorophenyl- | H | Cyclopropyl- | C—H | C—H | C—OMe | C—H | C—H | C—H | 18.06 | 586 [M + 2MeOH + H]+ | A | 235-236 |
| 2 | 3,5-dichlorophenyl- | H | Cyclopropyl- | C—H | C—H | C—H | C—H | C—H | C—Cl | 19.11 | 526 [M + H]+ | A | 83-85 |
| 3 | 3,5-dichlorophenyl- | cyclopropaneformyl- | Cyclopropyl- | C—H | C—H | C—H | C—H | C—CN | C—H | | 607 [M + Na]+ | A | 242-245 |
| 4 | 3,5-dichlorophenyl- | H | Cyclopropyl- | C—H | C—H | C—CN | C—H | C—H | C—H | 18.56 | 539 [M + Na]+ | A | 183-185 |
| 5 | 3,5-dichlorophenyl- | H | Cyclopropyl- | C—H | C—H | C—H | C—H | N | C—H | 18.03 | 515 [M − H]− | A | 115-118 |
| 6 | 3,5-dichlorophenyl- | H | Cyclopropyl- | C—H | C—H | C—H | C—H | C—CN | C—H | 13.86 | 491 [M − H]− | A | 232-235 |
| 7 | 3,5-dichlorophenyl- | H | Cyclopropyl- | C—H | C—H | C—Cl | C—H | C—H | C—H | 19.62 | 526 [M + H]+ | A | 82-84 |
| 8 | 3,5-dichlorophenyl- | H | Cyclopropyl- | C—H | C—H | C—H | C—H | C—H | C—H | 18.33 | 515 [M − H]− | A | 183-185 |
| 9 | 3,5-dichlorophenyl- | Et | Cyclopropyl- | C—H | C—H | C—CN | C—H | C—H | C—H | 19.65 | 542 [M + Na]+ | A | 135-138 |
| 10 | 3,5-dichlorophenyl- | H | Cyclopropyl- | C—H | C—H | C—H | C—H | C—F | C—H | 18.88 | 510 [M + H]+ | A | 191-193 |
| 11 | 3,5-dichlorophenyl- | H | Ethyl- | C—H | C—H | C—CN | C—H | C—CN | C—H | 18.55 | 505 [M + H]+ | A | 166-168 |
| 12 | 3,5-dichlorophenyl- | H | Ethyl- | C—H | C—H | C—H | C—H | C—H | C—H | 18.07 | 503 [M − H]− | A | 204-207 |
| 13 | 3,5-dichlorophenyl- | H | Ethyl- | C—H | C—H | C—H | C—H | C—H | C—H | 17.95 | — | A | 118-119 |
| 14 | 3,5-dichlorophenyl- | H | Ethyl- | C—H | C—H | C—H | C—H | C—H | C—H | 19.11 | 514 [M + H]+ | A | 64-66 |
| 15 | 3,5-dichlorophenyl- | Et | Cyclopropyl- | C—H | C—H | C—Cl | C—H | C—H | C—F | 20.36 | 560.28 [M + Na]+ | A | 146-149 |
| 16 | 3,5-dichlorophenyl- | H | 1-fluoro-1-phenylmethyl- | C—H | C—H | C—H | C—H | C—H | C—H | 2.36 | 560.28 [M + H]+ | B | |
| 17 | 3,5-dichlorophenyl- | H | Ethynyl- | C—H | C—H | C—H | C—H | C—H | C—H | 2.18 | 476.19 [M + H]+ | B | |
| 18 | 3,5-dichlorophenyl- | H | 1-chloro-2-methylprop-2-yl | C—H | C—H | C—H | C—H | C—H | C—H | 2.36 | 542.28 [M + H]+ | B | |
| 19 | 3,5-dichlorophenyl- | H | 4-pyrazolyl- | C—H | C—H | C—H | C—H | C—H | C—H | 2.01 | 518.24 [M + H]+ | B | |
| 20 | 3,5-dichlorophenyl- | H | 4-Pyridyl- | C—H | C—H | C—H | C—H | C—H | C—H | 2.14 | 529.14 [M + H]+ | B | |
| 21 | 3-trifluoromethylphenyl- | H | Benzyl- | C—H | C—H | C—H | C—H | C—H | C—H | 2.18 | 542.39 [M + H]+ | B | |
| 22 | 3-trifluoromethylphenyl- | H | iso-amyl- | C—H | C—H | C—H | C—H | C—H | C—H | 2.26 | 522.4 [M + H]+ | B | |
| 23 | 3-trifluoromethylphenyl- | H | cyclopentylmethyl- | C—H | C—H | C—H | C—H | C—H | C—H | 2.28 | 534.39 [M + H]+ | B | |
| 24 | 3-trifluoromethylphenyl- | H | 1-cyano-2-methoxyliminoyl-cyclopropyl- | C—H | C—H | C—H | C—H | C—H | C—H | 2.16 | 560.28 [M + H]+ | B | |
| 25 | 3-trifluoromethylphenyl- | H | 1,2,4-triazol-1-ylmethyl- | C—H | C—H | C—H | C—H | C—H | C—H | 1.84 | 533.36 [M + H]+ | B | |
| 26 | 3-trifluoromethylphenyl- | H | 1-fluoro-1-phenylmethyl- | C—H | C—H | C—H | C—H | C—H | C—H | 2.21 | 560.35 [M + H]+ | B | |
| 27 | 3-trifluoromethylphenyl- | H | Ethynyl- | C—H | C—H | C—H | C—H | C—H | C—H | 2.03 | 476.33 [M + H]+ | B | |
| 28 | 3-trifluoromethylphenyl- | H | 2-Pyridyl- | C—H | C—H | C—H | C—H | C—H | C—H | 2.26 | 529.32 [M + H]+ | B | |
| 29 | 3-trifluoromethylphenyl- | H | 4-imidazolyl- | C—H | C—H | C—H | N | C—H | C—H | 2.18 | 518.34 [M + H]+ | B | |
| 30 | 3-trifluoromethylphenyl- | H | propyn-1-yl- | C—H | C—H | C—H | C—H | C—H | C—H | 1.84 | 490.34 [M + H]+ | B | |
| 31 | 3-trifluoromethylphenyl- | H | tetrazol-1-yl- | C—H | C—H | C—H | C—H | C—H | C—H | 2.07 | 534.35 [M + H]+ | B | |
| 32 | 3-trifluoromethylphenyl- | H | 2-methylsulfanyl-ethenyl- | C—H | C—H | C—H | C—H | C—H | C—H | 1.88 | 524.34 [M + H]+ | B | |
| 33 | 3,5-dichlorophenyl- | H | Ethyl- | C—H | C—H | C—Me | C—H | C—H | C—H | 2.10 | 494 [M + H]+ | A | 104-107 |
| 34 | 3,5-dichlorophenyl- | H | Cyclopropyl- | C—H | C—H | C—Me | C—H | C—H | C—H | 18.88 | 506 [M + H]+ | A | 102-106 |
| 35 | 3,5-dichlorophenyl- | H | Ethyl- | C—H | C—Me | C—H | C—H | C—H | C—H | 18.50 | 496 [M + H]+ | A | |
| 36 | 3,5-dichlorophenyl- | H | Cyclopropyl- | C—H | C—Me | C—H | C—H | C—H | C—H | 17.74 | 508 [M + H]+ | A | 113-114 |
| 37 | 3,5-dichlorophenyl- | H | Ethyl- | C—H | C—H | C—H | C—H | C—H | N | 18.11 | 494 [M + H]+ | A | 121-123 |
| 38 | 3,5-dichlorophenyl- | H | Ethyl- | C—H | C—H | C—H | N | C—H | N | 18.41 | 494 [M + H]+ | A | 91-93 |
| 39 | 3,5-dichlorophenyl- | H | Cyclopropyl- | C—H | C—Cl | C—Cl | C—H | C—H | N | 19.11 | 562 [M + H]+ | A | 198-200 |
| 40 | 3,5-dichlorophenyl- | H | Cyclopropyl- | C—H | C—H | C—H | N | C—H | N | 13.38 | 482 [M + H]+ | A | 133-135 |
| 41 | 3,5-dichlorophenyl- | H | Cyclopropyl- | C—H | C—H | C—F | C—H | C—F | C—H | 14.93 | 527 [M + H]+ | A | 100-102 |
| 42 | 3,5-dichlorophenyl- | H | Cyclopropyl- | C—H | C—H | C—F | C—H | C—H | C—H | 17.95 | 508 [M − H]− | A | 230-232 |
| 43 | 3,5-dichlorophenyl- | H | Cyclopropyl- | C—H | C—H | C—H | C—H | C—F | C—H | 18.86 | 493 [M − H]− | A | 101-103 |
| 44 | 3,5-dichlorophenyl- | H | methylsulfanylmethyl- | C—H | C—H | C—H | C—H | C—H | C—H | 13.46 | 494 [M + H]+ | A | 187-189 |
| 45 | 3,5-dichlorophenyl- | H | methylsulfanylmethyl-methyl- | C—H | C—H | C—H | C—H | C—H | C—H | 12.54 | 552 [M + Na]+ | A | 81-84 |
| 46 | 3,5-dichlorophenyl- | H | Cyclopropyl- | C—H | C—Me | C—H | C—H | C—F | C—H | 19.12 | 482 [M − H]− | A | 102-103 |
| 47 | 3,5-dichlorophenyl- | H | Cyclopropyl- | C—H | C—Me | C—H | C—H | N | C—H | 18.45 | 527 [M + H]+ | A | 203-204 |
| 48 | 3,5-dichlorophenyl- | H | Cyclopropyl- | C—H | C—H | C—H | C—H | N | C—H | 15.44 | 505 [M − H]− | A | 111-113 |
| 49 | 3,5-dichlorophenyl- | H | Ethyl- | N | C—H | C—H | C—H | N | C—H | 13.99 | 479 [M − H]− | A | 80-81 |

-continued

| Entry | R4 | R1 | R2 | Y2 | Y3 | Y5 | Y6 | Y7 | Y8 | RT (min) | m/z | Method | MP (° C.) |
|---|---|---|---|---|---|---|---|---|---|---|---|---|---|
| 50 | 3,5-dichlorophenyl- | H | Ethyl- | C—H | C—H | C—H | C—H | C—H | C—Cl | 18.92 | 512 [M − H]− | A | 158-160 |
| 51 | 3,5-dichlorophenyl- | H | Ethyl- | C—H | C—H | C—H | C—H | C—Cl | C—H | 19.41 | 512 [M − H]− | A | 205-207 |
| 52 | 3,5-dichlorophenyl- | H | 1,2,4-triazol-1-ylmethyl- | C—H | C—H | C—H | C—H | C—H | C—H | 1.98 | 532.83 [M + H]+ | B | |
| 53 | 3,5-dichlorophenyl- | H | 2-pyrazinyl- | C—H | C—H | C—H | C—H | C—H | C—H | 2.29 | 530.21 [M + H]+ | B | |
| 54 | 3,5-dichlorophenyl- | H | 3-pyrazolyl- | C—H | C—H | C—H | C—H | C—H | C—H | 2.12 | 517.56 [M + H]+ | B | |
| 55 | 3-trifluoromethylphenyl- | H | 2-methylsulfanyl-ethyl- | C—H | C—H | C—H | C—H | C—H | C—H | 2.09 | 526.3 [M + H]+ | B | |
| 56 | 3-trifluoromethylphenyl- | H | pent-3-yl- | C—H | C—H | C—H | C—H | C—H | C—H | 2.24 | 522.41 [M + H]+ | B | |
| 57 | 3-trifluoromethylphenyl- | H | isoxazol-5-yl- | C—H | C—H | C—H | C—H | C—H | C—H | 2.06 | 519.29 [M + H]+ | B | |
| 58 | 3-trifluoromethylphenyl- | H | pyrazol-1-ylmethyl- | C—H | C—H | C—H | C—H | C—H | C—H | 1.97 | 531.71 [M + H]+ | B | |
| 59 | 3-trifluoromethylphenyl- | H | 2-pyrazinyl- | C—H | C—H | C—H | C—H | C—H | C—H | 2.13 | 530.34 [M + H]+ | B | |
| 60 | 3-trifluoromethylphenyl- | H | 1-chloro-2-methylprop-2-yl | C—H | C—H | C—H | C—H | C—H | C—H | 2.21 | 542.36 [M + H]+ | B | |
| 61 | 3-trifluoromethylphenyl- | H | 4-pyrazolyl- | C—H | C—H | C—H | C—H | C—H | C—H | 1.87 | 518.36 [M + H]+ | B | |
| 62 | 3-trifluoromethylphenyl- | H | 3-pyrazolyl- | C—H | C—H | C—H | C—H | C—H | C—H | 1.97 | 518.37 [M + H]+ | B | |
| 63 | 3-trifluoromethylphenyl- | H | 4-Pyridyl- | C—H | C—H | C—H | C—H | C—H | C—H | 1.98 | 529.37 [M + H]+ | B | |
| 64 | 3-trifluoromethylphenyl- | H | ethoxymethyl- | C—H | C—H | C—H | C—H | C—H | C—H | 2.13 | 510.35 [M + H]+ | B | |
| 65 | 3-trifluoromethylphenyl- | H | tetrahydrofuran-2-yl- | C—H | C—H | C—H | C—H | C—H | C—H | 2.11 | 521.75 [M + H]+ | B | |
| 66 | 3-trifluoromethylphenyl- | H | 2-methoxyethoxymethyl- | C—H | C—H | C—H | C—H | C—H | C—H | 2.06 | 540.35 [M + H]+ | B | |
| 67 | 3-trifluoromethylphenyl- | H | butyronitrile- | C—H | C—H | C—H | C—H | C—H | C—H | 1.99 | 519.34 [M + H]+ | B | |
| 68 | 3-trifluoromethylphenyl- | H | propargylhydroxylmethyl- | C—H | C—H | C—H | C—H | C—H | C—H | 2.06 | 520.28 [M + H]+ | B | |
| 69 | 3-trifluoromethylphenyl- | H | 1,2-dimethylprop-1-yl | C—H | C—H | C—H | C—H | C—H | C—H | 2.24 | 522.42 [M + H]+ | B | |
| 70 | 3-trifluoromethylphenyl- | H | 2-chloroeth-2-yl- | C—H | C—H | C—H | C—H | C—H | C—H | 2.27 | 528.32 [M + H]+ | B | |
| 71 | 3,5-dichlorophenyl- | H | 2-Thienyl- | C—H | C—H | C—H | C—H | C—H | C—H | 2.32 | 534.25 [M + H]+ | B | |
| 72 | 3,5-dichlorophenyl- | H | tetrahydropyran-4-yl- | C—H | C—H | C—H | C—H | C—H | C—H | 2.17 | 536.27 [M + H]+ | B | |
| 73 | 3,5-dichlorophenyl- | H | Ethyl- | C—H | C—H | N | C—H | C—H | N | 17.61 | 482 [M − H]+ | A | 182-184 |
| 74 | 3-trifluoromethylphenyl- | H | methylsulfanylmethyl- | C—H | C—H | C—H | C—F | C—H | C—H | 18.06 | 552 [M + Na]+ | A | 52-54 |
| 75 | 3,5-bis(trifluoromethyl)phenyl- | H | methylsulfanylmethyl- | C—H | C—H | C—H | C—H | C—H | C—H | 18.42 | 580 [M + H]+ | A | 124-126 |
| 76 | 3-trifluoromethylphenyl- | H | 2-chloroethylen-1-yl- | C—H | C—H | C—H | C—H | C—H | C—H | 2.08 | 512.28 [M − H]− | B | |
| 77 | 3,5-dichlorophenyl- | H | Cyclopropyl- | N | C—H | C—H | N | C—H | C—H | 17.29 | 491 [M − H]− | A | 228-229 |
| 78 | 3,5-dichlorophenyl- | H | Cyclopropyl- | C—H | C—H | C—H | N | C—H | C—H | 14.14 | 493 [M + H]+ | A | 98-100 |
| 79 | 3,5-dichlorophenyl- | H | methylsulfanylmethyl- | C—H | C—Me | C—H | C—H | C—H | C—H | 18.54 | 512 [M + H]+ | A | 68-70 |
| 80 | 3,5-dichlorophenyl- | H | Cyclopropyl- | C—H | C—H | C—F | C—H | C—H | C—F | 18.58 | 510 [M + H]+ | A | 134-136 |
| 81 | 3,5-dichlorophenyl- | H | methyl- | C—H | C—Me | C—H | C—F | C—H | C—H | 19.31 | 552 [M + Na]+ | A | 62-65 |
| 82 | 3,5-dichlorophenyl- | H | 2,2,2-trifluoro-ethyl- | C—H | C—H | C—H | C—H | C—H | C—H | 18.27 | 484 [M + Na]+ | A | 72-75 |
| 83 | 3,5-dichlorophenyl- | H | Ethyl- | C—H | C—Me | C—H | C—H | C—F | C—H | 18.64 | 574 [M + Na]+ | A | 118-121 |
| 84 | 3,5-dichlorophenyl- | H | methylsulfanylmethyl- | C—H | C—Cl | C—H | C—H | C—H | C—CN | 18.56 | 527 [M − H]− | A | 87-90 |
| 85 | 3,5-dichlorophenyl- | H | Ethyl- | N | C—H | N | C—H | C—H | N | 18.92 | 528 [M − H]− | A | 67-70 |
| 86 | 3,5-dichlorophenyl- | H | methylsulfanylmethyl- | C—H | C—H | C—H | C—H | C—F | C—H | 15.75 | 493 [M − H]− | A | 169-170 |
| 87 | 3,5-dichlorophenyl- | H | Ethyl- | C—H | C—H | C—H | N | C—H | C—H | 14.69 | 481 [M + H]+ | A | 88-90 |
| 88 | 3,5-dichlorophenyl- | H | Ethyl- | C—H | C—H | C—H | N | C—H | C—H | 14.13 | 493 [M + H]+ | A | 76-78 |
| 89 | 3,5-dichlorophenyl- | H | Cyclopropyl- | C—H | C—H | C—H | N | C—H | N | 13.73 | 481 [M + H]+ | A | 138-140 |
| 90 | 3,5-dichlorophenyl- | H | Cyclopropyl- | C—H | C—H | N | N | C—H | C—H | 14.95 | 507 [M + H]+ | A | 125-127 |
| 91 | 3,5-dichlorophenyl- | H | Ethyl- | C—H | C—H | C—H | N | C—H | C—H | 14.44 | 548 [M + H]+ | A | 125-127 |
| 92 | 3,5-dichlorophenyl- | H | Cyclopropyl- | C—H | C—H | C—H | N | C—H | C—F | 15.29 | 582 [M + H]+ | A | 150-152 |
| 93 | 3,5-dichlorophenyl- | H | 2,2,2-trifluoro-ethyl- | C—H | C—H | C—H | N | C—H | C—H | 15.16 | 494 [M + H]+ | A | 212-214 |
| 94 | 3,5-dichlorophenyl- | H | methyl- | C—H | C—H | C—H | C—H | C—F | C—F | 13.82 | 550 [M − H]− | A | 202-204 |
| 95 | 3,5-dichlorophenyl- | H | methylsulfanylmethyl- | C—H | C—H | C—H | C—H | C—F | C—F | 17.83 | 506 [M + H]+ | A | 198-200 |
| 96 | 3,5-dichlorophenyl- | H | 2-hydroxyiminoyl- | C—H | C—H | C—H | C—H | C—H | C—H | 18.67 | 528 [M − H]− | A | 159-161 |
| 97 | 3,5-dichlorophenyl- | H | 5-pyrimidyl- | C—H | C—H | C—H | C—H | C—H | C—H | 1.49 | 495.29 [M + H]+ | B | |
| 98 | 3,5-dichlorophenyl- | H | pyrazol-1-ylmethyl | C—H | C—H | C—H | C—H | C—H | C—H | 2.12 | 530.28 [M + H]+ | B | |
| 99 | 3,5-dichlorophenyl- | H | pyrazol-1-ylmethyl | C—H | C—H | C—H | C—H | C—H | C—H | 2.12 | 531.67 [M + H]+ | B | |

-continued

| Entry | R4 | R1 | R2 | Y2 | Y3 | Y5 | Y6 | Y7 | Y8 | RT (min) | m/z | Method | MP (° C.) |
|---|---|---|---|---|---|---|---|---|---|---|---|---|---|
| 100 | 3,5-dichlorophenyl- | H | 1-chloroprop-1-yl- | C–H | C–H | C–H | C–H | C–H | C–H | 2.36 | 528.24 [M + H]+ | B | |
| 101 | 3,5-dichlorophenyl- | H | 2-methylcyclopropryl- | C–H | C–H | C–H | C–H | C–H | C–H | 2.31 | 506.29 [M + H]+ | B | |
| 102 | 3,5-dichlorophenyl- | H | methylsulfonylmethyl- | C–H | C–H | C–H | C–H | C–H | C–H | 2.05 | 544.25 [M + H]+ | B | |
| 103 | 3,5-dichlorophenyl- | H | pyrid-3-yl- | C–H | C–H | N | C–H | C–H | C–H | 2.14 | 529.27 [M + H]+ | B | |
| 104 | 3,5-dichlorophenyl- | H | 2-chloroethylen-1-yl- | C–H | C–H | C–H | C–H | C–H | C–H | 2.23 | 512.19 [M + H]+ | B | |
| 105 | 3,5-dichlorophenyl- | H | 2-furyl- | C–H | C–H | C–H | C–H | C–H | C–H | 2.11 | 518 [M + H]+ | B | |
| 106 | 3-trifluoromethylphenyl- | H | tert-butyl- | C–H | C–H | C–H | C–H | C–H | C–H | 2.21 | 508.41 [M + H]+ | B | |
| 107 | 3-trifluoromethylphenyl- | H | propen-1-yl- | C–H | C–H | C–H | C–H | C–H | C–H | 2.09 | 492.36 [M + H]+ | B | |
| 108 | 3-trifluoromethylphenyl- | H | 2-Fluorophenyl- | C–H | C–H | C–H | C–H | C–H | C–H | 2.22 | 546.34 [M + H]+ | B | |
| 109 | 3-trifluoromethylphenyl- | H | 2-methylphenyl | C–H | C–H | C–H | C–H | C–H | C–H | 2.23 | 542.36 [M + H]+ | B | |
| 110 | 3-trifluoromethylphenyl- | H | phenyl- | C–H | C–H | C–H | C–H | C–H | C–H | 2.19 | 528.25 [M + H]+ | B | |
| 111 | 3-trifluoromethylphenyl- | H | 4-Fluorophenyl- | C–H | C–H | C–H | C–H | C–H | C–H | 2.20 | 546.34 [M + H]+ | B | |
| 112 | 3-trifluoromethylphenyl- | H | tert-butylmethyl- | C–H | C–H | C–H | C–H | C–H | C–H | 2.26 | 522.39 [M + H]+ | B | |
| 113 | 3-trifluoromethylphenyl- | H | 5-pyrimidyl- | C–H | C–H | N | C–H | C–H | C–H | 1.97 | 530.35 [M + H]+ | B | |
| 114 | 3-trifluoromethylphenyl- | H | pyrid-3-yl- | C–H | C–H | N | C–H | C–H | C–H | 2.21 | 528.3 [M + H]+ | B | |
| 115 | 3-trifluoromethylphenyl- | H | 1-chloroprop-1-yl- | C–H | C–H | C–H | C–H | C–H | C–H | 1.90 | 544.32 [M + H]+ | B | |
| 116 | 3-trifluoromethylphenyl- | H | methylsulfonylmethyl- | C–H | C–H | C–H | C–H | C–H | C–H | 1.98 | 529.41 [M + H]+ | B | |
| 117 | 3-trifluoromethylphenyl- | H | 1-methoxyeth-1-yl- | C–H | C–H | C–H | C–H | C–H | C–H | 2.10 | 510.37 [M + H]+ | B | |
| 118 | 3-trifluoromethylphenyl- | H | 2-cyano-ethyl- | C–H | C–H | C–H | C–H | C–H | C–H | 1.96 | 505.34 [M + H]+ | B | |
| 119 | 3-trifluoromethylphenyl- | H | N-formylaminomethyl- | C–H | C–H | C–H | C–H | C–H | C–H | 1.80 | 509.34 [M + H]+ | B | |
| 120 | 3-trifluoromethylphenyl- | H | 1-methoxyeth-1-yl- | C–H | C–H | C–H | C–H | C–H | C–H | 2.10 | 510.36 [M + H]+ | B | |
| 121 | 3-trifluoromethylphenyl- | H | 1-methoxyeth-1-yl- | C–H | C–H | C–H | C–H | C–H | C–H | 2.10 | 510.35 [M + H]+ | B | |
| 122 | 3-trifluoromethylphenyl- | H | 1-chloroeth-1-yl- | C–H | C–H | C–H | C–H | C–H | C–H | 2.14 | 514.35 [M + H]+ | B | |
| 123 | 3-trifluoromethylphenyl- | H | 1-methylcyclobutyl- | C–H | C–H | C–H | C–H | C–H | C–H | 2.22 | 520.38 [M + H]+ | B | |
| 124 | 3-trifluoromethylphenyl- | H | 1-methoxypropen-1-yl- | C–H | C–H | C–H | C–H | C–H | C–H | 2.18 | 522.34 [M + H]+ | B | |
| 125 | 3-trifluoromethylphenyl- | H | N-formylaminoeth-2-yl- | C–H | C–H | C–H | C–H | C–H | C–H | 1.86 | 523.35 [M + H]+ | B | |
| 126 | 3-trifluoromethylphenyl- | H | N-ethyl-N-formylaminomethyl- | C–H | C–H | C–H | C–H | C–H | C–H | 1.86 | 523.36 [M + H]+ | B | |
| 127 | 3-trifluoromethylphenyl- | H | spiro[2.2]pent-5-ylmethyl- | C–H | C–H | C–H | C–H | C–H | C–H | 2.24 | 532.39 [M + H]+ | B | |
| 128 | 3-trifluoromethylphenyl- | H | propen-1-yl- | C–H | C–H | C–H | C–H | C–H | C–H | 2.24 | 492.26 [M + H]+ | B | |
| 129 | 3,5-dichlorophenyl- | H | Cyclopropyl- | C–H | C–H Me | N | N | C–H | N | 17.12 | 508 [M + H]+ | A | 108–110 |
| 130 | 3,5-dichlorophenyl- | H | Ethyl- | C–H | C–H Me | C–H | C–H | C–H | C–H | 17.02 | 496 [M + H]+ | A | |
| 131 | 3,5-dichlorophenyl- | H | Cyclopropyl- | C–H | C–H | C–H | C–Me | C–H | C–H | 19.14 | 506 [M + H]+ | A | 136–139 |
| 132 | 3-trifluoromethylphenyl- | H | methylsulfanylmethyl- | C–H | C–H | C–H | C–H | C–H | C–H | 17.74 | 512 [M + H]+ | A | 59–61 |
| 133 | 3,4,5-trichlorophenyl- | H | methylsulfanylmethyl- | C–H | C–H | C–H | C–H | C–H | C–H | 19.36 | 568 [M + Na]+ | A | 69–72 |
| 134 | 3,5-dichloro-4-fluorophenyl- | H | methylsulfanylmethyl- | C–H | C–H | C–H | C–H | C–H | C–H | 18.82 | 532 [M + Na]+ | A | 73–76 |
| 135 | 3-trifluoromethylphenyl- | H | methylsulfanylmethyl- | C–H | C–H | C–H | C–CN | C–H | C–H | 17.69 | 559 [M + H]+ | A | 154–156 |
| 136 | 3,5-dichlorophenyl- | H | Ethyl- | C–H | C–Cl | C–H | C–H | C–H | N | 15.09 | 515 [M + H]+ | A | 83–85 |
| 137 | 3,5-dichlorophenyl- | H | Ethyl- | C–H | C–Cl | N | N | C–H | C–H | 17.85 | 513 [M − H]− | A | 85–87 |
| 138 | 3-trifluoromethylphenyl- | H | 2,6-difluorophenyl- | C–H | C–H | C–H | N | C–H | C–H | 2.17 | 564.32 [M + H]+ | B | |
| 139 | 3,5-dichlorophenyl- | H | Cyclopropyl- | C–H | C–Me | C–H | N | C–H | C–H | 19.25 | 576 [M + H]+ | A | 96–98 |
| 140 | 3-trifluoromethylphenyl- | H | Cyclopropyl- | C–H | C–H | C–H | N | C–H | C–H | 19.03 | 562 [M + H]+ | A | 173–174 |
| 141 | 3,5-dichlorophenyl- | cyclopropaneformyl- | Cyclopropyl- | C–H | C–H | C–H | N | C–H | C–H | 18.76 | 490 [M − H]− | A | 220–222 |
| 142 | 3,5-dichlorophenyl- | cyclopropaneformyl- | Ethyl- | C–H | C–Me | C–F | C–H | C–H | C–H | 18.74 | 496 [M − H]− | A | 147–149 |
| 143 | 3,5-dichlorophenyl- | H | Ethyl- | C–H | C–H | N | N | C–H | C–H | 14.38 | 496 [M + H]+ | A | 172–174 |
| 144 | 3,5-dichlorophenyl- | H | 1-fluoroprop-2-yl- | C–H | C–H | C–H | C–H | C–H | C–H | 2.34 | 512.26 [M + H]+ | B | |
| 145 | 3,5-dichlorophenyl- | H | 2-methoxy-ethyl- | C–H | C–H | C–H | C–H | C–H | C–H | 2.16 | 510.26 [M + H]+ | B | |

-continued

| Entry | R4 | R1 | R2 | Y2 | Y3 | Y5 | Y6 | Y7 | Y8 | RT (min) | m/z | Method | MP (° C.) |
|---|---|---|---|---|---|---|---|---|---|---|---|---|---|
| 146 | 3-trifluoromethylphenyl- | H | Cyclopentyl- | C—H | C—H | C—H | C—H | C—H | C—H | 2.23 | 520.55 [M + H]+ | B | |
| 147 | 3-trifluoromethylphenyl- | H | 2-methylcyclopropyl- | C—H | C—H | C—H | C—H | C—H | C—H | 2.16 | 506.37 [M + H]+ | B | |
| 148 | 3-trifluoromethylphenyl- | H | 2-methoxy-ethyl- | C—H | C—H | C—H | C—H | C—H | C—H | 2.00 | 510.41 [M + H]+ | B | |
| 149 | 3-trifluoromethylphenyl- | H | dihydrofuran-4-yl- | C—H | C—H | C—H | C—H | C—H | C—H | 2.04 | 520.36 [M + H]+ | B | |
| 150 | 3,5-dichlorophenyl- | H | 2,2,2-trifluoro-ethyl- | C—H | C—H | C—H | C—H | C—H | C—H | 18.56 | 532 [M − H]− | A | 117-118 |
| 151 | 3,5-dichlorophenyl- | H | Cyclopropyl- | C—H | C—H | C—H | C—H | C—H | C—H | 18.84 | 510 [M − H]− | A | 69-71 |
| 152 | 3,5-dichlorophenyl- | H | Cyclopropyl- | C—H | C—H | C—H | C—F | C—H | C—H | 19.95 | 524 [M − H]− | A | 79-81 |
| 153 | 3,5-dichlorophenyl- | H | methyl- | C—H | C—H | C—H | C—H | C—F | C—H | 18.67 | 484 [M + H]+ | A | 78-80 |
| 154 | 3,5-dichlorophenyl- | H | Ethyl- | C—H | C—H | C—H | C—F | C—H | C—H | 18.90 | 496 [M − H]− | A | 96-98 |
| 155 | 3,5-dichlorophenyl- | H | Ethyl- | C—H | C—H | C—H | C—H | C—H | N | 14.34 | 493 [M − H]− | A | 119-121 |
| 156 | 3,5-dichlorophenyl- | H | 2,2,2-trifluoro-ethyl- | C—H | C—Me | C—H | C—H | C—H | C—F | 18.40 | 550 [M − H]− | A | 169-171 |
| 157 | 3,5-dichlorophenyl- | H | cyclopropylmethyl- | C—H | C—H | C—H | C—H | C—H | C—H | 2.27 | 506.26 [M + H]+ | B | |
| 158 | 3,5-dichlorophenyl- | H | 1-methylcyclopropyl- | C—H | C—H | C—H | C—H | C—H | C—H | 2.32 | 506.35 [M + H]+ | B | |
| 159 | 3,5-dichlorophenyl- | H | 1-methylpropen-1-yl-methyl- | C—H | C—H | C—H | C—H | C—H | C—H | 2.17 | 466.31 [M + H]+ | B | |
| 160 | 3,5-dichlorophenyl- | H | 2-methylprop-1-yl- | C—H | C—H | C—H | C—H | C—H | C—H | 1.96 | 508.36 [M + H]+ | B | |
| 161 | 3,5-dichlorophenyl- | H | Cyclobutyl- | C—H | C—H | C—H | C—H | C—H | C—H | 2.18 | 506.56 [M + H]+ | B | |
| 162 | 3,5-dichlorophenyl- | H | sec-butyl- | C—H | C—H | C—H | C—H | C—H | C—H | 2.16 | 507.81 [M + H]+ | B | |
| 163 | 3,5-dichlorophenyl- | H | prop-1-yl- | C—H | C—H | C—H | C—H | C—H | C—H | 2.18 | 494.37 [M + H]+ | B | |
| 164 | 3-trifluoromethylphenyl- | H | 1-fluoropropan-2-yl- | C—H | C—H | C—H | C—H | C—H | C—H | 2.19 | 512.34 [M + H]+ | B | |
| 165 | 3-trifluoromethylphenyl- | H | cyclopropylmethyl- | C—H | C—H | C—H | C—H | C—H | C—H | 2.12 | 506.37 [M + H]+ | B | |
| 166 | 3-trifluoromethylphenyl- | H | 1-cyanocyclopropyl- | C—H | C—H | C—H | C—H | C—H | C—H | 2.11 | 517.38 [M + H]+ | B | |
| 167 | 3-trifluoromethylphenyl- | H | 2-fluoro-ethyl- | C—H | C—H | C—H | C—H | C—H | C—H | 2.00 | 498.35 [M + H]+ | B | |
| 168 | 3-trifluoromethylphenyl- | H | 1-fluoroethyl- | C—H | C—H | C—H | C—H | C—H | C—H | 2.09 | 498.33 [M + H]+ | B | |
| 169 | 3-trifluoromethylphenyl- | H | 3-methyloxetan-3-yl- | C—H | C—H | C—H | C—H | C—H | C—H | 2.00 | 522.38 [M + H]+ | B | |
| 170 | 3-trifluoromethylphenyl- | H | 2-chloropropen-1-yl- | C—H | C—H | C—H | C—H | C—H | C—H | 2.26 | 526.29 [M + H]+ | B | |
| 171 | 3-trifluoromethylphenyl- | H | 2-methylpropen-1-yl- | C—H | C—H | C—H | C—H | C—H | C—H | 2.34 | 506.31 [M + H]+ | B | |
| 172 | 3,5-dichlorophenyl- | H | Cyclopropyl- | C—H | C—H | N | N | C—H | C—H | 16.15 | 508 [M + H]+ | A | 194-196 |
| 173 | 3,5-dichlorophenyl- | H | Ethyl- | C—H | C—H | C—Me | C—H | C—H | C—H | 18.31 | 548 [M + H]+ | A | 167-169 |
| 174 | 3,5-bis(trifluoromethyl)phenyl- | | | | | | | | | | | | |
| 175 | 3,4-trichlorophenyl- | H | 2,2,2-trifluoro-ethyl- | C—H | C—H | C—H | C—H | C—H | C—H | 17.83 | 532 [M − H]− | A | 73-75 |
| 176 | 3,4,5-trichlorophenyl- | H | Ethyl- | C—H | C—Cl | N | C—H | C—H | C—H | 19.29 | 514 [M − H]− | A | 88-92 |
| 177 | 3,5-dichloro-4-fluorophenyl- | H | 2,2,2-trifluoro-ethyl- | C—H | C—Cl | N | C—H | C—H | C—H | 19.65 | 574 [M + Na]+ | A | 72-74 |
| 178 | 3,5-dichlorophenyl- | H | Cyclopropyl- | C—H | C—H | C—H | C—H | C—H | C—H | 19.59 | 527 [M + H]+ | A | 105-107 |
| 179 | 3,5-dichlorophenyl- | H | Ethyl- | C—H | C—H | C—H | C—H | C—H | C—H | 19.61 | 515 [M − H]− | A | 82-84 |
| 180 | 3,5-bis(trifluoromethyl)phenyl- | H | 2,2,2-trifluoro-ethyl- | C—H | C—H | C—H | C—H | C—H | C—H | 18.38 | 602 [M + H]+ | A | 78-81 |
| 181 | 3,4,5-trichlorophenyl- | H | 2,2,2-trifluoro-ethyl- | C—H | C—H | C—H | C—H | C—H | C—H | 19.25 | 568 [M + H]+ | A | 78-80 |
| 182 | 3-trifluoromethylphenyl- | H | Cyclopropyl- | C—H | C—H | C—H | C—H | C—H | C—H | 17.55 | 490 [M − H]− | A | 180-182 |
| 183 | 3,5-dichlorophenyl- | H | Ethyl- | C—H | C—H | C—H | C—H | C—H | C—H | 18.44 | 480 [M − H]− | A | 70-72 |
| 184 | 3,5-dichlorophenyl- | H | Cyclopropyl- | C—H | C—H | C—H | C—CN | C—H | C—H | 18.40 | 517 [M + H]+ | A | 85-88 |
| 185 | 3,5-dichlorophenyl- | H | Ethyl- | C—H | C—H | C—H | C—F | C—H | C—H | 20.18 | 496 [M + H]+ | A | 84-86 |
| 186 | 2,2,2-trifluoro-ethyl- | H | 2,2,2-trifluoro-ethyl- | C—H | C—H | C—H | C—F | C—H | C—H | 19.04 | 550 [M + H]+ | A | 73-75 |
| 187 | 3,5-dichlorophenyl- | H | Ethyl- | C—H | C—H | C—H | C—Cl | C—H | C—H | 18.60 | 496 [M − H]− | A | 93-95 |
| 188 | 3,5-dichlorophenyl- | H | Ethyl- | C—H | C—H | C—H | C—H | C—H | C—F | 19.41 | 512 [M − H]− | A | 134-136 |
| 189 | 3-trifluoromethylphenyl- | H | prop-2-yl- | C—H | C—H | C—H | C—H | C—H | C—H | 2.12 | 494.34 [M + H]+ | B | |
| 190 | 3-trifluoromethylphenyl- | H | 1-methylcyclopropyl- | C—H | C—H | C—H | C—H | C—H | C—H | 2.17 | 506.14 [M + H]+ | B | |
| 191 | 3-trifluoromethylphenyl- | H | 2-fluoro-cyclopropyl- | C—H | C—H | C—H | C—H | C—H | C—H | 2.02 | 510.33 [M + H]+ | B | |
| 192 | 3-trifluoromethylphenyl- | H | Ethyl- | C—H | C—H | C—H | C—H | C—H | C—H | 2.05 | 480.33 [M + H]+ | B | 87-89 |
| 193 | 3,5-dichlorophenyl- | H | propen-2-yl- | C—H | C—H | C—H | C—H | C—H | C—H | 2.27 | 492.28 [M + H]+ | B | |

-continued

| Entry | R4 | R1 | R2 | Y2 | Y3 | Y5 | Y6 | Y7 | Y8 | RT (min) | m/z | Method | MP (° C.) |
|---|---|---|---|---|---|---|---|---|---|---|---|---|---|
| 194 | 3,5-dichlorophenyl- | H | Ethyl- | C—H | C—H | C—H | C—Me | C—H | C—H | 18.28 | 494 [M + H]+ | A | 123-126 |
| 195 | 3,5-dichloro-4-fluorophenyl- | H | Ethyl- | C—H | C—H | C—H | C—H | C—H | C—H | 18.74 | 498 [M + H]+ | A | 175-177 |
| 196 | 3-trifluoromethylphenyl- | H | 2,2,2-trifluoro-ethyl- | C—H | C—H | C—H | C—F | C—H | C—H | 17.87 | 574 [M + Na]+ | A | 66-68 |
| 197 | 3-trifluoromethylphenyl- | H | 2,2,2-trifluoro-ethyl- | C—H | C—H | C—H | C—CN | C—H | C—H | 17.49 | 581 [M + Na]+ | A | 82-84 |
| 198 | 3,5-dichlorophenyl- | H | Ethyl- | C—H | C—H | C—H | C—CN | C—H | C—H | 19.58 | 505 [M + H]+ | A | 107-109 |

The Table 2 below represents compounds of formula I wherein $R^3$ is trifluoromethyl $Y^1$ and $G^1$ are oxygen:

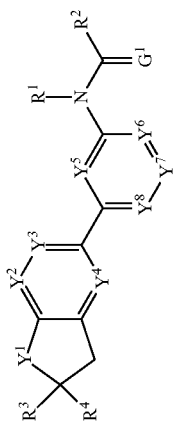

| Entry | Y2 | Y3 | R4 | R1 | R2 | Y4 | Y5 | Y6 | Y7 | Y8 | Y2 | Y3 | RT (min) | m/z | Ion obsd. | HPLC method |
|---|---|---|---|---|---|---|---|---|---|---|---|---|---|---|---|---|
| 199 | C—H | C—H | 3,5-dichlorophenyl- | H | Et | C—H | C—H | C—F | C—H | C—F | C—H | C—H | 18.02 | 516 | [M + H]+ | A |
| 200 | C—H | C—H | 3,5-dichlorophenyl- | H | Cyclopropyl | C—H | C—H | C—F | C—H | C—F | C—H | C—H | 18.23 | 528 | [M + H]+ | A |
| 201 | C—H | C—Cl | 3,5-dichlorophenyl- | H | Cyclopropyl | C—H | C—H | N | C—H | C—H | C—H | C—Cl | 17.53 | 516 | [M + H]+ | A |
| 202 | C—H | C—Cl | 3,5-dichlorophenyl- | H | Cyclopropyl | C—H | C—H | N | C—H | C—H | C—H | C—Cl | 17.80 | 550 | [M + Na]+ | A |
| 203 | C—H | C—Cl | 3,5-dichlorophenyl- | H | Et | C—H | N | N | C—H | C—H | C—H | C—Cl | 16.64 | 516 | [M + H]+ | A |
| 204 | C—H | C—Cl | 3,5-dichlorophenyl- | ethylformyl- | Cyclopropyl | C—H | C—H | N | C—H | C—H | C—H | C—Cl | 20.56 | 593 | [M + Na]+ | A |
| 205 | C—H | C—Cl | 3,5-dichlorophenyl- | H | Cyclopropyl | C—H | C—H | N | C—H | C—H | C—H | C—Cl | 16.48 | 550 | [M + Na]+ | A |
| 206 | C—H | C—Cl | 3,5-dichlorophenyl- | cyclopropylformyl- | Cyclopropyl | C—H | N | N | C—H | C—H | C—H | C—Cl | 18.45 | 617 | [M + Na]+ | A |
| 207 | C—H | C—H | 3,5-dichlorophenyl- | H | 3-thietanyl- | C—H | C—H | C—CN | C—H | C—H | C—H | C—H | 2.32 | 547 | [M + H]+ | B |
| 208 | C—H | C—H | 3,5-dichlorophenyl- | H | Cyclopropyl | C—H | C—H | C—CN | C—H | C—H | C—H | C—H | 18.53 | 526 | [M + H]+ | A |
| 209 | C—H | C—H | 3,5-dichlorophenyl- | H | 4-cyano-2-methylphenyl- | C—Cl | C—H | C—CN | C—H | C—H | C—H | C—H | 1.31 | 590 | [M + H]+ | B |
| 210 | C—H | C—H | 3,5-dichlorophenyl- | H | 1,1-dioxo-3-thietanyl- | C—H | C—H | C—CN | C—H | C—H | C—H | C—H | 1.22 | 579 | [M + H]+ | B |
| 211 | C—H | C—H | 3,5-dichlorophenyl- | H | 1-oxo-3-thietanyl- | C—H | C—H | C—CN | C—H | C—H | C—H | C—H | 1.18 | 563 | [M + H]+ | B |
| 212 | C—H | C—H | 3,5-bis(trifluoromethyl)phenyl- | H | Et | C—H | C—H | C—F | C—H | C—F | C—H | C—H | 17.60 | 584 | [M + H]+ | A |
| 213 | C—H | C—H | 3,5-bis(trifluoromethyl)phenyl- | H | 2,2,2-trifluoro-ethyl- | C—H | C—H | C—F | C—H | C—F | C—H | C—H | 17.61 | 636 | [M − H]− | A |
| 214 | C—H | C—H | 3,5-bis(trifluoromethyl)phenyl- | H | Me | C—H | C—H | C—F | C—H | C—F | C—H | C—H | 17.13 | 568 | [M − H]− | A |
| 215 | C—H | C—H | 3,5-bis(trifluoromethyl)phenyl- | H | Et | C—H | C—H | C—F | C—H | C—F | C—H | C—H | 17.66 | 566 | [M + H]+ | A |
| 216 | C—H | C—H | 3,5-bis(trifluoromethyl)phenyl- | H | 2,2,2-trifluoro-ethyl- | C—H | C—H | C—F | C—H | C—F | C—H | C—H | 17.61 | 620 | [M + H]+ | A |
| 217 | C—H | C—H | 3,5-bis(trifluoromethyl)phenyl- | H | i-Pr | C—H | C—H | C—CN | C—H | C—H | C—H | C—H | 17.97 | 602 | [M + Na]+ | A |
| 218 | C—H | C—H | 3,5-bis(trifluoromethyl)phenyl- | H | Et | C—H | C—H | C—CN | C—H | C—H | C—H | C—H | 17.21 | 595 | [M + Na]+ | A |
| 219 | C—H | C—H | 3,5-bis(trifluoromethyl)phenyl- | H | 2,2,2-trifluoro-ethyl- | C—H | C—H | C—CN | C—H | C—H | C—H | C—H | 17.20 | 649 | [M + Na]+ | A |
| 220 | C—H | C—H | 3,5-bis(trifluoromethyl)phenyl- | H | i-Pr | C—H | C—H | C—CN | C—H | C—H | C—H | C—H | 17.54 | 609 | [M + Na]+ | A |
| 221 | C—H | C—H | 3,5-bis(trifluoromethyl)phenyl- | Ac | Me | C—H | C—H | C—CN | C—H | C—H | C—H | C—H | 17.15 | 623 | [M + Na]+ | A |
| 222 | C—H | C—H | 3,5-bis(trifluoromethyl)phenyl- | H | Me | C—H | C—H | C—CN | C—H | C—H | C—H | C—H | 16.73 | 581 | [M + Na]+ | A |
| 223 | C—H | C—H | 3,5-bis(trifluoromethyl)phenyl- | H | i-Pr | C—H | C—H | C—Cl | C—H | C—H | C—H | C—H | 18.54 | 596 | [M + H]+ | A |
| 224 | C—H | C—H | 3,5-bis(trifluoromethyl)phenyl- | H | 2,2,2-trifluoro-ethyl- | C—H | C—H | C—Cl | C—H | C—H | C—H | C—H | 17.92 | 634 | [M − H]− | A |
| 225 | C—H | C—CN | 3,5-dichlorophenyl- | H | Me | C—H | C—H | C—CN | C—H | C—H | C—H | C—CN | 17.06 | 513 | [M + H]+ | A |
| 226 | C—H | C—CN | 3,5-dichlorophenyl- | H | i-Pr | C—H | C—H | C—CN | C—H | C—H | C—H | C—CN | 17.65 | 519 | [M + H]+ | A |
| 227 | C—H | C—H | 3,5-dichloro-4-fluorophenyl- | H | Me | C—H | C—H | C—CN | C—H | C—H | C—H | C—H | 17.56 | 580 | [M + Na]+ | A |
| 228 | C—H | C—H | 3,5-dichloro-4-fluorophenyl- | H | 2,2,2-trifluoro-ethyl- | C—H | C—H | C—CN | C—H | C—H | C—H | C—H | 17.07 | 531 | [M + Na]+ | A |
| 229 | C—H | C—H | 3,5-dichloro-4-fluorophenyl- | H | Et | C—H | C—H | C—CN | C—H | C—H | C—H | C—H | 17.56 | 545 | [M + Na]+ | A |
| 230 | C—H | C—H | 3,5-dichloro-4-fluorophenyl- | H | i-Pr | C—H | C—H | C—CN | C—H | C—H | C—H | C—H | 17.90 | 559 | [M + Na]+ | A |
| 231 | C—H | C—H | 3,5-dichlorophenyl- | H | 2,2,2-trifluoro-ethyl- | C—H | C—H | C—CN | C—H | C—H | C—H | C—H | 17.49 | 598 | [M + H]+ | A |
| 232 | C—H | C—CN | 3,5-dichlorophenyl- | H | i-Pr | C—H | C—H | C—CN | N | C—H | C—H | C—CN | 17.48 | 519 | [M + H]+ | A |
| 233 | C—H | C—CN | 3,5-dichlorophenyl- | H | i-Pr | C—H | C—H | C—CN | N | C—H | C—H | C—CN | 17.10 | 505 | [M + H]+ | A |
| 234 | C—H | C—H | 3,4,5-trichlorophenyl- | H | i-Pr | C—H | C—H | C—CN | C—H | C—H | C—H | C—H | 18.50 | 553 | [M + H]+ | A |
| 235 | C—H | C—H | 3,4,5-trichlorophenyl- | H | Et | C—H | C—H | C—CN | C—H | C—H | C—H | C—H | 18.20 | 536 | [M − H]− | A |
| 236 | C—H | C—H | 3,5-dichlorophenyl- | H | Me | C—H | C—H | C—Cl | C—H | C—H | C—H | C—H | 17.68 | 522 | [M − H]− | A |
| 237 | C—H | C—H | 3,5-dichlorophenyl- | H | Cyclopropyl | C—H | C—H | C—Cl | C—H | C—H | C—H | C—H | 2.11 | 527 | [M + H]+ | B |
| 238 | C—H | C—H | 3,5-dichlorophenyl- | H | Cyclopropyl | C—H | C—H | C—OCH3 | C—H | C—H | C—H | C—H | 2.15 | 523 | [M + H]+ | B |

-continued

| Entry | Y2 | Y3 | R4 | R1 | R2 | Y4 | Y5 | Y6 | Y7 | Y8 | Y2 | Y3 | RT (min) | m/z | Ion obsd. | HPLC method |
|---|---|---|---|---|---|---|---|---|---|---|---|---|---|---|---|---|
| 239 | C—H | C—H | 3,5-dichlorophenyl- | H | Cyclopropyl | C—H | C—H | C—NO2 | C—H | C—H | C—H | C—H | 2.25 | 537 | [M + H]+ | B |
| 240 | C—H | C—H | 3,5-dichlorophenyl- | H | Cyclopropyl | C—H | C—H | C—OCH3 | N | C—H | C—H | C—H | 2.16 | 522 | [M + H]+ | B |
| 241 | C—H | C—H | 3,5-dichlorophenyl- | H | Et | C—H | C—H | C—Cl | N | C—H | C—H | C—H | 2.06 | 515 | [M + H]+ | B |
| 242 | C—H | C—H | 3,5-dichlorophenyl- | H | Et | C—H | C—H | C—OCH3 | N | C—H | C—H | C—H | 2.11 | 511 | [M + H]+ | B |
| 243 | C—H | C—H | 3,5-dichlorophenyl- | H | Et | C—H | C—H | C—NO2 | C—H | C—H | C—H | C—H | 2.22 | 525 | [M + H]+ | B |
| 244 | C—H | C—H | 3,5-dichlorophenyl- | H | Et | C—H | C—H | C—OCH3 | C—H | C—H | C—H | C—H | 2.13 | 510 | [M + H]+ | B |
| 245 | C—H | C—H | 3,5-dichloro-4-fluorophenyl- | H | 2,2,2-trifluoro-ethyl- | C—H | C—H | C—Cl | C—H | C—F | C—H | C—H | 18.90 | 602 | [M − H]− | A |
| 246 | C—H | C—H | 3,5-dichloro-4-fluorophenyl- | H | Me | C—H | C—H | C—Cl | C—H | C—F | C—H | C—H | 18.70 | 518 | [M − H]− | A |
| 247 | C—H | C—H | 3,5-bis(trifluoromethyl)phenyl- | H | Me | C—H | C—H | C—Cl | C—H | C—F | C—H | C—H | 17.61 | 584 | [M − H]− | A |
| 248 | C—H | C—H | 3,5-bis(trifluoromethyl)phenyl- | H | Cyclopropyl | C—H | C—H | C—Cl | C—H | C—F | C—H | C—H | 18.25 | 610 | [M − H]− | A |
| 249 | C—H | C—H | 3-trifluoromethylphenyl- | H | i-Pr | C—H | C—H | C—F | C—H | C—F | C—H | C—H | 18.46 | 568 | [M + Na]+ | A |
| 250 | C—H | C—H | 3,4,5-trichlorophenyl- | H | Et | C—H | C—H | C—CN | C—H | C—F | C—H | C—H | 18.60 | 532 | [M − H]− | A |
| 251 | C—H | C—H | 3,4,5-trichlorophenyl- | H | i-Pr | C—H | C—H | C—CN | C—H | C—F | C—H | C—H | 18.86 | 562 | [M − H]− | A |
| 252 | C—H | C—H | 3,4,5-trichlorophenyl- | H | 2,2,2-trifluoro-ethyl- | C—H | C—H | C—CN | C—H | C—F | C—H | C—H | 18.12 | 591 | [M − H]− | A |
| 253 | C—H | C—H | 2-chloro-4-pyridyl- | H | (CH2)3 | C—H | C—H | C—H | C—H | C—H | C—H | C—H | 15.14 | 494 | [M + H]+ | A |
| 254 | C—H | C—H | 3,5-dichlorophenyl- | Et | 1-oxo-4-pyridyl- | C—H | C—H | C—CN | C—H | C—H | C—H | C—H | 18.92 | 492 | [M + H]+ | A |
| 255 | C—H | C—H | 2-trifluoromethyl-4-pyridyl- | H | Et | C—H | C—H | C—CN | C—H | C—H | C—H | C—H | 17.33 | 591 | [M + H]+ | A |
| 256 | C—H | C—H | 2,6-dichloro-4-pyridyl- | H | Et | C—H | C—H | C—CN | C—H | C—H | C—H | C—H | 18.45 | 506 | [M + H]+ | A |
| 257 | C—H | C—H | 3-trifluoromethylphenyl- | H | Et | C—H | C—H | C—F | C—H | C—H | C—H | C—H | 19.16 | 528 | [M + Na]+ | A |
| 258 | C—H | C—H | 3-trifluoromethylphenyl- | H | Et | C—H | C—H | C—CN | C—H | C—H | C—H | C—H | 19.54 | 498 | [M + H]+ | A |
| 259 | C—H | C—H | 3-trifluoromethylphenyl- | H | i-Pr | C—H | C—H | C—CN | C—H | C—H | C—H | C—H | 20.17 | 519 | [M + H]+ | A |
| 260 | C—H | C—H | 3,5-dichlorophenyl- | H | (CH2)3 | C—H | C—H | C—CN | C—H | C—H | C—H | C—H | 20.64 | 505 | [M + H]+ | A |
| 261 | C—H | C—H | 3,5-dichlorophenyl- | H | 3-thietanyl- | C—H | C—H | C—CN | C—H | C—H | C—H | C—H | 19.67 | 517 | [M + H]+ | A |
| 262 | C—H | C—H | 2-trifluoromethyl-4-pyridyl- | H | 1-oxo-3-thietanyl- | C—H | C—H | C—CN | C—H | C—H | C—H | C—H | 1.16 | 548 | [M + H]+ | B |
| 263 | C—H | C—H | 2-trifluoromethyl-4-pyridyl- | H | 1,1-dioxo-3-thietanyl- | C—H | C—H | C—CN | C—H | C—H | C—H | C—H | 1.04 | 564 | [M + H]+ | B |
| 264 | C—H | C—H | 2-trifluoromethyl-4-pyridyl- | H | Et | C—H | C—H | C—CN | C—H | C—H | C—H | C—H | 1.09 | 580 | [M + H]+ | B |

The table 3 below represents compounds of formula I** wherein R³ is trifluoromethyl Y¹ and G¹ are oxygen:

The compounds in the Table 3 were prepared from 2-amino-4-[(2S)-2-(3,5-dichlorophenyl)-2-(trifluoromethyl)-3H-benzofuran-5-yl]benzonitrile, which was obtained from 2-amino-4-[2-(3,5-dichlorophenyl)-2-(trifluoromethyl)-3H-benzofuran-5-yl]benzonitrile by separation on a preparative chiral HPLC, using standard amidation methods.

TABLE 3

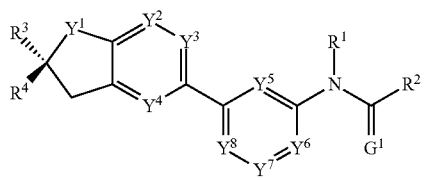

| Entry | Y2 | Y3 | Y4 | R4 | R1 | R2 | Y5 | Y6 | Y7 | Y8 | Y2 | Y3 | RT (min) | m/z | Ion | HPLC method |
|---|---|---|---|---|---|---|---|---|---|---|---|---|---|---|---|---|
| 265 | C—H | C—H | C—H | 3,5-dichlorophenyl- | H | 1-oxo-3-thietanyl- | C—H | C—CN | C—H | C—H | C—H | C—H | 1.18 | 563 | [M + H]+ | C |
| 266 | C—H | C—H | C—H | 3,5-dichlorophenyl- | H | Et | C—H | C—H | C—CN | C—H | C—H | C—H | 19.58 | 505 | [M + H]+ | A |

Chiral HPLC separation details for the preparation of 2-amino-4-[(2S)-2-(3,5-dichlorophenyl)-2-(trifluoromethyl)-3H-benzofuran-5-yl]benzonitrile:

Preparative Method:
 Column: 250×30 mm CHIRALPAK™ AD-H 5 um
 Mobile phase: Carbon dioxide/Methanol 75/25
 Flow rate: 120 mL/min
 Detection: UV 230 nm
 Temperature: 25° C.

Analytical Method:
 Column: 250×4.6 mm CHIRALPAK™ IF 5 um
 Mobile phase: Heptane/Ethanol/Diethylamine 90/10/0.1
 Flow rate: 0.7 mL/min
 Detection: DAD 280 nm
 Temperature: 25° C.

Results:
 From 442 mg of crude material:

| First eluting enantiomer (S) | | Second eluting enantiomer (R) | |
|---|---|---|---|
| CTE reference | P13013-1 | CTE reference | P13013-2 |
| Retention time (min) | 17.380 | Retention time (min) | 19.560 |
| Quantity (mg) | 198 | Quantity (mg) | 205 |
| Chemical purity (area % at 280 nm) | >99.5 | Chemical purity (area % at 280 nm) | >99 |
| Enantiomeric excess (%) | >99.5 | Enantiomeric excess (%) | >99.5 |

N-{2-Cyano-5-[2-(3,5-dichloro-phenyl)-2-trifluoromethyl-2,3-dihydro-benzo[b]thiophen-5-yl]-phenyl}-propionamide (267)

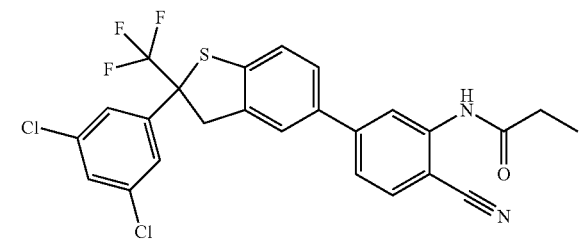 [SMILES: CCC(=O)Nc1cc(-c2ccc3c(c2)CC(c2cc(Cl)cc(Cl)c2)(C(F)(F)F)S3)ccc1C#N]

Step A: Synthesis of 5-Methoxy-2-methylsulfanyl-phenyl-diazene

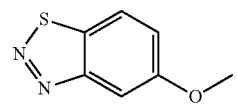

A mixture of 1-chloro-4-methoxy-2-nitrobenzene (37.6 g, 0.2 mol) and sodium sulfide (144 g, 0.6 mol) in 350 mL of water was reflux for 24 h. Then the mixture was poured into ice and extracted with ethyl acetate three times. The combined organic layers were dried over sodium sulfate, filtered and concentrated under reduced pressure to give the crude 2-amino-4-methoxybenzenethiol.

The above crude 2-amino-4-methoxybenzenethiol was added to a solution of 10 N aqueous HCl (50 mL, 0.5 mol) and 200 mL of water. Then, sodium nitrite (20.7 g, 0.3 mol) was slowly added at room temperature. After the addition, THF (200 mL) was added. The reaction mixture was stirred at room temperature for another 30 min, neutralized with saturated aqueous potassium carbonate and extracted with DCM. The organic layer was concentrated under reduced pressure and the residue was purified by column chromatography to afford 5-methoxy-1,2,3-benzothiadiazole (13.4 g, 37% yield).

Step B: Synthesis of 2-(3,5-Dichloro-phenyl)-5-methoxy-2-trifluoromethyl-2,3-dihydro-benzo[b]thiophene

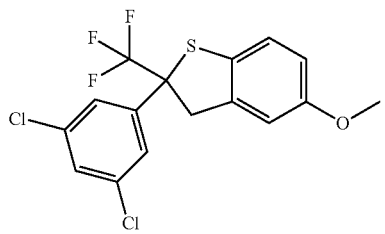 [SMILES: COc1ccc2c(c1)CC(c1cc(Cl)cc(Cl)c1)(C(F)(F)F)S2]

A mixture of 5-methoxy-1,2,3-benzothiadiazole (1.56 g, 6.48 mmol) and 1,3-dichloro-5-(1,1,1-trifluoroprop-2-en-2-yl)benzene (5 g, 21 mmol) in 20 mL of tert-butyl peroxide was refluxed for 16 h. Then the mixture was concentrated under reduced pressure. The residue was purified by column chromatography on silica gel to give 2-(3,5-Dichloro-phenyl)-5-methoxy-2-trifluoromethyl-2,3-dihydro-benzo[b]thiophene (1.05 g, 43% yield). $^1$H NMR (300 Mz, DMSO-d$_6$): δ:3.73 (s, 3H), 4.05 (q, 2H), 6.82 (d, 1H), 6.92 (s, 1H), 7.24 (d, 1H), 7.59 (s, 2H), 7.76 (s, 1H); $^{19}$F NMR (282 Mz, DMSO-d$_6$) δ: −73.37 (s, 3F).

Step C: Synthesis of 2-(3,5-Dichloro-phenyl)-2-trifluoromethyl-2,3-dihydro-benzo[b]thiophen-5-ol

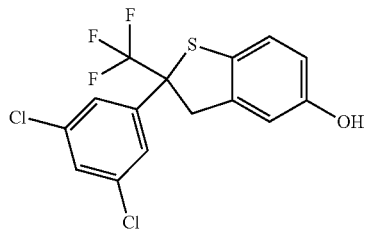 [SMILES: Oc1ccc2c(c1)CC(c1cc(Cl)cc(Cl)c1)(C(F)(F)F)S2]

BBr$_3$ (2.0M in CH$_2$Cl$_2$, 2 mL, 4 mmol) was added to a solution of 2-(3,5-Dichloro-phenyl)-5-methoxy-2-trifluoromethyl-2,3-dihydro-benzo[b]thiophene (378 mg, 1 mmol) in CH$_2$Cl$_2$ (10 mL) under nitrogen at −60° C. Then the mixture was refluxed for 16 h. 10 mL methanol was added to the mixture and stirring continued for 30 min at room temperature. The reaction mixture was poured into ice and extracted with ethyl acetate three times. The combined organic layers were dried over sodium sulfate, filtered and concentrated under reduce pressure. The residue was purified by column chromatography on silica gel to provide 2-(3,5-Dichloro-phenyl)-2-trifluoromethyl-2,3-dihydro-benzo[b]thiophen-5-ol (319 mg, 88% yield). $^1$H NMR (300 Mz, DMSO-d$_6$): δ: 3.98 (q, 2H), 6.60 (dd, 1H), 6.75 (s, 1H), 7.06 (d, 1H), 7.59 (s, 2H), 7.74 (s, 1H), 9.44 (s, 1H); $^{19}$F NMR (282 Mz, DMSO-d$_6$): δ: −73.21 (s, 3F). ESI-MS(−): 363 (M−H)$^-$.

Step D: Synthesis of trifluoro-methanesulfonic acid 2-(3,5-dichloro-phenyl)-2-trifluoromethyl-2,3-dihydro-benzo[b]thiophen-5-yl ester

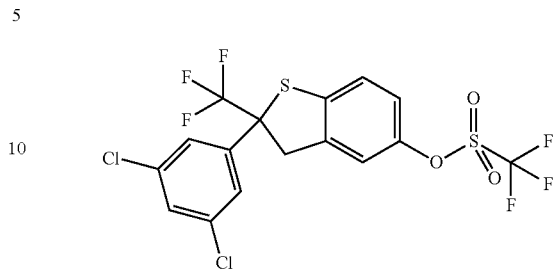

Trifluoromethanesulfonic anhydride (282 mg, 1 mmol) was added dropwise to a mixture of 2-(3,5-Dichloro-phenyl)-2-trifluoromethyl-2,3-dihydro-benzo[b]thiophen-5-ol (291 mg, 0.8 mmol), DMAP (10 mg, 0.1 mmol) and Et$_3$N (202 g, 2 mmol) in 20 mL of anhydrous CH$_2$Cl$_2$ under nitrogen at 0° C. After the addition, the reaction mixture was stirred at 0° C. for 30 min. Then the reaction mixture was poured into brine and extracted with CH$_2$Cl$_2$ three times. The combined organic layers were dried over sodium sulfate, filtered and concentrated in vacuo to dryness. The residue was purified by column chromatography on silica gel to give trifluoromethanesulfonic acid 2-(3,5-dichloro-phenyl)-2-trifluoromethyl-2,3-dihydro-benzo[b]thiophen-5-yl ester (388 mg, 98% yield). $^1$H NMR (300 Mz, DMSO-d$_6$): δ 4.14 (q, 2H), 7.39 (d, 1H), 7.46 (s, 1H), 7.53 (d, $^1$H), 7.59 (s, 2H), 7.80 (s, 1H); $^{19}$F NMR (282 Mz, DMSO-d$_6$): δ: −74.01 (s, 3F), −72.50 (s, 3F).

Step E: Synthesis of 2-amino-4-[2-(3,5-dichloro-phenyl)-2-trifluoromethyl-2,3-dihydro-benzo[b]thiophen-5-yl]-benzonitrile

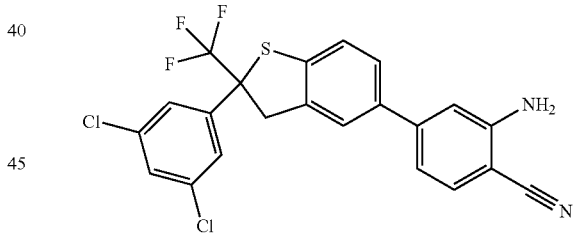

Under the protection of nitrogen, trifluoro-methanesulfonic acid 2-(3,5-dichloro-phenyl)-2-trifluoromethyl-2,3-dihydro-benzo[b]thiophen-5-yl ester (300 mg, 0.6 mmol), Pd(PPh$_3$)$_4$ (115 mg, 0.1 mmol), potassium carbonate (690 mg, 5 mmol) and 2-amino-4-(4,4,5,5-tetramethyl-1,3,2-dioxaborolan-2-yl)benzonitrile (244 mg, 1 mmol) were dissolved in 10 mL of ethylene glycol dimethyl ether and 2 mL of water. After the addition, the mixture was refluxed for 4 h. Then, it was poured into water and extracted with ethyl acetate three times. The combined organic layers were dried over sodium sulfate, filtered and concentrated under reduced pressure. The residue was purified by column chromatography on silica gel to provide 2-amino-4-[2-(3,5-dichloro-phenyl)-2-trifluoromethyl-2,3-dihydro-benzo[b]thiophen-5-yl]-benzonitrile (270 mg, 97% yield). $^1$H NMR (300 Mz, DMSO-d$_6$): δ 4.15 (d, 1H), 4.19 (d, 1H), 6.12 (s, 2H), 6.85 (dd, 1H), 7.03 (s, 1H), 7.45 (s, 2H), 7.48 (d, 1H), 7.53 (s, 1H), 7.63 (d, 2H), 7.78 (m, 1H); $^{19}$F NMR (282 Mz, DMSO-d$_6$): δ: −73.50 (s, 3F); ESI-MS(−): 463 (M−H)$^-$.

Step F: Synthesis of N-{2-Cyano-5-[2-(3,5-di-chloro-phenyl)-2-trifluoromethyl-2,3-dihydro-benzo[b]thiophen-5-yl]-phenyl}-propionamide (267)

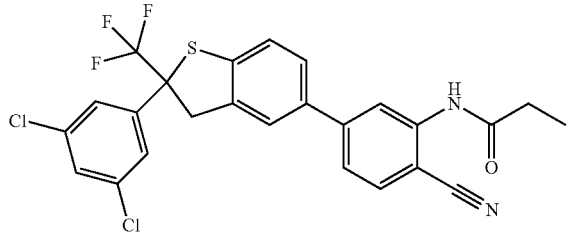 [SMILES: CCC(=O)Nc1cc(-c2ccc3c(c2)CC(c2cc(Cl)cc(Cl)c2)(C(F)(F)F)S3)ccc1C#N]

Propionyl chloride (92 mg, 1 mmol) was added to a mixture of 2-amino-4-[2-(3,5-dichloro-phenyl)-2-trifluoromethyl-2,3-dihydro-benzo[b]thiophen-5-yl]-benzonitrile (160 mg, 0.34 mmol) in 5 mL THF at room temperature. After the addition, the mixture was refluxed for 2 h. Then, the mixture was poured into water and extracted with ethyl acetate three times. The combined organic layers were dried over sodium sulfate, filtered and concentrated under reduced pressure. The residue was purified by column chromatography on silica gel to provide N-{2-Cyano-5-[2-(3,5-dichloro-phenyl)-2-trifluoromethyl-2,3-dihydro-benzo[b]thiophen-5-yl]-phenyl}-propionamide (158 mg, 89% yield). $^1$H NMR (300 Mz, DMSO-$d_6$): δ: 1.13 (t, 3H), 2.38 (q, 2H), 4.17 (q, 2H), 7.51 (d, 1H), 7.56-7.63 (m, 5H), 7.78 (s, 1H), 7.88 (d, 2H), 10.14 (s, 1H); $^{19}$F NMR (282 Mz, DMSO-$d_6$): δ: −73.52 (s, 3F); ESI-MS(−): 519 (M−H)$^-$.

N-[3-[2-(3,5-dichlorophenyl)-2-(trifluoromethyl)-3H-benzothiophen-5-yl]phenyl]propanamide (268)

This compounds was prepared using the methods described from compound 267.

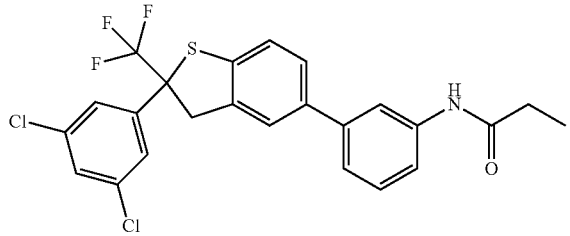 [SMILES: CCC(=O)Nc1cccc(-c2ccc3c(c2)CC(c2cc(Cl)cc(Cl)c2)(C(F)(F)F)S3)c1]

LC/Method A: RT=20.132 (min), m/z 496 [M+H]$^+$.

N-{3-[2-(3,5-Dichloro-phenyl)-1-oxo-2-trifluoromethyl-indan-5-yl]-phenyl}-propionamide (269)

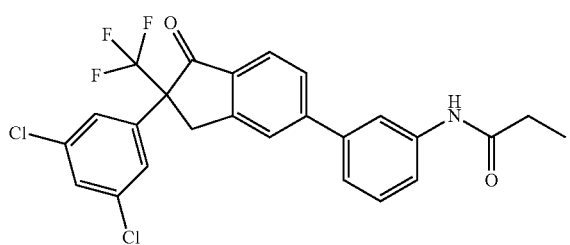 [SMILES: CCC(=O)Nc1cccc(-c2ccc3c(c2)CC(c2cc(Cl)cc(Cl)c2)(C(F)(F)F)C3=O)c1]

Step A: Synthesis of 1-bromomethyl-3-methoxy-benzene

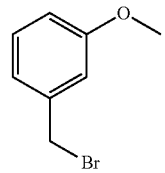

Phosphorous tribromide (29.0 g, 210 mmol) was added to a solution of (3-Methoxy-phenyl)-methanol (29.0 g, 210 mmol) in dry CH$_2$Cl$_2$ (300 mL) at 0° C. The reaction mixture was stirred at room temperature for 2 h before it was treated with cold water (100 mL). The organic layers were separated and the water phase was extracted with CH$_2$Cl$_2$ (3×100 mL). The combined organic layers were washed with water (2×100 mL), a saturated NaHCO$_3$ solution (100 mL), a saturated NaCl solution (100 mL), dried over MgSO$_4$, filtered, and concentrated in vacuo to afford 1-bromomethyl-3-methoxy-benzene (39.8 g, 94% yield). $^1$H NMR (300 Mz, DMSO-$d_6$): δ: 3.75 (s, 3H), 4.67 (s, 2H), 6.86-6.70 (m, 1H), 7.02 (q, 2H), 7.28 (m, 1H).

Step B: Synthesis of 2-(3,5-dichloro-phenyl)-3-(3-methoxy-phenyl)-propionic acid methyl ester

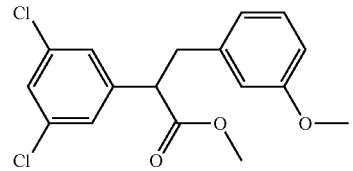 [SMILES: COC(=O)C(Cc1cccc(OC)c1)c1cc(Cl)cc(Cl)c1]

Freshly prepared LDA (1.0M in THF, 110 mL) was slowly added to a solution of methyl 3,5-dichlorophenylacetate (21.8 g, 100 mmol) in dry THF (200 mL) under nitrogen at −60° C. and stirring continued for 30 min. To this mixture was added 3-methoxybenzyl bromide (22.1 g, 110 mmol). After the addition, the mixture was stirred at −60° C. for another 3 h. Then, it was poured into diluted hydrochloric acid and extracted with ethyl acetate three times. The combined organic layers were dried over sodium sulfate, filtered and concentrated under reduced pressure. The crude product was purified by column chromatography on silica gel to give 2-(3,5-dichloro-phenyl)-3-(3-methoxy-phenyl)-propionic acid methyl ester (22.0 g, 65% yield). $^1$H NMR (300 Mz, DMSO-$d_6$): δ 2.93-3.02 (q, 1H), 3.20-3.27 (q, 1H), 3.57 (s, 3H), 3.69 (s, 3H), 4.15 (t, 1H), 6.71-6.77 (m, 3H), 7.14 (m, 1H), 7.41 (d, 2H), 7.49 (m, 1H).

Step C: Synthesis of 2-(3,5-dichloro-phenyl)-3-(3-methoxy-phenyl)-propionic acid

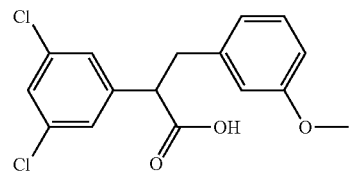 [SMILES: COc1cccc(CC(C(=O)O)c2cc(Cl)cc(Cl)c2)c1]

A mixture of 2-(3,5-dichloro-phenyl)-3-(3-methoxy-phenyl)-propionic acid methyl ester (33.8 g, 100 mmol) and LiOH (16.8 g, 400 mmol) in MeOH (100 mL)/H$_2$O (100 mL) were refluxed for 8 h. Then, the reaction mixture was poured into diluted hydrochloric acid and extracted with ethyl acetate three times. The combined organic layers were dried over sodium sulfate, filtered and concentrated in vacuo. The crude product was purified by column chromatography on silica gel to provide 2-(3,5-dichloro-phenyl)-3-(3-methoxy-phenyl)-propionic acid (29.2 g, 90% yield). $^1$H NMR (300 Mz, DMSO-d$_6$): δ 2.93-3.00 (q, 1H), 3.20-3.27 (q, 1H), 3.68 (s, 3H), 4.02 (t, 1H), 6.70-6.78 (m, 3H), 7.13 (t, 1H), 7.40 (d, 2H), 7.49 (t, 1H), 12.66 (s, 1H); ESI-MS(−): 323 (M−H)$^−$.

Step D: Synthesis of 2-(3,5-dichloro-phenyl)-3-(3-methoxy-phenyl)-propionyl chloride

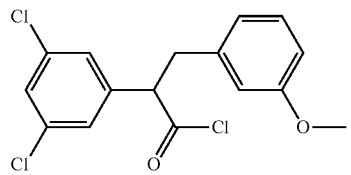 [SMILES: COc1cccc(CC(C(=O)Cl)c2cc(Cl)cc(Cl)c2)c1]

A mixture of 2-(3,5-dichloro-phenyl)-3-(3-methoxy-phenyl)-propionic acid (25.1 g, 77.5 mmol) in SOCl$_2$ (92.2 g, 775 mmol) was refluxed for 4 h. Then, the excess SOCl$_2$ was removed under reduced pressure to give the crude 2-(3,5-Dichloro-phenyl)-3-(3-methoxy-phenyl)-propionyl chloride in almost quantitative yield (28.2 g). The crude 2-(3,5-dichloro-phenyl)-3-(3-methoxy-phenyl)-propionyl chloride was directly used for the next step without further purification.

Step E: Synthesis of 2-(3,5-dichloro-phenyl)-5-methoxy-indan-1-one

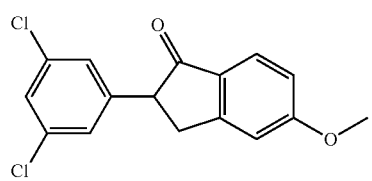 [SMILES: COc1ccc2c(c1)CC(c1cc(Cl)cc(Cl)c1)C2=O]

AlCl$_3$ (11.43 g, 86 mmol) was added to a solution of 2-(3,5-dichloro-phenyl)-3-(3-methoxy-phenyl)-propionyl chloride (28.20 g, 77.5 mmol) in CH$_2$Cl$_2$ (150 mL) at 0° C. Then the mixture was stirred at room temperature for 16 h. The reaction mixture was poured into ice and extracted with ethyl acetate three times. The combined organic layers were dried over sodium sulfate, filtered and concentrated in vacuo. The crude product was purified by column chromatography on silica gel to give 2-(3,5-dichloro-phenyl)-5-methoxy-indan-1-one (13.69 g, 58% yield). ESI-MS(+): 361 (M+Na+CH$_3$OH)$^+$; M.p.: 154-155V.

Step F: Synthesis of 2-(3,5-dichloro-phenyl)-5-methoxy-2-trifluoromethyl-indan-1-one

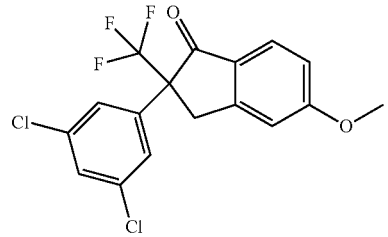 [SMILES: COc1ccc2c(c1)CC(c1cc(Cl)cc(Cl)c1)(C(F)(F)F)C2=O]

To a three-neck flask equipped with septum and magnetic stirrer were added 2-(3,5-dichloro-phenyl)-5-methoxy-indan-1-one (13.35 g, 43.6 mmol), DBU (13.25 g, 87.2 mmol) and CH$_3$CN (200 mL). A solution of CF$_3$I (35 g, 177.6 mmol) in CH$_3$CN (90.8 g) was also added. Then a solution of sodium dithionite (7.6 g, 43.6 mmol) in 180 mL of H$_2$O was added and the mixture was stirred for 4 h at room temperature. The reaction mixture was diluted with 200 mL of water and extracted with ethyl acetate three times. The combined organic layers were dried over sodium sulfate and evaporated in vacuo to dryness. The residue was purified by column chromatography on silica gel to give 2-(3,5-dichloro-phenyl)-5-methoxy-2-trifluoromethyl-indan-1-one (11.43 g, 70% yield). $^1$H NMR (300 Mz, DMSO-d$_6$): δ 3.86 (d, 1H), 3.90 (s, 3H), 3.98 (d, 1H), 7.06-7.10 (m, 1H), 7.15 (d, 1H), 7.74 (s, 3H), 7.77 (d, 1H); M.p.: 109-110° C. HPLC: 93.4%.

Step G: Synthesis of 2-(3,5-dichloro-phenyl)-5-hydroxy-2-trifluoromethyl-indan-1-one

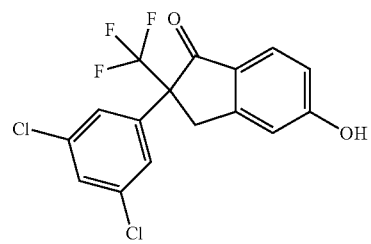 [SMILES: O=C1c2ccc(O)cc2CC1(c1cc(Cl)cc(Cl)c1)C(F)(F)F]

BBr$_3$ (2.0M in CH$_2$Cl$_2$, 90 mL, 180 mmol) was added to a solution of 2-(3,5-dichloro-phenyl)-5-methoxy-2-trifluoromethyl-indan-1-one (12.81 g, 34.3 mmol) in CH$_2$Cl$_2$ (100 mL) under nitrogen at −60° C. Then the mixture was refluxed for 24 h. 90 mL methanol was added to the mixture and stirring continued for 30 min at room temperature. The reaction mixture was poured into ice and extracted three times with ethyl acetate. The combined organic layers were dried over sodium sulfate, filtered and concentrated under reduce pressure. The residue was purified by column chromatography on silica gel to give 2-(3,5-dichloro-phenyl)-5-hydroxy-2-trifluoromethyl-indan-1-one (9.52 g, 77% yield). $^1$H NMR (300 Mz, DMSO-d$_6$): δ 3.87 (q, 2H), 6.86-6.89 (m, 2H), 7.85-7.70 (m, 4H), 11.07 (s, 1H); ESI-MS(−): 359 (M−H)$^−$; M.p.: 212-213° C.

Step H: Synthesis of trifluoro-methanesulfonic acid 2-(3,5-dichloro-phenyl)-1-oxo-2-trifluoromethyl-indan-5-yl ester

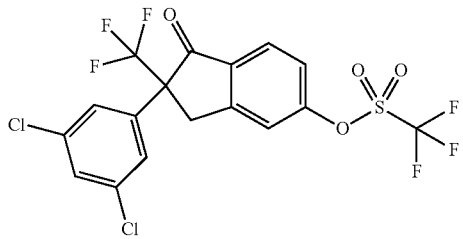 [SMILES: O=C1c2ccc(OS(=O)(=O)C(F)(F)F)cc2CC1(c1cc(Cl)cc(Cl)c1)C(F)(F)F]

Trifluoromethanesulonic anhydride (9.4 g, 26.1 mmol) was added dropwise to a mixture of 2-(3,5-dichloro-phenyl)-5-hydroxy-2-trifluoromethyl-indan-1-one (9.4 g, 21.6 mmol), DMAP (0.7 g, 5.7 mmol), and $Et_3N$ (3.3 g, 32.6 mmol) in 200 mL of anhydrous $CH_2Cl_2$ under nitrogen at 0° C. After the addition, the reaction mixture was stirred at 0° C. for 30 min. Then it was poured into brine and extracted with $CH_2Cl_2$ three times. The combined organic layers were dried over sodium sulfate, filtered and concentrated in vacuo to dryness. The residue was purified by column chromatography on silica gel to give trifluoro-methanesulfonic acid 2-(3,5-dichloro-phenyl)-1-oxo-2-trifluoromethyl-indan-5-yl ester (13.717 g, 100% yield). $^1$H NMR (300 Mz, $CDCl_3$): δ: 3.80 (d, 1H), 4.04 (d, 1H), 7.43-7.45 (m, 2H), 7.51 (s, 1H), 7.60 (s, 2H), 8.04 (d, 1H).

Step I: Synthesis of N-{3-[2-(3,5-dichloro-phenyl)-1-oxo-2-trifluoromethyl-indan-5-yl]-phenyl}-propionamide (269)

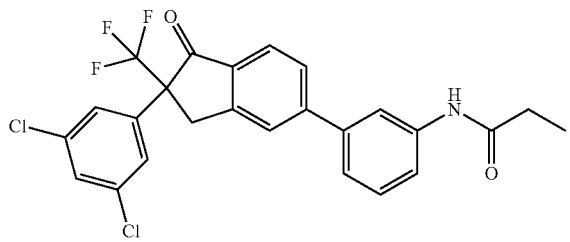 [SMILES: CCC(=O)Nc1cccc(-c2ccc3c(c2)CC(c2cc(Cl)cc(Cl)c2)(C(F)(F)F)C3=O)c1]

Under the protection of nitrogen, trifluoro-methanesulfonic acid 2-(3,5-dichloro-phenyl)-1-oxo-2-trifluoromethyl-indan-5-yl ester (492 mg, 1 mmol), Pd $(PPh_3)_4$ (230 mg, 0.2 mmol), potassium carbonate (552 mg, 4 mmol) and 3-aminobenzeneboronic acid (186 mg, 1.2 mmol) were dissolved in 30 mL of ethylene glycol dimethyl ether and 10 mL of water. After the addition, the mixture was refluxed for 4 h. Then, it was poured into water and extracted with ethyl acetate three times. The combined organic layers were dried over sodium sulfate, filtered and concentrated under reduced pressure to give the crude 5-(3-amino-phenyl)-2-(3,5-dichloro-phenyl)-2-trifluoromethyl-indan-1-one, which was added to a solution of compound $Et_3N$ (303 mg, 3 mmol) in 30 mL of THF. To the above solution, propionyl chloride (92 mg, 1 mmol) was added at room temperature. After the addition, the mixture was stirred at the same temperature for another 2 h. Then, the mixture was poured into water and extracted with ethyl acetate three times. The combined organic layers were dried over sodium sulfate, filtered and concentrated under reduced pressure. The residue was purified by column chromatography on silica gel to provide N-{3-[2-(3,5-dichloro-phenyl)-1-oxo-2-trifluoromethyl-indan-5-yl]-phenyl}-propionamide (113 mg, 23% yield). 1H NMR (300 Mz, DMSO-$d_6$): δ: 1.11 (t, 3H), 2.37 (q, 2H), 4.10 (q, 2H), 7.41-7.48 (m, 2H), 7.61-7.63 (m, 1H), 7.77-7.79 (m, 4H), 7.87 (s, 1H), 7.92 (d, 1H), 8.11 (s, 1H), 10.05 (s, 1H); ESI-MS(-): 490 (M-H)$^-$ N-{3-[2-(3,5-Dichloro-phenyl)-1-hydroxy-2-trifluoromethyl-indan-5-yl]-phenyl}-propionamide (270)

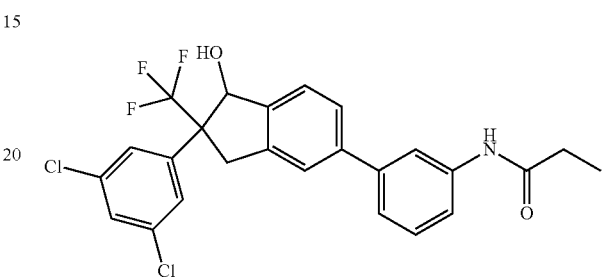

Sodium borohydride (38 mg, 1 mmol) was added to a mixture of N-{3-[2-(3,5-dichloro-phenyl)-1-oxo-2-trifluoromethyl-indan-5-yl]-phenyl}-propionamide (145 mg, 0.3 mmol) in 0.5 mL of water and 10 mL of tetrahydrofuran. After the addition, the reaction mixture was stirred at room temperature for 2 h. Then it was poured into water and extracted with ethyl acetate three times. The combined organic layers were dried over sodium sulfate, filtered and concentrated in vacuo to dryness. The residue was purified by column chromatography on silica gel to give N-{3-[2-(3,5-Dichloro-phenyl)-1-hydroxy-2-trifluoromethyl-indan-5-yl]-phenyl}-propionamide (140 mg, 95% yield). $^1$H NMR (300 Mz, DMSO-$d_6$): δ: 1.10 (t, 3H), 2.34 (q, 2H), 3.53 (d, 1H), 3.82 (d, 1H), 5.67 (s, 1H), 6.70 (d, 1H), 7.29-7.50 (m, 5H), 7.56 (d, 1H), 7.69 (t, 1H), 7.78 (s, 2H), 7.94 (s, 1H), 9.97 (s, 1H). $^{19}$F NMR (300 Mz, DMSO-$d_6$): δ: -61.55 (s, 3F); ESI-MS(-): 492 (M-H)$^-$.

BIOLOGICAL EXAMPLES

These Examples illustrate the pesticidal/insecticidal properties of compounds of formula (I). Tests were performed as follows:

Spodoptera Littoralis (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality, anti-feedant effect, and growth inhibition in comparison to untreated samples 3 days after infestation. Control of Spodoptera littoralis by a test sample is when at least one of mortality, anti-feedant effect, and growth inhibition is higher than the untreated sample.

The following compounds resulted in at least 80% control at an application rate of 200 ppm: 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 203, 204, 205, 209, 210, 211, 212, 213, 214, 215, 216, 217, 218, 219, 220, 221, 222, 223, 224, 225, 226, 227, 228, 229, 230, 231, 232, 233, 234, 235, 236, 237 239, 241, 242, 243, 244, 245, 246, 247, 249, 250, 251, 252, 253, 256, 257, 258, 259, 260, 261, 264, 265, 266, 267, 268, 269, 270

*Heliothis virescens* (Tobacco Budworm):

Eggs (0-24 h old) were placed in 24-well microtiter plates on artificial diet and treated with aqueous test solutions prepared from 10,000 ppm DMSO stock solutions by pipetting. The samples were assessed for egg and larval mortality 5 days after infestation.

The following compounds resulted in at least 80% egg or larval mortality at an application rate of 200 ppm:

1, 2, 5, 6, 9, 11, 15, 16, 19, 20, 21, 22, 23, 25, 26, 27, 28, 29, 30, 31, 32, 36, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 73, 7477, 78, 79, 80, 81, 82, 83, 84, 85, 86, 87, 88, 89, 90, 91, 92, 93, 94, 95, 96, 97, 98, 99, 100, 101, 102, 103, 105, 106, 107, 108, 109, 110, 111, 112, 113, 114, 115, 116, 117, 118, 119, 120, 121, 122, 123, 124, 125, 126, 127, 131, 132, 133, 134, 135, 136, 137, 138, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 174, 175, 176, 177, 178, 179, 180, 181, 182, 183, 184, 185, 186, 187, 188, 189, 190, 191, 194, 195, 196, 197, 198, 199, 200, 202, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 249, 250, 251, 252, 253, 255, 266, 269, 270

*Plutella xylostella* (Diamond Back Moth):

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

2, 6, 9, 15, 19, 20, 25, 27, 29, 30, 31, 32, 34, 35, 36, 40, 41, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 77, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 209, 210, 211, 212, 213, 214, 215, 216, 217, 218, 219, 220, 221, 222, 223, 224, 225, 226, 227, 228, 229, 230, 231, 232, 233, 234, 235, 236, 237, 241, 242, 243, 245, 246, 247, 249, 250, 251, 252, 253, 254, 255, 256, 257, 258, 259 260, 261, 262, 263, 264, 265, 266, 267, 268, 269, 270

*Diabrotica balteata* (Corn Root Worm):

24-well microtiter plates with artificial diet were treated with aqueous test solutions prepared from 10,000 ppm DMSO stock solutions by pipetting. After drying, the plates were infested with L2 larvae (6 to 10 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

9, 15, 25, 32, 46, 74, 75, 79, 80, 81, 86, 87, 88, 89, 90, 91, 94, 95, 96, 98, 102, 110, 111, 113, 114, 117, 118, 120, 121, 122, 123, 127, 128, 130, 132, 133, 134, 135, 137, 139, 141, 143, 144, 145, 146, 147, 148, 150, 151, 152, 153, 154, 155, 156, 157, 158, 160, 161, 162, 164, 165, 166, 167, 168, 169, 170, 172, 173, 174, 175, 176, 177, 178, 180, 181, 183, 184, 185, 186, 187, 188, 189, 190, 191, 192, 193, 195, 196, 197, 198, 199, 200, 205, 207, 208, 209, 210, 211, 212, 213, 214, 215, 216, 217, 218, 219, 220, 221, 222, 224, 225, 226, 227, 228, 229, 230, 231, 232, 233, 234, 235, 236, 237, 239, 243, 269, 270

*Myzus persicae* (Green Peach Aphid)

Test compounds from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:

61, 74, 81, 107, 115, 118, 119, 131, 132, 133, 134, 135, 141, 145, 148, 149, 150, 151, 153, 156, 157, 159, 160, 161, 162, 164, 166, 168, 169, 175, 176, 177, 180, 181, 183, 184, 185, 186, 187, 188, 189, 190, 191, 192, 193, 194, 195, 196, 197, 198, 199, 210, 211, 215, 216, 217, 218, 219, 220, 221, 222, 224, 225, 226, 227, 228, 229, 230, 231, 232, 233, 234, 235, 236, 243, 246, 249, 250, 251, 252, 253, 256, 258, 259, 260, 262, 263, 265, 266, 268

*Thrips tabaci* (Onion *Thrips*):

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation. The following compounds resulted in at least 80% mortality at an application rate of 200 ppm:

9, 49, 75, 79, 80, 81, 85, 91, 94, 95, 96, 98, 102, 113, 118, 128, 131, 133, 134, 141, 144, 145, 148, 150, 151, 152, 153, 154, 155, 156, 157, 158, 160, 162, 165, 166, 167, 168, 169, 170, 174, 175, 176, 177, 178, 179, 180, 181, 183, 184, 185, 186, 187, 188, 189, 190, 191, 192, 193, 194, 195, 196, 197, 198, 199, 200, 205, 209, 210, 211, 212, 214, 215, 217, 218, 219, 220, 221, 222, 223, 224, 225, 226, 227, 228, 229, 230, 231, 232, 233, 234, 235, 236, 237, 241, 245, 246, 249, 250, 251, 252, 253, 256, 257, 258, 259, 260, 262, 263, 265, 266, 268, 269

*Tetranychus urticae* (Two-Spotted Spider Mite):

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: 10, 24, 31, 32, 52, 59, 64, 74, 78, 98, 102, 103, 107, 113, 115, 118, 119, 122, 125, 128, 134, 147, 149, 150, 152, 156, 157, 158, 160, 161, 164, 166, 168, 170, 175, 176, 177, 181, 183, 184, 185, 189, 190, 191, 195, 196, 197, 198, 209, 210, 211, 218, 220, 222, 225, 226, 227, 228, 229, 230, 231, 234, 235, 236, 250, 251, 252, 253, 255, 256, 259, 260, 263, 264, 265, 266

The invention claimed is:

1. A compound of formula I

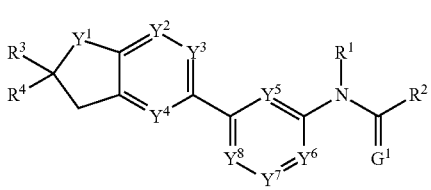

(I)

wherein
$G^1$ is oxygen or sulfur;
$Y^1$ is oxygen, sulfur, C(O), CHOR or CH$_2$;
$Y^2$, $Y^3$ and $Y^4$ are each independently C—H, C—$R^5$ or nitrogen, wherein no more than one of $Y^2$, $Y^3$ and $Y^4$ is C—$R^5$;
$Y^5$ is C—H, C—F or nitrogen;
$Y^6$ is C—H, C—$R^{6a}$ or nitrogen;
$Y^7$ is C—H, C—$R^{6b}$ or nitrogen;
$Y^8$ is C—H, C—$R^{6c}$ or nitrogen;
R is hydrogen, $C_1$-$C_8$alkyl;
$R^1$ is hydrogen, $C_1$-$C_8$alkyl, $C_1$-$C_8$alkoxy, $C_1$-$C_8$alkylcarbonyl, $O_3$—$C_8$cycloalkylcarbonyl or $C_1$-$C_8$alkoxycarbonyl;
$R^2$ is $C_1$-$C_8$alkyl or $C_1$-$C_8$alkyl substituted by one to five $R^7$, $C_2$-$C_8$alkenyl or $C_2$-$C_8$alkenyl substituted by one to five $R^7$, $C_2$-$C_8$alkynyl or $C_2$-$C_8$alkynyl substituted by one to five $R^7$, $C_1$-$C_8$alkoxy-$C_1$-$C_8$alkyl or $C_1$-$C_8$alkoxy-$C_1$-$C_8$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-$C_1$-$C_4$alkylene or $C_3$-$C_{10}$cycloalkyl-$C_1$-$C_4$alkylene substituted by one to five $R^8$, aryl-$C_1$-$C_4$alkylene- or aryl-$C_1$-$C_4$alkylene- substituted by one to five $R^9$, heterocyclyl-$C_1$-$C_4$alkylene- or heterocyclyl-$C_1$-$C_4$alkylene- substituted by one to five $R^9$, aryl or aryl substituted by one to five $R^9$, heterocyclyl or heterocyclyl substituted by one to five $R^9$;
or $R^1$ and $R^2$ form a four to six membered ring together with the atoms to which they are attached substituted by one to five $R^7$
$R^3$ is $C_1$-$C_8$haloalkyl;
$R^4$ is aryl or aryl substituted by one to five $R^{10}$, or heteroaryl or heteroaryl substituted by one to five $R^{10}$;
each $R^5$ is independently halogen, cyano, $C_1$-$C_4$alkyl, $C_1$-$C_4$haloalkyl, $C_1$-$C_4$alkoxy or $C_1$-$C_4$haloalkoxy;
$R^{6a}$ is halogen, cyano, $C_1$-$C_4$alkyl, $C_1$-$C_4$haloalkyl, $C_1$-$C_4$alkoxy or $C_1$-$C_4$haloalkoxy;
$R^{6b}$ is fluoro or chloro;
$R^{6c}$ is halogen, cyano, $C_1$-$C_4$alkyl, $C_1$-$C_4$haloalkyl, $C_1$-$C_4$alkoxy or $C_1$-$C_4$haloalkoxy;
each $R^7$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, carbonylamino, (carbonyl)($C_1$-$C_8$alkyl)amino, ($C_1$-$C_8$alkylcarbonyl)($C_1$-$C_8$alkyl)amino, ($C_1$-$C_8$haloalkylcarbonyl)($C_1$-$C_8$alkyl)amino, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, aryl-$C_1$-$C_4$alkylthio or aryl-$C_1$-$C_4$alkylthio wherein the aryl moiety is substituted by one to five $R^{11}$, or $R^7$ is OH—N= or $C_1$-$C_6$alkoxy-N=;
each $R^8$ is independently halogen, cyano, $C_1$-$C_8$alkyl, $C_2$-$C_8$alkenyl, $C_2$-$C_8$alkynyl, $C_1$-$C_8$alkoxy, or $C_1$-$C_8$akoxycarbonyl;
each $R^9$ is independently halogen, cyano, nitro, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_5$haloalkynyl, $C_3$-$C_{10}$cycloalkyl, $C_3$-$C_{10}$cycloalkyl-$C_1$-$C_4$alkylene, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylaminosulfonyl, ($C_1$-$C_8$alkyl)$_2$aminosulfonyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl;
each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;
each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy;
or a salt or N-oxide thereof.

2. A compound according to claim 1, wherein $Y^1$ is oxygen.

3. A compound according to claim 1, wherein $G^1$ is oxygen.

4. A compound according to claim 1, wherein $Y^2$ and $Y^4$ are C—H, and $Y^3$ is C—H or C—$R^5$.

5. A compound according to claim 4, wherein $R^5$ is halogen, cyano, methyl, halomethyl, methoxy or halomethoxy.

6. A compound according to claim 1, wherein $Y^5$, $Y^7$ and $Y^8$ are C—H or nitrogen and $Y^6$ is C—H, C—$R^{6a}$ or nitrogen, wherein no more than two of $Y^5$, $Y^6$, $Y^7$ and $Y^8$ are nitrogen.

7. A compound according to claim 6, wherein $R^{6a}$ is halogen, cyano, methyl, halomethyl, methoxy or halomethoxy.

8. A compound according to claim 1, wherein $R^2$ is $C_1$-$C_6$alkyl or $C_1$-$C_6$alkyl substituted by one to five $R^7$, $C_2$-$C_6$alkenyl or $C_2$-$C_6$alkenyl substituted by one to five $R^{12}$, $C_2$-$C_6$alkynyl or $C_2$-$C_6$alkynyl substituted by one to five $R^7$, $C_1$-$C_6$alkoxy-$C_1$-$C_6$alkyl or $C_1$-$C_6$alkoxy-$C_1$-$C_6$alkyl substituted by one to five $R^7$, $C_3$-$C_{10}$cycloalkyl or $C_3$-$C_{10}$cycloalkyl substituted by one to five $R^8$, $C_3$-$C_{10}$cycloalkyl-C($R^{12}$)($R^{13}$)— or $C_3$-$C_{10}$cycloalkyl-C($R^{12}$)($R^{13}$)— substituted by one to five $R^9$, aryl-C($R^{12}$)($R^{13}$)— or aryl-C($R^{12}$)($R^{13}$)— substituted by one to five $R^9$, heterocyclyl-C($R^{12}$)($R^{13}$)— or heterocyclyl-C($R^{12}$)($R^{13}$)— substituted by one to five $R^9$, aryl or aryl substituted by one to five $R^9$, heterocyclyl or heterocyclyl substituted by one to five $R^9$;
wherein aryl is phenyl;
wherein heterocyclyl is a 4- to 7-membered heterocyclic ring containing one to four heteroatoms independently selected from O, S, SO, SO$_2$, N and N($R^{14}$) as ring atoms; and wherein $R^{12}$ and $R^{13}$ are independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;
wherein $R^{14}$ is hydrogen or $R^9$.

9. A compound according to claim 1, wherein $R^3$ is chlorodifluoromethyl, difluoromethyl or trifluoromethyl.

10. A compound according to claim 1, wherein $R^4$ is group A

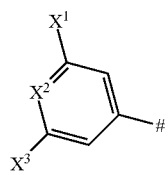

(A)

wherein $X^2$ is C—$X^4$ or nitrogen and $X^1$, $X^3$ and $X^4$ are independently hydrogen, halogen or trihalomethyl, providing that at least one of $X^1$, $X^3$ and $X^4$ is not hydrogen, wherein # is the attachment point.

11. An insecticidal, acaricidal, nematicidal or molluscicidal composition comprising an insecticidally, acaricidally, nematicidally or molluscicidally effective amount of a compound of formula (I) as defined in claim 1.

12. An insecticidal, acaricidal, nematicidal or molluscicidal composition according to claim 11 comprising at least one additional compound having biological activity.

13. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene, clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

14. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

* * * * *

UNITED STATES PATENT AND TRADEMARK OFFICE
CERTIFICATE OF CORRECTION

| | | |
|---|---|---|
| PATENT NO. | : 9,598,389 B2 | Page 1 of 1 |
| APPLICATION NO. | : 14/771600 | |
| DATED | : March 21, 2017 | |
| INVENTOR(S) | : Long Lu et al. | |

It is certified that error appears in the above-identified patent and that said Letters Patent is hereby corrected as shown below:

In the Claims

Column 145, Line 30, the O3 should be C3.

Column 146, Line 12, the C5 should be C8.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*